(12) United States Patent
Hayflick

(10) Patent No.: US 6,479,256 B1
(45) Date of Patent: *Nov. 12, 2002

(54) LECTOMEDIN MATERIALS AND METHODS

(75) Inventor: Joel S. Hayflick, Seattle, WA (US)

(73) Assignee: ICOS Corporation, Bothell, WA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/262,537

(22) Filed: Mar. 4, 1999

Related U.S. Application Data

(60) Provisional application No. 60/076,782, filed on Mar. 4, 1998.

(51) Int. Cl.[7] .......................... C12P 21/06; C12N 1/20; C12N 15/00; C12N 15/74; C07H 21/04
(52) U.S. Cl. ................ 435/69.1; 435/252.3; 435/320.1; 435/471; 536/23.5
(58) Field of Search .............................. 435/69.1, 70.1, 435/71.1, 71.2, 252.3, 325, 471, 320.1; 536/23.5

(56) References Cited

U.S. PATENT DOCUMENTS

| | | | |
|---|---|---|---|
| 5,350,836 A | * | 9/1994 | Kopchick et al. |
| 5,869,632 A | * | 2/1999 | Soppet et al. |

FOREIGN PATENT DOCUMENTS

| | | | |
|---|---|---|---|
| WO | WO 91/09955 | | 7/1991 |
| WO | WO 92/20808 | | 11/1992 |
| WO | WO 93/11236 | | 6/1993 |
| WO | WO 94/12650 | | 6/1994 |
| WO | WO 97/07209 | * | 2/1997 |
| WO | WO 97/09433 | | 3/1997 |
| WO | WO 98/49289 | | 11/1998 |

OTHER PUBLICATIONS

Vukicevic et al. PNAS USA 93:9021–9026, 1996.*
Massague J. Cell 49:437–8, 1987.*
Pilbeam et al. Bone 14:717–720, 1993.*
Skolnick et al. Trends in Biotech. 18:34–39, 2000.*
Bork P. Genome Research 10:398–400, 2000.*
Doerks et al. Trends in Genetics 14:248–250, 1998.*
Smith et al. Nature Biotechnology 15:1222–1223, 1997.*
Brenner SE. Trends in Genetics 15:132–133, 1999.*
Bork et al. Trends in Genetics 12:425–427, 1996.*
Rudinger J. et al. Characteristics of the amino acids as components of a peptide hormone sequence. in Peptide Hormones. pp. 1–7. Edited by Parsons, JA; Mill Hill, London, 1976.*
George et al. Current methods in sequence comparison and analysis. In Macromolecular Sequencing and Synthesis—selected methods and applications. Ed. Schlesinger, Alan R. Liss, Inc, NY. pp. 127–149, 1988.*
Lelianova VG. et al. a Latrotoxin receptor, latrophilin, is a novel member of the secretin family of G protein–coupled receptors. J. Biol. Chem. vol. 272, pp. 21504–21508, 1997.*

Krasnoperov VG. a–Latrotoxin stimulates exocytosis by the interaction with a neuronal G–protein–coupled receptor. Neuron. vol. 18, pp. 925–937, 1997.*

Danielson PE, et al. Four structurally distinct neuron–specific olfactomedin–related glycoproteins produced by differential promoter utilization and alternative mRNA splicing from a single gene. J. Neurosci. Res. vol. 38, pp. 468–478, 1994.

Sambrook J, et al. Molecular cloning: a laboratory manual. Second Ed. Cold Spring Harbor Laboratory Press. pp. 17.3–17.44, 1989.

Anderson, "Human gene therapy," *Nature*, supplement to vol. 392:25–30 (1998).

Arar, et al., "Galectin–3 gene (LGALS3) expression in experimental atherosclerosis and cultured smooth muscle cells," *FEBS Letts.* 430:307–311 (1998).

Ausubel, et al., "Screening of Recombinant DNA Libraries," *Protocols in Molecular Biology*, pp. 6.0.3–6.4.10 (1994).

Baud V., "EMR1, an Unusual Member in the Family of Hormone Receptors with Seven Transmembrane Segments," *Genomics* 26:334–344 (1995).

Bramlage, et al., "Designing ribozymes for the inhibition of gene expression," *Trends in Biotech* 16:434–438 (1998).

Campbell, et al., "Epidermal growth factor–like modules," *Curr. Opin. Struct. Biol.* 3:385–392 (1993).

Cane, et al., "Harnessing the Biosynthetic Code: Combinations, Permutations, and Mutations," *Science* 282:63–68 (1998).

Capecchi, "Altering the Genome by Homologous Recombination," *Science* 244:1288–1292 (1989).

Clapham, "The G–protein nanomachine," *Nature* 379:297–299 (1996).

Davletov, et al., "Isolation and Biochemical Characterization of a $Ca^{2+}$–independent α–Latrotoxin–binding Protein*," *J. Biol. Chem.* 271:23239–23245 (1996).

Dayhoff, *Atlas of Protein Sequence and Structure*, 5:124 (1972).

D'Souza, et al., "Arginyl–glycyl–aspartic acid (RGD): a cell adhesion motif," *Trends Biochem. Sci.*, 16:246–250 (1991).

Friedmann, "Progress Toward Human Gene Therapy," *Science*, 244:1275–1281 (1989).

(List continued on next page.)

Primary Examiner—Gary L. Kunz
Assistant Examiner—Robert S. Landsman
(74) *Attorney, Agent, or Firm*—Marshall, Gerstein & Borun

(57) ABSTRACT

Disclosed are novel seven transmembrane receptor polypeptides having characteristic extracellular structure including lectin-binding, olfactomedin-like and mucin-like domains.

13 Claims, No Drawings

OTHER PUBLICATIONS

Gibson et al., "Ribozymes; Their Function and Strategies for Their Use," *Mol. Biotech.* 7:125–137 (1997).

Gray, et al., "CD97 is a Processed, Seven–Transmembrane, Heterodimeric Receptor Associated with Inflammation[1]," *J. Immunol* 157:5438–5447 (1996).

Hamann, et al., "The Seven–Span Transmembrane Receptor CD97 Has a Cellular Ligand (CD55, DAF)," *J. Exp. Med.* 184:1185–1189 (1996).

Hamann J., et al., "Expression Cloning and Chromosomal Mapping of the Leukocyte Activation Antigen CD97, a New Seven–Span Transmembrane Molecule of the Secretin Receptor Superfamily with an Unusual Extracellular Domain[1]," *Immunol* 155:1942–1950 (1996).

Harlow, et al., "Monoclonal Antibodies," *Antibodies: A Laboratory Manual*, Chapter 6 (1988).

Houston et al., "The chemical–biological interface: developments in automated and miniaturised screening technology," *Curr. Opin. Biotechnol.* 8:734–740 (1997).

Inohara, et al., "Galectin–3 Stimulates Cell Proliferation," *Exp. Cell. Res.* 245:294–302 (1998).

Jayawickreme and Kost, "Gene expression systems in the development of high–throughout screens," *Curr. Opin. Biotechnol.* 8:629–634 (1997).

Kashishian, et al., "AKAP79 Inhibits Calcineurin through a Site Distinct from the Immunophilin–binding Region*," *J. Bio. Chem.* 273:27412–27419 (1998).

Kobilka, et al., "Cloning, Sequencing, and Expression of the Gene Coding for the Human Platelet $\alpha_2$–Adrenergic Receptor," *Science* 238:650–656 (1987).

Krasnoperov, et al., "α–Latrotoxin Stimulates Exocytosis by the Interaction with a Neuronal G–Protein–Coupled Receptor," *Neuron* 18:925–937 (1997).

Lavrovsky, et al., "Therapeutic Potential and Mechanism of Action of Oligonucleotides and Ribozymes," *Biochem. Mol. Med.* 62:11–22 (1997).

Lehninger, "The Amino Acid Building Blocks of Proteins," *Biochemistry*, pp. 71–77 (1975).

Lelianova, et al., "α–Latroxin Receptor, Latrophilin, Is a Novel Member of the Secretin Family of G Protein–coupled Receptors*," *J. Biol. Chem.* 272:21504–21508 (1997).

Lewin, B., "Mechanisms of RNA Splicing," *GENES IV*, p. 597 (1992).

McKnight, et al., "Molecular Cloning of F4/80, a Murine Macrophage–restricted Cell Surface Glycoprotein with Homology to the G–protein–linked Transmembrane 7 Hormone Receptor Family*," *J. Biol. Chem.* 271:486–489 (1996).

McKnight, et al., "EGF–TM7: a novel subfamily of seven–transmembrane–region leukocyte cell–surface molecules," *Immunol Today* 17:283–287 (1996).

Meldolesi, "Studies on α–Latrotoxin Receptors in Rat Brain Synaptosomes: Correlation Between Toxin Binding and Stimulation of Transmitter Release," *J. Neurochem.* 38:1559–1569 (1982).

Miller, "Human gene therapy comes of age," *Nature* 357:455–460 (1992).

Myers, "Will combinatorial chemistry deliver real medicines?," *Curr. Opin. Biotechnol.* 8:701–707 (1997).

Nachtigal, et al., "Galectin–3 Expression in Human Atherosclerotic Lesions," *Am. J. Pathol.* 152:1199–1208 (1998).

Nishimori, et al., "A Novel brain–specific p53–target gene, BAI1, containing thrombospondin type 1 repeats inhibits experimental angiogenesis," *Oncogene* 15:2145–2150 (1997).

Ozeki, et al., "Amino Acid Sequence and Molecular Characterization of a $_D$–Galactoside–Specific Lectin Purified from Seq Urchin (*Anthocidaris crassispina*) Eggs[†]," *Biochemistry* 30:2391–2394 (1991).

Perillo, et al., "Galectins: versatile modulators of cell adhesion, cell proliferation, and cell death," *J. Mol. Med.* 76:402–412 (1998).

Pesheva, et al., "Galectin–3 Promotes Neural Cell Adhesion and Neurite Growth," *J. Neurosci. Res.* 54:639–654 (1998).

Petrenko, et al., "Isolation and properties of the α–latrotoxin receptor," *EMBO J* 9:2023–2027 (1990).

Petrenko, et al., "*Minireview*: α–Latrotoxin receptor; Implications in nerve terminal funciton," *F.E.B.S. Letts.* 325:81–85 (1993).

Rao, et al., "The Structure of a $Ca^{2+}$–Binding epidermal Growth Factor–like Domain: Its Role in Protein–Protein Interactions," *Cell* 82:131–141 (1995).

Remington's Pharmaceutical Sciences, 18th Ed. (1990, Mack Publishing Co., Easton, PA 18042) 1435–1712.

Ross, "The pathogenesis of atherosclerosis: a perspective for the 1990s," *Nature* 362:801–809 (1993).

Sadhu, et al., "LFA–1 Binding Site in ICAM–3 Contains a Conserved Motif and Non–Contiguous Amin oAcids," *Cell Adhesion and Commun.* 2:429–440 (1994).

Sambrook, et al., (Eds.), *Molecular Cloning: A Laboratory Manual*, Cold Spring Harbor Laboratory Press: Cold Spring Harbor, New York (1989), pp. 9.47–9.51.

Van der Vieren, M., et al., "A Novel Leukointegrin, $\alpha d \beta 2$, Binds Preferentially to ICAM–3," *Immunity* 3:683–690 (1995).

Verma, "Gene Therapy: Treatment of disease by introducing healthy genes into the body is becoming feasible. But the therapy will not reach its full potential until the genes can be coaxed to work throughout life," *Scientific American* 68–84 (1990).

Yokoe and Anholt, "Molecular cloning of olfactomedin, an extracellular matrix protein specific to olfactory neuroepithelium," *Proc. Natl. Acad. Sci.* (*USA*) 90:4655–4659 (1993).

* cited by examiner

LECTOMEDIN MATERIALS AND METHODS

The application claims priority of U.S. Provisional Application Serial No. 60/076,782, filed Mar. 4, 1998.

BACKGROUND OF THE INVENTION

G-protein coupled receptors (GPCRs) are proteins that interact with G-proteins to transmit an intracellular signal. Upon ligand binding, GPCRs trigger the hydrolysis of GTP to GDP by G-protein subunits; GTP hydrolysis is accompanied by a switch from activity to inactivity. It is estimated that there are roughly 1,000 GPCRs [Clapham, *Nature* 379:297–299 (1996)] and all characterized to date include a seven transmembrane domain that anchors the receptor to the cell. GPCRs include receptors for opiates, adrenaline, histamine, polypeptide hormones, and photons, among other ligands. These receptors are coupled to a wide variety of cellular second messenger pathways including, for example, pathways that alter intracellular calcium concentrations and cAMP levels.

Among the various GPCRs identified, CD97 appears to be representative of a sub-family of proteins which effect cellular adhesion [McKnight, et al., *Immunol Today* 17:283–287(1996)]. CD97 and related receptors are unique in that their structure includes a transmembrane domain that directly links a cytoplasmic domain that participates in GTP hydrolysis with extracellular protein binding domains that specifically participate in cell-cell adhesion. The extracellular, amino terminal region of CD97 includes numerous cell-cell adhesive motifs, including multiple epidermal growth factor-like (EGF-like) repeats and an integrin binding site [Hamann J, et al., Immunol 155:1942—1950 (1996); Gray, et al., *J. Immunol* 157:5438–5447 (1996)]. Proteins that contain EGF-like repeats have been shown to be involved in cell adhesion events [Campbell, et al., *Curr. Opin. Struct. Biol.* 3:385–392 (1993); Rao,et al., *Cell* 82:131–141 (1995)], and consistent with this observation, heterologous expression of CD97 in COS cells elicits homotypic cell aggregation that can be blocked in the presence of anti-CD97 monoclonal antibodies [Hamann, et al., *J. Exp. Med.* 184:1185–1189 (1996)]. CD97 and related proteins have been referred to as the EGF-7TM subfamily of seven transmembrane receptors [McKNight and Gordon, *Immunol. Today* 17:283–2887 (1996)]. Ligands identified for CD97 include members of the integrin family of cell surface adhesion receptors. Various integlins recognize and interact with their cognate ligands through a trimeric amino acid sequence of arginine-glycine-aspartic acid (denoted RGD in the single letter amino acid code) [D'Souza, et al., *Trends Biochem. Sci.*, 16:246–250 (1991)] and this sequence has been identified in the extracellular region of CD97, between the EGF-like repeats and the transmembrane domain.

CD97 has been shown to undergo post-translational proteolytic processing which results in an extracellular (and potentially soluble) alpha subunit and a smaller, integral membrane beta subunit [Gray, et al., *J. Immunol.* 157:5438–5447 (1996)]. The two subunits are associated in a non-covalent manner and the alpha subunit is held at the cell surface through its interaction with the beta subunit. The role of proteolysis is unclear, but it may be a mechanism for receptor down-regulation which is common among proteins, such as selectins and intercellular adhesion molecules (ICAMs), that participate in cell adhesion.

Other members of the CD97 sub-family of GPCRs have been identified by amino acid sequence and structural homology and include human EMR1, HE6, BAI1, the calcium-independent receptor of latrotoxin (CIRL), latrophilin, and proteins encoded by the *Caenorhabditis elegans* open reading frames designated B0457.1 and B0286.2 [Baud V, et al., *Genomics* 26:334–344 (1995); McKnight, et al., *J. Biol. Chem.* 271:486–489 (1996); Krasnoperov, et al., *Neuron* 18:925–937 (1997); Lelianova, et al., *J. Biol. Chem.* 272:21504–21508 (1997); Davletov, et al., *J. Biol. Chem.* 271:23239–23245 (1996); Nishimori, et al., *Oncogene* 15:2145–2150 (1997)]. EMR1, and its murine homolog F4/80, are macrophage-specific in expression and structurally related to CD97 in that they contain multiple extracellular EGF-like repeats, a rod-like stalk region, and the characteristic transmembrane domain of GPCRs [Baud V, et al., *Genomics* 26:334–344 (1995); McKnight, et al., *J. Biol. Chem.* 271:486–489 (1996)]. No ligands have been identified for EMR-1 and it is uncertain if the protein undergoes post-translational proteolytic processing.

CIRL [Krasnoperov, et al., *Neuron* 18:925–937 (1997); Lelianova, et al., *J. Biol. Chem.* 272:21504–21508 (1997); Davletov, et al., *J. Biol. Chem.* 271:23239–23245 (1996)] is believed to be expressed specifically in the central nervous system at neuronal presynaptic terminals and, like CD97, undergoes proteolytic cleavage resulting in an extracellular alpha subunit in non-covalent association with an integral membrane seven-transmembrane beta subunit. Cleavage of latrophilin is believed to occur at a Ser-His-Leu/Thr-Asn-Phe site that is conserved in CD97 [Krasnoperov, et al., *Neuron* 18:925–937 (1997)]. CIRL has been shown to bind latrotoxin, a component of black widow spider venom, in the 0.5 to 1.0 nM range, and binding of the ligand to CIRL expressed in bovine chromaffin cells has been shown to result in exocytosis, a hallmark of toxin binding [Krasnoperov, et al., *Neuron* 18:925–937 (1997)]. Alpha latrotoxin binding has also been demonstrated at neuromuscular motor endplates, and this interaction elicits explosive secretory granule release of acetylcholine from presynaptic granules, resulting in muscle paralysis characteristic of the spider's bite [Petrenko, et al., *F.E.B.S. Letts.* 325:81–85 (1993)]. It is unclear, however, if the peripheral toxin effects result from binding to CIRL or some other related protein.

Thus there exists a need in the art to identify and characterize other members of the CD97-like family of GPCRs, in particular human receptors which participate in cellular adhesion and those that participate in cytoplasmic metabolic pathways modulated by extracellular signals. Identification of CD97-like receptors can permit identification and diagnosis of disease states which arise from aberrant signaling by the receptor, as well as disease states that arise from aberrant expression of the receptor itself.

SUMMARY OF THE INVENTION

The present invention provides purified and isolated human seven transmembrane receptor lectomedin polypeptides or fragments thereof, said polypeptides comprising extracellular lectin-binding, olfactomedin-like, and mucin-like domains. Mature lectomedin polypeptides are also provided wherein signal or leader sequences are cleaved. Preferred polypeptides of the invention comprise the amino acid sequence set out in SEQ ID NO: 2 or a fragment thereof, the amino acid sequence set out in SEQ ID NO: 4 or fragment thereof the amino acid sequence set out in SEQ ID NO: 6 or fragment thereof, and the amino acid sequence set out in SEQ ID NO: 58 or fragment thereof.

The invention also provides polynucleotides encoding polypeptides of the invention. Preferred polynucleotides comprising the sequence set forth in SEQ ID NO: 1, SEQ ID NO: 3, SEQ ID NO: 5, and SEQ ID NO: 57. The invention also provides polynucleotides a) encoding a human lectomedin polypeptide selected from the group consisting of the polynucleotide set out in SEQ ID NO: 1, SEQ ID NO: 3, SEQ ID NO: 5, or SEQ ID NO: 57; b) a DNA which hybridizes under moderately stringent conditions to the non-coding strand of the polynucleotide of (a); and c) a DNA which would hybridize to the non-coding strand of the polynucleotide of (a) but for the redundancy of the genetic code. Preferred polynucleotides of the invention are DNA molecules. Preferred DNA molecules are cDNA molecules and genomic DNA molecules. The invention also provides DNA which is a wholly or partially chemically synthesized. Anti-sense polynucleotide which specifically hybridizes with a polynucleotide of the invention are also comprehended.

The invention also proved expression construct comprising the a polynucleotide of the invention, as well as host cells transformed or transfected with a polynucleotide or expression construct of the invention.

The invention also provides polynucleotide of the invention operably linked to a heterologous promoter, and host cells polynucleotides operably linked to a heterologous promoter.

In another aspect, the invention provides methods for producing a human lectomedin polypeptide comprising the steps of: a) growing the host cell of the invention under conditions appropriate for expression of the lectomedin polypeptide and b) isolating the lectomedin polypeptide from the host cell or the medium of its growth.

The invention also proved antibodies specifically immunoreactive with a polypeptide of the invention. Preferably, antibodies of the invention are monoclonal antibodies. The invention also provides cells, e.g. hybridomas, that produce antibodies of the invention. Anti-idiotype antibodies specifically immunoreactive with an antibody of the invention are also comprehended.

The invention also provides methods to identify a specific binding partner compound of a lectomedin polypeptide comprising the steps of: a) contacting the lectomedin polypeptide with a compound under conditions which permit binding between the compound and the lectomedin polypeptide; b) detecting binding of the compound to the lectomedin polypeptide; and c) identifying the compound as a specific binding partner of the lectomedin polypeptide. Methods of the invention embrace specific binding partner that modulate activity of the lectomedin polypeptide. In one aspect, the compound inhibits activity of the lectomedin polypeptide, and in another aspect, the compound enhances activity of the lectomedin polypeptide.

The invention also provides methods to identify a specific binding partner compound of a lectomedin polynucleotide comprising the steps of: a) contacting the lectomedin polynucleotide with a compound under conditions which permit binding between the compound and the lectomedin polynucleotide; b) detecting binding of the compound to the lectomedin polynucleotide; and c) identifying the compound as a specific binding partner of the lectomedin polynucleotide. Methods of the invention embrace specific binding partner that modulates expression of a lectomedin polypeptide encoded by the lectomedin polynucleotide. In one aspect, the compound inhibits expression of the lectomedin polypeptide, and in another aspect, the compound enhances expression of the lectomedin polypeptide. The invention also provides compounds identified by a method of the invention.

In another aspect, the invention comprehends composition comprising the compound identified by a method of the invention and a pharmaceutically acceptable carrier. The invention also provides use of a compound identified by a method of the invention for the preparation of a medicament to treat lectomedin related pathologies.

The invention also provides for use of a lectomedin polypeptide in the preparation of a medicament for the treatment of a lectomedin related disorder.

DETAILED DESCRIPTION OF THE INVENTION

The present invention provides purified and isolated polypeptides and underlying polynucleotides for a novel family of transmembrane proteins designated lectomedins. The invention includes both naturally occurring and non-naturally occurring lectomedin polynucleotides and polypeptide products thereof. Naturally occurring lectomedin products include distinct gene and polypeptide species within the lectomedin family, including, for example, allelic variants, which are expressed within cells of the same animal, as well as corresponding species homologs expressed in cells of other animals. The invention further provides splice variants encoded by the same polynucleotide but which arise from distinct mRNA transcripts. Non-naturally occurring lectomedin products include variants of the naturally occurring products such as analogs, fragments, fusion (or chimeric) proteins, and lectomedin products having covalent modifications. The lectomedin family of proteins is distinguished from previously known seven transmembrane families of proteins in that the lectomedin proteins include at least one extracellular lectin binding-like domain and at least one extracellular olfactomedin domain. Unlike many other seven transmembrane proteins, the structure of proteins in the lectomedin family of proteins does not include EGF-like binding domains which effect cell/cell interactions. In a preferred embodiment, the invention provides polynucleotides comprising the sequences set forth in SEQ ID NOs: 1, 3, 5 and 57. The invention also embraces polynucleotides encoding the amino acid sequences set out in SEQ ID NOs: 2, 4, 6, and 58. Presently preferred polypeptides of the invention comprises the amino acid sequences set out in SEQ ID NOs: 2, 4, 6, and 58.

The invention also provides expression constructs (or vectors) comprising polynucleotides of the invention, as well as host cells transformed, transfected, or electroporated to include a polynucleotide or expression construct of the invention. Methods to produce a polypeptide of the invention are also comprehended. The invention further provides antibodies, preferably monoclonal antibodies, specifically immunoreactive with a polypeptide of the invention, as well as cell lines, e.g., hybridomas, that secrete the antibodies.

The present invention provides novel purified and isolated human polynucleotides (e.g., DNA sequences and RNA transcripts, both sense and complementary antisense strands, including splice variants thereof) encoding the human lectomedins. DNA sequences of the invention include genomic and cDNA sequences as well as wholly or partially chemically synthesized DNA sequences. Genomic DNA of the invention comprises the protein coding region for a polypeptide of the invention and includes allelic variants of the preferred polynucleotides of the invention. Genomic DNA of the invention is distinguishable from genomic DNAs encoding polypeptides other than lectomedin in that it includes the lectomedin coding region found in lectomedin cDNA of the invention. Genomic DNA of the invention can be transcribed into RNA, and the resulting RNA transcript may undergo one or more splicing events wherein one or more introns (i.e., non-coding regions) of the transcript are removed, or "spliced out." RNA transcripts that can be spliced by alternative mechanisms, and therefore be subjected to removal of different non-coding RNA sequences but still encode a lectomedin polypeptide, are referred to in the art as splice variants, which are embraced by the invention. Splice variants comprehended by the invention, therefore, are encoded by the same DNA sequences but arise from distinct mRNA transcripts. Allelic variants are known in the art to be modified forms of a wild type (predominant) gene sequence, the modification resulting from recombination during chromosomal segregation or exposure to conditions which give rise to genetic mutation. Allelic variants, like wild type genes, are inherently naturally occurring sequences (as opposed to non-naturally occurring variants which arise from in vitro manipulation).

The invention also comprehends cDNA that is obtained through reverse transcription of an RNA polynucleotide encoding lectomedin, followed by second strand synthesis of a complementary strand to provide a double stranded DNA. "Chemically synthesized" as used herein and understood in the art, refers to polynucleotides produced by purely chemical, as opposed to enzymatic, methods. "Wholly" synthesized DNA sequences are therefore produced entirely by chemical means, and "partially" synthesized DNAs embrace those wherein only portions of the resulting DNA were produced by chemical means.

Preferred DNA sequences encoding human lectomedin polypeptides are set out in SEQ ID NOs: 1, 3, 5, and 57. The worker of skill in the art will readily appreciate that preferred DNAs of the invention comprise double stranded molecules, for example, the molecule having the sequence set forth in either SEQ ID NOs: 1, 3, 5, or 57, along with the complementary molecule (the "non-coding strand" or "complement") having a sequence deducible from the sequence of SEQ ID NO: 1 according to Watson-Crick base pairing rules for DNA. Also preferred are polynucleotides encoding the lectomedin polypeptides of SEQ ID NOs: 2, 4, 6, and 58.

The invention further embraces species, preferably mammalian, homologs of the human lectomedin DNA. Species homologs, in general, share at least 35%, at least 40%, at least 45%, at least 50%, at least 60%, at least 65%, at least 70%, at least 75%, at least 80%, at least 85%, at least 90%, at least 95%, at least 98%, or at least 99% homology with human DNA of the invention. Percent sequence "homology" with respect to polynucleotides of the invention is defined herein as the percentage of nucleotide bases in the candidate sequence that are identical to nucleotides in the lectomedin coding sequence after aligning the sequences and introducing gaps, if necessary, to achieve the maximum percent sequence identity.

The polynucleotide sequence information provided by the invention makes possible large scale expression of the encoded polypeptide by techniques well known and routinely practiced in the art. Polynucleotides also permit identification and isolation of polynucleotides encoding related lectomedin polypeptides by well known techniques including Southern and/or Northern hybridization, and polymerase chain reaction (PCR), ligase chain reaction, as well as other amplification techniques. Examples of related polynucleotides include human and non-human genomic sequences, including allelic variants, as well as polynucleotides encoding polypeptides homologous to lectomedins and structurally related polypeptides sharing one or more biological, immunological, and/or physical properties of lectomedin.

The disclosure of full length polynucleotides encoding lectomedin polypeptides makes readily available to the worker of ordinary skill in the art every possible fragment of the full length polynucleotides. The invention therefore provides fragments of lectomedin coding polynucleotides. Such fragments comprise at least 10 to 20, and preferably at least 15, consecutive nucleotides of the polynucleotide. The invention comprehends, however, fragments of various lengths. Preferably, fragment polynucleotides of the invention comprise sequences unique to the lectomedin coding polynucleotide sequence, and therefore hybridize under highly stringent or moderately stringent conditions only (i.e., "specifically") to polynucleotides encoding lectomedin, or lectomedin fragments thereof containing the unique sequence. Polynucleotide fragments of genomic sequences of the invention comprise not only sequences unique to the coding region, but also include fragments of the full length sequence derived from introns, regulatory regions, and/or other non-translated sequences. Sequences unique to polynucleotides of the invention are recognizable through sequence comparison to other known polynucleotides, and can be identified through use of alignment programs routinely utilized in the art, e.g., those made available in public sequence databases.

The invention also provides fragment polynucleotides that are conserved in one or more polynucleotides encoding members of the lectomedin family of polypeptides. Such fragments include sequences characteristic of the family of lectomedin polynucleotides, and are also referred to as "signature sequences." The conserved signature sequences are readily discernable following simple sequence comparison of polynucleotides encoding members of the lectomedin family. Fragments of the invention can be labeled in a manner that permits their detection, including radioactive and non-radioactive labeling.

Fragment polynucleotides are particularly useful as probes for detection of full length or other fragment lectomedin coding polynucleotides. One or more fragment polynucleotides can be included in kits that are used to detect the presence of a polynucleotide encoding lectomedin, or used to detect variations in a polynucleotide sequence encoding lectomedin.

The invention also embraces DNA sequences encoding lectomedin species which hybridize under moderately or highly stringent conditions to the non-coding strand, or complement, of the polynucleotide in SEQ ID NOs: 1, 3, 5, or 57. DNA sequences encoding lectomedin polypeptides which would hybridize thereto but for the redundancy of the genetic code are further comprehended by the invention. Exemplary highly stringent conditions are include hybridization at 45° C. in 5×SSPE and 45% formamide, and a final wash at 65° C. in 0.1×SSC. Exemplary moderately stringent condition include a final wash at 55° C. in 1×SSC. It is understood in the art that conditions of equivalent stringency can be achieved through variation of temperature and buffer, or salt concentration as described Ausubel, et al. (Eds.), *Protocols in Molecular Biology,* John Wiley & Sons (1994), pp.6.0.3 to 6.4.10. Modifications in hybridization conditions can be empirically determined or precisely calculated based on the length and the percentage of guanosine/cytosine (GC) base pairing of the probe. The hybridization conditions can be calculated as described in Sambrook, et al., (Eds.), *Molecular Cloning: A Laboratory Manual,* Cold Spring Harbor Laboratory Press: Cold Spring Harbor, N.Y. (1989), pp. 9.47 to 9.5 1.

Autonomously replicating recombinant expression constructs such as plasmid and viral DNA vectors incorporating lectomedin coding sequences are also provided. Expression constructs wherein lectomedin-encoding polynucleotides are operably linked to an endogenous or exogenous expression control DNA sequence and a transcription terminator are also provided. Expression control DNA sequences include promoters, enhancers, and operator, and are generally selected based on the expression systems in which the expression construct is to be utilized. Preferred promoter and enhancer sequences are generally selected for the ability to increase gene expression, while operator sequences are generally selected for the ability to regulate gene expression. Expression constructs of the invention may also include sequences encoding one or more selectable markers that permit identification of host cells bearing the construct. Expression constructs may also include sequences that facilitate, and preferably promote, homologous recombination in a host cell. Preferred constructs of the invention also include sequences necessary for replication in a host cell. Expression constructs are preferably utilized for production of an encoded lectomedin protein, but may also be utilized to amplify the construct itself.

According to another aspect of the invention, host cells are provided, including prokaryotic and eukaryotic cells, comprising a polynucleotide of the invention in a manner which permits expression of the encoded lectomedin polypeptide. Polynucleotides of the invention may be introduced into the host cell as part of a circular plasmid, or as linear DNA comprising an isolated protein coding region or a viral vector. Methods for introducing DNA into the host cell well known and routinely practiced in the art include transformation, transfection, electroporation, nuclear injection, or fusion with carriers such as liposomes, micelles, ghost cells, and protoplasts. Expression systems of the invention include bacterial, yeast, fungal, plant, insect, invertebrate, and mammalian cells systems. Host cells of the invention are a valuable source of immunogen for development of antibodies specifically immunoreactive with lectomedin. Host cells of the invention are also useful in methods for large scale production of lectomedin polypeptides wherein the cells are grown in a suitable culture medium and the desired polypeptide products are isolated from the cells or from the medium in which the cells are grown by purification methods known in the art, e.g., conventional chromatographic methods including immunoaffinity chromatography, receptor affinity chromatography, hydrophobic interaction chromatography, lectin affinity chromatography, size exclusion filtration, cation or anion exchange chromatography, high pressure liquid chromatography (HPLC), reverse phase HPLC and the like. Still other methods of purification include those wherein the desired protein is expressed and purified as a fusion protein having a specific tag, label, or chelating moiety that is recognized by a specific binding partner or agent. The purified protein can be cleaved to yield the desired protein, or be left as an intact fusion protein. Cleavage of the fusion component may produce a form of the desired protein having additional amino acid residues as a result of the cleavage process.

Knowledge of lectomedin coding DNA sequences allows for modification of cells to permit, or increase, expression of endogenous lectomedin. Cells can be modified (e.g., by homologous recombination) to provide increased lectomedin expression by replacing, in whole or in part, the naturally occurring lectomedin promoter with all or part of a heterologous promoter so that the cells express lectomedin at higher levels. The heterologous promoter is inserted in such a manner that it is operably linked to lectomedin-encoding sequences. See, for example, PCT International Publication No. WO 94/12650, PCT International Publication No. WO 92/20808, and PCT International Publication No. WO 91/09955. It is also contemplated that, in addition to heterologous promoter DNA, amplifiable marker DNA (e.g., ada, dhfr, and the multifunctional CAD gene which encodes carbamyl phosphate synthase, aspartate transcarbamylase, and dihydroorotase) and/or intron DNA may be inserted along with the heterologous promoter DNA. If linked to the lectomedin coding sequence, amplification of the marker DNA by standard selection methods results in co-amplification of the lectomedin coding sequences in the cells.

The DNA sequence information provided by the present invention also makes possible the development through, e.g. homologous recombination or "knock-out" strategies [Capecchi, *Science* 244:1288–1292 (1989)], of animals that fail to express functional lectomedin or that express a variant of lectomedin. Such animals are useful as models for studying the in vivo activities of lectomedin and modulators of lectomedin.

The invention also provides purified and isolated mammalian lectomedin polypeptides encoded by a polynucleotide of the invention. Presently preferred are lectomedin polypeptides comprising the amino acid sequence set out in SEQ ID NO: 2, 4, 6, or 58. The invention also embraces lectomedin polypeptides encoded by a DNA selected from the group consisting of: a) the DNA sequence set out in SEQ ID NO: 1, 3, 5 or 57; b) a DNA molecule which hybridizes under high stringent conditions to the noncoding strand of the protein coding portion of (a); and c) a DNA molecule that would hybridize to the DNA of (a) but for the degeneracy of the genetic code.

The invention also embraces variant (or analog) lectomedin polypeptides. In one example, insertion variants are provided wherein one or more amino acid residues supplement a lectomedin amino acid sequence. Insertions may be located at either or both termini of the protein, or may be positioned within internal regions of the lectomedin amino acid sequence. Insertional variants with additional residues at either or both termini can include for example, fusion proteins and proteins including amino acid tags or labels.

In another aspect, the invention provides deletion variants wherein one or more amino acid residues in a lectomedin polypeptide are removed. Deletions can be effected at one or both termini of the lectomedin polypeptide, or with removal of one or more residues within the lectomedin amino acid sequence. Deletion variants, therefore, include all fragments of a lectomedin polypeptide.

In still another aspect, the invention provides substitution variants of lectomedin polypeptides. Substitution variants include those polypeptides wherein one or more amino acid residues of a lectomedin polypeptide are removed and replaced with alternative residues. In one aspect, the substitutions are conservative in nature, however, the invention embraces substitutions that are also non-conservative. Conservative substitutions for this purpose may be defined as set out in Tables A, B, or C below.

The invention also provides derivatives of lectomedin polypeptides. Derivatives include lectomedin polypeptides bearing modifications other than insertion, deletion, or substitution of amino acid residues. Preferably, the modifications are covalent in nature, and include, for example, chemical bonding with polymers, lipids, non-naturally occurring amino acids, other organic, and inorganic moieties. Derivatives of the invention may be prepared to increase circulating half-life of a lectomedin polypeptide, or may be designed to improve targeting capacity for the polypeptide to desired cells, tissues, or organs.

The invention also embraces polypeptides have at least 99%, at least 95%, at least 90%, at least 85%, at least 80%, at least 75%, at least 70%, at least 65%, at least 60%, at least 55% or at least 50% identity and/or homology to the preferred polypeptide of the invention. Percent amino acid sequence "identity" with respect to the preferred polypeptide of the invention is defined herein as the percentage of amino acid residues in the candidate sequence that are identical with the residues in the lectomedin sequence after aligning both sequences and introducing gaps, if necessary, to achieve the maximum percent sequence identity, and not considering any conservative substitutions as part of the sequence identity. Percent sequence "homology" with respect to the preferred polypeptide of the invention is defined herein as the percentage of amino acid residues in the candidate sequence that are identical with the residues in the lectomedin sequence after aligning the sequences and introducing gaps, if necessary, to achieve the maximum percent sequence identity, and also considering any conservative substitutions as part of the sequence identity.

In one aspect, percent homology is calculated as the percentage of amino acid residues in the smaller of two sequences which align with identical amino acid residue in the sequence being compared, when four gaps in a length of 100 amino acids may be introduced to maximize alignment [Dayhoff, in *Altas of Protein Sequence and Structure*, Vol. 5, p. 124, National Biochemical Research Foundation, Washington, D.C. (1972), incorporated herein by reference].

Polypeptides of the invention may be isolated from natural cell sources or may be chemically synthesized, but are preferably produced by recombinant procedures involving host cells of the invention. Use of mammalian host cells is expected to provide for such post-translational modifications (e.g., glycosylation, truncation, lipidation, and phosphorylation) as may be needed to confer optimal biological activity on recombinant expression products of the invention. Glycosylated and non-glycosylated form of lectomedin polypeptides are embraced.

Insertion variants include lectomedin polypeptides wherein one or more amino acid residues are added to a lectomedin acid sequence, or fragment thereof. Variant products of the invention also include mature lectomedin products, i.e., lectomedin products wherein leader or signal sequences are removed, with additional amino terminal residues. The additional amino terminal residues may be derived from another protein, or may include one or more residues that are not identifiable as being derived from a specific proteins. Lectomedin products with an additional methionine residue at position −1 (Met$^{-1}$-lectomedin) are contemplated, as are lectomedin products with additional methionine and lysine residues at positions −2 and −1 (Met$^{-2}$-Lys$^{-1}$-lectomedin). Variants of lectomedin with multiple, additional Met, Met-Lys, Lys residues are particularly useful for enhanced recombinant protein production in bacterial host cell.

The invention also embraces lectomedin variants having additional amino acid residues which result from use of specific expression systems. For example, use of commercially available vectors that express a desired polypeptide as part of glutathione-S-transferase (GST) fusion product provides the desired polypeptide having an additional glycine residue at position −1 after cleavage of the GST component from the desired polypeptide. Variants which result from expression in other vector systems are also contemplated.

Insertional variants also include fusion proteins wherein the amino and/or carboxy termini of the lectomedin polypeptide is fused to another polypeptide. Examples of such fusion proteins are immunogenic polypeptides, proteins with long circulating half life, such as immunoglobulin constant regions, marker proteins (e.g., fluorescent) and proteins or polypeptide that facilitate purification of the desired lectomedin polypeptide, e.g. FLAG® tags or poly-histidine sequences.

Deletion variants include lectomedin polypeptides wherein one or more amino acid residues are deleted from the lectomedin amino acid sequence. Deletion variants of the invention embrace polypeptide fragments of the sequence set out in SEQ ID NO: 2, 4, 6, or 58 wherein the fragments maintain biological or immunological properties of a lectomedin polypeptide. Fragments comprising at least 5, 10, 15, 20, 25, 30, 35, or 40 consecutive amino acids of SEQ ID NO: 2, 4, 6, or 58 are comprehended by the invention. Preferred polypeptide fragments display antigenic properties unique to or specific for the lectomedin family of polypeptides. Fragments of the invention having the desired biological and immunological properties can be prepared by any of the methods well known and routinely practiced in the art.

Substitution variants of the invention include lectomedin polypeptides, or fragments thereof wherein one or more amino acid residues in the lectomedin amino acid sequence are deleted and replaced with another amino acid residue. Variant polypeptides include those wherein conservative substitutions have been introduced by modification of polynucleotides encoding polypeptides of the invention. Amino acids can be classified according to physical properties and contribution to secondary and tertiary protein structure. A conservative substitution is recognized in the art as a substitution of one amino acid for another amino acid that has similar properties. Exemplary conservative substitutions are set out in Table A (from WO 97/09433, page 10, published Mar. 13, 1997 (PCT/GB96/02197, filed Sep. 6, 1996), immediately below.

TABLE A

| Conservative Substitutions I | | |
|---|---|---|
| SIDE CHAIN CHARACTERISTIC | | AMINO ACID |
| Aliphatic | Non-polar | G A P |
| | | I L V |
| | Polar - uncharged | C S T M |
| | | N Q |
| | Polar - charged | D E |
| | | K R |
| Aromatic | | H F W Y |
| Other | | N Q D E |

Alternatively, conservative amino acids can be grouped as described in Lehninger, [*Biochemistry*, Second Edition; Worth Publishers, Inc. NY:N.Y. (1975), pp.71–77] as set out in Table B, immediately below.

TABLE B

Conservative Substitutions II

| SIDE CHAIN CHARACTERISTIC | AMINO ACID |
|---|---|
| Non-polar (hydrophobic) | |
| A. Aliphatic: | A L I V P |
| B. Aromatic: | F W |
| C. Sulfur-containing: | M |
| D. Borderline: | G |
| Uncharged-polar | |
| A. Hydroxyl: | S T Y |
| B. Amides: | N Q |
| C. Sulfhydryl: | C |
| D. Borderline: | G |
| Positively Charged (Basic): | K R H |
| Negatively Charged (Acidic): | D E |

As still an another alternative, exemplary conservative substitutions are set out in Table C, below.

The invention further embraces lectomedin products, or fragments thereof, covalently modified or derivatized, e.g., to include one or more water soluble polymer attachments such as polyethylene glycol, polyoxyethylene glycol, or polypropylene glycol. Particularly preferred are lectomedin products covalently modified with polyethylene glycol (PEG) subunits. Water soluble polymers may be bonded at specific positions, for example at the amino terminus of the lectomedin products, or randomly attached to one or more side chains of the polypeptide. Additional derivatives include lectomedin species immobilized on a solid support, pin microparticle, or chromatographic resin, as well as lectomedin polypeptides modified to include one or more non-protein labels, tags, or chelating agents.

TABLE C

Conservative Substitutions III

| Original Residue | Exemplary Substitution |
|---|---|
| Ala (A) | Val, Leu, Ile |
| Arg (R) | Lys, Gln, Asn |
| Asn (N) | Gln, His, Lys, Arg |
| Asp (D) | Glu |
| Cys (C) | Ser |
| Gln (Q) | Asn |
| Glu (E) | Asp |
| His (H) | Asn, Gln, Lys, Arg |
| Ile (I) | Leu, Val, Met, Ala, Phe, |
| Leu (L) | Ile, Val, Met, Ala, Phe |
| Lys (K) | Arg, Gln, Asn |
| Met (M) | Leu, Phe, Ile |
| Phe (F) | Leu, Val, Ile, Ala |
| Pro (P) | Gly |
| Ser (S) | Thr |
| Thr (T) | Ser |
| Trp (W) | Tyr |
| Tyr (Y) | Trp, Phe, Thr, Ser |
| Val (V) | Ile, Leu, Met, Phe, Ala |

Also comprehended by the present invention are antibodies (e.g., monoclonal and polyclonal antibodies, single chain antibodies, chimeric antibodies, bifunctional/bispecific antibodies, humanized antibodies, human antibodies, and CDR-grafted antibodies, including compounds which include CDR sequences which specifically recognize a polypeptide of the invention) and other binding proteins specific for lectomedin products or fragments thereof. Preferred antibodies of the invention are human antibodies which are produced and identified according to methods described in WO93/11236, published Jun. 20, 1993, which is incorporated herein by reference in its entirety. Antibody fragments, including Fab, Fab', F(ab')$_2$, and F$_v$, are also provided by the invention. The term "specific for" indicates that the variable regions of the antibodies of the invention recognize and bind lectomedin polypeptides exclusively (i.e., able to distinguish single lectomedin polypeptides from the family of lectomedin polypeptides despite sequence identity, homology, or similarity found in the family of polypeptides), but may also interact with other proteins (for example, S. aureus protein A or other antibodies in ELISA techniques) through interactions with sequences outside the variable region of the antibodies, and in particular, in the constant region of the molecule. Screening assays to determine binding specificity of an antibody of the invention are well known and routinely practiced in the art. For a comprehensive discussion of such assays, see Harlow et al. (Eds), Antibodies: A Laboratory Manual; Cold Spring Harbor Laboratory; Cold Spring Harbor, N.Y. (1988), Chapter 6. Antibodies that recognize and bind fragments of the lectomedin polypeptides of the invention are also contemplated, provided that the antibodies are first and foremost specific for, as defined above, lectomedin polypeptides. As with antibodies that are specific for full length lectomedin polypeptides, antibodies of the invention that recognize lectomedin fragments are those which can distinguish single and distinct lectomedin polypeptides from the family of lectomedin polypeptides despite inherent sequence identity, homology, or similarity found in the family of proteins. Antibodies of the invention can be produced using any method well known and routinely practiced in the art.

Non-human antibodies may be humanized by any methods known in the art. In one method, the non-human complementarity determining regions (CDRs) are inserted into a human antibody or consensus antibody framework sequence. Further changes can then be introduced into the antibody framework to modulate affinity or immunogenicity.

Antibodies of the invention are useful for, for example, therapeutic purposes (by modulating activity of lectomedin), diagnostic purposes to detect or quantitate lectomedin, as well as purification of lectomedin. Antibodies are particularly useful for detecting and/or quantitating lectomedin expression in cells, tissues, organs and lysates and extracts thereof, as well as fluids, including serum, plasma, cerebrospinal fluind, urine, sputum, peritoneal fluid, pleural fluid, or pulmonary lavage. Kits comprising an antibody of the invention for any of the purposes described herein are also comprehended. In general, a kit of the invention also includes a control antigen for which the antibody is immunospecific.

Specific binding proteins can be identified or developed using isolated or recombinant lectomedin products, lectomedin variants, or cells expressing such products. Binding proteins are useful for purifying lectomedin products and detection or quantification of lectomedin products in fluid and tissue samples using known immunological procedures. Binding proteins are also manifestly useful in modulating (i.e., blocking, inhibiting or stimulating) biological activities of lectomedin, especially those activities involved in signal transduction.

The DNA and amino acid sequence information provided by the present invention also makes possible the systematic analysis of the structure and function of lectomedins. DNA and amino acid sequence information for lectomedin also permits identification of binding partner compounds with which a lectomedin polypeptide or polynucleotide will interact. Agents that modulate (i.e., increase, decrease, or block) lectomedin activity or expression may be identified by incubating a putative modulator with a lectomedin polypeptide or polynucleotide and determining the effect of the putative modulator on lectomedin activity or expression. The selectivity of a compound that modulates the activity of the lectomedin can be evaluated by comparing its binding activity to one particular lectomedin to its activity to other lectomedin polypeptides. Cell based methods, such as di-hybrid assays to identify DNAs encoding binding compounds and split hybrid assays to identify inhibitors of lectomedin polypeptide interaction with a known binding polypeptide, as well as in vitro methods, including assays wherein a lectomedin polypeptide, lectomedin polynucleotide, or a binding partner are immobilized, and solution assays are contemplated by the invention.

Selective modulators may include, for example, antibodies and other proteins or peptides which specifically bind to a lectomedin polypeptide or a lectomedin-encoding nucleic acid, oligonucleotides which specifically bind to a lectomedin polypeptide or a lectomedin gene sequence, and other non-peptide compounds (e.g., isolated or synthetic organic and inorganic molecules) which specifically react with a lectomedin polypeptide or its underlying nucleic acid. Mutant lectomedin polypeptides which affect the enzymatic activity or cellular localization of the wild-type lectomedin polypeptides are also contemplated by the invention. Presently preferred targets for the development of selective modulators include, for example: (1) regions of the lectomedin polypeptide which contact other proteins, (2) regions that localize the lectomedin polypeptide within a cell, (3) regions of the lectomedin polypeptide which bind substrate, (4) allosteric regulatory binding site(s) of the lectomedin polypeptide, (5) site(s) of the lectomedin polypeptide wherein covalent modification regulates biological activity and (6) regions of the lectomedin polypeptide which are involved in multimerization of lectomedin subunits. Still other selective modulators include those that recognize specific lectomedin encoding and regulatory polynucleotide sequences. Modulators of lectomedin activity may be therapeutically useful in treatment of a wide range of diseases and physiological conditions in which lectomedin activity is known or suspected to be involved.

Lectomedin polypeptides of the invention are amenable to numerous cell based high throughput screening (HTS) assays known in the art, including melanophore assay to investigate receptor-ligand interaction, yeast based assay systems, and mammalian cell expression systems. For a review, see Jayawickreme and Kost, *Curr. Opin. Biotechnol.* 8:629–634 (1997). Automated and miniaturized HTS assays are also comprehended as described, for example, in Houston and Banks, *Curr. Opin. Biotechnol.* 8:734–740 (1997).

There are a number of different libraries used for the identification of small molecule modulators, including, (1) chemical libraries, (2) natural product libraries, and (3) combinatorial libraries comprised of random or designed peptides, oligonucleotides or organic molecules.

Chemical libraries consist of structural analogs of known compounds or compounds that are identified as "hits" or "leads" via natural product screening. Natural product libraries are collections of microorganisms, animals, plants, or marine organisms which are used to create mixtures for screening by: (1) fermentation and extraction of broths from soil, plant or marine microorganisms or (2) extraction of plants or marine organisms. Natural product libraries include polyketides, non-ribosomal peptides, and variants (non-naturally occurring) variants thereof. For a review, see Science 282:63–68 (1998). Combinatorial libraries are composed of large numbers of peptides, oligonucleotides or organic compounds as a mixture. They are relatively easy to prepare by traditional automated synthesis methods, PCR, cloning or proprietary synthetic methods. Of particular interest are peptide and oligonucleotide combinatorial libraries. Still other libraries of interest include peptide, protein, peptidomimetic, multiparallel synthetic collection, recombinatorial, and polypeptide libraries. For a review of combinatorial chemistry and libraries created therefrom, see Myers, *Curr. Opin. Biotechnol.* 8:701–707 (1997).

Identification of modulators through use of the various libraries described herein permits modification of the candidate "hit" (or "lead") to optimize the capacity of the "hit" to modulate activity.

The scientific value of the information contributed through the disclosures of DNA and amino acid sequences of the present invention is manifest. As one series of examples, knowledge of the sequence of a cDNA for lectomedin makes possible through use of Southern hybridization or polymerase chain reaction (PCR) the identification of genomic DNA sequences encoding lectomedin and lectomedin expression control regulatory sequences such as promoters, operators, enhancers, repressors, and the like. DNA/DNA hybridization procedures carried out with DNA sequences of the invention under moderately to highly stringent conditions are likewise expected to allow the isolation of DNAs encoding allelic variants of lectomedin; allelic variants are known in the art to include structurally related proteins sharing one or more of the biochemical and/or immunological properties specific to lectomedin. Similarly, non-human species genes encoding proteins homologous to human lectomedin can also be identified by Southern and/or PCR analysis; species homologs of the invention are particularly useful in animal models for the study of lectomedin-related disorders. As an alternative, complementation studies can be useful for identifying other human lectomedin products as well as non-human proteins, and DNAs encoding the proteins, sharing one or more biological properties of lectomedin.

Polynucleotides of the invention are also useful in hybridization assays to detect the capacity of cells to express lectomedin. Polynucleotides of the invention may also be the basis for diagnostic methods useful for identifying a genetic alteration(s) in a lectomedin locus that underlies a disease state or states.

Also made available by the invention are anti-sense polynucleotides which recognize and hybridize to polynucleotides encoding lectomedin. Full length and fragment anti-sense polynucleotides are provided. The worker of ordinary skill will appreciate that fragment antisense molecules of the invention include (i) those which specifically recognize and hybridize to lectomedin RNA (as determined by sequence comparison of DNA encoding lectomedin to DNA encoding other known molecules) as well as (ii) those which recognize and hybridize to RNA encoding variants of the lectomedin family of proteins. Antisense polynucleotides that hybridize to RNA encoding other members of the lectomedin family of proteins are also identifiable through sequence comparison to identify characteristic, or signature, sequences for the family of molecules. Anti-sense polynucleotides are particularly relevant to regulating expression of lectomedin by those cells expressing lectomedin mRNA.

Antisense nucleic acids (preferably 10 to 20 base pair oligonucleotides) capable of specifically binding to lectomedin expression control sequences or lectomedin RNA are introduced into cells (e.g., by a viral vector or colloidal dispersion system such as a liposome). The antisense nucleic acid binds to the lectomedin target nucleotide sequence in the cell and prevents transcription or translation of the target sequence. Phosphorothioate and methylphosphonate antisense oligonucleotides are specifically contemplated for therapeutic use by the invention. The antisense oligonucleotides may be further modified by poly-L-lysine, transferrin polylysine, or cholesterol moieties at their 5' end.

The invention further contemplates methods to modulate lectomedin expression through use of ribozymes. For a review, see Gibson and Shillitoe, *Mol. Biotech.* 7:125–137 (1997). Ribozyme technology can be utilized to inhibit translation of lectomedin mRNA in a sequence specific manner through (i) the hybridization of a complementary RNA to a target mRNA and (ii) cleavage of the hybridized mRNA through nuclease activity inherent to the complementary strand. Ribozymes can identified by empirical methods but more preferably are specifically designed based on accessible sites on the target mRNA (Bramlage, et al., *Trends in Biotech* 16:434–438 (1998). Delivery of ribozymes to target cells can be accomplished using either exogenous or endogenous delivery techniques well known and routinely practiced in the art. Exogenous delivery methods can include use of targeting liposomes or direct local injection. Endogenous methods include use of viral vectors and non-viral plasmids.

Ribozymes can specifically modulate expression of lectomedin when designed to be complementary to regions unique to a polynucleotide encoding lectomedin. "Specifically modulate" therefore is intended to mean that ribozymes of the invention recognizes only a polynucleotide encoding lectomedin. Similarly, ribozymes can be designed to modulate expression of all or some of the lectomedin family of proteins. Ribozymes of this type are designed to recognize polynucleotide sequences conserved in all or some of the polynucleotides which encode the family of proteins.

The invention further embraces methods to modulate transcription of lectomedin through use of oligonucleotide-directed triplet helix formation. For a review, see Lavrovsky, et al., *Biochem. Mol. Med.* 62:11–22 (1997). Triplet helix formation is accomplished using sequence specific oligonucleotides which hybridize to double stranded DNA in the major groove as defined in the Watson-Crick model. Hybridization of a sequence specific oligonucleotide can thereafter modulate activity of DNA-binding proteins, including, for example, transcription factors and polymerases. Preferred target sequences for hybridization include promoter and enhancer regions to permit transcriptional regulation of lectomedin expression.

Oligonucleotides which are capable of triplet helix formation are also useful for site-specific covalent modification of target DNA sequences. Oligonucleotides useful for covalent modification are coupled to various DNA damaging agents as described in Lavrovsky, et al. [supra].

Mutations in a lectomedin gene that results in loss of normal function of the lectomedin gene product may underlie lectomedin-related human disease states. The invention comprehends gene therapy to restore lectomedin activity would thus be indicated in treating those disease states (for example, various forms of cancer described herein). Delivery of a functional lectomedin gene to appropriate cells is effected ex vivo, in situ, or in vivo by use of vectors, and more particularly viral vectors (e.g., adenovirus, adeno-associated virus, or a retrovirus), or ex vivo by use of physical DNA transfer methods (e.g., liposomes or chemical treatments). See, for example, Anderson, *Nature,* supplement to vol. 392, no. 6679, pp.25 (1998). For additional reviews of gene therapy technology see Friedmann, *Science,* 244: 1275–1281 (1989); Verma, *Scientific American:* 68–84 (1990); and Miller, *Nature,* 357: 455–460 (1992). Alternatively, it is contemplated that in other human disease states, preventing the expression of or inhibiting the activity of lectomedin will be useful in treating the disease states. It is contemplated that antisense therapy or gene therapy could be applied to negatively regulate the expression of lectomedin.

The invention further embraces pharmaceutical compositions comprising a lectomedin polypeptide of the invention, generally in combination with a pharmaceutically acceptable carrier. The pharmaceutical compositions optionally may include pharmaceutically acceptable (i.e., sterile and non-toxic) liquid, semisolid, or solid diluents that serve as pharmaceutical vehicles, excipients, or media. Any diluent known in the art may be used. Exemplary diluents include, but are not limited to, polyoxyethylene sorbitan monolaurate, magnesium stearate, methyl- and propylhydroxybenzoate, talc, alginates, starches, lactose, sucrose, dextrose, sorbitol, mannitol, gum acacia, calcium phosphate, mineral oil, cocoa butter, and oil of theobroma.

The pharmaceutical compositions can be packaged in forms convenient for delivery. The compositions can be enclosed within a capsule, sachet, cachet, gelatin, paper, or other container. These delivery forms are preferred when compatible with entry of the immunogenic composition into the recipient organism and, particularly, when the immunogenic composition is being delivered in unit dose form. The dosage units can be packaged, e.g., in tablets, capsules, suppositories or cachets.

The pharmaceutical compositions may be introduced into the subject to be treated by any conventional method including, e.g., by intravenous, intradermal, intramuscular, intramammary, intraperitoneal, intrathecal, intraocular, retrobulbar, intrapulmonary (e.g., aerosolized drug solutions) or subcutaneous injection (including depot administration for long term release); by oral, sublingual, nasal, anal, vaginal, or transdermal delivery; or by surgical implantation, e.g., embedded under the splenic capsule, brain, or in the cornea. The treatment may consist of a single dose or a plurality of doses over a period of time.

When given parenterally, lectomedin product compositions are generally injected in doses ranging from 1 $\mu$g/kg to 100 mg/kg per day, preferably at doses ranging from 0.1 mg/kg to 50 mg/kg per day, and more preferably at doses ranging from 1 to 20 mg/kg/day. The lectomedin product composition may be administered by an initial bolus followed by a continuous infusion to maintain therapeutic circulating levels of drug product. Those of ordinary skill in the art will readily optimize effective dosages and administration regimens as determined by good medical practice and the clinical condition of the individual patient. The frequency of dosing will depend on the pharmacokinetic parameters of the agents and the route of administration. The optimal pharmaceutical formulation will be determined by one skilled in the art depending upon the route of administration and desired dosage. See for example, Remington's Pharmaceutical Sciences, 18th Ed. (1990, Mack Publishing Co., Easton, Pa. 18042) pages 1435–1712, the disclosure of which is hereby incorporated by reference. Such formulations may influence the physical state, stability, rate of in vivo release, and rate of in vivo clearance of the administered agents. Depending on the route of administration, a suitable dose may be calculated according to body weight, body surface area or organ size. Further refinement of the calculations necessary to determine the appropriate dosage for treatment involving each of the above mentioned formulations is routinely made by those of ordinary skill in the art without undue experimentation, especially in light of the dosage information and assays disclosed herein, as well as the pharmacokinetic data observed in the human clinical trials discussed above. Appropriate dosages may be ascertained through use of established assays for determining blood levels dosages in conjunction with appropriate dose-response data. The final dosage regimen will be determined by the attending physician, considering various factors which modify the action of drugs, e.g. the drug's specific activity, the severity of the damage and the responsiveness of the patient, the age, condition, body weight, sex and diet of the patient, the severity of any infection, time of administration and other clinical factors. As studies are conducted, further information will emerge regarding the appropriate dosage levels and duration of treatment for various diseases and conditions.

It will be appreciated that the pharmaceutical compositions and treatment methods of the invention may be useful in the fields of human medicine and veterinary medicine. Thus, the subject to be treated may be a mammal, preferably human, or other animals. For veterinary purposes, subjects include, for example, farm animals including cows, sheep, pigs, horses, and goats, companion animals such as dogs and cats; exotic and/or zoo animals; laboratory animals including mice, rats, rabbits, guinea pigs, and hamsters; and poultry such as chickens, turkeys, ducks and geese.

The present invention is illustrated by the following examples. Example 1 describes identification and characterization of cDNA encoding lectomedin polypeptides. Example 2 relates to expression of recombinant lectomedin. Example 3 described characterization of recombinant lectomedin. Ligand affinity chromatography with immobilized lectomedin is described in Example 4. Example 5 describes Northern analysis of lectomedin expression. Example 5 provides an assessment of tissue distribution of lectomedin in mammalian cell types, while Example 6 describes results from in situ hybridization. The chromosome localization of lectomedin is disclosed in Example 7. Example 8 provides production of polyclonal and monoclonal antibodies specific for lectomedin. Example 9 addresses lectomedin expression.

EXAMPLE 1

Isolation and Characterization of Human Lectomedin

Identification of Lectomedin-1α

In an attempt to identify genes encoding novel seven transmembrane receptor proteins related to CD97, a TBLASTN search of the National Center for Biotechnology Information (NCBI, Bethesda, Md.) Expressed Sequence Tag (EST) database was carried out with an amino acid query sequence for full length CD97 (SEQ ID NO: 12). This database contains DNA sequences representing one or both ends of cDNAs collected from a variety of tissue sources. The TBLASTN program was used to determine homology between the protein sequence of CD97 and the six different amino acid sequences encoded by each EST. In the search, ESTs are translated in six reading frames and the amino acid sequences generated are compared to the query CD97 amino acid sequence. Sequences identified as homologous at the amino acid level were examined and any ESTs positively identified as corresponding to a known protein were discarded.

Among the CD97-related sequences identified as corresponding to known proteins were ESTs representing CD97, human EMR1, and murine F4/80. In addition, several ESTs showed statistically significant values for relatedness in the transmembrane region of CD97, but they were not CD97, EMR1, or F4/80. One of the identified ESTs, designated GenBank® Accession No: T47902 (SEQ ID NO: 13), was chosen to attempt identification of a full length cDNA. The basis for choosing T47902 was disclosure in GenBank® that the EST was derived from a human fetal spleen library.

A library probe was first generated by PCR based on the Genbank sequence of T47902. Primers used to amplify a T47902 sequence are set out in SEQ ID NOs: 14 and 15 below.

```
5' TGGAGTTTCAGCTGCTATTG SEQ ID NO: 14

5' TGCCCATCCACAATAGTCTC SEQ ID NO: 15
```

Mixed human adult spleen cDNA was prepared by standard methods and ligated into vector pcDNA1.amp (Invitrogen) [Van der Vieren, M. et al. *Immunity* 3:683–690 (1995)]. The resulting plasmid mixture was transformed into *E. coli* and the bacteria were plated onto LB bacterial plates containing carbenicillin (100 ug/nl). Surviving colonies were collected by scraping and plasmid DNA was prepared by the alkaline lysis method. The cDNA mixture was used as a template for PCR in a reaction mixture including 350 ng cDNA, 100 ng each primer (SEQ ID NO. 14 and NO. 15), 200 $\mu$M each deoxynucleotide triphosphate (adenosine, thymidine, cytidine and guanosine), 10 mM Tris-HCl, pH 8.3 (at 25° C.), 50 mM KCl, 1.5 mM MgCl$_2$, and 5 units Taq polymerase (Perkin Elmer Corp., Foster City, Calif.). PCR was carried out with an initial denaturation step of seven minutes at 95° C. followed by 30 cycles of denaturation for one minute at 95° C., hybridization for one minute at 55° C., and extension two minutes at 74° C. After PCR, 10 $\mu$l of the reaction was separated on a 1.5% agarose gel and an amplification product of 306 bp was detected following ethidium bromide staining. The 306 bp product was eluted from the gel using GeneClean® (BIO101 Inc., Vista Calif.) according to the manufacturer's suggested protocol and ligated into vector pCR2.1 (TA Cloning kit, Invitrogen, Carlsbad, Calif.). The resulting plasmid preparation was transformed into *E. coli* and the cells plated as described above. Several colonies were selected for DNA minipreps and the cDNA inserts were sequenced.

The 306 bp insert was excised from the pCR2.1® TA Cloning® vector by digestion with EcoRI. Following digestion, DNA fragments were fractionated on an agarose gel. A band of approximately 306 bp was eluted from the gel and labeled by random priming according to standard procedures. The labeled probe was used to screen the human spleen adult cDNA pcDNA1 library (described above) immobilized on nylon membranes following colony lifts from cells spread on LB/carbenicillin plates.

Two cDNA clones, designated 3.3 and 15.3.1, were obtained and purified. Clone 3.3 included an insert of approximately 4200 bp and clone 15.3.1 contained an insert of approximately 2750 bp. Both clones were sequenced by standard automated methods. The nucleotide sequence for clone 3.3 is set out in SEQ ID NO: 9 and the predicted amino acid encoded is set out in SEQ ID NO: 10. The nucleotide sequence for clone 15.3.1 is set out in SEQ ID NO: 16. It was initially presumed that the two clones represented a single cDNA sequence and, relying predominantly on the larger 3.3 insert, a contiguous cDNA was predicted. Neither insert, however, encoded a complete open reading frame, as evidenced by the fact that an in frame ATG translation start site preceded by a Kozak translation initiator sequence and an in-frame stop codon were not found.

In an attempt to isolate the 5' end of the complete cDNA, RACE PCR was carried out using a human spleen cDNA library (Marathon™ cDNA, Clontech, La Jolla, Calif.). Nested primers (SEQ ID NOs: 17 and 18) utilized in the PCR were designed based on the library vector and clone 3.3 sequences.

```
5' GTGATCCAGCTACAGTTGTGCTCAT   SEQ ID NO: 17

5' CTAATGCTTCACAGAATCTCTCTGGC  SEQ ID NO: 18
```

Five microliters of cDNA prepared from human spleen RNA or peripheral blood leukocyte RNA was added to separate reactions with 100 ng downstream nested gene specific primer, adapter primer AP1 (Marathon™ cDNA kit; Clontech Inc., Palo Alto Calif.), 200 µM each deoxynucleotide triphosphate (adenosine, thymidine, cytidine, and guanosine), 10 mM Tris-HCl, pH 8.3 (at 25° C.), 50 mM KCl, 1.5 mM MgCl2, 5 units Taq polymerase. PCR was carried out with an initial denaturation step for two minutes at 94° C., followed by (i) five cycles of 0.05 minutes at 94° C. and seven minutes at 74° C., (ii) five cycles of 0.05 minutes at 94° C. and seven minutes at 72° C., and (iii) 25 cycles of 0.05 minutes at 94° C. and seven minutes at 70° C. Following amplification, the reaction mixture was diluted 1:50, and 5 µl was used in a second amplification reaction including 100 ng upstream internal gene specific primer and adapter primer AP2 (Marathon™ cDNA kit, Clontech) with the same cycling conditions as in the first amplification. Amplification products from the second reaction were separated on a 0.9% agarose gel and a band of approximately 2 kb in the gel was eluted for subcloning into vector pCR2.1® as above. The isolated fragment was designated RACE3.3. The nucleotide and predicted amino acid sequences for the fragment are set out in SEQ ID NOs: 7 and 8, respectively.

When the RACE3.3 sequence was correlated with the sequence for the spleen clone 3.3 to account for overlap, an open reading frame (SEQ ID NO: 33) was deduced encoding a polypeptide of 1114 amino acids (SEQ ID NO: 34) and a predicted molecular weight of approximately 125 kD. Even thought the EST used to screen the spleen library was selected based on sequence similarity to CD97, the polypeptide encoded by the overlapping clones was presumed to represent a unique family of human proteins, related to, but distinct from, any previously identified in GenBank®. The putative extracellular domain in the predicted amino acid sequence did not include EGF domains characteristic of the CD97-like protein family and the amino acid sequence of the transmembrane domain in the predicted protein was only about 45–60% identical to the transmembrane domains of CD97. In addition, the predicted amino acid sequence deduced from the combined RACE3.3 and clone 3.3 open reading frame included potential lectin-binding, olfactomedin-ike, and mucin-like extracellular domains not found in CD97. Based on the presence of the extracellular lectin binding-like and olfactomedin-like domains, the polypeptide encoded by the RACE3.3 and clone 3.3 sequences was designated lectomedin-1α.

A later BLAST search of the GenBank® database using the lectomedin-1α sequence indicated that lectomedin-1α was related to the rat receptor for α-latrotoxin designated latrophilin [Lenianova, et al., *J. Biol. Chem.* 272:21504–21508 (1997)], and the calcium-independent receptor of α-latrotoxin (CIRL) [Krasnoperov, supra]. Both human lectomedin-1α and rat latrophilin have extracellular lectin binding-like and olfactomedin-like domains, in addition to a seven transmembrane region and a cytoplasmic domain also found in CD97. Lectomedin-1α also includes a sequence at amino acid residues 809 to 814 (in SEQ ID NO: 2) which is similar to a proposed cleavage site conserved in both CD97 and latrophilin. It is possible that these three proteins are processed by an endoprotease (or related proteases) with similar primary sequence specificity. In view of these similarities, lectomedin-1α may be related to a human homolog of the rat latrophilin and may participate in stimulation/secretion coupling in presynaptic termini and/or secretory granule release. Expression of lectomedin in cell and tissue types outside the central nervous system (discussed below), however, indicates that lectomedin is functionally distinct from latrophilin.

The overall amino acid sequence of lectomedin-1α was found to be approximately 80% identical to that of latrophilin, but the amino acid sequence of the latrophilin cytoplasmic domain was unrelated to the predicted cytoplasmic domain of lectomedin-1α. In addition, the location of the initiating methionine in latrophilin differed from that in the predicted open reading frame of lectomedin-1α. After further analysis of the lectomedin-1α polynucleotide sequence, however, a methionine codon in a different reading frame was identified upstream from the originally predicted open reading frame. The location of the upstream methionine codon (with respect to the transmembrane region) more closely corresponded to the position of the latrophilin initiating methionine and the first few amino acids in reading frame with the upstream methionine codon also corresponded to the sequence in latrophilin.

In view of the potential similarity to latrophilin, the polynucleotide sequence encoding the 1114 amino acid lectomedin-1α open reading frame was again compared to the raw data obtained during automated sequencing of the RACE3.3 cDNA. Further inspection showed that a guanosine nucleotide at position 454 had been entered in SEQ ID NO: 33, but was not present in the raw sequence data. The corrected nucleotide sequence for RACE3.3 (i.e., having the extraneous guanosine nucleotide deleted) together with the sequence of clone 3.3 (SEQ ID NO: 9) showed an open reading frame encoding 1177 amino acids. The corrected open reading frame began with the newly identified initiating methionine and included the previously identified lectin binding-like, olfactomedin-like, mucin-like, transmembrane and cytoplasmic domains of lectomedin-1α (SEQ ID NO: 1).

Based on sequence homology with known proteins, domains in various regions of the lectomedin-1α protein were identified. An extracellular region of approximately 831 amino acids showed homology to a previously reported D-galactoside binding lectin binding-like domain [Ozeki, et al., *Biochemistry* 30:2391–2394 (1991)] (lectomedin-1α amino acids 36 to 131 of SEQ ID NO: 2) and an olfactomedin-like domain [Yokoe and Anholt, *Proc. Natl. Acad. Sci. (USA)* 90:4655–4659 (1993)] (lectomedin-1α amino acids 135 to 327 of SEQ ID NO: 2). Three extracellular and three intracellular domains were separated by seven transmembrane domains (amino acids 832 to 1075 of SEQ ID NO: 2) characteristic of G-protein coupled receptors (GPCR) [Kobilka, etal., *Science* 238:650–656 (1987)]. A cytoplasmic region of 102 amino acids was adjacent the transmembrane region. Based on the observation that lectomedin-1α contained a region from amino acids 354 to 563 (SEQ ID NO: 2) with many serine and threonine residues (which may be O-glycosylated), as well as many proline residues (which break up alpha helices resulting in an extended structure with many beta turns), a mucin-like domain was identified.

Identification of Additional Lectomedin-1 Species

The sequence for lectomedin-1α was based on the sequences determined for clone 3.3 and the fragment RACE3.3. A second lectomedin cDNA could also be deduced based on the sequence of the second spleen clone 15.3.1. In comparing the sequences for clones 3.3 and 15.3.1, it was first noted that the clones were substantially identical throughout both 5' regions, except that an adenosine required at position 1620 of clone 3.3 (SEQ ID NO: 7) was apparently not present in clone 15.3.1. As a result, the reading frame of clone 15.3.1 was shifted in comparison to the reading frame of clone 3.3, and thus, clone 15.3.1 did not encode a protein having the characteristic seven transmembrane domain found in lectomedin-1α. When the variant adenosine was inserted into the sequence for clone 15.3.1, the predicted protein sequence was consistent with the lectomedin-1α amino acid sequence up to the first amino acid residue in the cytoplasmic domain. This sequence suggested an alternative splice site in the cytoplasmic region of clone 15.3.1 that produced a shorter cDNA comprising a cytoplasmic domain of approximately forty-eight amino acids (as compared to 107 amino acids in the cytoplasmic domain of the lectomedin-1α cDNA derived solely from clone 3.3 sequences). The lectomedin-1α cDNA deduced from clone 3.3 also terminated at an alternative poly(A$^+$) site 210 nucleotides upstream from the corresponding poly(A$^+$) site identified in clone 15.3.1. The differences suggested that clone 15.3.1 represents a second member of the lectomedin family, which was designated lectomedin-1β. A deduced polynucleotide sequence for lectomedin-1β was therefore generated using the overlapping sequence from clone 3.3 (which extended the 5' region of clone 15.3.1) and the RACE3.3 sequence (to provide an appropriate 5' end); the complete predicted cDNA and deduced amino acid sequences for lectomedin-1β are set out in SEQ ID NOs: 3 and 4, respectively.

Characterization of the predicted amino acid sequence for lectomedin-1β provides various domains similar (in both sequence and position) to those identified for lectomedin-1α. An extracellular region of approximately 831 amino acids is predicted, including a D-galactoside-binding lectin-like domain (amino acids 36 to 131 of SEQ ID NO: 4), an olfactomedin-like domain (amino acids 135 to 327 of SEQ ID NO: 4), and a mucin-like domain (amino acids 354 to 563 of SEQ ID NO: 4). A seven transmembrane domain (amino acids 832 to 1075 of SEQ ID NO: 4) was located adjacent the extracellular domain, and a cytoplasmic region of 48 amino acids (residues 1076 to 1123 of SEQ ID NO: 4) was located adjacent the transmembrane region.

The originally identified EST designated T49702 (SEQ ID NO: 13) was described in GenBank® to represent the 5' end of a cDNA clone designated 71509 (SEQ ID NO: 21), and when GenBank® was further searched for a DNA sequence representing the 3' end of clone 71509, a second EST designated T47903 (SEQ ID NO: 30) was identified. Clone 71509 (SEQ ID NO: 21) was purchased, sequenced, and compared to the corresponding regions in lectomedin-1α and lectomedin-1β. The sequence of clone 71509 was identical to portions of the lectomedin-1α and 1β sequences, but, like the alternative splicing apparent from comparing lectomedin-1α and lectomedin-1β, yet another alternative splicing event was found based on the sequence of clone 71509. Specifically, the sequence of clone 71509 was found to lack a 106 bp sequence found in clone 3.3. Clone 15.3.1 also lacked the same 106 bp and an additional 97 bp of 5' upstream DNA. Clone 15.3.1 therefore lacked 203 bp of sequence found in the lectomedin-1α clone. The 106 bp deletion resulted in a frame shift in the region encoding the cytoplasmic domain, providing a third lectomedin protein. This third alternative lectomedin polynucleotide and predicted amino acid sequence (SEQ ID NO: 5 and 6, respectively) was designated lectomedin-1γ.

As with the other lectomedin polypeptides, lectomedin-1γ is predicted to include (i) an extracellular region of approximately 831 amino acids with a D-galactoside binding lectin-like domain (amino acids 36 to 131 of SEQ ID NO: 6), an olfactomedin-like domain (amino acids 135 to 327 of SEQ ID NO: 6) and a mucin-like domain (amino acids 354 to 563 of SEQ ID NO: 6), (ii) a seven transmembrane region (amino acids 832 to 1075 of SEQ ID NO: 6), and (iii) a cytoplasmic region of 328 amino acids (amino acids 1076 to 1403 of SEQ ID NO: 6).

The sequences at which the three clones diverged showed hallmarks of the canonical 3 exon sequence with the presence of an AG dinucleotide. However, these regions differed from the accepted intron junction sequences which have been found to include highly conserved GT dinucleotides [*GENES IV*, B. Lewin, Cell Press, Cambridge Mass. (1992), p. 597]. The identification of these sequences indicated that the clones were derived from alternatively spliced RNAs rather than from incomplete RNA splicing wherein the canonical exon/intron junction sequence (AG/GT) would be expected.

Identification of Lectomedin-2 and Lectomedin-3 Species

Lectomedin 1α and rat latrophilin (SEQ ID NO: 19) were used as query sequences in a subsequent BLAST search in an attempt to identify any additional ESTs with sequence homology. Two human ESTs designated AA683020 (SEQ ID NO: 22) and M79057 (SEQ ID NO: 23) were identified as being closely related to both lectomedin-1α and rat latrophilin. The sequence for EST AA683020 corresponds to the region from nucleotide 3275 to 3643 in the lectomedin-1α sequence (SEQ ID NO: 22) and the sequence for EST M79057 corresponds to nucleotides 2561 to 2842 in lectomedin-1α.

The BLAST search results indicated that both ESTs were more closely related to the sequence encoding rat latrophilin than to the nucleotide sequence encoding lectomedin-1α, further distinguishing lectomedin-1α from the rat protein and suggesting that the human ESTs may be more closely related to a putative human homolog of rat latrophilin. In view of the apparent relatedness between the human EST sequences and human lectomedin-1α, however, the AA683020 and M79057 ESTs were determined to represent unique lectomedin-2 and lectomedin-3 species.

In an effort to isolate cDNAs encoding full length lectomedin-2 and lectomedin-3 proteins, primers were designed based on the EST sequences for both lectomedin-2 and lectomedin-3 to amplify probes for library screening. Primers for amplifying a lectomedin-2 sequence were NHlect2.5 (SEQ ID NO: 35) and NHlect2.3 (SEQ ID NO: 36), and primers for the lectomedin-3 sequence were Nhlct.5 (SEQ ID NO: 37) and NHlct.3 (SEQ ID NO: 38).

NHlect2.5  GGGCCTCACCTGGGCTTTCGGCCTCCTC SEQ ID NO:35

NHlect2.3  GGACTGGTGCCCCCACGCGTGTCAGCAC SEQ ID NO:36

Nhlct.5    CCAACAAGACCCATACCAGCTGTG SEQ ID NO:37

Nhlct 3    CTGAGTCTTGTCGATCCCGACC SEQ ID NO:38

PCR was carried out using a Clontech human brain Marathon-Ready™ cDNA library as template. Reaction conditions included an initial incubation at 94° C. for five minutes, followed by 25 cycles at 94° C. for 30 seconds, 55° C. for 30 seconds, and 72° C. for 30 seconds, followed by a final extension step of 72° C. for 7 minutes and cooling to 4° C. in a Perkin-Elmer GeneAmp™ PCR System 9700. The resulting PCR products were gel purified using low melting point agarose (Gibco/BRL) and a QIAGEN® gel extraction kit according to the manufacturer's suggested protocol. The purified amplification products were separately cloned into vector pCRII® with a TA Cloning kit (Invitrogen), and sequencing was carried out to identify errors associated with PCR.

Probes for cDNA library screening were prepared by purifying EcoRI fragments from the pCRII® clones. The lectomedin-2 digestion products provided two fragments, 274 and 158 bp, and the 274 bp fragment was purified. The lectomedin-3 digestion resulted in a 297 bp EcoRI fragment.

A human fetal brain cDNA library in the LAMBDA ZAP® II vector was purchased from Stratagene (La Jolla, Calif.). Approximately 50,000 pfu were plated on twenty 150 mm LBM agar plates with LE392 E. coli. Plates were inverted and incubated at 37° C. overnight. The next day, the plates were chilled at 4° C. for two hours before preparing filter replicas. Amersham Hybond®N+ nylon transfer membrane filters, with a diameter of 132 mm and a removal rating of 0.45 µm, were used to prepare two replicas of each plate. Filters were soaked in denaturing solution for two minutes, soaked in neutralizing solution for two minutes, and UV crosslinked in a Stratagene UV Stratalinker 2400. Filters were prehybridized overnight at 65° C. with 20 filters in 80 ml of prehybridization solution.

Hybridization probes were prepared by labeling the EcoRI fragments with $^{32}$P-dCTP and $^{32}$P-dTTP (800 Ci/mmol each, NEN Life Sciences Products) using a random priming kit (Boehringer Mannheim GmbH, Germany). The labeled probes were added to 20 ml hybridization solution per 20 filters and hybridization was carried out at 65° C. overnight. The filters were washed the next day and air dried before autoradiography at −70° C. for one to three days. Once films were developed, positive plaques were picked and removed to 500 µl of phage diluent buffer including one drop of chloroform. Dilutions of the positive plaques were prepared and plated on 100 mm LBM agar plates.

The plates were screened a second time as described above using 82 mm Amersham Hybond® N+ filters, except that only one set of replica filters was prepared. Positive plaques from the second screening were screened for a third time to ensure that only positive plaques were picked for the phage rescue.

Positive plaques were prepared using an Exassist®/SOLR phage rescue system (Stratagene, La Jolla, Calif.) according to the manufacturer's suggested protocol. The rescue procedure produced E. coli colonies containing the DNA of interest cloned into a pBluescript® SK vector with flanking EcoRI restriction sites. Plasmid DNA was purified using the Wizard® Plus Miniprep Kit (Promega, Madison, Wis.) and digested with EcoRI to determine relative size.

The resulting purified clones were analyzed by DNA sequencing at both the 5' and 3' ends. Of the positive clones identified by the probe derived from EST M79057, several of the longest isolates were chosen for complete DNA sequence analysis. Two clones (designated 2.1 and 2.4) were found to comprise overlapping DNA sequences totaling 5611 bp including a complete open reading fame encoding 1470 amino acids. Of the clones identified with the AA683020 probe, all comprised sequences identical to clones derived from EST M79057. These results indicated that the AA683020 and M79057 ESTs represented non-overlapping regions from a single mRNA species. The two clones therefore were derived from the same lectomedin-2 gene. The polynucleotide encoding lectomedin-2 is set out in SEQ ID NO: 57, and its amino acid sequence is set out in SEQ ID NO: 58.

The organization of various domains in the predicted polypeptide sequence of lectomedin-2 was related to that in lectomedin-1. The approximately 851 amino acid extracellular domain of lectomedin-2 included a region with homology to the D-galactoside binding lectin-like domain (amino acids 36 to 131 of SEQ ID NO.: 57), an olfactomedin-like domain (amino acids 135 to 325 of SEQ ID NO: 57), three extracellular and three intracellular domains separated by seven transmembrane domains (approximately amino acids 852 to 1095 of SEQ ID NO: 57) and a cytoplasmic region (approximately amino acids 1096 to 1470 of SEQ ID NO: 57). The cytoplasmic region of lectomedin-2 was most similar in length and sequence identity to lectomedin-1γ. Comparison of the overall polypeptide sequences of lectomedin-1γ and lectomedin-2 showed 62.5% amino acid identity. Comparison of the overall polypeptide sequences of lectomedin-2 and CIRL showed 97.6% amino acid identity. These comparisons indicated that lectomedin-2 is more closely related by sequence to CIRL than lectomedin-1γ.

A strategy was designed to assemble the overlapping clones 2-1 and 2-4 in the mammalian expression vector pcDNA3 to produce full length lectomedin-2 open reading frame. Two primers (SEQ ID NOs: 61 and 62) were used to amplify a region of cDNA clone 2–1.

```
JD#1       ATATAAGCTTGCTGCCACCATGGCCCGC SEQ ID NO:61

Lecto-     ATGACCCACAGCCCGTTCTC SEQ ID NO:62
3#31
```

Primer JD#1 (SEQ ID NO: 61) incorporated a HindIII site to facilitate cloning. The resulting 843 bp amplified product was digested with HindIII and BamHI and a 535 bp DNA fragment was isolated. The 535 bp fragment from clone 2-1 was ligated with a 1912 bp BamHI/SalI fragment from clone 2–1, a 2904 bp SalI/EcoRV DNA fragment from clone 2-4, and pcDNA3 (Invitrogen) previously digested with HindlII and EcoRV.

Identification of Additional Lectomedin Species

A BLAST search of the GenBank EST database with lectomedin-1α or lectomedin-2 as query sequences identified EST sequences identical to lectomedin-1, EST sequences identical to lectomedin-2 and ESTs that were significantly related to but distinct from both known lectomedins. See Table 1. One of these unique lectomedin ESTs (GenBank Acc# R50822) was derived from clone #37438. Clone #37438 was purchased and its DNA sequence completely determined. The polynucleotide sequence for clone #37438 is set out in SEQ ID NO: 59, and the encoded amino acid sequence is set out in SEQ ID NO: 60. The 3' sequence of clone #37438 is comprised of an untranslated region preceded by a predicted coding sequence for a protein with significant amino acid homology to the cytoplasmic domains of lectomedin-1γ and lectomedin-2. The 5' end of the sequence of clone #37438 was unrelated to the lectomedins, but was identical to the nucleotide sequence for a tRNA synthetase. This clone may represent a partially spliced mRNA or it might be a cloning artifact.

The cDNA clone #37438 was used to generate a labeled probe to screen approximately one million clones from a human fetal brain cDNA library by techniques standard in the art. Hybridization was carried out at 43° C. in the presence of 45% formamide and filters were washed in 0.1×SSC at 68° C. for 90 minutes. Positive clones identified were isolated to homogeneity and partial sequence analysis was carried out with eleven of the clones. The DNA sequence of one clone (#11) was determined to have 3' sequences identical to clone #37438 and 5' sequences within the upstream coding sequences similar to, but distinct from, lectomedin-1 and lectomedin-2.

TABLE 1

Additional Lectomedin Species

| Lectomedin-4 | T10363 | (SEQ ID NO: 39), |
|---|---|---|
| | R19057 | (SEQ ID NO: 40), |
| Lectomedin-5 | R50822 | (SEQ ID NO: 41) |
| Lectomedin-6 | W03697 | (SEQ ID NO: 42) |
| Lectomedin-7 | H18951 | (SEQ ID NO: 43) |
| Lectomedin-8 | AA769730 | (SEQ ID NO: 44) |
| Lectomedin-9 | C17798 | (SEQ ID NO: 45) |
| Lectomedin-10 | Z44961 | (SEQ ID NO: 46) |
| Lectomedin-11 | AA369669 | (SEQ ID NO: 47) |
| Lectomedin-12 | AB011122 | (SEQ ID NO: 48) |

EXAMPLE 2

Recombinant Expression of Lectomedin

Lectomedin-1α

A. Expression vectors encoding lectomedin isoforms were constructed by combining DNA fragments from clone 3.3 and RACE3.3 described above.

In one approach, both clone 3.3 and RACE3.3 polynucleotides are first modified in the overlapping regions by insertion of a silent mutation to introduce a SacI restriction site. PCR is employed using primers (SEQ ID NOs: 25 and 26) to amplify a 5' sequence from the RACE3.3 cDNA template that changes G to C at position 1455 to create the desired restriction site. In amplification of the RACE3.3 fragment, the 5' primer (SEQ ID NO: 26) is designed based on sequences at the ATG start codon; the primer introduces a BamHI restriction site to facilitate cloning and a Kozak consensus start sequence.

```
5'-TCTTCAGCTGAGCTCTTCAAAACC SEQ ID NO:24

5'-GGTTTTGAAGAGCTCAGCTGAAGA SEQ ID NO:25

5'-CAGCAGGGATCCACCATGGTGTCTT- SEQ ID NO:26
   CTGGTTGCAGAATGCGAAGTCTGTGG

5'-GACGATGACGCGGCCGCCTATTAAAGAC- SEQ ID NO:27
   TTGTAACCAGCTGCATTTGTCCTTCTC
```

In amplification of the clone 3.3 DNA with primers set out in SEQ ID NOs: 24 and 27, the 3' primer is based on sequences at the stop site of translation and is designed to introduce a NotI restriction site.

The resulting amplification products, a RACE3.3 fragment with a 5' BamHI site and a 3' SacI site, and a clone 3.3 DNA with a 5' SacI site and a 3' NotI site, are digested with appropriate enzymes, ligated together, and cloned into the mammalian expression vector pcDNA+3, (Invitrogen, Carlsbad, Calif.) previously digested with BamHI and NotI.

B. As an alternative approach, a lectomedin-1α-encoding DNA is generated using PCR with the 5' primer used to amplify RACE3.3 described above and the 3' primer used to amplify the clone 3.3 DNA also described above.

In the PCR, both RACE3.3 and clone 3.3 DNA are combined with the two primers. After an initial denaturing step, the RACE3.3 and clone 3.3 DNA will anneal across the overlapping regions and the double stranded region will serve as primers in the first extension that produces a complete double stranded lectomedin-1α DNA. Subsequent amplifications will result from extension from the 5' and 3' primers. The amplification product is then purified, digested with BamHI and NotI, and inserted into the pcDNA vector previously digested with the same enzymes.

C. In another approach, an expression vector encoding lectomedin-1α was constructed in a two step procedure. First, PCR was carried out using a XbaI fragments of clone 3.3 and primers 3.3.24 (SEQ ID NO: 52) and Lecto 3' express (SEQ ID NO: 27) along with Taq polymerase.

```
CCTACCACAGCTGTGACAATAACTTCTTCAGCTGAGC SEQ ID NO:52
```

A second PCR was carried out using an EcoRI fragment of RACE 3.3 as template DNA and primers Lecto 5' express (SEQ ID NO: 26) and Lecto6 (SEQ ID NO: 25) with Vent® polymerase (New England Biolabs, Beverly, Mass.). The two amplification products were purified, denatured, and annealed. Because the two fragments overlap in a region of approximately 100 nucleotides, annealing results in a partially double stranded molecule spanning the entire lectomedin-1α coding region. Extension with Taq polymerase first produces a double stranded lectomedin-1α coding region. The double stranded molecule was then amplified using primers in SEQ ID NOs: 26 and 27. The SEQ ID NO: 26 primer was designed to introduce a BamHI restriction site, followed by a Kozak consensus start site. The resulting amplification product was digested with NotI and BamHI, and the lectomedin-1α fragment was gel purified. The fragment was ligated into pcDNA3 (Invitrogen, Carlsbad, Calif.) previously digested with BamHI and NotI. Sequence analysis of the resulting plasmid, designated pcDNA3 Lectomedin-1α#2, indicated that several errors were introduced in the amplification process. The correct lectomedin-1α coding sequence was constructed from regions of pcDNA3 Lectomedin-1α#2 without errors ligated to fragments of RACE3.3 and clone 3.3 as follows.

A 166 bp HindIII/BglII fragment from pcDNA3 Lectomedin-1α#2, a 628 bp BglII/BstXI fragment from RACE3.3, and a 775 bp BstXI/ApaI fragment from pcDNA3 Lectomedin-1α#2 were ligated in the presence of pBluescript® KS+ (pBSKS) (Stratagene) previously digested with BstXI and ApaI. The resulting plasmid was designated pBSKSlectoHindIII/ApaI#14.

In a another reaction, a 306 bp ApaI/EcoRI fragment from clone 3.3 and a 2486 bp EcoRI/EcoRI fragment from clone 3.3 were ligated in the presence of pB SKS previously digested with ApaI and EcoRI. The resulting plasmid was designated pBSKSlecto I alphaEcoRI/ApaI#6.

Plasmids pNEF6 and pDEF2 encode promoter regions and a 5' intron from the gene encoding Chinese hamster ovary elongation factor 1, in addition to neomycin (G418) resistance for selection. Construction of pNEF6 and pDEF2 was carried out as follows.

Plasmid pEF1/XN was generated by ligation of an 11 kb NotI/XbaI fragment from pSK/EF1.12 (WO 98/49289, published Nov. 5, 1998, incorporated herein by reference), having the XbaI site blunt ended with Klenow polymerase, with a 2.22 NotI/SmaI fragment from pDC31 (WO 98/49289).

Plasmid pNEF3 was generated by ligation of a 4.19 kb SalI/NsiI fragment (the NsiI site blunt ended with Klenow polymerase) from pSKEF1.7 (WO 98/49289) with a 7.96 kb SalI/PmeI fragment from pNEF1 (WO 98/49289).

Plasmid pNEF5 was constructed with a 9.2 kb AscI/NotI fragment from pNEF3 and an 11 kb AscI/NotI fragment from pEX1/XN.

Plasmid pNEF6 was constructed by ligation of a 19.7 kb XbaI/Asp718 fragment fom pNEF5 with a 0.844 kb XbaI/Asp718 fragment from pRc/CMv (Invitrogen).

A 736 bp NotI/HindIII fragment (including the intron sequence) was isolated from pDEF2 and combined with a 1571 HindIII/ApaI fragment (including the Kozak sequence, translation start site, and coding region for amino acids 1 to 515) from pBSKSlectoHindIII/ApaI#14, a 3714 bp ApaI/XbaI fragment (encoding amino acids 516 to 1177 of lectomedin-1α and including a stop codon and untranslated sequences) from pBSKSlectolalphaEcoRI/Apa#6, and pNEF6 previously digested with XbaI and NotI. The resulting plasmid was designated pNEF6Lectomedin1A#3.1.

Lectomedin-1β and Lectomedin-1γ

Clone 15.3.1 and clone 71509 were separately amplified with primers lecto3.3.10 and 3.3.19.

```
TCAGACACTCATACTGCTGTG  SEQ ID NO:49

CACAGTCCACAACTTGCAC    SEQ ID NO:50
```

The resulting amplification products were digested with StuI and NcoI, and a 113 bp fragment from 15.3.1 (lectomedin-1β) and a 210 bp fragment from 71509 (lectomedin-1γ) were purified. Each fragment was separately ligated into pBSKSlecto1alphaEcoRI/ApaI#6 previously digested with StuI and NcoI. The resulting plasmids were designated pBSKSlecto1betaEcoRI/ApaI#7 and pBSKSlecto1gammaEcoRI/ApaI#6.

To create a lectomedin-1β expression plasmid, the reaction described above for construction of the lectomedin-1α expression plasmid was repeated except that a 2586 bp ApaI/XbaI fragment from pBSKSlecto1betaEcoRI/ApaI#7 was substituted for the 3714 bp ApaI/XbaI from pBSKSlecto1alphaEcoRI/ApaI#6 to provide plasmid pNEF6Lectomedin1B#4.2.

To create a lectomedin-1γ expression plasmid, the same lectomedin-1α reaction above was carried out except that a 2683 bp ApaI/XbaI fragment from pBSKSlecto1gammaEcoRI/ApaI#6 was substituted for the 3714 bp ApaI/XbaI from pBSKSlecto11alphaEcoRI/ApaI#6 to provide plasmid pNEF6Lectomedin1G.

Expression of a Soluble Lectomedin-1 Ig Fusion Protein

An expression construct was also prepared in parental vector pDC37 encoding a soluble, truncated form of lectomedin-1 as a fusion protein with human immunoglobulin G1 hinge and constant heavy chain regions 2 and 3 [hinge CH2-CH3] sequence [Sadhu, et al., *Cell Adhesion and Commun.* 2:429–440 (1994)]. Plasmid pDC37, encoding human VCAM-1 with human IgG1 hinge-CH2 coding sequences, is a derivative of pDC31 generated by digestion with SalI, filled in with Klenow polymerase, and blunt end ligated to eliminate the SalI site.

Plasmid pDC37/VCAM1.Ig1.2c was digested with HindIII and SalI and a fragment lacking the VACM-1 coding region was isolated. The isolated HindIII/SalI fragment was ligated with a 1571 bp HindIII/ApaI fragment from pcDNA3Lectomedin-1a#2 and an amplification product from clone 3.3 prepared using primers lecto Sal Ig (SEQ ID NO: 51) and 3.3.24 (SEQ ID NO: 52).

```
       lecto SaL Ig            SEQ ID NO:51
   GACGCTGGTCGACTAGGTGGCTGCATGCACACGTTGTTCG 3.3.24                  SEQ ID NO:52
     CCTACCACAGCTGTGACAATAACTTCTTCAGCTGAGC
```

Primer lecto Sal Ig generated a unique SalI site in the amplification product (after codon 811 of lectomedin-1) to permit in-frame ligation to IgG1 coding sequences. The resulting plasmid was designated pDC37Lecto.Ig#7.

A 736 bp NotI/HindIII fragment from pDEF2 was ligated with a 1571 bp HindIII/ApaIII fragment (encoding the Kozak sequence, start site, and amino acids 1 to 515 from lectomedin-1α) from pcDNA3 Lectomedin-1a#2, a 1788 bp ApaI/XbaI fragment (encoding amino acids 516 to 811 from lectomedin-1 fused to IgG sequences) from pDC37Lecto.Ig#7, and pDEF14 previously digested with NotI and XbaI. The resulting plasmid was designated pDEF14Lecto.Ig#2.

Plasmid pDEF14Lecto.Ig#2 was transfected into DHFR⁻ DG44 CHO cells and stably transfected cells were selected.

EXAMPLE 3

Characterization of Recombinant Lectomedin

Characterization of the protein expression level in recombinant cells is carried out using polyclonal antisera (produced as described in Example 8), and functional analysis, with respect to latrotoxin binding (discussed below) and/or release of secretory granule contents, is performed as previously described.

In initial characterization, Chinese hamster ovary (CHO) cells were transfected by standard methods (i.e., calcium phosphate or cationic lipids) with lectomedin-1α expression construct. After 48 hours incubation, the cells were lysed in PBS containing 1% Triton® X-100 and protease inhibitors, and proteins in the detergent soluble fraction were separated by SDS-PAGE. After transfer to nitrocellulose membrane, the blot was incubated with rabbit antiserum immunospecific for lectomedin-1α (generated against amino acids 432–852 as immunogen). Immunoreactivity was detected using a goat anti-rabbit IgG (conjugated with horseradish peroxidase) followed by chemiluminescence detection and exposure to X-ray film (using a Renaissance® detection kit, NEN Life Sciences, Boston, Mass.).

For functional characterization, secretory cells of the endocrine system are employed which readily accept DNA constructs by transfection. Cell lines useful in functional characterization include, for example, mouse anterior pituitary corticotroph continuous cells (AtT20; ATCC CCL 89), rat pancreatic islet insulinoma continuous cells (RinM5F), or human pituitary somatotroph continuous cells (GH3; ATCC CCL 82.1). After an appropriate amount of time to allow protein synthesis, incubation of the transfected cells with alpha-latrotoxin, or another ligand, is followed by detection of stimulated secretion of proteins using enzyme-linked immunosorbant assay or radioimmunoassay (RIA). For example, increased secretion from the exemplified cells lines is accomplished through detection of adrenocorticotrophic hormone (ACTH) release from AtT20 cells, insulin release from RinM5F cells, or growth hormone release from GH3 cells.

In addition, since lectomedin-1 is a G-protein coupled receptor, ligand binding would be expected to trigger intracellular second messenger effector pathway activity changes such as, for example, increased production of cyclic AMP (cAMP) or changes in intracellular calcium concentration. Changes of these types are measured by standard techniques, for example, RIA detection of cAMP or fluorescence detection of calcium binding indicators (i.e., Fura 2).

An exemplary alpha-latrotoxin binding assay has been previously described [Meldolesi, *J. Neurochem.*

38:1559–1569 (1982), Petrenko, et al., *EMBO J*, 9:2023–2027 (1990)]. Cells are transfected with either vector DNA alone (control cells) or a lectomedin 1-encoding expression plasmid (assay cells). Both assay and control cells are homogenized in buffer (120 mM NaCl, 4.7 mM KCl, 1.2 mM each $MgSO_4$, $K_2HPO_4$, and $CaCl_2$, 20 mM $Na_2HPO_4$—HCl, pH 7.4, and 10 mM glucose) and protein concentrations are determined by standard methods. Known amounts of protein from control or transfected assay cell membranes are spotted on nitrocellulose paper and placed in separate wells of a 24 well dish. The paper is rinsed once with buffer containing 100 mM KCl, 2 mM $CaCl_2$, and 20 mM Tris, pH 7.7, and incubated for one hour in the same buffer supplemented to 1.5% (w/v) with bovine serum albumin (BSA) (blocking buffer). Solutions of blocking buffer containing from 0.1 to 1.2 nM of $^{125}$I-labeled alpha-latrotoxin, labeled to a specific activity of 1500 to 2000 Ci/mmol, without or with a large excess (100 nM) of unlabeled toxin are incubated for thirty minutes with the immobilized protein. The paper is rinsed three times with 1 ml of blocking buffer over a 20 minute time period and counts per minute remaining are determined with a gamma counter. Nonspecific binding is determined to be the value of radioactive counts remaining after incubation of labeled toxin in the presence of a large excess of unlabeled toxin. Specific counts are converted to nanomoles of toxin bound per milligram of protein spotted and the data is plotted as nanomoles bound toxin versus nanomoles free toxin. The data are converted to bound toxin divided by free toxin versus bound toxin to derive a Scatchard plot for number of binding sites (a linear plot being the expected result for a single toxin binding site on the receptor).

In additional characterizations, the lectomedin fusion protein Lecto-1Ig (Example 2) was purified using protein A Sepharose® (Amersham Pharmacia Biotech, Piscataway, N.J.) affinity chromatography and conditioned growth media derived from one of two clones designated G10 and E10. Media was loaded onto the column which was then washed extensively with 50 mM Tris, pH 7.5, 50 mM NaCl. Protein was eluted in buffer containing 50 mM citric acid, pH 4.0, and 50 mM citric acid, pH 3.0. The majority of the protein eluted in the pH 3.0 buffer. Protein fractions were pooled, neutralized with 1 M Tris, pH 8.0, and dialyzed against PBS. Purified protein was filtered, aliquoted, flash frozen and stored at −70° C.

Amino terminal sequencing indicated that the mature amino terminus of the protein was identified as a phenylalanine residue at position 26. This observation indicated that the recombinant protein was recognized and cleaved by a signal peptidase in the CHO cells and that the amino terminus was not blocked.

Size exclusion chromatography suggested a protein with a molecular weight of approximately 650 kDal as compared to the molecular weight determined on SDS PAGE of approximately 170 kDal. The gel filtration result suggested that four monomers combined to produce the 650 kDal protein.

Treatment of the protein with N-glycosidase F, O-glycosidase, and/or neurominidase (Boehringer Mannheim) in 10 mM $Na_2HPO_4$ (pH 6.8), 5 mM EDTA, 0.25% Triton® X-100, 0.5% SDS, and 0.5% β-mercaptoethanol (BME), at 37° C., resulted in reduction of protein molecular weight. After treatment with N-glycosidase F alone, monomeric protein molecular weight was approximately 130 kDal. After treatment with N-glycosidase F, O-glycosidase, and neuraminidase, monomeric protein molecular weight was approximately 125 kDal. These observations suggest that the observed SDS PAGE molecular weight may be attributable to approximately 40 kDal N-linked carbohydrate and approximately 5 kDal O-linked carbohydrate.

EXAMPLE 4

Ligand Affinity Chromatography

In an attempt to isolate a ligand for lectomedin-1, an affinity column was generated with immobilized lectomedin-1. In short, 10 mg of purified sLecto-1Ig was coupled to CNBr-activated Sepharose 4B resin (AmershamPharmacia) according to the manufacturer's suggested protocol. Greater than 96% of the lectomedin protein was coupled to the resin.

A detergent extract was prepared from human spleen (3.48 g wet weight). Tissue was homogenized in 15 ml buffer containing 1% Triton® X-100, 25 mM Tris, pH 8, 150 mM NaCl, 5 mM iodoacetamide, 5 mM EDTA, 1 mM phenylnethylsulfonyl fluoride (PMSF), and 1 μg/ml pepstatin and aprotinin using a Waring blender. Homogenization was carried out at low speed. The resulting homogenate was cooled on ice for one hour and centrifuged at 100,000×g for 60 min. The supernatant (approximately 120 mg total protein) was mixed with the sLecto-1Ig-coupled resin with rotation overnight at 4° C. The resin was drained and washed extensively with 10 mM Tris (pH 8), 150 mM NaCl, and 10 mM Tris (pH 8), 1 M NaCl. Protein was eluted with five bed volumes of 100 mM D-lactose, 10 mM Tris, pH 8.0, 150 mM NaCl. Five equal fractions were collected. The resin was further eluted with four bed volumes of 100 mM glycine, pH 2.0, and four equal fractions were collected and neutralized with 1 M Tris, pH 8.0. The resin was then neutralized in 10 mM Tris, pH 8.0/150 mM NaCl. Fractions from the resin were analyzed by SDS-PAGE and bands of approximately 95, 71, 55 and 30 kDal were detected.

Fractions with the highest protein yields were spin concentrated (Ultrafree® 10, Millipore, New Bedford, Mass.) and proteins were separated with 12% SDS-PAGE. Coomassie staining revealed four prominent bands in the lactose eluate of approximately 30–32, 55, 70, and 80–95 kDal. Bands were excised from the gel, rinsed twice in 50:50 acetonitrile:water, and stored at −70° C. until sequence analyses were performed. Sequence results indicated that the 30–32 kDal protein was Mac-2 (also called galectin-3, GenBank® Accession No: g106937), the 55 kDal protein was fibrinogen γ A chain (GenBank® Accession No: g71827) and the 80–95 kDal protein was immunoglobulin mu chain constant region.

Mac-2 (galectin-3) is synthesized by numerous immune cell populations and epithelia, and is a major non-integrin laminin binding protein [Perillo, et al., *J. Mol. Med.* 76:402–412 (1998)]. Recent observations indicated that Mac-2 was expressed in vessels in early atherosclerotic lesions in association with infiltrating monocytes. Expression was not detected in normal vessels. Expression was also detected in aortic smooth muscle cells in culture, as well as in animals following a hypercholesterolemic feeding regimen and post balloon angioplasty [Arar, et al., FEBS Letts.430:307–311 (1998), Nachtigal, et al., *Am.J.Pathol.* 152:1199–1208 (1998)]. Mac-2 stimulates normal fibroblast proliferation, neural cell adhesion, and neurite outgrowth [Inohjara, et la., *Exp. Cell. Res.* 245:294–302 (1998); Pesheva, et al., *J. Neurosci. Res.* 54:639–654 (1998)].

The binding results from lectomedin affinity chromatography, in view of the art, suggest that secretion of Mac-2 by infiltrating macrophages during atherogenesis and binding to lectomedin-1 expressed on smooth muscle cells of vascular tunica media may be required for smooth muscle proliferation in atherosclerosis. [Ross, Nature 362:801–809 (1993)].

Previous work has indicated that circulating components of the thrombolytic pathway, including firinogen, are associated with chronic vascular disease (i.e. , hypertension, atherosclerosis). Studied showed that circulating fibrinogen levels may be elevated in hypertensive patient populations. These observations suggest a role for lectomedin in various vascular disease states.

EXAMPLE 5

Northern Analysis

In an attempt to assess human lectomedin-1α expression, Northern blot analysis was performed using a commercial multi-tissue blot (Clontech, Palo Alto, Calif.) with RNA derived from various human tissue sources. The probe used was a 531 bp BstM fragment derived from the extracellular region of clone 3.3 (bases 1860 to 2350 in SEQ ID NO: 7). Hybridization was carried out in Express-Hyb™ Solution (Clontech) at 68° C. for two hours; the final wash was carried out at 68° C. in 0.1×SSC for one hour.

Results indicated expression of two predominant transcripts of 6.6 and 7 kb. The highest levels of expression were detected in spleen, prostate, and lung. Lower signals were in duodenum, placenta, thymus, testis, colonic mucosa, heart, and liver. Lowest levels were found in skeletal muscle, kidney, pancreas, and brain. No signal was observed in ovary and peripheral blood leukocytes.

EXAMPLE 6

In situ Hybridization

In order to verify results from Northern analysis, in situ hybridization was carried out using various human tissue sections.

Probes for in situ hybridization analysis were prepared as follows. Clone 3.3 was engineered by PCR to include a SacI site near the 5' end of the cDNA by changing a G nucleotide to C at position 1459 of the composite sequence. A 626 bp SacI/EcoRI fragment was prepared and subcloned into pBSSK (Stratagene, La Jolla, Calif.). The resulting plasmid was linearized with either EcoRI or SacI. The ends of the SacI linearized DNA were made blunt by standard procedures using T4 DNA polymerase. Linear DNAs were used to generate $^{35}$S-labeled sense or antisense strand probes for in situ hybridization with tissue sections from spleen, lung, prostate, heart, thymus, duodenum.

The results obtained from hybridization experiments were inconclusive due to high background with sense strand control probe.

In another approach to localizing the lectomedin-1 mRNA, two other fragments of the lectomedin-1 cDNA were subcloned into the pBluescript vector. A 1238 bp BamHI/SacI fragment of lectomedin-1α (SEQ ID NO: 1) was subcloned. A representative clone containing this fragment was designated as probe BS. A 2855 bp BamHI/XbaI fragment of lectomedin-1 α (SEQ ID NO: 1) was subcloned and a representative clone was isolated and designated as probe BX. $^{35}$S-labeled sense and antisense probes from both BS and BX were prepared by methods standard in the art and hybridized with tissue sections from human brain occipital cortex, cerebellum and thalamus; interventricular septum, sino-atrial node and atrium of the heart; small intestine, spleen, lung, prostate, adrenal gland and pancreas.

Specific signals were observed with the antisense BS probe in cardiac myocytes (heart), endocrine secretory cells of the adrenal cortex, occipital cortex neurons and cerebellar purkinje neurons, granule layer neurons and some molecular layer neurons. The antisense BX probe produced similar patterns except for the presence of specific signals in a subset of secretory cells of the prostate.

EXAMPLE 7

Human Lectomedin Chromosomal Localization

The contiguous lectomedin-1α cDNA deduced from combining clone 3.3 and RACE3.3 sequences was used as a query to search the NCBI Sequence-Tagged Sites (STS) database in an attempt to map the chromosomal location of a gene encoding lectomedin-1α.

Two STSs were identified, designate SHGC-36772 and WI-1 1936, which were mapped to chromosome 1 by radiation hybrid mapping techniques. The STS WI-11936 mapping has been further refined to chromosome locus 1p31.

In an effort to identify the chromosomal localization of the gene for lectomedin-2, the full length nucleotide sequence was used to query the GenBank® high throughput genomic sequences nucleotide database using the BLAST algorithm. Results indicated that a portion of chromosome 17 had identity with a portion of the lectomedin-2 DNA sequence. Query of the human Genemap '98 at NCBI for the localization of this region of chromosome 17, showed that the lectomedin-2 gene mapped to chromosome 17p11.1-q12.

To identify the chromosomal localization of the gene for lectomedin-3, an accession number query (using EST R50822) of the Unigene database at the National Center for Biotechnology Information (NCBI) was carried out. The results identified a cluster of ESTs, including R50822 that mapped to human chromosome 4. Refinement of the localization was carried by searching the human GeneMap '98 out at NCBI, which showed that EST the cluster containing R80522 was assigned to 4q12–13.3.

EXAMPLE 8

Preparation of Antibodies to Lectomedin

Generation of Polyclonal Anti-sera with Extracellular Lectomedin-1 Fragments

An *E. coli* expression vector was constructed encoding the extracellular region of lectomedin-1α (residues 432 to 852 of SEQ ID NO: 1) as a fusion protein with a biotinylated tag at the amino terminus. The plasmid, designed "Biolecto 1st ECD" was constructed as follows.

PCR primers "lecto-1" and "lecto-2" (SEQ ID NOs: 31 and 32, respectively) were used to amplify a 1283 bp fragment of clone 3.3 (nucleotides 1508–2772 in SEQ ID NO: 9 which encodes the amino acid sequence from residue 432 to residue 852 of SEQ ID NO: 10). This region of the lectomedin-1 polypeptide is approximately 69% identical with latrophilin.

```
primer lecto-1                      SEQ ID NO:31
    5'-TACAACCATGGGCACAACTGTAGCTGG primer lecto-2                      SEQ ID NO:32
    5'-TACAAGATCTAGCAGATAGCCAGGCAAACAAGGG
```

Primer lecto-1 introduced an NcoI restriction site (underlined above) in the amplification product and primer lecto-2 introduced a BglII restriction site (underlined above) and a translational termination site. The amplified fragment was subcloned into plasmid arabio1b previously digested with NcoI and BglII to form plasmid Biolecto1stECD. The plasmid arabio1b contains the *Salmonella typhimurium* arabinose promoter and araC gene, as well as the biotin transferase gene [Kashishian, et al., *J. Bio. Chem.* 273:27412–27419 (1998)]. The expression product of the final construct provides a fusion protein of approximately 55 kDa with the biotin tag at the N-terminus, and the lectomedin-1 amino acids 432 to 852 at the C-terminus.

The plasmid Biolecto1stECD was transformed into *E. coli* using standard procedures and single colonies were isolated and grown for plasmid preparation. A culture including the desired plasmid was grown at 30° C. in LB/carbenicillin supplemented with biotin (4 μM) and induced in the presence of arabinose (0.5%) for 16 hours. Bacteria were collected by centrifugation and lysed with hen egg lysozyme (10 μg/ml) in TEN buffer (50 mM Tris-HCl, pH 7.5 at 25° C., 0.5 mM EDTA, 0.3 M NaCl) on ice for 15 minutes. After incubation on ice, NP-40 detergent was added to 0.2% final concentration and the resulting mixture sonicated briefly on ice. Insoluble material was removed by centrifugation at 15,000×g for ten minutes, after which the pellet washed five times with the additional of TEN buffer followed by sonication and centrifugation. The final pellet was solubilized in 2× sample loading buffer for preparative SDS-PAGE separation.

A major band of 55 kDa was detected after treating the gel for 30 minutes in 0.4 M KCl. The 55 kDa band was excised from the gel and the fusion protein eluted in dialysis tubing using 0.5% SDS-PAGE running buffer. The collected protein was concentrated, spin-dialyzed (30,000 MW cutoff Ultrafree® Centrifugal Filter Device; Millipore Corp. Bedford, Mass.), and stored.

The purified protein was used to immunize two rabbits to generate antisera according to well known procedures.

Briefly, two New Zealand white rabbits (designated #7234 and #7278) were prebled to obtain preimmune serum and then immunized with 250 μg of purified BiolectolstECD fusion protein emulsified with complete Freund's adjuvant. The rabbits were boosted repeatedly with 250 μg of purified fusion protein in incomplete Fruend's adjuvant. The first three boosts were given at one month intervals, the third and fourth boosts following a three month interval, and the fourth and fifth boost following an additional one month interval. Blood was drawn by ear vein puncture two weeks after the second, third, fourth, and fifth boosts to determine antibody titers.

Immunoprecipitation was carried out with the resulting polyclonal sera using extracts from tissues/cell lines, including brain cortex, lung, spleen, liver, skeletal muscle, hippocampus, and prostate carcinoma cell line PC-3 (ATCC, CRL 1435). Protein species having molecular weights of 200, 180, 170, and 70 kDa were detected which may have represented full length proteins, proteolytic fragments, or isoforms of lectomedin including the α, β, and γ proteins.

Serum obtained from rabbit #7234 after the fifth boost was subjected to antigen-specific affinity chromatography by methods standard in the art. Briefly, 10 ml of 0.45 or 0.8 microfiltered serum (100×g supernatant) adjusted to 10 mM Tris, pH 7.5, was incubated with sLecto-1Ig agarose beads for 16 hours at 4° C. with rotation. The beads were drained and washed with 20 bed volumes of 0.5 M NaCl, 10 mM Tris, pH 7.5, until absorbance $OD_{280}$ reached 0.03. Bound antibody was eluted with five bed volumes of 100 mM glycine, pH 2.5. The eluates were collected as 0.5 ml fractions and neutralized with 1 M Tris, pH 8. The sLecto-1Ig agarose beads were neutralized with 50 mM Tris, pH 7.5/150 mM NaCl and stored at 4° C. in the same buffer supplemented with 0.1% timerool. Fractions were analyzed by SDS-PAGE for the presence of immunoglobulin heavy and light chains. The peak fractions were pooled, the buffer was exchanged with PBS, and the volume reduced by 90%. The final product was mixed with an equal volume of sterile glycerol, aliquoted, flash frozen, and stored at –70° C. until use.

Generation of Polyclonal Antisera with Synthetic Lectomedin-1 Cytoplasmic Peptides Peptides specific to the carboxy terminal cytoplasmic regions of α, β, and γ isoforms of lectomedin-1 were synthesized as immunogens for producing polyclonal antisera in New Zealand White rabbits. The peptides were designed from the DNA sequence in the cytoplasmic region of lectomedin 1α (SEQ ID NO: 53), lectomedin 1β (SEQ ID NO: 54), and lectomedin 1γ (SEQ ID NO: 55).

```
Cys-Leu-Gln-Asp-Leu-Tyr-His-Leu-Glu-Leu-Leu-Leu-Gly-Gln-Ile-Ala    SEQ ID NO:53

Cys-Thr-Arg-Thr-Ser-Ala-Arg-Tyr-Ser-Ser-Gyl-Thr-Gln-Asp-Ile-His    SEQ ID NO:54

Cys-Glu-Gly-Asp-Val-Arg-Glu-Gly-Gln-Met-Gln-Leu-Val-Thr-Ser-Leu    SEQ ID NO:55
```

Peptides comprising the carboxy terminal regions of the related lectomedin-2 (SEQ ID NO: 63) and lectomedin-3 (SEQ ID NO: 64) proteins were also synthesized.

```
Cys-Pro-Gly-Pro-Asp-Gly-Asp-Gly-Asp-Gly-Gln-Met-Gln-Leu-Val-Thr-Ser-Leu  SEQ ID NO:63

Cys-Pro-Glu-Gly-Ser-Ser-Lys-Gly-Pro-Ala-His-Leu-Val-Thr-Ser-Leu  SEQ ID NO:64
```

The synthesized peptides were individually conjugated to Keyhole Limpet Hemocyanin (KLH) (Imject, Pierce) according to the manufacturer's suggested protocol. Rabbits were prebled, and 100 μg of conjugated peptide in complete Freund's adjuvant was injected per rabbit, two rabbits per isoform. At three week intervals, the rabbits were boosted with the same dose of antigen in incomplete Freud's adjuvant. Animals were bled 10 days after the third injection and serum titer determined by ELISA.

Briefly, Immulon® 4 (Dynax Technologies, Chantilly, Va.) plates were coated with unconjugated peptide at 2 μg/ml. Plates were blocked with 0.5% fish skin gelatin and washed. Serial dilutions of the pre-immune serum and test bleeds from each rabbit were incubated on the peptide-coated plates. After washing, goat anti-rabbit-horseradish peroxidase (HRP) conjugated secondary antibody was added. The plates were washed and signal detected by tetramethyl benzidine (TMB) (Sigma) reagent.

Serum from rabbits #6484 and #6453 immunized with the lectomedin-1β peptide showed reactivity three-fold greater than pre-immune serum at a 3000-fold dilution. Serum from rabbits #6868 and #6307 immunized with lectomedin-1γ showed three-fold greater reactivity over pre-immune serum at a 3000-fold dilution. Serum from rabbits #7347 and #6490 immunized with lectomedin-1α, showed three-fold greater reactivity at a 200-fold dilution.

In view of these results, a second lectomedin-1α peptide (SEQ ID NO: 56) was synthesized and the immunization protocol described above was repeated with two additional rabbits. Serum from these rabbits is assayed for specific reactivity as described above.

bovine serum [FBS] for three days prior to fusion). The cells are collectedy centrifugation and the supernatant is aspirated. The cell pellet is dislodged and 2 ml of 37° C. PEG 1500 (50% in 75 mM HEPES, pH 8.0) (Boehringer Mannheim) is added while stirring over the course of one minute, followed by the addition of 14 ml of serum free RPMI over seven minutes. Additional RPMI can be added and the cells are centrifuged at 200×g for 10 minutes. After discarding the supernatant, the pellet is resuspended in 200 ml RPMI containing 15% FBS, 100 mM sodium hypoxanthine, 0.4 mM aminopterin, 16 mM thymidine (HAT) (Gibco), 25 units/ml IL-6 (Boehringer Mannheim), and $1.5 \times 10^6$ thymocytes/mil. The suspension is dispensed into ten 96-well flat bottom tissue culture plates (Corning, United Kingdom) at 200 μl/well. Cells are fed on days 2, 4, and 6 days post-fusion by aspirating 100 μl from each well and adding 100 μl/well plating medium containing 10 U/ml IL-6 and lacking thymocytes.

When cell growth reaches 60–80% confluence (day 8 to 10), culture supernatants are taken from each well and

```
Cys-Ser-Arg-Ile-Arg-Arg-Met-Trp-Asn-Asp-Thr-Val-Arg-Lys-Gln-Ser  SEQ ID NO:56
```

Monoclonal Antibody Production

In an attempt to produce monoclonal antibodies immunospecific for lectomedin polypeptides, the following procedure was carried out.

Five 6 to 12 week old BALB/c mice were prebled on day 0 and immunized by subcutaneous injection with 20 μg of the lectomedin-1α, lectomedin-1β, or lectomedin-1γ peptides (SEQ ID NOs: 53, 54, and 55) described above (60 μg total) in complete Freund's adjuvant. On Days 21, 41, and 62, each mouse was boosted with 10 μg of each peptide (30 μg total) in incomplete Freund's adjuvant. Test bleeds were drawn on day 72 and reactivity determined by ELISA against individual peptides as described in generation of polyclonal antisera, with the exception that specific mouse antibody was detected with a goat anti-mouse-HRP.

Immune serum from all five mice showed reactivity to lectomedin-1β and lectomedin-1γ peptides greater than pre-immune serum at a 12800-fold dilution. Serum from all of the mice showed modest reactivity to lectomedin-1α peptide.

Additional peptides comprising the carboxyl termini of lectomedin-2 and lectomedin-3 (SEQ ID NOs: 58 and ) were synthesized to screen for cross reactive antibodies recognizing similar epitopes found in termini of lectomedin-1γ, lectomedin-2 and lectomedin-3.

In an another approach to generate an immune response to lectomedin-1α, five additional mice were immunized with the second lectomedin-1α peptide (SEQ ID NO: 56) described above. Immune serum from each of the mice is tested for lectomedin-1α reactivity by ELISA (described above) prior to fusion and hybridoma cloning.

The spleen of the immunized animal is removed aseptically and a single-cell suspension is formed by grinding the spleen between the frosted ends of two glass microscope slides submerged in serum free RPMI 1640 (Gibco, Canada) supplemented with 2 mM L-glutamine, 1 mM sodium pyruvate, 100 units/ml penicillin, and 100 μg/ml streptomycin. The cell suspension is filtered with a sterile 70-mesh Nitex cell strainer (Becton Dickinson, Parsippany, N.J.), and washed twice by centrifuging at 200×g for five minutes and resuspending the pellet in 20 ml serum free RPMI. Thymocytes taken from naive Balb/c mice are prepared in the same manner.

Approximately $2\times10^8$ spleen cells are combined with $4\times10^7$ NS-1 cells (kept in log phase in RPMI with 11% fetal screened for reactivity to lectomedin by ELISA. ELISAs are performed as follows. Immulon 4 plates (Dynatech, Cambridge, Mass.) are coated at 4° C. with 50 μl/well with 100 ng/well of inmmunogen in 50 mM carbonate buffer, pH 9.6. Plates are washed with PBS with 0.05%, Tween® 20 (PBST) and blocked 30 minutes at 37° C. with 0.5% fish skin gelatin. Plates are washed as described above and 50 μl culture supernatant is added. After incubation at 37° C. for 30 minutes, plates were washed as above, then 50 μl of horseradish peroxidase conjugated goat anti-mouse IgG(fc) (Jackson ImmunoResearch, West Grove, Pa.) [diluted 1:10,000 in PBST] is added. Plates are incubated at 37° C. for 30 minutes, washed with PBST and 100 μl of substrate, consisting of 1 mg/ml TMB (Sigma) and 0.15 ml/ml 30% $H_2O_2$ in 100 mM citrate, pH 4.5, is added. The color reaction is stopped with the addition of 50 μl of 15% $H_2SO_4$. Absorbance at 450 nm is read on a plate reader (Dynatech).

EXAMPLE 9

Immunocytochemistry for Expression of Lectomedin

Polyclonal antisera generated in rabbit #7234 (and affinity purified) as described above was used to determine lectomedin expression patterns in human and rat tissues. Human tissues were obtained from the National Disease Research Interchange (NDRI, Philadelphia, Pa.), including human brain (cortex and cerebellum), heart (septum and atrium), prostate, lung, liver, spleen, small intestines, adrenal gland, and artery (renal, pulmonary and subclavian). Aorta was obtained from the Pathological Determinants of Atherosclerosis in Youth (PDAY) Study, Louisiana State University Medical Center. Rat tissue was prepared using procedures well known and routinely practiced in the art.

Frozen tissues were embedded in OCT (Tissue-Tek), sectioned at 6 micron thickness, mounted onto Superfrost Plus (VWR Scientific) slides, and stored at −20° C. until the assay was performed. Paraffin-embedded, formalin-fixed tissues were stored at room temperature until the assay was performed. Prior to assay, frozen tissue was fixed in acetone for two minutes at 4° C., except for brain tissue which was fixed in ether for five minutes at room temperature. Formalin-fixed tissue was deparaffinized with two three-minute washes in each of xylene, 100% ethanol, 95% ethanol, and 70% ethanol. Endogenous peroxidase activity was quenched by incubating the fixed cryosections in buffer containing 0.1% sodium azide and 0.33% hydrogen peroxide in phosphate buffered saline (PBS) during a 15 minute incubation. All incubations were carried out at room temperature unless otherwise indicated. Slides were rinsed in TBST (20 mM Trizma® base [Sigma], 150 mM NaCl, 0.05% Tween®, pH 7.2) and blocked in a solution containing 30% normal human serum albumin (Boston Biomedica), 5% normal goat serum (Harlan), and 2% bovine serum albumin (Sigma) in TBST for 30 minutes. Nonspecific binding was blocked using sequential 15 minute incubations with avidin and biotin blocking solution (SP-2001, Vector Labs, Burlingame Calif.). Slides were rinsed in TSBT after each incubation. Primary antibody at concentrations ranging from 1 µg/ml to 5 µg/ml was applied to each section for one hour, after which sides were washed in TSBT three times. Biotinylated goat anti-rabbit antibody conjugated to peroxidase (Vector Labs) was diluted 1:200 in blocking solution and applied to the slides for 30 minutes. Slides were washed for five minutes and incubated for 30 minutes with ABC Elite reagent (avidin-biotin-peroxidase kit PK-6100, Vector Labs). Slides were washed twice for five minutes per wash in TSBT. Substrate solution (DAB substrate kit for peroxidase, Vector Labs) was applied to the slides and the desired color intensity was allowed to develop over approximately five minutes. The reaction was stopped with deionized water, and the slides were counterstained with Gill's hematoxylin (Sigma) solution, rinsed in water, dehydrated in ethanol, and mounted with Cytoseal mounting medium (Stephens Scientific) for light microscopic evaluation.

In human brain cortex, labeling with 7234 sera was detected in a subset of neurons (including large and small pyrimidal neurons), granule cells, and smooth muscle cells of the vasculature. Human cerebellum staining with 7234 sera was localized to purkinje neurons and neurons of the granular cell layer. Human heart (septal and atrial sections) showed cardiomyocyte immunoreactivity, most prominently at cardial myocyte cell junctions transverse to the plane of the contractile apparatus called intercalated dicks.

In double label experiments using a commercially available connexin antibody (Zymed, San Francisco, Calif.), which stains connexin found at the intercalated disks, the previous results were confirmed as results indicated that connexin antibody and 7234 antisera staining co-localized on the intercalated disks.

Sections of human prostate showed weak stromal cell labeling and cytoplasmic skeletal muscle staining. Lung staining was found in cartilage and some bronchial smooth muscle cells, with certain cells staining more strongly than others. The medulla of the adrenal gland showed strong positive staining.

Human liver, spleen, and small intestines exhibited a non-specific pattern of immunoreactivity. Human aorta showed immunoreactivity with 7234 sera in the vessel wall that was primarily located in the tunica intima (lumenal muscle layer) and tunica media (intermediate muscle layer). Thoracic aorta, pulmonary artery, and renal antery each showed similar staining patterns. When compared with staining with an antibody to smooth muscle α-actin (an accepted marker for smooth muscle cells), lectomedin-1 immunoreactivity was found primarily in the same cells (i.e., smooth muscle cells).

Staining in rat tissues with 7234 sera demonstrated similar patterns as observed in human tissues. In brain, some neuronal populations and the smooth muscle of the vasculature were stained. In the heart, disks, cardiomyocytes, and vascular smooth muscle all showed immunoreactivity.

While the present invention has been described in terms of specific embodiments, it is understood that variations and modifications will occur to those skilled in the art. Accordingly, only such limitations as appear in the appended claims should be placed on the invention.

What is claimed is:

1. A polynuclcotidc encoding a lectomedin polypeptide, said polypeptide characterized by the ability to bind one or more lectomedin ligands Mac-2 (galectin 3), fibrinogen γ A, and immunoglobulin mu chain constant region, said polypeptide selected from the group consisting of:

(a) a mature lectomedin polypeptide encoded by SEQ ID NO: 1; and (b) a polypeptide comprising of the amino acid sequence set out in SEQ ID NO:2.

2. The polynucleotide according to claim 1 comprising the sequence set forth in SEQ ID NO: 1.

3. The polynucleotide according to claim 1 comprising the sequence set forth in SEQ ID NO: 3.

4. The polynucleotide according to claim 1 comprising the sequence set forth in SEQ ID NO: 5.

5. A polynucleotide encoding a human lectomedin polypeptide, comprising extracellular lectin-binding, olfactomedin-like, and mucin-like domains, said polypeptide characterized by the ability to bind one or more lectomedin ligands Mac-2 (galeclin-3), fibrinogen γA, and immunoglobulin mu chain constant region, wherein said polynucleotide is selected from the group consisting of:

(a) the polynucleotide according to claim 1; and (b) a DNA which hybridizes under highly stringent conditions to the non-coding strand of the polynucleotide of (a), said conditions including a final wash in 1×SSC at 65° C. for 1 hour.

6. The polynucleotide of claim 5 which is a DNA molecule.

7. The DNA of claim 6 which is a cDNA molecule.

8. A fully complementary polynucleotide which specifically hybridizes with the polynucleotide of claim 6.

9. A expression construct comprising the polynucleotide according to claim 5.

10. A host cell transformed or transfected with the polynucleotide according to claim 9.

11. The polynucleotide according to claim 5 operably linked to a heterologous promoter.

12. A host cell comprising the polynucleotide according to claim 11.

13. A method for producing a human lectomedin polypeptide comprising the steps of a) growing the host cell according to claim 10 or 12 under conditions appropriate for expression of the lectomedin polypeptide and b) isolating the lectomedin polypeptide from the host cell or the medium of its growth.

* * * * *

UNITED STATES PATENT AND TRADEMARK OFFICE
CERTIFICATE OF CORRECTION

PATENT NO.   : 6,479,256 B1
DATED        : November 12, 2002
INVENTOR(S)  : Joel S. Hayflick It is certified that error appears in the above-identified patent and that said Letters Patent is hereby corrected as shown below:

Column 1,
Line 47, please delete "integlins" and insert -- integrins --.
Line 50, please delete "D'Souza, et al." and insert -- D'Souza et al. --.

Column 2,
Line 2, please delete "Davletov, etal." and insert -- Davletov, et al. --.

Column 6,
Line 50, please delete "conditions are include" and insert -- conditions include --.
Line 65, please delete "9.47 to 9.5 1" and insert -- 9.47 to 9.51 --.

Column 22,
Line 18, please delete "canonical 3 exon" and insert -- canonical 3'exon --.

Column 23,
Line 10, please insert a -- ® -- between "Cloning kit".

Column 26,
Line 47, please delete "pB SKS" and insert -- pBSKS --.
Line 49, please delete "pBSKSlectolalphaEcoRI/Apal#6" and insert
-- pBSKSlecto I alphaEcoRI/Apal#6 --.

Column 27,
Line 41, please delete "pBSKSlectollalphaEcoRI/Apal#6" and insert
-- pBSKSlecto I alphaEcoRI/Apal#6 --.

UNITED STATES PATENT AND TRADEMARK OFFICE
CERTIFICATE OF CORRECTION

PATENT NO. : 6,479,256 B1
DATED : November 12, 2002
INVENTOR(S) : Joel S. Hayflick It is certified that error appears in the above-identified patent and that said Letters Patent is hereby corrected as shown below:

Column 31,
Line 21, please delete "BstM fragment" and insert -- BstXI fragment --.

Column 32,
Line 21, please delete "WI-I 1936" and insert -- WI-1936 --.

Column 36,
Line 12, please delete "thymocytes/mil." and insert -- thymocytes/ml --.
Line 26, please delete "Immulon 4 plates" and insert -- Immulon® 4 plates --.

Column 192,
Line 66, please delete "A expression" and insert -- An expressopm --.

Signed and Sealed this

First Day of June, 2004

JON W. DUDAS
*Acting Director of the United States Patent and Trademark Office*

SEQUENCE LISTING

<160> NUMBER OF SEQ ID NOS: 64

<210> SEQ ID NO 1
<211> LENGTH: 5597
<212> TYPE: DNA
<213> ORGANISM: Homo sapiens
<220> FEATURE:
<221> NAME/KEY: CDS
<222> LOCATION: (217)..(3747)

<400> SEQUENCE: 1

```
cggcgaacag acgttctttc tcctccatgc agttacacaa aaggagggct acggaaacta         60
aaagtttcgg ggcctctggc tcggtgtgtg gagaaaagag aaaacctgga gacgggatat        120
gaagatcaat gatgcagact gatggtcttg atgaagctgg gcatttataa ctagattcat        180
taaggaatac aaagaaaata cttaaaggga tcaata atg gtg tct tct ggt tgc         234
                                         Met Val Ser Ser Gly Cys
                                           1               5 aga atg cga agt ctg tgg ttt atc att gta atc agc ttc tta cca aat         282
Arg Met Arg Ser Leu Trp Phe Ile Ile Val Ile Ser Phe Leu Pro Asn
         10                  15                  20 aca gaa ggt ttc agc aga gca gct tta cca ttt ggg ctg gtg agg cga         330
Thr Glu Gly Phe Ser Arg Ala Ala Leu Pro Phe Gly Leu Val Arg Arg
```

-continued

```
             25                  30                  35
gaa tta tcc tgt gaa ggt tat tct ata gat ctg cga tgc ccg ggc agt      378
Glu Leu Ser Cys Glu Gly Tyr Ser Ile Asp Leu Arg Cys Pro Gly Ser
         40                  45                  50 gat gtc atc atg att gag agc gct aac tat ggt cgg acg gat gac aag      426
Asp Val Ile Met Ile Glu Ser Ala Asn Tyr Gly Arg Thr Asp Asp Lys
 55                  60                  65                  70 att tgt gat gct gac cca ttt cag atg gag aat aca gac tgc tac ctc      474
Ile Cys Asp Ala Asp Pro Phe Gln Met Glu Asn Thr Asp Cys Tyr Leu
                 75                  80                  85 ccc gat gcc ttc aaa att atg act caa agg tgc aac aat cga aca cag      522
Pro Asp Ala Phe Lys Ile Met Thr Gln Arg Cys Asn Asn Arg Thr Gln
             90                  95                 100 tgt ata gta gtt act ggg tca gat gtg ttt cct gat cca tgt cct gga      570
Cys Ile Val Val Thr Gly Ser Asp Val Phe Pro Asp Pro Cys Pro Gly
        105                 110                 115 aca tac aaa tac ctt gaa gtc caa tat gaa tgt gtc cct tac att ttt      618
Thr Tyr Lys Tyr Leu Glu Val Gln Tyr Glu Cys Val Pro Tyr Ile Phe
    120                 125                 130 gtg tgt cct ggg acc ttg aaa gca att gtg gac tca cca tgt ata tat      666
Val Cys Pro Gly Thr Leu Lys Ala Ile Val Asp Ser Pro Cys Ile Tyr
135                 140                 145                 150 gaa gct gaa caa aag gcg ggt gct tgg tgc aag gac cct ctt cag gct      714
Glu Ala Glu Gln Lys Ala Gly Ala Trp Cys Lys Asp Pro Leu Gln Ala
                155                 160                 165 gca gat aaa att tat ttc atg ccc tgg act ccc tat cgt acc gat act      762
Ala Asp Lys Ile Tyr Phe Met Pro Trp Thr Pro Tyr Arg Thr Asp Thr
            170                 175                 180 tta ata gaa tat gct tct tta gaa gat ttc caa aat agt cgc caa aca      810
Leu Ile Glu Tyr Ala Ser Leu Glu Asp Phe Gln Asn Ser Arg Gln Thr
        185                 190                 195 aca aca tat aaa ctt cca aat cga gta gat ggt act gga ttt gtg gtg      858
Thr Thr Tyr Lys Leu Pro Asn Arg Val Asp Gly Thr Gly Phe Val Val
    200                 205                 210 tat gat ggt gct gtc ttc ttt aac aaa gaa aga acg agg aat att gtg      906
Tyr Asp Gly Ala Val Phe Phe Asn Lys Glu Arg Thr Arg Asn Ile Val
215                 220                 225                 230 aaa ttt gac ttg agg act aga att aag agt ggc gag gcc ata att aac      954
Lys Phe Asp Leu Arg Thr Arg Ile Lys Ser Gly Glu Ala Ile Ile Asn
                235                 240                 245 tat gcc aac tac cat gat acc tca cca tac aga tgg gga gga aag act     1002
Tyr Ala Asn Tyr His Asp Thr Ser Pro Tyr Arg Trp Gly Gly Lys Thr
            250                 255                 260 gat atc gac cta gca gtt gat gaa aat ggt tta tgg gtc att tac gcc     1050
Asp Ile Asp Leu Ala Val Asp Glu Asn Gly Leu Trp Val Ile Tyr Ala
        265                 270                 275 act gaa cag aac aat gga atg ata gtt att agc cag ctg aat cca tac     1098
Thr Glu Gln Asn Asn Gly Met Ile Val Ile Ser Gln Leu Asn Pro Tyr
    280                 285                 290 act ctt cga ttt gaa gca acg tgg gag act gta tac gac aaa cgt gcc     1146
Thr Leu Arg Phe Glu Ala Thr Trp Glu Thr Val Tyr Asp Lys Arg Ala
295                 300                 305                 310 gca tca aat gct ttt atg ata tgc gga gtc ctc tat gtg gtt agg tca     1194
Ala Ser Asn Ala Phe Met Ile Cys Gly Val Leu Tyr Val Val Arg Ser
                315                 320                 325 gtt tat caa gac aat gaa agt gaa aca ggc aag aac tca att gat tac     1242
Val Tyr Gln Asp Asn Glu Ser Glu Thr Gly Lys Asn Ser Ile Asp Tyr
            330                 335                 340 att tat aat acc cga tta aac cga gga gaa tat gta gac gtt ccc ttc     1290
```

-continued

```
Ile Tyr Asn Thr Arg Leu Asn Arg Gly Glu Tyr Val Asp Val Pro Phe
            345                 350                 355 ccc aac cag tat cag tat att gct gca gtg gat tac aat cca aga gat      1338
Pro Asn Gln Tyr Gln Tyr Ile Ala Ala Val Asp Tyr Asn Pro Arg Asp
    360                 365                 370 aac caa ctt tac gtg tgg aac aat aac ttc att tta cga tat tct ctg      1386
Asn Gln Leu Tyr Val Trp Asn Asn Asn Phe Ile Leu Arg Tyr Ser Leu
375                 380                 385                 390 gag ttt ggt cca cct gat cct gcc caa gtg cct acc aca gct gtg aca      1434
Glu Phe Gly Pro Pro Asp Pro Ala Gln Val Pro Thr Thr Ala Val Thr
                395                 400                 405 ata act tct tca gct gag ctg ttc aaa acc ata ata tca acc aca agc      1482
Ile Thr Ser Ser Ala Glu Leu Phe Lys Thr Ile Ile Ser Thr Thr Ser
            410                 415                 420 act act tca cag aaa ggc ccc atg agc aca act gta gct gga tca cag      1530
Thr Thr Ser Gln Lys Gly Pro Met Ser Thr Thr Val Ala Gly Ser Gln
        425                 430                 435 gaa gga agc aaa ggg aca aaa cca cct cca gca gtt tct aca acc aaa      1578
Glu Gly Ser Lys Gly Thr Lys Pro Pro Pro Ala Val Ser Thr Thr Lys
    440                 445                 450 att cca cct ata aca aat att ttt ccc ctg cca gag aga ttc tgt gaa      1626
Ile Pro Pro Ile Thr Asn Ile Phe Pro Leu Pro Glu Arg Phe Cys Glu
455                 460                 465                 470 gca tta gac tcc aag ggg ata aag tgg cct cag aca caa agg gga atg      1674
Ala Leu Asp Ser Lys Gly Ile Lys Trp Pro Gln Thr Gln Arg Gly Met
                475                 480                 485 atg gtt gaa cga cca tgc cct aag gga aca aga gga act gcc tca tat      1722
Met Val Glu Arg Pro Cys Pro Lys Gly Thr Arg Gly Thr Ala Ser Tyr
            490                 495                 500 ctc tgc atg att tcc act gga aca tgg aac cct aag ggc ccc gat ctt      1770
Leu Cys Met Ile Ser Thr Gly Thr Trp Asn Pro Lys Gly Pro Asp Leu
        505                 510                 515 agc aac tgt acc tca cac tgg gtg aat cag ctg gct cag aag atc aga      1818
Ser Asn Cys Thr Ser His Trp Val Asn Gln Leu Ala Gln Lys Ile Arg
    520                 525                 530 agc gga gaa aat gct gct agt ctt gcc aat gaa ctg gct aaa cat acc      1866
Ser Gly Glu Asn Ala Ala Ser Leu Ala Asn Glu Leu Ala Lys His Thr
535                 540                 545                 550 aaa ggg cca gtg ttt gct ggg gat gta agt tct tca gtg aga ttg atg      1914
Lys Gly Pro Val Phe Ala Gly Asp Val Ser Ser Ser Val Arg Leu Met
                555                 560                 565 gag cag ttg gtg gac atc ctt gat gca cag ctg cag gaa ctg aaa cct      1962
Glu Gln Leu Val Asp Ile Leu Asp Ala Gln Leu Gln Glu Leu Lys Pro
            570                 575                 580 agt gaa aaa gat tca gct gga cgg agt tat aac aag gca att gtt gac      2010
Ser Glu Lys Asp Ser Ala Gly Arg Ser Tyr Asn Lys Ala Ile Val Asp
        585                 590                 595 aca gtg gac aac ctt ctg aga cct gaa gct ttg gaa tca tgg aaa cat      2058
Thr Val Asp Asn Leu Leu Arg Pro Glu Ala Leu Glu Ser Trp Lys His
    600                 605                 610 atg aat tct tct gaa caa gca cat act gca aca atg tta ctc gat aca      2106
Met Asn Ser Ser Glu Gln Ala His Thr Ala Thr Met Leu Leu Asp Thr
615                 620                 625                 630 ttg gaa gaa gga gct ttt gtc cta gct gac aat ctt tta gaa cca aca      2154
Leu Glu Glu Gly Ala Phe Val Leu Ala Asp Asn Leu Leu Glu Pro Thr
                635                 640                 645 agg gtc tca atg ccc aca gaa aat att gtc ctg gaa gtt gcc gta ctc      2202
Arg Val Ser Met Pro Thr Glu Asn Ile Val Leu Glu Val Ala Val Leu
            650                 655                 660
```

-continued

```
agt aca gaa gga cag atc caa gac ttt aaa ttt cct ctg ggc atc aaa    2250
Ser Thr Glu Gly Gln Ile Gln Asp Phe Lys Phe Pro Leu Gly Ile Lys
        665                 670                 675 gga gca ggc agc tca atc caa ctg tcc gca aat acc gtc aaa cag aac    2298
Gly Ala Gly Ser Ser Ile Gln Leu Ser Ala Asn Thr Val Lys Gln Asn
680                 685                 690 agc agg aat ggg ctt gca aag ttg gtg ttc atc att tac cgg agc ctg    2346
Ser Arg Asn Gly Leu Ala Lys Leu Val Phe Ile Ile Tyr Arg Ser Leu
695                 700                 705                 710 gga cag ttc ctt agt aca gaa aat gca acc att aaa ctg ggt gct gat    2394
Gly Gln Phe Leu Ser Thr Glu Asn Ala Thr Ile Lys Leu Gly Ala Asp
            715                 720                 725 ttt att ggt cgt aat agc acc att gca gtg aac tct cac gtc att tca    2442
Phe Ile Gly Arg Asn Ser Thr Ile Ala Val Asn Ser His Val Ile Ser
        730                 735                 740 gtt tca atc aat aaa gag tcc agc cga gta tac ctg act gat cct gtg    2490
Val Ser Ile Asn Lys Glu Ser Ser Arg Val Tyr Leu Thr Asp Pro Val
    745                 750                 755 ctt ttt acc ctg cca cac att gat cct gac aat tat ttc aat gca aac    2538
Leu Phe Thr Leu Pro His Ile Asp Pro Asp Asn Tyr Phe Asn Ala Asn
760                 765                 770 tgc tcc ttc tgg aac tac tca gag aga act atg atg gga tat tgg tct    2586
Cys Ser Phe Trp Asn Tyr Ser Glu Arg Thr Met Met Gly Tyr Trp Ser
775                 780                 785                 790 acc cag ggc tgc aag ctg gtt gac act aat aaa act cga aca acg tgt    2634
Thr Gln Gly Cys Lys Leu Val Asp Thr Asn Lys Thr Arg Thr Thr Cys
            795                 800                 805 gca tgc agc cac cta acc aat ttt gca att ctc atg gcc cac agg gaa    2682
Ala Cys Ser His Leu Thr Asn Phe Ala Ile Leu Met Ala His Arg Glu
        810                 815                 820 att gca tat aaa gat ggc gtt cat gaa tta ctt ctt aca gtc atc acc    2730
Ile Ala Tyr Lys Asp Gly Val His Glu Leu Leu Leu Thr Val Ile Thr
    825                 830                 835 tgg gtg gga att gtc att tcc ctt gtt tgc ctg gct atc tgc atc ttc    2778
Trp Val Gly Ile Val Ile Ser Leu Val Cys Leu Ala Ile Cys Ile Phe
840                 845                 850 acc ttc tgc ttt ttc cgt ggc cta cag agt gac cga aat act att cac    2826
Thr Phe Cys Phe Phe Arg Gly Leu Gln Ser Asp Arg Asn Thr Ile His
855                 860                 865                 870 aag aac ctt tgt atc aac ctt ttc att gct gaa ttt att ttc cta ata    2874
Lys Asn Leu Cys Ile Asn Leu Phe Ile Ala Glu Phe Ile Phe Leu Ile
            875                 880                 885 ggc att gat aag aca aaa tat gcg att gca tgc cca ata ttt gca gga    2922
Gly Ile Asp Lys Thr Lys Tyr Ala Ile Ala Cys Pro Ile Phe Ala Gly
        890                 895                 900 ctt cta cac ttt ttc ttt ttg gca gct ttt gct tgg atg tgc cta gaa    2970
Leu Leu His Phe Phe Phe Leu Ala Ala Phe Ala Trp Met Cys Leu Glu
    905                 910                 915 ggt gtg cag ctc tac cta atg tta gtt gaa gtt ttt gaa agt gaa tat    3018
Gly Val Gln Leu Tyr Leu Met Leu Val Glu Val Phe Glu Ser Glu Tyr
920                 925                 930 tca agg aaa aaa tat tac tat gtt gct ggt tac ttg ttt cct gcc aca    3066
Ser Arg Lys Lys Tyr Tyr Tyr Val Ala Gly Tyr Leu Phe Pro Ala Thr
935                 940                 945                 950 gtg gtt gga gtt tca gct gct att gac tat aag agc tat gga aca gaa    3114
Val Val Gly Val Ser Ala Ala Ile Asp Tyr Lys Ser Tyr Gly Thr Glu
            955                 960                 965 aaa gct tgc tgg ctt cat gtt gat aac tac ttt ata tgg agc ttc att    3162
Lys Ala Cys Trp Leu His Val Asp Asn Tyr Phe Ile Trp Ser Phe Ile
        970                 975                 980
```

```
                                                                -continued gga cct gtt acc ttc att att ctg cta aat att atc ttc ttg gtg atc    3210
Gly Pro Val Thr Phe Ile Ile Leu Leu Asn Ile Ile Phe Leu Val Ile
            985                 990                 995 aca ttg tgc aaa atg gtg aag cat tca aac act ttg aaa cca gat tct    3258
Thr Leu Cys Lys Met Val Lys His Ser Asn Thr Leu Lys Pro Asp Ser
    1000                1005                1010 agc agg ttg gaa aac att aag tct tgg gtg ctt ggc gct ttc gct ctt    3306
Ser Arg Leu Glu Asn Ile Lys Ser Trp Val Leu Gly Ala Phe Ala Leu
1015                1020                1025                1030 ctg tgt ctt ctt ggc ctc acc tgg tcc ttt ggg ttg ctt ttt att aat    3354
Leu Cys Leu Leu Gly Leu Thr Trp Ser Phe Gly Leu Leu Phe Ile Asn
                1035                1040                1045 gag gag act att gtg atg gca tat ctc ttc act ata ttt aat gct ttc    3402
Glu Glu Thr Ile Val Met Ala Tyr Leu Phe Thr Ile Phe Asn Ala Phe
            1050                1055                1060 cag gga gtg ttc att ttc atc ttt cac tgt gct ctc caa aag aaa gta    3450
Gln Gly Val Phe Ile Phe Ile Phe His Cys Ala Leu Gln Lys Lys Val
        1065                1070                1075 cga aaa gaa tat ggc aag tgc ttc aga cac tca tac tgc tgt gga ggc    3498
Arg Lys Glu Tyr Gly Lys Cys Phe Arg His Ser Tyr Cys Cys Gly Gly
    1080                1085                1090 ctc cca act gag agt ccc cac agt tca gtg aag gca tca acc acc aga    3546
Leu Pro Thr Glu Ser Pro His Ser Ser Val Lys Ala Ser Thr Thr Arg
1095                1100                1105                1110 acc agt gct cgc tat tcc tct ggc aca cag agt cgt ata aga aga atg    3594
Thr Ser Ala Arg Tyr Ser Ser Gly Thr Gln Ser Arg Ile Arg Arg Met
                1115                1120                1125 tgg aat gat act gtg aga aaa caa tca gaa tct tct ttt atc tca ggt    3642
Trp Asn Asp Thr Val Arg Lys Gln Ser Glu Ser Ser Phe Ile Ser Gly
            1130                1135                1140 gac atc aat agc act tca aca ctt aat caa gga ctg aca tca cat ggt    3690
Asp Ile Asn Ser Thr Ser Thr Leu Asn Gln Gly Leu Thr Ser His Gly
        1145                1150                1155 ctg aga gcc cat ctt caa gat tta tat cat tta gag cta ctc tta ggc    3738
Leu Arg Ala His Leu Gln Asp Leu Tyr His Leu Glu Leu Leu Leu Gly
    1160                1165                1170 cag ata gcc tgagcagaca gacatgatgt gagttgtcca aagacattca            3787
Gln Ile Ala
1175 ctgaacaatg ccagggatac aagtgccatg gatactctac cgctaaatgg taatttaac   3847 aacagctact cgctgcacaa gggtgactat aatgacagcg tgcaagttgt ggactgtgga  3907 ctaagtctga atgatactgc ttttgagaaa atgatcattt cagaattagt gcacaacaac  3967 ttacggggca gcagcaagac tcacaacctc gagctcacgc taccagtcaa acctgtgatt  4027 ggaggtagca gcagtgaaga tgatgctatt gtggcagatg cttcatcttt aatgcacagc  4087 gacaacccag ggctggagct ccatcacaaa gaactcgagg caccacttat tcctcagcgg  4147 actcactccc ttctgtacca accccagaag aaagtgaagt ccgagggaac tgacagctat  4207 gtctcccaac tgcagcagaa ggctgaagat cacctacagt cccccaacag agactctctt  4267 tatacaagca tgcccaatct tagagactct ccctatccgg agagcagccc tgacatggaa  4327 gaagacctct ctccctccag gaggagtgag aatgaggaca tttactataa aagcatgcca  4387 aatcttggag ctggccatca gcttcagatg tgctaccaga tcagcagggg caatagtgat  4447 ggttatataa tccccattaa caagaagggg tgtattccag aaggagatgt tagagaagga  4507 caaatgcagc tggttacaag tctttaatca tacagctaag gaattccaag ggccacatgc  4567
```

-continued

```
gagtattaat aaataaagac accattggcc tgacgcagct ccctcaaact ctgcttgaag    4627
agatgactct tgacctgtgg ttctctggtg taaaaaagat gactgaacct tgcagttctg    4687
tgaattttta taaacatac aaaaactttg tatatacaca gagtatacta aagtgaatta    4747
tttgttacaa agaaaagaga tgccagccag gtattttaag attctgctgc tgtttagaga    4807
aattgtgaaa caagcaaaac aaaacttttcc agccattta ctgcagcagt ctgtgaacta    4867
aatttgtaaa tatggctgca ccatttttgt aggcctgcat tgtattatat acaagacgta    4927
ggctttaaaa tcctgtggga caaatttact gtaccttact attcctgaca agacttggaa    4987
aagcaggaga gatattctgc atcagtttgc agttcactgc aaatctttta cattaaggca    5047
aagattgaaa acatgcttaa ccactagcaa tcaagccaca ggccttatt catatgtttc    5107 ctcaactgta caatgaacta ttctcatgaa aaatggctaa agaaattata ttttgttcta    5167
ttgctagggt aaaataaata catttgtgtc caactgaaat ataattgtca ttaaaataat    5227
tttaaagagt gaagaaaata ttgtgaaaag ctcttggttg cacatgttat gaaatgtttt    5287
ttcttacact ttgtcatggt aagttctact cattttcact tctttccac tgtatacagt    5347 gttctgcttt gacaaagtta gtctttatta cttacattta aatttcttat tgccaaaaga    5407
acgtgtttta tggggagaaa caaactcttt gaagccagtt atgtcatgcc ttgcacaaaa    5467
gtgatgaaat ctagaaaaga ttgtgtgtca cccctgttta ttcttgaaca gagggcaaag    5527
agggcactgg gcacttctca caaactttct agtgaacaaa aggtgcctat tctttttaa    5587 aaaaaaaaaa                                                          5597
```

<210> SEQ ID NO 2
<211> LENGTH: 1177
<212> TYPE: PRT
<213> ORGANISM: Homo sapiens

<400> SEQUENCE: 2

```
Met Val Ser Ser Gly Cys Arg Met Arg Ser Leu Trp Phe Ile Ile Val
  1               5                  10                  15

Ile Ser Phe Leu Pro Asn Thr Glu Gly Phe Ser Arg Ala Ala Leu Pro
             20                  25                  30

Phe Gly Leu Val Arg Arg Glu Leu Ser Cys Glu Gly Tyr Ser Ile Asp
         35                  40                  45

Leu Arg Cys Pro Gly Ser Asp Val Ile Met Ile Glu Ser Ala Asn Tyr
     50                  55                  60

Gly Arg Thr Asp Asp Lys Ile Cys Asp Ala Asp Pro Phe Gln Met Glu
 65                  70                  75                  80

Asn Thr Asp Cys Tyr Leu Pro Asp Ala Phe Lys Ile Met Thr Gln Arg
                 85                  90                  95

Cys Asn Asn Arg Thr Gln Cys Ile Val Val Thr Gly Ser Asp Val Phe
            100                 105                 110

Pro Asp Pro Cys Pro Gly Thr Tyr Lys Tyr Leu Glu Val Gln Tyr Glu
        115                 120                 125

Cys Val Pro Tyr Ile Phe Val Cys Pro Gly Thr Leu Lys Ala Ile Val
    130                 135                 140

Asp Ser Pro Cys Ile Tyr Glu Ala Glu Gln Lys Ala Gly Ala Trp Cys
145                 150                 155                 160

Lys Asp Pro Leu Gln Ala Ala Asp Lys Ile Tyr Phe Met Pro Trp Thr
                165                 170                 175

Pro Tyr Arg Thr Asp Thr Leu Ile Glu Tyr Ala Ser Leu Glu Asp Phe
            180                 185                 190
```

```
Gln Asn Ser Arg Gln Thr Thr Tyr Lys Leu Pro Asn Arg Val Asp
        195                 200                 205

Gly Thr Gly Phe Val Val Tyr Asp Gly Ala Val Phe Phe Asn Lys Glu
    210                 215                 220

Arg Thr Arg Asn Ile Val Lys Phe Asp Leu Arg Thr Arg Ile Lys Ser
225                 230                 235                 240

Gly Glu Ala Ile Ile Asn Tyr Ala Asn Tyr His Asp Thr Ser Pro Tyr
                245                 250                 255

Arg Trp Gly Gly Lys Thr Asp Ile Asp Leu Ala Val Asp Glu Asn Gly
            260                 265                 270

Leu Trp Val Ile Tyr Ala Thr Glu Gln Asn Asn Gly Met Ile Val Ile
        275                 280                 285

Ser Gln Leu Asn Pro Tyr Thr Leu Arg Phe Glu Ala Thr Trp Glu Thr
    290                 295                 300

Val Tyr Asp Lys Arg Ala Ala Ser Asn Ala Phe Met Ile Cys Gly Val
305                 310                 315                 320

Leu Tyr Val Val Arg Ser Val Tyr Gln Asp Asn Glu Ser Glu Thr Gly
                325                 330                 335

Lys Asn Ser Ile Asp Tyr Ile Tyr Asn Thr Arg Leu Asn Arg Gly Glu
            340                 345                 350

Tyr Val Asp Val Pro Phe Pro Asn Gln Tyr Gln Tyr Ile Ala Ala Val
        355                 360                 365

Asp Tyr Asn Pro Arg Asp Asn Gln Leu Tyr Val Trp Asn Asn Asn Phe
    370                 375                 380

Ile Leu Arg Tyr Ser Leu Glu Phe Gly Pro Pro Asp Pro Ala Gln Val
385                 390                 395                 400

Pro Thr Thr Ala Val Thr Ile Thr Ser Ser Ala Glu Leu Phe Lys Thr
                405                 410                 415

Ile Ile Ser Thr Thr Ser Thr Ser Gln Lys Gly Pro Met Ser Thr
            420                 425                 430

Thr Val Ala Gly Ser Gln Glu Gly Ser Lys Gly Thr Lys Pro Pro Pro
        435                 440                 445

Ala Val Ser Thr Thr Lys Ile Pro Pro Ile Thr Asn Ile Phe Pro Leu
    450                 455                 460

Pro Glu Arg Phe Cys Glu Ala Leu Asp Ser Lys Gly Ile Lys Trp Pro
465                 470                 475                 480

Gln Thr Gln Arg Gly Met Met Val Glu Arg Pro Cys Pro Lys Gly Thr
                485                 490                 495

Arg Gly Thr Ala Ser Tyr Leu Cys Met Ile Ser Thr Gly Thr Trp Asn
            500                 505                 510

Pro Lys Gly Pro Asp Leu Ser Asn Cys Thr Ser His Trp Val Asn Gln
        515                 520                 525

Leu Ala Gln Lys Ile Arg Ser Gly Glu Asn Ala Ala Ser Leu Ala Asn
    530                 535                 540

Glu Leu Ala Lys His Thr Lys Gly Pro Val Phe Ala Gly Asp Val Ser
545                 550                 555                 560

Ser Ser Val Arg Leu Met Glu Gln Leu Val Asp Ile Leu Asp Ala Gln
                565                 570                 575

Leu Gln Glu Leu Lys Pro Ser Glu Lys Asp Ser Ala Gly Arg Ser Tyr
            580                 585                 590

Asn Lys Ala Ile Val Asp Thr Val Asp Asn Leu Leu Arg Pro Glu Ala
        595                 600                 605
```

```
Leu Glu Ser Trp Lys His Met Asn Ser Ser Glu Gln Ala His Thr Ala
    610                 615                 620

Thr Met Leu Leu Asp Thr Leu Glu Glu Gly Ala Phe Val Leu Ala Asp
625                 630                 635                 640

Asn Leu Leu Glu Pro Thr Arg Val Ser Met Pro Thr Glu Asn Ile Val
                645                 650                 655

Leu Glu Val Ala Val Leu Ser Thr Glu Gly Gln Ile Gln Asp Phe Lys
            660                 665                 670

Phe Pro Leu Gly Ile Lys Gly Ala Gly Ser Ser Ile Gln Leu Ser Ala
        675                 680                 685

Asn Thr Val Lys Gln Asn Ser Arg Asn Gly Leu Ala Lys Leu Val Phe
    690                 695                 700

Ile Ile Tyr Arg Ser Leu Gly Gln Phe Leu Ser Thr Glu Asn Ala Thr
705                 710                 715                 720

Ile Lys Leu Gly Ala Asp Phe Ile Gly Arg Asn Ser Thr Ile Ala Val
                725                 730                 735

Asn Ser His Val Ile Ser Val Ser Ile Asn Lys Glu Ser Ser Arg Val
            740                 745                 750

Tyr Leu Thr Asp Pro Val Leu Phe Thr Leu Pro His Ile Asp Pro Asp
        755                 760                 765

Asn Tyr Phe Asn Ala Asn Cys Ser Phe Trp Asn Tyr Ser Glu Arg Thr
    770                 775                 780

Met Met Gly Tyr Trp Ser Thr Gln Gly Cys Lys Leu Val Asp Thr Asn
785                 790                 795                 800

Lys Thr Arg Thr Thr Cys Ala Cys Ser His Leu Thr Asn Phe Ala Ile
                805                 810                 815

Leu Met Ala His Arg Glu Ile Ala Tyr Lys Asp Gly Val His Glu Leu
            820                 825                 830

Leu Leu Thr Val Ile Thr Trp Val Gly Ile Val Ile Ser Leu Val Cys
        835                 840                 845

Leu Ala Ile Cys Ile Phe Thr Phe Cys Phe Phe Arg Gly Leu Gln Ser
    850                 855                 860

Asp Arg Asn Thr Ile His Lys Asn Leu Cys Ile Asn Leu Phe Ile Ala
865                 870                 875                 880

Glu Phe Ile Phe Leu Ile Gly Ile Asp Lys Thr Lys Tyr Ala Ile Ala
                885                 890                 895

Cys Pro Ile Phe Ala Gly Leu Leu His Phe Phe Leu Ala Ala Phe
            900                 905                 910

Ala Trp Met Cys Leu Glu Gly Val Gln Leu Tyr Leu Met Leu Val Glu
        915                 920                 925

Val Phe Glu Ser Glu Tyr Ser Arg Lys Lys Tyr Tyr Tyr Val Ala Gly
    930                 935                 940

Tyr Leu Phe Pro Ala Thr Val Val Gly Val Ser Ala Ala Ile Asp Tyr
945                 950                 955                 960

Lys Ser Tyr Gly Thr Glu Lys Ala Cys Trp Leu His Val Asp Asn Tyr
                965                 970                 975

Phe Ile Trp Ser Phe Ile Gly Pro Val Thr Phe Ile Ile Leu Leu Asn
            980                 985                 990

Ile Ile Phe Leu Val Ile Thr Leu Cys Lys Met Val Lys His Ser Asn
        995                 1000                1005

Thr Leu Lys Pro Asp Ser Ser Arg Leu Glu Asn Ile Lys Ser Trp Val
    1010                1015                1020

Leu Gly Ala Phe Ala Leu Leu Cys Leu Leu Gly Leu Thr Trp Ser Phe
```

```
1025                1030                1035                1040
Gly Leu Leu Phe Ile Asn Glu Glu Thr Ile Val Met Ala Tyr Leu Phe
                1045                1050                1055

Thr Ile Phe Asn Ala Phe Gln Gly Val Phe Ile Phe Ile Phe His Cys
                1060                1065                1070

Ala Leu Gln Lys Lys Val Arg Lys Glu Tyr Gly Lys Cys Phe Arg His
            1075                1080                1085

Ser Tyr Cys Cys Gly Gly Leu Pro Thr Glu Ser Pro His Ser Ser Val
            1090                1095                1100

Lys Ala Ser Thr Thr Arg Thr Ser Ala Arg Tyr Ser Ser Gly Thr Gln
1105                1110                1115                1120

Ser Arg Ile Arg Arg Met Trp Asn Asp Thr Val Arg Lys Gln Ser Glu
                1125                1130                1135

Ser Ser Phe Ile Ser Gly Asp Ile Asn Ser Thr Ser Thr Leu Asn Gln
                1140                1145                1150

Gly Leu Thr Ser His Gly Leu Arg Ala His Leu Gln Asp Leu Tyr His
                1155                1160                1165

Leu Glu Leu Leu Leu Gly Gln Ile Ala
    1170                1175

<210> SEQ ID NO 3
<211> LENGTH: 5617
<212> TYPE: DNA
<213> ORGANISM: Homo sapiens
<220> FEATURE:
<221> NAME/KEY: CDS
<222> LOCATION: (217)..(3585)

<400> SEQUENCE: 3
```

| | |
|---|---|
| cggcgaacag acgttctttc tcctccatgc agttacacaa aaggagggct acggaaacta | 60 |
| aaagtttcgg ggcctctggc tcggtgtgtg gagaaaagag aaaacctgga gacgggatat | 120 |
| gaagatcaat gatgcagact gatggtcttg atgaagctgg gcatttataa ctagattcat | 180 |
| taaggaatac aaagaaaata cttaaaggga tcaata atg gtg tct tct ggt tgc | 234 |

```
                                              Met Val Ser Ser Gly Cys
                                                1               5 aga atg cga agt ctg tgg ttt atc att gta atc agc ttc tta cca aat    282
Arg Met Arg Ser Leu Trp Phe Ile Ile Val Ile Ser Phe Leu Pro Asn
            10                  15                  20 aca gaa ggt ttc agc aga gca gct tta cca ttt ggg ctg gtg agg cga   330
Thr Glu Gly Phe Ser Arg Ala Ala Leu Pro Phe Gly Leu Val Arg Arg
        25                  30                  35 gaa tta tcc tgt gaa ggt tat tct ata gat ctg cga tgc ccg ggc agt   378
Glu Leu Ser Cys Glu Gly Tyr Ser Ile Asp Leu Arg Cys Pro Gly Ser
    40                  45                  50 gat gtc atc atg att gag agc gct aac tat ggt cgg acg gat gac aag   426
Asp Val Ile Met Ile Glu Ser Ala Asn Tyr Gly Arg Thr Asp Asp Lys
55                  60                  65                  70 att tgt gat gct gac cca ttt cag atg gag aat aca gac tgc tac ctc   474
Ile Cys Asp Ala Asp Pro Phe Gln Met Glu Asn Thr Asp Cys Tyr Leu
                75                  80                  85 ccc gat gcc ttc aaa att atg act caa agg tgc aac aat cga aca cag   522
Pro Asp Ala Phe Lys Ile Met Thr Gln Arg Cys Asn Asn Arg Thr Gln
            90                  95                  100 tgt ata gta gtt act ggg tca gat gtg ttt cct gat cca tgt cct gga   570
Cys Ile Val Val Thr Gly Ser Asp Val Phe Pro Asp Pro Cys Pro Gly
        105                 110                 115 aca tac aaa tac ctt gaa gtc caa tat gaa tgt gtc cct tac att ttt   618
```

```
                                                                -continued

Thr Tyr Lys Tyr Leu Glu Val Gln Tyr Glu Cys Val Pro Tyr Ile Phe
    120                 125                 130 gtg tgt cct ggg acc ttg aaa gca att gtg gac tca cca tgt ata tat      666
Val Cys Pro Gly Thr Leu Lys Ala Ile Val Asp Ser Pro Cys Ile Tyr
135                 140                 145                 150 gaa gct gaa caa aag gcg ggt gct tgg tgc aag gac cct ctt cag gct      714
Glu Ala Glu Gln Lys Ala Gly Ala Trp Cys Lys Asp Pro Leu Gln Ala
                155                 160                 165 gca gat aaa att tat ttc atg ccc tgg act ccc tat cgt acc gat act      762
Ala Asp Lys Ile Tyr Phe Met Pro Trp Thr Pro Tyr Arg Thr Asp Thr
            170                 175                 180 tta ata gaa tat gct tct tta gaa gat ttc caa aat agt cgc caa aca      810
Leu Ile Glu Tyr Ala Ser Leu Glu Asp Phe Gln Asn Ser Arg Gln Thr
        185                 190                 195 aca aca tat aaa ctt cca aat cga gta gat ggt act gga ttt gtg gtg      858
Thr Thr Tyr Lys Leu Pro Asn Arg Val Asp Gly Thr Gly Phe Val Val
    200                 205                 210 tat gat ggt gct gtc ttc ttt aac aaa gaa aga acg agg aat att gtg      906
Tyr Asp Gly Ala Val Phe Phe Asn Lys Glu Arg Thr Arg Asn Ile Val
215                 220                 225                 230 aaa ttt gac ttg agg act aga att aag agt ggc gag gcc ata att aac      954
Lys Phe Asp Leu Arg Thr Arg Ile Lys Ser Gly Glu Ala Ile Ile Asn
                235                 240                 245 tat gcc aac tac cat gat acc tca cca tac aga tgg gga gga aag act     1002
Tyr Ala Asn Tyr His Asp Thr Ser Pro Tyr Arg Trp Gly Gly Lys Thr
            250                 255                 260 gat atc gac cta gca gtt gat gaa aat ggt tta tgg gtc att tac gcc     1050
Asp Ile Asp Leu Ala Val Asp Glu Asn Gly Leu Trp Val Ile Tyr Ala
        265                 270                 275 act gaa cag aac aat gga atg ata gtt att agc cag ctg aat cca tac     1098
Thr Glu Gln Asn Asn Gly Met Ile Val Ile Ser Gln Leu Asn Pro Tyr
    280                 285                 290 act ctt cga ttt gaa gca acg tgg gag act gta tac gac aaa cgt gcc     1146
Thr Leu Arg Phe Glu Ala Thr Trp Glu Thr Val Tyr Asp Lys Arg Ala
295                 300                 305                 310 gca tca aat gct ttt atg ata tgc gga gtc ctc tat gtg gtt agg tca     1194
Ala Ser Asn Ala Phe Met Ile Cys Gly Val Leu Tyr Val Val Arg Ser
                315                 320                 325 gtt tat caa gac aat gaa agt gaa aca ggc aag aac tca att gat tac     1242
Val Tyr Gln Asp Asn Glu Ser Glu Thr Gly Lys Asn Ser Ile Asp Tyr
            330                 335                 340 att tat aat acc cga tta aac cga gga gaa tat gta gac gtt ccc ttc     1290
Ile Tyr Asn Thr Arg Leu Asn Arg Gly Glu Tyr Val Asp Val Pro Phe
        345                 350                 355 ccc aac cag tat cag tat att gct gca gtg gat tac aat cca aga gat     1338
Pro Asn Gln Tyr Gln Tyr Ile Ala Ala Val Asp Tyr Asn Pro Arg Asp
    360                 365                 370 aac caa ctt tac gtg tgg aac aat aac ttc att tta cga tat tct ctg     1386
Asn Gln Leu Tyr Val Trp Asn Asn Asn Phe Ile Leu Arg Tyr Ser Leu
375                 380                 385                 390 gag ttt ggt cca cct gat cct gcc caa gtg cct acc aca gct gtg aca     1434
Glu Phe Gly Pro Pro Asp Pro Ala Gln Val Pro Thr Thr Ala Val Thr
                395                 400                 405 ata act tct tca gct gag ctg ttc aaa acc ata ata tca acc aca agc     1482
Ile Thr Ser Ser Ala Glu Leu Phe Lys Thr Ile Ile Ser Thr Thr Ser
            410                 415                 420 act act tca cag aaa ggc ccc atg agc aca act gta gct gga tca cag     1530
Thr Thr Ser Gln Lys Gly Pro Met Ser Thr Thr Val Ala Gly Ser Gln
        425                 430                 435
```

| | | |
|---|---|---|
| gaa gga agc aaa ggg aca aaa cca cct cca gca gtt tct aca acc aaa<br>Glu Gly Ser Lys Gly Thr Lys Pro Pro Pro Ala Val Ser Thr Thr Lys<br>440 445 450 | | 1578 |
| att cca cct ata aca aat att ttt ccc ctg cca gag aga ttc tgt gaa<br>Ile Pro Pro Ile Thr Asn Ile Phe Pro Leu Pro Glu Arg Phe Cys Glu<br>455 460 465 470 | | 1626 |
| gca tta gac tcc aag ggg ata aag tgg cct cag aca caa agg gga atg<br>Ala Leu Asp Ser Lys Gly Ile Lys Trp Pro Gln Thr Gln Arg Gly Met<br>475 480 485 | | 1674 |
| atg gtt gaa cga cca tgc cct aag gga aca aga gga act gcc tca tat<br>Met Val Glu Arg Pro Cys Pro Lys Gly Thr Arg Gly Thr Ala Ser Tyr<br>490 495 500 | | 1722 |
| ctc tgc atg att tcc act gga aca tgg aac cct aag ggc ccc gat ctt<br>Leu Cys Met Ile Ser Thr Gly Thr Trp Asn Pro Lys Gly Pro Asp Leu<br>505 510 515 | | 1770 |
| agc aac tgt acc tca cac tgg gtg aat cag ctg gct cag aag atc aga<br>Ser Asn Cys Thr Ser His Trp Val Asn Gln Leu Ala Gln Lys Ile Arg<br>520 525 530 | | 1818 |
| agc gga gaa aat gct gct agt ctt gcc aat gaa ctg gct aaa cat acc<br>Ser Gly Glu Asn Ala Ala Ser Leu Ala Asn Glu Leu Ala Lys His Thr<br>535 540 545 550 | | 1866 |
| aaa ggg cca gtg ttt gct ggg gat gta agt tct tca gtg aga ttg atg<br>Lys Gly Pro Val Phe Ala Gly Asp Val Ser Ser Ser Val Arg Leu Met<br>555 560 565 | | 1914 |
| gag cag ttg gtg gac atc ctt gat gca cag ctg cag gaa ctg aaa cct<br>Glu Gln Leu Val Asp Ile Leu Asp Ala Gln Leu Gln Glu Leu Lys Pro<br>570 575 580 | | 1962 |
| agt gaa aaa gat tca gct gga cgg agt tat aac aag gca att gtt gac<br>Ser Glu Lys Asp Ser Ala Gly Arg Ser Tyr Asn Lys Ala Ile Val Asp<br>585 590 595 | | 2010 |
| aca gtg gac aac ctt ctg aga cct gaa gct ttg gaa tca tgg aaa cat<br>Thr Val Asp Asn Leu Leu Arg Pro Glu Ala Leu Glu Ser Trp Lys His<br>600 605 610 | | 2058 |
| atg aat tct tct gaa caa gca cat act gca aca atg tta ctc gat aca<br>Met Asn Ser Ser Glu Gln Ala His Thr Ala Thr Met Leu Leu Asp Thr<br>615 620 625 630 | | 2106 |
| ttg gaa gaa gga gct ttt gtc cta gct gac aat ctt tta gaa cca aca<br>Leu Glu Glu Gly Ala Phe Val Leu Ala Asp Asn Leu Leu Glu Pro Thr<br>635 640 645 | | 2154 |
| agg gtc tca atg ccc aca gaa aat att gtc ctg gaa gtt gcc gta ctc<br>Arg Val Ser Met Pro Thr Glu Asn Ile Val Leu Glu Val Ala Val Leu<br>650 655 660 | | 2202 |
| agt aca gaa gga cag atc caa gac ttt aaa ttt cct ctg ggc atc aaa<br>Ser Thr Glu Gly Gln Ile Gln Asp Phe Lys Phe Pro Leu Gly Ile Lys<br>665 670 675 | | 2250 |
| gga gca ggc agc tca atc caa ctg tcc gca aat acc gtc aaa cag aac<br>Gly Ala Gly Ser Ser Ile Gln Leu Ser Ala Asn Thr Val Lys Gln Asn<br>680 685 690 | | 2298 |
| agc agg aat ggg ctt gca aag ttg gtg ttc atc att tac cgg agc ctg<br>Ser Arg Asn Gly Leu Ala Lys Leu Val Phe Ile Ile Tyr Arg Ser Leu<br>695 700 705 710 | | 2346 |
| gga cag ttc ctt agt aca gaa aat gca acc att aaa ctg ggt gct gat<br>Gly Gln Phe Leu Ser Thr Glu Asn Ala Thr Ile Lys Leu Gly Ala Asp<br>715 720 725 | | 2394 |
| ttt att ggt cgt aat agc acc att gca gtg aac tct cac gtc att tca<br>Phe Ile Gly Arg Asn Ser Thr Ile Ala Val Asn Ser His Val Ile Ser<br>730 735 740 | | 2442 |
| gtt tca atc aag aaa gag tcc agc cga gta tac ctg act gat cct gtg<br>Val Ser Ile Lys Lys Glu Ser Ser Arg Val Tyr Leu Thr Asp Pro Val<br>745 750 755 | | 2490 |

```
ctt ttt acc ctg cca cac att gat cct gac aat tat ttc aat gca aac    2538
Leu Phe Thr Leu Pro His Ile Asp Pro Asp Asn Tyr Phe Asn Ala Asn
        760                 765                 770 tgc tcc ttc tgg aac tac tca gag aga act atg atg gga tat tgg tct    2586
Cys Ser Phe Trp Asn Tyr Ser Glu Arg Thr Met Met Gly Tyr Trp Ser
775                 780                 785                 790 acc cag ggc tgc aag ctg gtt gac act aat aaa act cga aca acg tgt    2634
Thr Gln Gly Cys Lys Leu Val Asp Thr Asn Lys Thr Arg Thr Thr Cys
                795                 800                 805 gca tgc agc cac cta acc aat ttt gca att ctc atg gcc cac agg gaa    2682
Ala Cys Ser His Leu Thr Asn Phe Ala Ile Leu Met Ala His Arg Glu
            810                 815                 820 att gca tat aaa gat ggc gtt cat gaa tta ctt ctt aca gtc atc acc    2730
Ile Ala Tyr Lys Asp Gly Val His Glu Leu Leu Leu Thr Val Ile Thr
        825                 830                 835 tgg gtg gga att gtc att tcc ctt gtt tgc ctg gct atc tgc atc ttc    2778
Trp Val Gly Ile Val Ile Ser Leu Val Cys Leu Ala Ile Cys Ile Phe
840                 845                 850 acc ttc tgc ttt ttc cgt ggc cta cag agt gac cga aat act att cac    2826
Thr Phe Cys Phe Phe Arg Gly Leu Gln Ser Asp Arg Asn Thr Ile His
855                 860                 865                 870 aag aac ctt tgt atc aac ctt ttc att gct gaa ttt att ttc cta ata    2874
Lys Asn Leu Cys Ile Asn Leu Phe Ile Ala Glu Phe Ile Phe Leu Ile
                875                 880                 885 ggc att gat aag aca aaa tat gcg att gca tgc cca ata ttt gca gga    2922
Gly Ile Asp Lys Thr Lys Tyr Ala Ile Ala Cys Pro Ile Phe Ala Gly
            890                 895                 900 ctt cta cac ttt ttc ttt ttg gca gct ttt gct tgg atg tgc cta gaa    2970
Leu Leu His Phe Phe Phe Leu Ala Ala Phe Ala Trp Met Cys Leu Glu
        905                 910                 915 ggt gtg cag ctc tac cta atg tta gtt gaa gtt ttt gaa agt gaa tat    3018
Gly Val Gln Leu Tyr Leu Met Leu Val Glu Val Phe Glu Ser Glu Tyr
920                 925                 930 tca agg aaa aaa tat tac tat gtt gct ggt tac ttg ttt cct gcc aca    3066
Ser Arg Lys Lys Tyr Tyr Tyr Val Ala Gly Tyr Leu Phe Pro Ala Thr
935                 940                 945                 950 gtg gtt gga gtt tca gct gct att gac tat aag agc tat gga aca gaa    3114
Val Val Gly Val Ser Ala Ala Ile Asp Tyr Lys Ser Tyr Gly Thr Glu
                955                 960                 965 aaa gct tgc tgg ctt cat gtt gat aac tac ttt ata tgg agc ttc att    3162
Lys Ala Cys Trp Leu His Val Asp Asn Tyr Phe Ile Trp Ser Phe Ile
            970                 975                 980 gga cct gtt acc ttc att att ctg cta aat att atc ttc ttg gtg atc    3210
Gly Pro Val Thr Phe Ile Ile Leu Leu Asn Ile Ile Phe Leu Val Ile
        985                 990                 995 aca ttg tgc aaa atg gtg aag cat tca aac act ttg aaa cca gat tct    3258
Thr Leu Cys Lys Met Val Lys His Ser Asn Thr Leu Lys Pro Asp Ser
    1000                1005                1010 agc agg ttg gaa aac att aag tct tgg gtg ctt ggc gct ttc gct ctt    3306
Ser Arg Leu Glu Asn Ile Lys Ser Trp Val Leu Gly Ala Phe Ala Leu
1015                1020                1025                1030 ctg tgt ctt ctt ggc ctc acc tgg tcc ttt ggg ttg ctt ttt att aat    3354
Leu Cys Leu Leu Gly Leu Thr Trp Ser Phe Gly Leu Leu Phe Ile Asn
                1035                1040                1045 gag gag act att gtg atg gca tat ctc ttc act ata ttt aat gct ttc    3402
Glu Glu Thr Ile Val Met Ala Tyr Leu Phe Thr Ile Phe Asn Ala Phe
            1050                1055                1060 cag gga gtg ttc att ttc atc ttt cac tgt gct ctc caa aag aaa gta    3450
Gln Gly Val Phe Ile Phe Ile Phe His Cys Ala Leu Gln Lys Lys Val
```

```
                1065              1070              1075
cga aaa gaa tat ggc aag tgc ttc aga cac tca tac tgc tgt gga ggc    3498
Arg Lys Glu Tyr Gly Lys Cys Phe Arg His Ser Tyr Cys Cys Gly Gly
   1080              1085              1090 ctc cca act gag agt ccc cac agt tca gtg aag gca tca acc acc aga    3546
Leu Pro Thr Glu Ser Pro His Ser Ser Val Lys Ala Ser Thr Thr Arg
 1095              1100              1105              1110 acc agt gct cgc tat tcc tct ggc aca cag gac att cac tgaacaatgc     3595
Thr Ser Ala Arg Tyr Ser Ser Gly Thr Gln Asp Ile His
             1115              1120 cagggataca agtgccatgg atactctacc gctaaatggt aattttaaca acagctactc   3655
gctgcacaag ggtgactata atgacagcgt gcaagttgtg gactgtggac taagtctgaa   3715
tgatactgct tttgagaaaa tgatcatttc agaattagtg cacaacaact tacggggcag   3775
cagcaagact cacaacctcg agctcacgct accagtcaaa cctgtgattg gaggtagcag   3835
cagtgaagat gatgctattg tggcagatgc ttcatcttta atgcacagcg acaacccagg   3895
gctggagctc catcacaaag aactcgaggc accacttatt cctcagcgga ctcactccct   3955
tctgtaccaa ccccagaaga aagtgaagtc cgagggaact gacagctatg tctcccaact   4015
gacagcagag gctgaagatc acctacagtc ccccaacaga gactctcttt atacaagcat   4075
gcccaatctt agagactctc cctatccgga gagcagccct gacatggaag aagacctctc   4135
tccctccagg aggagtgaga atgaggacat ttactataaa agcatgccaa atcttggagc   4195
tggccatcag cttcagatgt gctaccagat cagcaggggc aatagtgatg ttatatataat  4255 ccccattaac aaagaagggt gtattccaga aggagatgtt agagaaggac aaatgcagct   4315
ggttacaagt ctttaatcat acagctaagg aattccaagg ccacatgcg agtattaata    4375 aataaagaca ccattggcct gacgcagctc cctcaaactc tgcttgaaga gatgactctt   4435
gacctgtggt tctctggtgt aaaaaagatg actgaacctt gcagttctgt gaatttttat   4495
aaaacataca aaactttgt atatacacag agtatactaa agtgaattat tgttacaaa    4555 gaaaagagat gccagccagg tattttaaga ttctgctgct gtttagagaa attgtgaaac   4615
aagcaaaaca aaactttcca gccatttac tgcagcagtc tgtgaactaa atttgtaaat    4675
atggctgcac cattttgta ggcctgcatt gtattatata caagacgtag gctttaaaat    4735
cctgtgggac aaatttactg taccttacta ttcctgacaa gacttggaaa gcaggagag    4795 atattctgca tcagttttgca gttcactgca aatcttttac attaaggcaa agattgaaaa   4855
catgcttaac cactagcaat caagccacag gccttatttc atatgtttcc tcaactgtac   4915
aatgaactat tctcatgaaa aatggctaaa gaaattatat tttgttctat tgctagggta   4975
aaataaatac atttgtgtcc aactgaaata taattgtcat taaaataatt ttaaagagtg   5035
aagaaaatat tgtgaaaagc tcttggttgc acatgttatg aaatgttttt tcttacactt   5095
tgtcatggta agttctactc atttttcactt cttttccact gtatacagtg ttctgctttg   5155
acaaagttag tctttattac ttacatttaa atttcttatt gccaaaagaa cgtgtttttat  5215 ggggagaaac aaactctttg aagccagtta tgtcatgcct tgcacaaaag tgatgaaatc   5275
tagaaaagat tgtgtgtcac ccctgtttat tcttgaacag agggcaaaga gggcactggg   5335
cacttctcac aaactttcta gtgaacaaaa ggtgcctatt ctttttttaaa aaaataaaat   5395 aaaacataaa tattactctt ccatattcct tctgcctata tttagtaatt aatttatttt   5455
atgataaagt tctaatgaaa tgtaaattgt ttcagcaaaa ttctgctttt ttttcatccc   5515
tttgtgtaaa cctgttaata atgagcccat cactaatatc cagtgtaaag tttaacacgg   5575
```
tttgacagta ataaatgtg aatttttca aaaaaaaaaa aa    5617

<210> SEQ ID NO 4
<211> LENGTH: 1123
<212> TYPE: PRT
<213> ORGANISM: Homo sapiens

<400> SEQUENCE: 4

Met Val Ser Ser Gly Cys Arg Met Arg Ser Leu Trp Phe Ile Ile Val
1               5                   10                  15

Ile Ser Phe Leu Pro Asn Thr Glu Gly Phe Ser Arg Ala Ala Leu Pro
            20                  25                  30

Phe Gly Leu Val Arg Arg Glu Leu Ser Cys Glu Gly Tyr Ser Ile Asp
        35                  40                  45

Leu Arg Cys Pro Gly Ser Asp Val Ile Met Ile Glu Ser Ala Asn Tyr
    50                  55                  60

Gly Arg Thr Asp Asp Lys Ile Cys Asp Ala Asp Pro Phe Gln Met Glu
65                  70                  75                  80

Asn Thr Asp Cys Tyr Leu Pro Asp Ala Phe Lys Ile Met Thr Gln Arg
                85                  90                  95

Cys Asn Asn Arg Thr Gln Cys Ile Val Val Thr Gly Ser Asp Val Phe
            100                 105                 110

Pro Asp Pro Cys Pro Gly Thr Tyr Lys Tyr Leu Glu Val Gln Tyr Glu
        115                 120                 125

Cys Val Pro Tyr Ile Phe Val Cys Pro Gly Thr Leu Lys Ala Ile Val
    130                 135                 140

Asp Ser Pro Cys Ile Tyr Glu Ala Glu Gln Lys Ala Gly Ala Trp Cys
145                 150                 155                 160

Lys Asp Pro Leu Gln Ala Ala Asp Lys Ile Tyr Phe Met Pro Trp Thr
                165                 170                 175

Pro Tyr Arg Thr Asp Thr Leu Ile Glu Tyr Ala Ser Leu Glu Asp Phe
            180                 185                 190

Gln Asn Ser Arg Gln Thr Thr Thr Tyr Lys Leu Pro Asn Arg Val Asp
        195                 200                 205

Gly Thr Gly Phe Val Val Tyr Asp Gly Ala Val Phe Phe Asn Lys Glu
    210                 215                 220

Arg Thr Arg Asn Ile Val Lys Phe Asp Leu Arg Thr Arg Ile Lys Ser
225                 230                 235                 240

Gly Glu Ala Ile Ile Asn Tyr Ala Asn Tyr His Asp Thr Ser Pro Tyr
                245                 250                 255

Arg Trp Gly Gly Lys Thr Asp Ile Asp Leu Ala Val Asp Glu Asn Gly
            260                 265                 270

Leu Trp Val Ile Tyr Ala Thr Glu Gln Asn Asn Gly Met Ile Val Ile
        275                 280                 285

Ser Gln Leu Asn Pro Tyr Thr Leu Arg Phe Glu Ala Thr Trp Glu Thr
    290                 295                 300

Val Tyr Asp Lys Arg Ala Ala Ser Asn Ala Phe Met Ile Cys Gly Val
305                 310                 315                 320

Leu Tyr Val Val Arg Ser Val Tyr Gln Asp Asn Glu Ser Glu Thr Gly
                325                 330                 335

Lys Asn Ser Ile Asp Tyr Ile Tyr Asn Thr Arg Leu Asn Arg Gly Glu
            340                 345                 350

Tyr Val Asp Val Pro Phe Pro Asn Gln Tyr Gln Tyr Ile Ala Ala Val
        355                 360                 365

-continued

```
Asp Tyr Asn Pro Arg Asp Asn Gln Leu Tyr Val Trp Asn Asn Asn Phe
        370                 375                 380
Ile Leu Arg Tyr Ser Leu Glu Phe Gly Pro Pro Asp Pro Ala Gln Val
385                 390                 395                 400
Pro Thr Thr Ala Val Thr Ile Thr Ser Ser Ala Glu Leu Phe Lys Thr
                405                 410                 415
Ile Ile Ser Thr Thr Ser Thr Thr Ser Gln Lys Gly Pro Met Ser Thr
                420                 425                 430
Thr Val Ala Gly Ser Gln Glu Gly Ser Lys Gly Thr Lys Pro Pro Pro
                435                 440                 445
Ala Val Ser Thr Thr Lys Ile Pro Pro Ile Thr Asn Ile Phe Pro Leu
450                 455                 460
Pro Glu Arg Phe Cys Glu Ala Leu Asp Ser Lys Gly Ile Lys Trp Pro
465                 470                 475                 480
Gln Thr Gln Arg Gly Met Met Val Glu Arg Pro Cys Pro Lys Gly Thr
                485                 490                 495
Arg Gly Thr Ala Ser Tyr Leu Cys Met Ile Ser Thr Gly Thr Trp Asn
                500                 505                 510
Pro Lys Gly Pro Asp Leu Ser Asn Cys Thr Ser His Trp Val Asn Gln
        515                 520                 525
Leu Ala Gln Lys Ile Arg Ser Gly Glu Asn Ala Ala Ser Leu Ala Asn
        530                 535                 540
Glu Leu Ala Lys His Thr Lys Gly Pro Val Phe Ala Gly Asp Val Ser
545                 550                 555                 560
Ser Ser Val Arg Leu Met Glu Gln Leu Val Asp Ile Leu Asp Ala Gln
                565                 570                 575
Leu Gln Glu Leu Lys Pro Ser Glu Lys Asp Ser Ala Gly Arg Ser Tyr
                580                 585                 590
Asn Lys Ala Ile Val Asp Thr Val Asp Asn Leu Leu Arg Pro Glu Ala
        595                 600                 605
Leu Glu Ser Trp Lys His Met Asn Ser Ser Glu Gln Ala His Thr Ala
        610                 615                 620
Thr Met Leu Leu Asp Thr Leu Glu Glu Gly Ala Phe Val Leu Ala Asp
625                 630                 635                 640
Asn Leu Leu Glu Pro Thr Arg Val Ser Met Pro Thr Glu Asn Ile Val
                645                 650                 655
Leu Glu Val Ala Val Leu Ser Thr Glu Gly Gln Ile Gln Asp Phe Lys
                660                 665                 670
Phe Pro Leu Gly Ile Lys Gly Ala Gly Ser Ser Ile Gln Leu Ser Ala
        675                 680                 685
Asn Thr Val Lys Gln Asn Ser Arg Asn Gly Leu Ala Lys Leu Val Phe
        690                 695                 700
Ile Ile Tyr Arg Ser Leu Gly Gln Phe Leu Ser Thr Glu Asn Ala Thr
705                 710                 715                 720
Ile Lys Leu Gly Ala Asp Phe Ile Gly Arg Asn Ser Thr Ile Ala Val
                725                 730                 735
Asn Ser His Val Ile Ser Val Ser Ile Lys Lys Glu Ser Ser Arg Val
                740                 745                 750
Tyr Leu Thr Asp Pro Val Leu Phe Thr Leu Pro His Ile Asp Pro Asp
        755                 760                 765
Asn Tyr Phe Asn Ala Asn Cys Ser Phe Trp Asn Tyr Ser Glu Arg Thr
        770                 775                 780
```

Met Met Gly Tyr Trp Ser Thr Gln Gly Cys Lys Leu Val Asp Thr Asn
785                 790                 795                 800

Lys Thr Arg Thr Thr Cys Ala Cys Ser His Leu Thr Asn Phe Ala Ile
            805                 810                 815

Leu Met Ala His Arg Glu Ile Ala Tyr Lys Asp Gly Val His Glu Leu
        820                 825                 830

Leu Leu Thr Val Ile Thr Trp Val Gly Ile Val Ile Ser Leu Val Cys
    835                 840                 845

Leu Ala Ile Cys Ile Phe Thr Phe Cys Phe Arg Gly Leu Gln Ser
850                 855                 860

Asp Arg Asn Thr Ile His Lys Asn Leu Cys Ile Asn Leu Phe Ile Ala
865                 870                 875                 880

Glu Phe Ile Phe Leu Ile Gly Ile Asp Lys Thr Lys Tyr Ala Ile Ala
                885                 890                 895

Cys Pro Ile Phe Ala Gly Leu Leu His Phe Phe Phe Leu Ala Ala Phe
            900                 905                 910

Ala Trp Met Cys Leu Glu Gly Val Gln Leu Tyr Leu Met Leu Val Glu
        915                 920                 925

Val Phe Glu Ser Glu Tyr Ser Arg Lys Lys Tyr Tyr Tyr Val Ala Gly
    930                 935                 940

Tyr Leu Phe Pro Ala Thr Val Val Gly Val Ser Ala Ala Ile Asp Tyr
945                 950                 955                 960

Lys Ser Tyr Gly Thr Glu Lys Ala Cys Trp Leu His Val Asp Asn Tyr
                965                 970                 975

Phe Ile Trp Ser Phe Ile Gly Pro Val Thr Phe Ile Ile Leu Leu Asn
            980                 985                 990

Ile Ile Phe Leu Val Ile Thr Leu Cys Lys Met Val Lys His Ser Asn
        995                 1000                1005

Thr Leu Lys Pro Asp Ser Ser Arg Leu Glu Asn Ile Lys Ser Trp Val
    1010                1015                1020

Leu Gly Ala Phe Ala Leu Leu Cys Leu Leu Gly Leu Thr Trp Ser Phe
025                 1030                1035                1040

Gly Leu Leu Phe Ile Asn Glu Glu Thr Ile Val Met Ala Tyr Leu Phe
                1045                1050                1055

Thr Ile Phe Asn Ala Phe Gln Gly Val Phe Ile Phe Ile Phe His Cys
            1060                1065                1070

Ala Leu Gln Lys Lys Val Arg Lys Glu Tyr Gly Lys Cys Phe Arg His
        1075                1080                1085

Ser Tyr Cys Cys Gly Gly Leu Pro Thr Glu Ser Pro His Ser Ser Val
    1090                1095                1100

Lys Ala Ser Thr Thr Arg Thr Ser Ala Arg Tyr Ser Ser Gly Thr Gln
105                 1110                1115                1120

Asp Ile His

<210> SEQ ID NO 5
<211> LENGTH: 5491
<212> TYPE: DNA
<213> ORGANISM: Homo sapiens
<220> FEATURE:
<221> NAME/KEY: CDS
<222> LOCATION: (217)..(4425)

<400> SEQUENCE: 5
cggcgaacag acgttctttc tcctccatgc agttacacaa aaggagggct acggaaacta    60
aaagtttcgg ggcctctggc tcggtgtgtg gagaaaagag aaaacctgga gacgggatat    120

-continued

```
gaagatcaat gatgcagact gatggtcttg atgaagctgg gcatttataa ctagattcat      180
taaggaatac aaagaaaata cttaaaggga tcaata atg gtg tct tct ggt tgc        234
                                       Met Val Ser Ser Gly Cys
                                         1               5 aga atg cga agt ctg tgg ttt atc att gta atc agc ttc tta cca aat        282
Arg Met Arg Ser Leu Trp Phe Ile Ile Val Ile Ser Phe Leu Pro Asn
            10                  15                  20 aca gaa ggt ttc agc aga gca gct tta cca ttt ggg ctg gtg agg cga        330
Thr Glu Gly Phe Ser Arg Ala Ala Leu Pro Phe Gly Leu Val Arg Arg
                25                  30                  35 gaa tta tcc tgt gaa ggt tat tct ata gat ctg cga tgc ccg ggc agt        378
Glu Leu Ser Cys Glu Gly Tyr Ser Ile Asp Leu Arg Cys Pro Gly Ser
        40                  45                  50 gat gtc atc atg att gag agc gct aac tat ggt cgg acg gat gac aag        426
Asp Val Ile Met Ile Glu Ser Ala Asn Tyr Gly Arg Thr Asp Asp Lys
 55                  60                  65                  70 att tgt gat gct gac cca ttt cag atg gag aat aca gac tgc tac ctc        474
Ile Cys Asp Ala Asp Pro Phe Gln Met Glu Asn Thr Asp Cys Tyr Leu
                 75                  80                  85 ccc gat gcc ttc aaa att atg act caa agg tgc aac aat cga aca cag        522
Pro Asp Ala Phe Lys Ile Met Thr Gln Arg Cys Asn Asn Arg Thr Gln
                90                  95                 100 tgt ata gta gtt act ggg tca gat gtg ttt cct gat cca tgt cct gga        570
Cys Ile Val Val Thr Gly Ser Asp Val Phe Pro Asp Pro Cys Pro Gly
            105                 110                 115 aca tac aaa tac ctt gaa gtc caa tat gaa tgt gtc cct tac att ttt        618
Thr Tyr Lys Tyr Leu Glu Val Gln Tyr Glu Cys Val Pro Tyr Ile Phe
        120                 125                 130 gtg tgt cct ggg acc ttg aaa gca att gtg gac tca cca tgt ata tat        666
Val Cys Pro Gly Thr Leu Lys Ala Ile Val Asp Ser Pro Cys Ile Tyr
135                 140                 145                 150 gaa gct gaa caa aag gcg ggt gct tgg tgc aag gac cct ctt cag gct        714
Glu Ala Glu Gln Lys Ala Gly Ala Trp Cys Lys Asp Pro Leu Gln Ala
                155                 160                 165 gca gat aaa att tat ttc atg ccc tgg act ccc tat cgt acc gat act        762
Ala Asp Lys Ile Tyr Phe Met Pro Trp Thr Pro Tyr Arg Thr Asp Thr
            170                 175                 180 tta ata gaa tat gct tct tta gaa gat ttc caa aat agt cgc caa aca        810
Leu Ile Glu Tyr Ala Ser Leu Glu Asp Phe Gln Asn Ser Arg Gln Thr
        185                 190                 195 aca aca tat aaa ctt cca aat cga gta gat ggt act gga ttt gtg gtg        858
Thr Thr Tyr Lys Leu Pro Asn Arg Val Asp Gly Thr Gly Phe Val Val
200                 205                 210 tat gat ggt gct gtc ttc ttt aac aaa gaa aga acg agg aat att gtg        906
Tyr Asp Gly Ala Val Phe Phe Asn Lys Glu Arg Thr Arg Asn Ile Val
215                 220                 225                 230 aaa ttt gac ttg agg act aga att aag agt ggc gag gcc ata att aac        954
Lys Phe Asp Leu Arg Thr Arg Ile Lys Ser Gly Glu Ala Ile Ile Asn
                235                 240                 245 tat gcc aac tac cat gat acc tca cca tac aga tgg gga gga aag act       1002
Tyr Ala Asn Tyr His Asp Thr Ser Pro Tyr Arg Trp Gly Gly Lys Thr
            250                 255                 260 gat atc gac cta gca gtt gat gaa aat ggt tta tgg gtc att tac gcc       1050
Asp Ile Asp Leu Ala Val Asp Glu Asn Gly Leu Trp Val Ile Tyr Ala
        265                 270                 275 act gaa cag aac aat gga atg ata gtt att agc cag ctg aat cca tac       1098
Thr Glu Gln Asn Asn Gly Met Ile Val Ile Ser Gln Leu Asn Pro Tyr
280                 285                 290
```

-continued

```
act ctt cga ttt gaa gca acg tgg gag act gta tac gac aaa cgt gcc   1146
Thr Leu Arg Phe Glu Ala Thr Trp Glu Thr Val Tyr Asp Lys Arg Ala
295                 300                 305                 310 gca tca aat gct ttt atg ata tgc gga gtc ctc tat gtg gtt agg tca   1194
Ala Ser Asn Ala Phe Met Ile Cys Gly Val Leu Tyr Val Val Arg Ser
                315                 320                 325 gtt tat caa gac aat gaa agt gaa aca ggc aag aac tca att gat tac   1242
Val Tyr Gln Asp Asn Glu Ser Glu Thr Gly Lys Asn Ser Ile Asp Tyr
            330                 335                 340 att tat aat acc cga tta aac cga gga gaa tat gta gac gtt ccc ttc   1290
Ile Tyr Asn Thr Arg Leu Asn Arg Gly Glu Tyr Val Asp Val Pro Phe
        345                 350                 355 ccc aac cag tat cag tat att gct gca gtg gat tac aat cca aga gat   1338
Pro Asn Gln Tyr Gln Tyr Ile Ala Ala Val Asp Tyr Asn Pro Arg Asp
    360                 365                 370 aac caa ctt tac gtg tgg aac aat aac ttc att tta cga tat tct ctg   1386
Asn Gln Leu Tyr Val Trp Asn Asn Asn Phe Ile Leu Arg Tyr Ser Leu
375                 380                 385                 390 gag ttt ggt cca cct gat cct gcc caa gtg cct acc aca gct gtg aca   1434
Glu Phe Gly Pro Pro Asp Pro Ala Gln Val Pro Thr Thr Ala Val Thr
                395                 400                 405 ata act tct tca gct gag ctg ttc aaa acc ata ata tca acc aca agc   1482
Ile Thr Ser Ser Ala Glu Leu Phe Lys Thr Ile Ile Ser Thr Thr Ser
            410                 415                 420 act act tca cag aaa ggc ccc atg agc aca act gta gct gga tca cag   1530
Thr Thr Ser Gln Lys Gly Pro Met Ser Thr Thr Val Ala Gly Ser Gln
        425                 430                 435 gaa gga agc aaa ggg aca aaa cca cct cca gca gtt tct aca acc aaa   1578
Glu Gly Ser Lys Gly Thr Lys Pro Pro Pro Ala Val Ser Thr Thr Lys
    440                 445                 450 att cca cct ata aca aat att ttt ccc ctg cca gag aga ttc tgt gaa   1626
Ile Pro Pro Ile Thr Asn Ile Phe Pro Leu Pro Glu Arg Phe Cys Glu
455                 460                 465                 470 gca tta gac tcc aag ggg ata aag tgg cct cag aca caa agg gga atg   1674
Ala Leu Asp Ser Lys Gly Ile Lys Trp Pro Gln Thr Gln Arg Gly Met
                475                 480                 485 atg gtt gaa cga cca tgc cct aag gga aca aga gga act gcc tca tat   1722
Met Val Glu Arg Pro Cys Pro Lys Gly Thr Arg Gly Thr Ala Ser Tyr
            490                 495                 500 ctc tgc atg att tcc act gga aca tgg aac cct aag ggc ccc gat ctt   1770
Leu Cys Met Ile Ser Thr Gly Thr Trp Asn Pro Lys Gly Pro Asp Leu
        505                 510                 515 agc aac tgt acc tca cac tgg gtg aat cag ctg gct cag aag atc aga   1818
Ser Asn Cys Thr Ser His Trp Val Asn Gln Leu Ala Gln Lys Ile Arg
    520                 525                 530 agc gga gaa aat gct gct agt ctt gcc aat gaa ctg gct aaa cat acc   1866
Ser Gly Glu Asn Ala Ala Ser Leu Ala Asn Glu Leu Ala Lys His Thr
535                 540                 545                 550 aaa ggg cca gtg ttt gct ggg gat gta agt tct tca gtg aga ttg atg   1914
Lys Gly Pro Val Phe Ala Gly Asp Val Ser Ser Ser Val Arg Leu Met
                555                 560                 565 gag cag ttg gtg gac atc ctt gat gca cag ctg cag gaa ctg aaa cct   1962
Glu Gln Leu Val Asp Ile Leu Asp Ala Gln Leu Gln Glu Leu Lys Pro
            570                 575                 580 agt gaa aaa gat tca gct gga cgg agt tat aac aag gca att gtt gac   2010
Ser Glu Lys Asp Ser Ala Gly Arg Ser Tyr Asn Lys Ala Ile Val Asp
        585                 590                 595 aca gtg gac aac ctt ctg aga cct gaa gct ttg gaa tca tgg aaa cat   2058
Thr Val Asp Asn Leu Leu Arg Pro Glu Ala Leu Glu Ser Trp Lys His
    600                 605                 610
```

-continued

| | | |
|---|---|---|
| atg aat tct tct gaa caa gca cat act gca aca atg tta ctc gat aca<br>Met Asn Ser Ser Glu Gln Ala His Thr Ala Thr Met Leu Leu Asp Thr<br>615                     620                   625                   630 | 2106 |
| ttg gaa gaa gga gct ttt gtc cta gct gac aat ctt tta gaa cca aca<br>Leu Glu Glu Gly Ala Phe Val Leu Ala Asp Asn Leu Leu Glu Pro Thr<br>                               635                   640                   645 | 2154 |
| agg gtc tca atg ccc aca gaa aat att gtc ctg gaa gtt gcc gta ctc<br>Arg Val Ser Met Pro Thr Glu Asn Ile Val Leu Glu Val Ala Val Leu<br>                     650                   655                   660 | 2202 |
| agt aca gaa gga cag atc caa gac ttt aaa ttt cct ctg ggc atc aaa<br>Ser Thr Glu Gly Gln Ile Gln Asp Phe Lys Phe Pro Leu Gly Ile Lys<br>665                     670                   675 | 2250 |
| gga gca ggc agc tca atc caa ctg tcc gca aat acc gtc aaa cag aac<br>Gly Ala Gly Ser Ser Ile Gln Leu Ser Ala Asn Thr Val Lys Gln Asn<br>                   680                   685                   690 | 2298 |
| agc agg aat ggg ctt gca aag ttg gtg ttc atc att tac cgg agc ctg<br>Ser Arg Asn Gly Leu Ala Lys Leu Val Phe Ile Ile Tyr Arg Ser Leu<br>695                     700                   705                   710 | 2346 |
| gga cag ttc ctt agt aca gaa aat gca acc att aaa ctg ggt gct gat<br>Gly Gln Phe Leu Ser Thr Glu Asn Ala Thr Ile Lys Leu Gly Ala Asp<br>                   715                   720                   725 | 2394 |
| ttt att ggt cgt aat agc acc att gca gtg aac tct cac gtc att tca<br>Phe Ile Gly Arg Asn Ser Thr Ile Ala Val Asn Ser His Val Ile Ser<br>                730                   735                   740 | 2442 |
| gtt tca atc aat aaa gag tcc agc cga gta tac ctg act gat cct gtg<br>Val Ser Ile Asn Lys Glu Ser Ser Arg Val Tyr Leu Thr Asp Pro Val<br>               745                   750                   755 | 2490 |
| ctt ttt acc ctg cca cac att gat cct gac aat tat ttc aat gca aac<br>Leu Phe Thr Leu Pro His Ile Asp Pro Asp Asn Tyr Phe Asn Ala Asn<br>760                     765                   770 | 2538 |
| tgc tcc ttc tgg aac tac tca gag aga act atg atg gga tat tgg tct<br>Cys Ser Phe Trp Asn Tyr Ser Glu Arg Thr Met Met Gly Tyr Trp Ser<br>775                     780                   785                   790 | 2586 |
| acc cag ggc tgc aag ctg gtt gac act aat aaa act cga aca acg tgt<br>Thr Gln Gly Cys Lys Leu Val Asp Thr Asn Lys Thr Arg Thr Thr Cys<br>                   795                   800                   805 | 2634 |
| gca tgc agc cac cta acc aat ttt gca att ctc atg gcc cac agg gaa<br>Ala Cys Ser His Leu Thr Asn Phe Ala Ile Leu Met Ala His Arg Glu<br>                810                   815                   820 | 2682 |
| att gca tat aaa gat ggc gtt cat gaa tta ctt ctt aca gtc atc acc<br>Ile Ala Tyr Lys Asp Gly Val His Glu Leu Leu Leu Thr Val Ile Thr<br>               825                   830                   835 | 2730 |
| tgg gtg gga att gtc att tcc ctt gtt tgc ctg gct atc tgc atc ttc<br>Trp Val Gly Ile Val Ile Ser Leu Val Cys Leu Ala Ile Cys Ile Phe<br>840                     845                   850 | 2778 |
| acc ttc tgc ttt ttc cgt ggc cta cag agt gac cga aat act att cac<br>Thr Phe Cys Phe Phe Arg Gly Leu Gln Ser Asp Arg Asn Thr Ile His<br>855                     860                   865                   870 | 2826 |
| aag aac ctt tgt atc aac ctt ttc att gct gaa ttt att ttc cta ata<br>Lys Asn Leu Cys Ile Asn Leu Phe Ile Ala Glu Phe Ile Phe Leu Ile<br>                875                   880                   885 | 2874 |
| ggc att gat aag aca aaa tat gcg att gca tgc cca ata ttt gca gga<br>Gly Ile Asp Lys Thr Lys Tyr Ala Ile Ala Cys Pro Ile Phe Ala Gly<br>                890                   895                   900 | 2922 |
| ctt cta cac ttt ttc ttt ttg gca gct ttt gct tgg atg tgc cta gaa<br>Leu Leu His Phe Phe Phe Leu Ala Ala Phe Ala Trp Met Cys Leu Glu<br>905                     910                   915 | 2970 |
| ggt gtg cag ctc tac cta atg tta gtt gaa gtt ttt gaa agt gaa tat<br>Gly Val Gln Leu Tyr Leu Met Leu Val Glu Val Phe Glu Ser Glu Tyr | 3018 |

```
                920               925                930
tca agg aaa aaa tat tac tat gtt gct ggt tac ttg ttt cct gcc aca    3066
Ser Arg Lys Lys Tyr Tyr Tyr Val Ala Gly Tyr Leu Phe Pro Ala Thr
935                 940                 945                 950 gtg gtt gga gtt tca gct gct att gac tat aag agc tat gga aca gaa    3114
Val Val Gly Val Ser Ala Ala Ile Asp Tyr Lys Ser Tyr Gly Thr Glu
                955                 960                 965 aaa gct tgc tgg ctt cat gtt gat aac tac ttt ata tgg agc ttc att    3162
Lys Ala Cys Trp Leu His Val Asp Asn Tyr Phe Ile Trp Ser Phe Ile
        970                 975                 980 gga cct gtt acc ttc att att ctg cta aat att atc ttc ttg gtg atc    3210
Gly Pro Val Thr Phe Ile Ile Leu Leu Asn Ile Ile Phe Leu Val Ile
    985                 990                 995 aca ttg tgc aaa atg gtg aag cat tca aac act ttg aaa cca gat tct    3258
Thr Leu Cys Lys Met Val Lys His Ser Asn Thr Leu Lys Pro Asp Ser
1000                1005                1010 agc agg ttg gaa aac att aag tct tgg gtg ctt ggc gct ttc gct ctt    3306
Ser Arg Leu Glu Asn Ile Lys Ser Trp Val Leu Gly Ala Phe Ala Leu
1015                1020                1025                1030 ctg tgt ctt ctt ggc ctc acc tgg tcc ttt ggg ttg ctt ttt att aat    3354
Leu Cys Leu Leu Gly Leu Thr Trp Ser Phe Gly Leu Leu Phe Ile Asn
            1035                1040                1045 gag gag act att gtg atg gca tat ctc ttc act ata ttt aat gct ttc    3402
Glu Glu Thr Ile Val Met Ala Tyr Leu Phe Thr Ile Phe Asn Ala Phe
        1050                1055                1060 cag gga gtg ttc att ttc atc ttt cac tgt gct ctc caa aag aaa gta    3450
Gln Gly Val Phe Ile Phe Ile Phe His Cys Ala Leu Gln Lys Lys Val
    1065                1070                1075 cga aaa gaa tat ggc aag tgc ttc aga cac tca tac tgc tgt gga ggc    3498
Arg Lys Glu Tyr Gly Lys Cys Phe Arg His Ser Tyr Cys Cys Gly Gly
1080                1085                1090 ctc cca act gag agt ccc cac agt tca gtg aag gca tca acc acc aga    3546
Leu Pro Thr Glu Ser Pro His Ser Ser Val Lys Ala Ser Thr Thr Arg
1095                1100                1105                1110 acc agt gct cgc tat tcc tct ggc aca cag agt cgt ata aga aga atg    3594
Thr Ser Ala Arg Tyr Ser Ser Gly Thr Gln Ser Arg Ile Arg Arg Met
            1115                1120                1125 tgg aat gat act gtg aga aaa caa tca gaa tct tct ttt atc tca ggt    3642
Trp Asn Asp Thr Val Arg Lys Gln Ser Glu Ser Ser Phe Ile Ser Gly
        1130                1135                1140 gac atc aat agc act tca aca ctt aat caa gga cat tca ctg aac aat    3690
Asp Ile Asn Ser Thr Ser Thr Leu Asn Gln Gly His Ser Leu Asn Asn
    1145                1150                1155 gcc agg gat aca agt gcc atg gat act cta ccg cta aat ggt aat ttt    3738
Ala Arg Asp Thr Ser Ala Met Asp Thr Leu Pro Leu Asn Gly Asn Phe
1160                1165                1170 aac aac agc tac tcg ctg cac aag ggt gac tat aat gac agc gtg caa    3786
Asn Asn Ser Tyr Ser Leu His Lys Gly Asp Tyr Asn Asp Ser Val Gln
1175                1180                1185                1190 gtt gtg gac tgt gga cta agt ctg aat gat act gct ttt gag aaa atg    3834
Val Val Asp Cys Gly Leu Ser Leu Asn Asp Thr Ala Phe Glu Lys Met
            1195                1200                1205 atc att tca gaa tta gtg cac aac aac tta cgg ggc agc agc aag act    3882
Ile Ile Ser Glu Leu Val His Asn Asn Leu Arg Gly Ser Ser Lys Thr
        1210                1215                1220 cac aac ctc gag ctc acg cta cca gtc aaa cct gtg att gga ggt agc    3930
His Asn Leu Glu Leu Thr Leu Pro Val Lys Pro Val Ile Gly Gly Ser
    1225                1230                1235 agc agt gaa gat gat gct att gtg gca gat gct tca tct tta atg cac    3978
```

-continued

| | | |
|---|---|---|
| Ser Ser Glu Asp Asp Ala Ile Val Ala Asp Ala Ser Ser Leu Met His<br>　　1240　　　　　　　　　1245　　　　　　　　　1250 | | |
| agc gac aac cca ggg ctg gag ctc cat cac aaa gaa ctc gag gca cca<br>Ser Asp Asn Pro Gly Leu Glu Leu His His Lys Glu Leu Glu Ala Pro<br>1255　　　　　　　　　1260　　　　　　　　　1265　　　　　　　　　1270 | | 4026 |
| ctt att cct cag cgg act cac tcc ctt ctg tac caa ccc cag aag aaa<br>Leu Ile Pro Gln Arg Thr His Ser Leu Leu Tyr Gln Pro Gln Lys Lys<br>　　　　　　　　　1275　　　　　　　　　1280　　　　　　　　　1285 | | 4074 |
| gtg aag tcc gag gga act gac agc tat gtc tcc caa ctg aca gca gag<br>Val Lys Ser Glu Gly Thr Asp Ser Tyr Val Ser Gln Leu Thr Ala Glu<br>　　1290　　　　　　　　　1295　　　　　　　　　1300 | | 4122 |
| gct gaa gat cac cta cag tcc ccc aac aga gac tct ctt tat aca agc<br>Ala Glu Asp His Leu Gln Ser Pro Asn Arg Asp Ser Leu Tyr Thr Ser<br>1305　　　　　　　　　1310　　　　　　　　　1315 | | 4170 |
| atg ccc aat ctt aga gac tct ccc tat ccg gag agc agc cct gac atg<br>Met Pro Asn Leu Arg Asp Ser Pro Tyr Pro Glu Ser Ser Pro Asp Met<br>　　1320　　　　　　　　　1325　　　　　　　　　1330 | | 4218 |
| gaa gaa gac ctc tct ccc tcc agg agg agt gag aat gag gac att tac<br>Glu Glu Asp Leu Ser Pro Ser Arg Arg Ser Glu Asn Glu Asp Ile Tyr<br>1335　　　　　　　　　1340　　　　　　　　　1345　　　　　　　　　1350 | | 4266 |
| tat aaa agc atg cca aat ctt gga gct ggc cat cag ctt cag atg tgc<br>Tyr Lys Ser Met Pro Asn Leu Gly Ala Gly His Gln Leu Gln Met Cys<br>　　　　　　　　　1355　　　　　　　　　1360　　　　　　　　　1365 | | 4314 |
| tac cag atc agc agg ggc aat agt gat ggt tat ata atc ccc att aac<br>Tyr Gln Ile Ser Arg Gly Asn Ser Asp Gly Tyr Ile Ile Pro Ile Asn<br>　　1370　　　　　　　　　1375　　　　　　　　　1380 | | 4362 |
| aaa gaa ggg tgt att cca gaa gga gat gtt aga gaa gga caa atg cag<br>Lys Glu Gly Cys Ile Pro Glu Gly Asp Val Arg Glu Gly Gln Met Gln<br>1385　　　　　　　　　1390　　　　　　　　　1395 | | 4410 |
| ctg gtt aca agt ctt taatcataca gctaaggaat ccaagggcc acatgcgagt<br>Leu Val Thr Ser Leu<br>　　1400 | | 4465 |
| attaataaat aaagacacca ttggcctgac gcagctccct caaactctgc ttgaagagat | | 4525 |
| gactcttgac ctgtggttct ctggtgtaaa aaagatgact gaaccttgca gttctgtgaa | | 4585 |
| tttttataaa acatacaaaa actttgtata tacacagagt atactaaagt gaattatttg | | 4645 |
| ttacaaagaa aagagatgcc agccaggtat tttaagattc tgctgctgtt tagagaaatt | | 4705 |
| gtgaaacaag caaaacaaaa ctttccagcc attttactgc agcagtctgt gaactaaatt | | 4765 |
| tgtaaatatg gctgcaccat ttttgtaggc ctgcattgta ttatatacaa gacgtaggct | | 4825 |
| ttaaaatcct gtgggacaaa tttactgtac cttactattc ctgacaagac ttggaaaagc | | 4885 |
| aggagagata ttctgcatca gtttgcagtt cactgcaaat cttttacatt aaggcaaaga | | 4945 |
| ttgaaaacat gcttaaccac tagcaatcaa gccacaggcc ttatttcata tgtttcctca | | 5005 |
| actgtacaat gaactattct catgaaaaat ggctaaagaa attatatttt gttctattgc | | 5065 |
| tagggtaaaa taaatacatt tgtgtccaac tgaaatataa ttgtcattaa ataattttta | | 5125 |
| aagagtgaag aaaatattgt gaaaagctct tggttgcaca tgttatgaaa tgttttttct | | 5185 |
| tacactttgt catggtaagt tctactcatt ttcacttctt ttccactgta tacagtgttc | | 5245 |
| tgctttgaca aagttagtct ttattactta catttaaatt tcttattgcc aaaagaacgt | | 5305 |
| gttttatggg gagaaacaaa ctctttgaag ccagttatgt catgccttgc acaaaagtga | | 5365 |
| tgaaatctag aaaagattgt gtgtcacccc tgtttattct tgaacagagg gcaaagaggg | | 5425 |
| cactgggcac ttctcacaaa ctttctagtg aacaaaggt gcctattctt ttttaaaaaa | | 5485 |
| aaaaaa | | 5491 |

-continued

```
<210> SEQ ID NO 6
<211> LENGTH: 1403
<212> TYPE: PRT
<213> ORGANISM: Homo sapiens

<400> SEQUENCE: 6

Met Val Ser Ser Gly Cys Arg Met Arg Ser Leu Trp Phe Ile Ile Val
  1               5                  10                  15

Ile Ser Phe Leu Pro Asn Thr Glu Gly Phe Ser Arg Ala Ala Leu Pro
                 20                  25                  30

Phe Gly Leu Val Arg Arg Glu Leu Ser Cys Glu Gly Tyr Ser Ile Asp
             35                  40                  45

Leu Arg Cys Pro Gly Ser Asp Val Ile Met Ile Glu Ser Ala Asn Tyr
 50                  55                  60

Gly Arg Thr Asp Asp Lys Ile Cys Asp Ala Asp Pro Phe Gln Met Glu
 65                  70                  75                  80

Asn Thr Asp Cys Tyr Leu Pro Asp Ala Phe Lys Ile Met Thr Gln Arg
                 85                  90                  95

Cys Asn Asn Arg Thr Gln Cys Ile Val Val Thr Gly Ser Asp Val Phe
            100                 105                 110

Pro Asp Pro Cys Pro Gly Thr Tyr Lys Tyr Leu Glu Val Gln Tyr Glu
        115                 120                 125

Cys Val Pro Tyr Ile Phe Val Cys Pro Gly Thr Leu Lys Ala Ile Val
130                 135                 140

Asp Ser Pro Cys Ile Tyr Glu Ala Glu Gln Lys Ala Gly Ala Trp Cys
145                 150                 155                 160

Lys Asp Pro Leu Gln Ala Ala Asp Lys Ile Tyr Phe Met Pro Trp Thr
                165                 170                 175

Pro Tyr Arg Thr Asp Thr Leu Ile Glu Tyr Ala Ser Leu Glu Asp Phe
            180                 185                 190

Gln Asn Ser Arg Gln Thr Thr Thr Tyr Lys Leu Pro Asn Arg Val Asp
        195                 200                 205

Gly Thr Gly Phe Val Val Tyr Asp Gly Ala Val Phe Phe Asn Lys Glu
210                 215                 220

Arg Thr Arg Asn Ile Val Lys Phe Asp Leu Arg Thr Arg Ile Lys Ser
225                 230                 235                 240

Gly Glu Ala Ile Ile Asn Tyr Ala Asn Tyr His Asp Thr Ser Pro Tyr
                245                 250                 255

Arg Trp Gly Gly Lys Thr Asp Ile Asp Leu Ala Val Asp Glu Asn Gly
            260                 265                 270

Leu Trp Val Ile Tyr Ala Thr Glu Gln Asn Asn Gly Met Ile Val Ile
        275                 280                 285

Ser Gln Leu Asn Pro Tyr Thr Leu Arg Phe Glu Ala Thr Trp Glu Thr
290                 295                 300

Val Tyr Asp Lys Arg Ala Ala Ser Asn Ala Phe Met Ile Cys Gly Val
305                 310                 315                 320

Leu Tyr Val Val Arg Ser Val Tyr Gln Asp Asn Glu Ser Glu Thr Gly
                325                 330                 335

Lys Asn Ser Ile Asp Tyr Ile Tyr Asn Thr Arg Leu Asn Arg Gly Glu
            340                 345                 350

Tyr Val Asp Val Pro Phe Pro Asn Gln Tyr Gln Tyr Ile Ala Ala Val
        355                 360                 365

Asp Tyr Asn Pro Arg Asp Asn Gln Leu Tyr Val Trp Asn Asn Asn Phe
370                 375                 380
```

-continued

```
Ile Leu Arg Tyr Ser Leu Glu Phe Gly Pro Pro Asp Pro Ala Gln Val
385                 390                 395                 400

Pro Thr Thr Ala Val Thr Ile Thr Ser Ser Ala Glu Leu Phe Lys Thr
                405                 410                 415

Ile Ile Ser Thr Thr Ser Thr Thr Ser Gln Lys Gly Pro Met Ser Thr
                420                 425                 430

Thr Val Ala Gly Ser Gln Glu Gly Ser Lys Gly Thr Lys Pro Pro Pro
            435                 440                 445

Ala Val Ser Thr Thr Lys Ile Pro Pro Ile Thr Asn Ile Phe Pro Leu
450                 455                 460

Pro Glu Arg Phe Cys Glu Ala Leu Asp Ser Lys Gly Ile Lys Trp Pro
465                 470                 475                 480

Gln Thr Gln Arg Gly Met Met Val Glu Arg Pro Cys Pro Lys Gly Thr
                485                 490                 495

Arg Gly Thr Ala Ser Tyr Leu Cys Met Ile Ser Thr Gly Thr Trp Asn
                500                 505                 510

Pro Lys Gly Pro Asp Leu Ser Asn Cys Thr Ser His Trp Val Asn Gln
                515                 520                 525

Leu Ala Gln Lys Ile Arg Ser Gly Glu Asn Ala Ala Ser Leu Ala Asn
530                 535                 540

Glu Leu Ala Lys His Thr Lys Gly Pro Val Phe Ala Gly Asp Val Ser
545                 550                 555                 560

Ser Ser Val Arg Leu Met Glu Gln Leu Val Asp Ile Leu Asp Ala Gln
                565                 570                 575

Leu Gln Glu Leu Lys Pro Ser Glu Lys Asp Ser Ala Gly Arg Ser Tyr
                580                 585                 590

Asn Lys Ala Ile Val Asp Thr Val Asp Asn Leu Leu Arg Pro Glu Ala
                595                 600                 605

Leu Glu Ser Trp Lys His Met Asn Ser Ser Glu Gln Ala His Thr Ala
                610                 615                 620

Thr Met Leu Leu Asp Thr Leu Glu Glu Gly Ala Phe Val Leu Ala Asp
625                 630                 635                 640

Asn Leu Leu Glu Pro Thr Arg Val Ser Met Pro Thr Glu Asn Ile Val
                645                 650                 655

Leu Glu Val Ala Val Leu Ser Thr Glu Gly Gln Ile Gln Asp Phe Lys
                660                 665                 670

Phe Pro Leu Gly Ile Lys Gly Ala Gly Ser Ser Ile Gln Leu Ser Ala
                675                 680                 685

Asn Thr Val Lys Gln Asn Ser Arg Asn Gly Leu Ala Lys Leu Val Phe
                690                 695                 700

Ile Ile Tyr Arg Ser Leu Gly Gln Phe Leu Ser Thr Glu Asn Ala Thr
705                 710                 715                 720

Ile Lys Leu Gly Ala Asp Phe Ile Gly Arg Asn Ser Thr Ile Ala Val
                725                 730                 735

Asn Ser His Val Ile Ser Val Ser Ile Asn Lys Glu Ser Ser Arg Val
                740                 745                 750

Tyr Leu Thr Asp Pro Val Leu Phe Thr Leu Pro His Ile Asp Pro Asp
                755                 760                 765

Asn Tyr Phe Asn Ala Asn Cys Ser Phe Trp Asn Tyr Ser Glu Arg Thr
                770                 775                 780

Met Met Gly Tyr Trp Ser Thr Gln Gly Cys Lys Leu Val Asp Thr Asn
785                 790                 795                 800
```

-continued

```
Lys Thr Arg Thr Thr Cys Ala Cys Ser His Leu Thr Asn Phe Ala Ile
                805                 810                 815
Leu Met Ala His Arg Glu Ile Ala Tyr Lys Asp Gly Val His Glu Leu
            820                 825                 830
Leu Leu Thr Val Ile Thr Trp Val Gly Ile Val Ile Ser Leu Val Cys
            835                 840                 845
Leu Ala Ile Cys Ile Phe Thr Phe Cys Phe Arg Gly Leu Gln Ser
        850                 855                 860
Asp Arg Asn Thr Ile His Lys Asn Leu Cys Ile Asn Leu Phe Ile Ala
865                 870                 875                 880
Glu Phe Ile Phe Leu Ile Gly Ile Asp Lys Thr Lys Tyr Ala Ile Ala
                885                 890                 895
Cys Pro Ile Phe Ala Gly Leu Leu His Phe Phe Leu Ala Ala Phe
                900                 905                 910
Ala Trp Met Cys Leu Glu Gly Val Gln Leu Tyr Leu Met Leu Val Glu
                915                 920                 925
Val Phe Glu Ser Glu Tyr Ser Arg Lys Lys Tyr Tyr Tyr Val Ala Gly
            930                 935                 940
Tyr Leu Phe Pro Ala Thr Val Val Gly Val Ser Ala Ala Ile Asp Tyr
945                 950                 955                 960
Lys Ser Tyr Gly Thr Glu Lys Ala Cys Trp Leu His Val Asp Asn Tyr
                965                 970                 975
Phe Ile Trp Ser Phe Ile Gly Pro Val Thr Phe Ile Ile Leu Leu Asn
                980                 985                 990
Ile Ile Phe Leu Val Ile Thr Leu Cys Lys Met Val Lys His Ser Asn
            995                 1000                1005
Thr Leu Lys Pro Asp Ser Ser Arg Leu Glu Asn Ile Lys Ser Trp Val
    1010                1015                1020
Leu Gly Ala Phe Ala Leu Leu Cys Leu Leu Gly Leu Thr Trp Ser Phe
1025                1030                1035                1040
Gly Leu Leu Phe Ile Asn Glu Glu Thr Ile Val Met Ala Tyr Leu Phe
                1045                1050                1055
Thr Ile Phe Asn Ala Phe Gln Gly Val Phe Ile Phe Ile Phe His Cys
        1060                1065                1070
Ala Leu Gln Lys Lys Val Arg Lys Glu Tyr Gly Lys Cys Phe Arg His
            1075                1080                1085
Ser Tyr Cys Cys Gly Gly Leu Pro Thr Glu Ser Pro His Ser Ser Val
        1090                1095                1100
Lys Ala Ser Thr Thr Arg Thr Ser Ala Arg Tyr Ser Ser Gly Thr Gln
1105                1110                1115                1120
Ser Arg Ile Arg Arg Met Trp Asn Asp Thr Val Arg Lys Gln Ser Glu
                1125                1130                1135
Ser Ser Phe Ile Ser Gly Asp Ile Asn Ser Thr Ser Thr Leu Asn Gln
            1140                1145                1150
Gly His Ser Leu Asn Asn Ala Arg Asp Thr Ser Ala Met Asp Thr Leu
        1155                1160                1165
Pro Leu Asn Gly Asn Phe Asn Asn Ser Tyr Ser Leu His Lys Gly Asp
    1170                1175                1180
Tyr Asn Asp Ser Val Gln Val Asp Cys Gly Leu Ser Leu Asn Asp
1185                1190                1195                1200
Thr Ala Phe Glu Lys Met Ile Ile Ser Glu Leu Val His Asn Asn Leu
                1205                1210                1215
Arg Gly Ser Ser Lys Thr His Asn Leu Glu Leu Thr Leu Pro Val Lys
```

-continued

```
                    1220                1225                1230
Pro Val Ile Gly Gly Ser Ser Glu Asp Asp Ala Ile Val Ala Asp
                1235                1240                1245

Ala Ser Ser Leu Met His Ser Asp Asn Pro Gly Leu Glu Leu His His
    1250                1255                1260

Lys Glu Leu Glu Ala Pro Leu Ile Pro Gln Arg Thr His Ser Leu Leu
1265                1270                1275                1280

Tyr Gln Pro Gln Lys Lys Val Lys Ser Glu Gly Thr Asp Ser Tyr Val
                1285                1290                1295

Ser Gln Leu Thr Ala Glu Ala Glu Asp His Leu Gln Ser Pro Asn Arg
                1300                1305                1310

Asp Ser Leu Tyr Thr Ser Met Pro Asn Leu Arg Asp Ser Pro Tyr Pro
            1315                1320                1325

Glu Ser Ser Pro Asp Met Glu Glu Asp Leu Ser Pro Ser Arg Arg Ser
        1330                1335                1340

Glu Asn Glu Asp Ile Tyr Tyr Lys Ser Met Pro Asn Leu Gly Ala Gly
1345                1350                1355                1360

His Gln Leu Gln Met Cys Tyr Gln Ile Ser Arg Gly Asn Ser Asp Gly
            1365                1370                1375

Tyr Ile Ile Pro Ile Asn Lys Glu Gly Cys Ile Pro Glu Gly Asp Val
        1380                1385                1390

Arg Glu Gly Gln Met Gln Leu Val Thr Ser Leu
        1395                1400
```

<210> SEQ ID NO 7
<211> LENGTH: 1527
<212> TYPE: DNA
<213> ORGANISM: Homo sapiens
<220> FEATURE:
<221> NAME/KEY: CDS
<222> LOCATION: (217)..(1527)

<400> SEQUENCE: 7

```
cggcgaacag acgttctttc tcctccatgc agttacacaa aaggagggct acggaaacta      60
aaagtttcgg ggcctctggc tcggtgtgtg gagaaaagag aaaacctgga gacgggatat     120
gaagatcaat gatgcagact gatggtcttg atgaagctgg gcatttataa ctagattcat     180
taaggaatac aaagaaaata cttaaaggga tcaata atg gtg tct tct ggt tgc       234
                                        Met Val Ser Ser Gly Cys
                                        1               5 aga atg cga agt ctg tgg ttt atc att gta atc agc ttc tta cca aat       282
Arg Met Arg Ser Leu Trp Phe Ile Ile Val Ile Ser Phe Leu Pro Asn
            10                  15                  20 aca gaa ggt ttc agc aga gca gct tta cca ttt ggg ctg gtg agg cga       330
Thr Glu Gly Phe Ser Arg Ala Ala Leu Pro Phe Gly Leu Val Arg Arg
        25                  30                  35 gaa tta tcc tgt gaa ggt tat tct ata gat ctg cga tgc ccg ggc agt       378
Glu Leu Ser Cys Glu Gly Tyr Ser Ile Asp Leu Arg Cys Pro Gly Ser
    40                  45                  50 gat gtc atc atg att gag agc gct aac tat ggt cgg acg gat gac aag       426
Asp Val Ile Met Ile Glu Ser Ala Asn Tyr Gly Arg Thr Asp Asp Lys
55                  60                  65                  70 att tgt gat gct gac cca ttt cag atg gag aat aca gac tgc tac ctc       474
Ile Cys Asp Ala Asp Pro Phe Gln Met Glu Asn Thr Asp Cys Tyr Leu
                75                  80                  85 ccc gat gcc ttc aaa att atg act caa agg tgc aac aat cga aca cag       522
Pro Asp Ala Phe Lys Ile Met Thr Gln Arg Cys Asn Asn Arg Thr Gln
            90                  95                 100
```

```
tgt ata gta gtt act ggg tca gat gtg ttt cct gat cca tgt cct gga    570
Cys Ile Val Val Thr Gly Ser Asp Val Phe Pro Asp Pro Cys Pro Gly
        105                 110                 115 aca tac aaa tac ctt gaa gtc caa tat gaa tgt gtc cct tac att ttt    618
Thr Tyr Lys Tyr Leu Glu Val Gln Tyr Glu Cys Val Pro Tyr Ile Phe
        120                 125                 130 gtg tgt cct ggg acc ttg aaa gca att gtg gac tca cca tgt ata tat    666
Val Cys Pro Gly Thr Leu Lys Ala Ile Val Asp Ser Pro Cys Ile Tyr
135                 140                 145                 150 gaa gct gaa caa aag gcg ggt gct tgg tgc aag gac cct ctt cag gct    714
Glu Ala Glu Gln Lys Ala Gly Ala Trp Cys Lys Asp Pro Leu Gln Ala
                155                 160                 165 gca gat aaa att tat ttc atg ccc tgg act ccc tat cgt acc gat act    762
Ala Asp Lys Ile Tyr Phe Met Pro Trp Thr Pro Tyr Arg Thr Asp Thr
            170                 175                 180 tta ata gaa tat gct tct tta gaa gat ttc caa aat agt cgc caa aca    810
Leu Ile Glu Tyr Ala Ser Leu Glu Asp Phe Gln Asn Ser Arg Gln Thr
        185                 190                 195 aca aca tat aaa ctt cca aat cga gta gat ggt act gga ttt gtg gtg    858
Thr Thr Tyr Lys Leu Pro Asn Arg Val Asp Gly Thr Gly Phe Val Val
        200                 205                 210 tat gat ggt gct gtc ttc ttt aac aaa gaa aga acg agg aat att gtg    906
Tyr Asp Gly Ala Val Phe Phe Asn Lys Glu Arg Thr Arg Asn Ile Val
215                 220                 225                 230 aaa ttt gac ttg agg act aga att aag agt ggc gag gcc ata att aac    954
Lys Phe Asp Leu Arg Thr Arg Ile Lys Ser Gly Glu Ala Ile Ile Asn
                235                 240                 245 tat gcc aac tac cat gat acc tca cca tac aga tgg gga gga aag act    1002
Tyr Ala Asn Tyr His Asp Thr Ser Pro Tyr Arg Trp Gly Gly Lys Thr
            250                 255                 260 gat atc gac cta gca gtt gat gaa aat ggt tta tgg gtc att tac gcc    1050
Asp Ile Asp Leu Ala Val Asp Glu Asn Gly Leu Trp Val Ile Tyr Ala
        265                 270                 275 act gaa cag aac aat gga atg ata gtt att agc cag ctg aat cca tac    1098
Thr Glu Gln Asn Asn Gly Met Ile Val Ile Ser Gln Leu Asn Pro Tyr
        280                 285                 290 act ctt cga ttt gaa gca acg tgg gag act gta tac gac aaa cgt gcc    1146
Thr Leu Arg Phe Glu Ala Thr Trp Glu Thr Val Tyr Asp Lys Arg Ala
295                 300                 305                 310 gca tca aat gct ttt atg ata tgc gga gtc ctc tat gtg gtt agg tca    1194
Ala Ser Asn Ala Phe Met Ile Cys Gly Val Leu Tyr Val Val Arg Ser
                315                 320                 325 gtt tat caa gac aat gaa agt gaa aca ggc aag aac tca att gat tac    1242
Val Tyr Gln Asp Asn Glu Ser Glu Thr Gly Lys Asn Ser Ile Asp Tyr
            330                 335                 340 att tat aat acc cga tta aac cga gga gaa tat gta gac gtt ccc ttc    1290
Ile Tyr Asn Thr Arg Leu Asn Arg Gly Glu Tyr Val Asp Val Pro Phe
        345                 350                 355 ccc aac cag tat cag tat att gct gca gtg gat tac aat cca aga gat    1338
Pro Asn Gln Tyr Gln Tyr Ile Ala Ala Val Asp Tyr Asn Pro Arg Asp
        360                 365                 370 aac caa ctt tac gtg tgg aac aat aac ttc att tta cga tat tct ctg    1386
Asn Gln Leu Tyr Val Trp Asn Asn Asn Phe Ile Leu Arg Tyr Ser Leu
375                 380                 385                 390 gag ttt ggt cca cct gat cct gcc caa gtg cct acc aca gct gtg aca    1434
Glu Phe Gly Pro Pro Asp Pro Ala Gln Val Pro Thr Thr Ala Val Thr
                395                 400                 405 ata act tct tca gct gag ctg ttc aaa acc ata ata tca acc aca agc    1482
Ile Thr Ser Ser Ala Glu Leu Phe Lys Thr Ile Ile Ser Thr Thr Ser
```

```
                        410              415              420
act act tca cag aaa ggc ccc atg agc aca act gta gct gga tca              1527
Thr Thr Ser Gln Lys Gly Pro Met Ser Thr Thr Val Ala Gly Ser
            425                 430                 435

<210> SEQ ID NO 8
<211> LENGTH: 437
<212> TYPE: PRT
<213> ORGANISM: Homo sapiens

<400> SEQUENCE: 8

Met Val Ser Ser Gly Cys Arg Met Arg Ser Leu Trp Phe Ile Ile Val
 1               5                  10                  15

Ile Ser Phe Leu Pro Asn Thr Glu Gly Phe Ser Arg Ala Ala Leu Pro
             20                  25                  30

Phe Gly Leu Val Arg Arg Glu Leu Ser Cys Glu Gly Tyr Ser Ile Asp
         35                  40                  45

Leu Arg Cys Pro Gly Ser Asp Val Ile Met Ile Glu Ser Ala Asn Tyr
     50                  55                  60

Gly Arg Thr Asp Asp Lys Ile Cys Asp Ala Asp Pro Phe Gln Met Glu
 65                  70                  75                  80

Asn Thr Asp Cys Tyr Leu Pro Asp Ala Phe Lys Ile Met Thr Gln Arg
                 85                  90                  95

Cys Asn Asn Arg Thr Gln Cys Ile Val Val Thr Gly Ser Asp Val Phe
            100                 105                 110

Pro Asp Pro Cys Pro Gly Thr Tyr Lys Tyr Leu Glu Val Gln Tyr Glu
        115                 120                 125

Cys Val Pro Tyr Ile Phe Val Cys Pro Gly Thr Leu Lys Ala Ile Val
    130                 135                 140

Asp Ser Pro Cys Ile Tyr Glu Ala Glu Gln Lys Ala Gly Ala Trp Cys
145                 150                 155                 160

Lys Asp Pro Leu Gln Ala Ala Asp Lys Ile Tyr Phe Met Pro Trp Thr
                165                 170                 175

Pro Tyr Arg Thr Asp Thr Leu Ile Glu Tyr Ala Ser Leu Glu Asp Phe
            180                 185                 190

Gln Asn Ser Arg Gln Thr Thr Thr Tyr Lys Leu Pro Asn Arg Val Asp
        195                 200                 205

Gly Thr Gly Phe Val Val Tyr Asp Gly Ala Val Phe Phe Asn Lys Glu
    210                 215                 220

Arg Thr Arg Asn Ile Val Lys Phe Asp Leu Arg Thr Arg Ile Lys Ser
225                 230                 235                 240

Gly Glu Ala Ile Ile Asn Tyr Ala Asn Tyr His Asp Thr Ser Pro Tyr
                245                 250                 255

Arg Trp Gly Gly Lys Thr Asp Ile Asp Leu Ala Val Asp Glu Asn Gly
            260                 265                 270

Leu Trp Val Ile Tyr Ala Thr Glu Gln Asn Asn Gly Met Ile Val Ile
        275                 280                 285

Ser Gln Leu Asn Pro Tyr Thr Leu Arg Phe Glu Ala Thr Trp Glu Thr
    290                 295                 300

Val Tyr Asp Lys Arg Ala Ala Ser Asn Ala Phe Met Ile Cys Gly Val
305                 310                 315                 320

Leu Tyr Val Val Arg Ser Val Tyr Gln Asp Asn Glu Ser Glu Thr Gly
                325                 330                 335

Lys Asn Ser Ile Asp Tyr Ile Tyr Asn Thr Arg Leu Asn Arg Gly Glu
            340                 345                 350
```

```
Tyr Val Asp Val Pro Phe Pro Asn Gln Tyr Gln Tyr Ile Ala Ala Val
            355                 360                 365

Asp Tyr Asn Pro Arg Asp Asn Gln Leu Tyr Val Trp Asn Asn Asn Phe
        370                 375                 380

Ile Leu Arg Tyr Ser Leu Glu Phe Gly Pro Pro Asp Pro Ala Gln Val
385                 390                 395                 400

Pro Thr Thr Ala Val Thr Ile Thr Ser Ser Ala Glu Leu Phe Lys Thr
                405                 410                 415

Ile Ile Ser Thr Thr Ser Thr Thr Ser Gln Lys Gly Pro Met Ser Thr
                420                 425                 430

Thr Val Ala Gly Ser
            435

<210> SEQ ID NO 9
<211> LENGTH: 4190
<212> TYPE: DNA
<213> ORGANISM: Homo sapiens
<220> FEATURE:
<221> NAME/KEY: CDS
<222> LOCATION: (1)..(2340)

<400> SEQUENCE: 9 gcc caa gtg cct acc aca gct gtg aca ata act tct tca gct gag ctg      48
Ala Gln Val Pro Thr Thr Ala Val Thr Ile Thr Ser Ser Ala Glu Leu
 1               5                  10                  15 ttc aaa acc ata ata tca acc aca agc act act tca cag aaa ggc ccc      96
Phe Lys Thr Ile Ile Ser Thr Thr Ser Thr Thr Ser Gln Lys Gly Pro
             20                  25                  30 atg agc aca act gta gct gga tca cag gaa gga agc aaa ggg aca aaa     144
Met Ser Thr Thr Val Ala Gly Ser Gln Glu Gly Ser Lys Gly Thr Lys
         35                  40                  45 cca cct cca gca gtt tct aca acc aaa att cca cct ata aca aat att     192
Pro Pro Pro Ala Val Ser Thr Thr Lys Ile Pro Pro Ile Thr Asn Ile
     50                  55                  60 ttt ccc ctg cca gag aga ttc tgt gaa gca tta gac tcc aag ggg ata     240
Phe Pro Leu Pro Glu Arg Phe Cys Glu Ala Leu Asp Ser Lys Gly Ile
 65                  70                  75                  80 aag tgg cct cag aca caa agg gga atg atg gtt gaa cga cca tgc cct     288
Lys Trp Pro Gln Thr Gln Arg Gly Met Met Val Glu Arg Pro Cys Pro
                 85                  90                  95 aag gga aca aga gga act gcc tca tat ctc tgc atg att tcc act gga     336
Lys Gly Thr Arg Gly Thr Ala Ser Tyr Leu Cys Met Ile Ser Thr Gly
            100                 105                 110 aca tgg aac cct aag ggc ccc gat ctt agc aac tgt acc tca cac tgg     384
Thr Trp Asn Pro Lys Gly Pro Asp Leu Ser Asn Cys Thr Ser His Trp
        115                 120                 125 gtg aat cag ctg gct cag aag atc aga agc gga gaa aat gct gct agt     432
Val Asn Gln Leu Ala Gln Lys Ile Arg Ser Gly Glu Asn Ala Ala Ser
    130                 135                 140 ctt gcc aat gaa ctg gct aaa cat acc aaa ggg cca gtg ttt gct ggg     480
Leu Ala Asn Glu Leu Ala Lys His Thr Lys Gly Pro Val Phe Ala Gly
145                 150                 155                 160 gat gta agt tct tca gtg aga ttg atg gag cag ttg gtg gac atc ctt     528
Asp Val Ser Ser Ser Val Arg Leu Met Glu Gln Leu Val Asp Ile Leu
                165                 170                 175 gat gca cag ctg cag gaa ctg aaa cct agt gaa aaa gat tca gct gga     576
Asp Ala Gln Leu Gln Glu Leu Lys Pro Ser Glu Lys Asp Ser Ala Gly
            180                 185                 190 cgg agt tat aac aag gca att gtt gac aca gtg gac aac ctt ctg aga     624
```

-continued

```
Arg Ser Tyr Asn Lys Ala Ile Val Asp Thr Val Asp Asn Leu Leu Arg
            195                 200                 205 cct gaa gct ttg gaa tca tgg aaa cat atg aat tct tct gaa caa gca      672
Pro Glu Ala Leu Glu Ser Trp Lys His Met Asn Ser Ser Glu Gln Ala
210                 215                 220 cat act gca aca atg tta ctc gat aca ttg gaa gaa gga gct ttt gtc      720
His Thr Ala Thr Met Leu Leu Asp Thr Leu Glu Glu Gly Ala Phe Val
225                 230                 235                 240 cta gct gac aat ctt tta gaa cca aca agg gtc tca atg ccc aca gaa      768
Leu Ala Asp Asn Leu Leu Glu Pro Thr Arg Val Ser Met Pro Thr Glu
            245                 250                 255 aat att gtc ctg gaa gtt gcc gta ctc agt aca gaa gga cag atc caa      816
Asn Ile Val Leu Glu Val Ala Val Leu Ser Thr Glu Gly Gln Ile Gln
        260                 265                 270 gac ttt aaa ttt cct ctg ggc atc aaa gga gca ggc agc tca atc caa      864
Asp Phe Lys Phe Pro Leu Gly Ile Lys Gly Ala Gly Ser Ser Ile Gln
    275                 280                 285 ctg tcc gca aat acc gtc aaa cag aac agc agg aat ggg ctt gca aag      912
Leu Ser Ala Asn Thr Val Lys Gln Asn Ser Arg Asn Gly Leu Ala Lys
290                 295                 300 ttg gtg ttc atc att tac cgg agc ctg gga cag ttc ctt agt aca gaa      960
Leu Val Phe Ile Ile Tyr Arg Ser Leu Gly Gln Phe Leu Ser Thr Glu
305                 310                 315                 320 aat gca acc att aaa ctg ggt gct gat ttt att ggt cgt aat agc acc     1008
Asn Ala Thr Ile Lys Leu Gly Ala Asp Phe Ile Gly Arg Asn Ser Thr
            325                 330                 335 att gca gtg aac tct cac gtc att tca gtt tca atc aat aaa gag tcc     1056
Ile Ala Val Asn Ser His Val Ile Ser Val Ser Ile Asn Lys Glu Ser
        340                 345                 350 agc cga gta tac ctg act gat cct gtg ctt ttt acc ctg cca cac att     1104
Ser Arg Val Tyr Leu Thr Asp Pro Val Leu Phe Thr Leu Pro His Ile
    355                 360                 365 gat cct gac aat tat ttc aat gca aac tgc tcc ttc tgg aac tac tca     1152
Asp Pro Asp Asn Tyr Phe Asn Ala Asn Cys Ser Phe Trp Asn Tyr Ser
370                 375                 380 gag aga act atg atg gga tat tgg tct acc cag ggc tgc aag ctg gtt     1200
Glu Arg Thr Met Met Gly Tyr Trp Ser Thr Gln Gly Cys Lys Leu Val
385                 390                 395                 400 gac act aat aaa act cga aca acg tgt gca tgc agc cac cta acc aat     1248
Asp Thr Asn Lys Thr Arg Thr Thr Cys Ala Cys Ser His Leu Thr Asn
            405                 410                 415 ttt gca att ctc atg gcc cac agg gaa att gca tat aaa gat ggc gtt     1296
Phe Ala Ile Leu Met Ala His Arg Glu Ile Ala Tyr Lys Asp Gly Val
        420                 425                 430 cat gaa tta ctt ctt aca gtc atc acc tgg gtg gga att gtc att tcc     1344
His Glu Leu Leu Leu Thr Val Ile Thr Trp Val Gly Ile Val Ile Ser
    435                 440                 445 ctt gtt tgc ctg gct atc tgc atc ttc acc ttc tgc ttt cgt ggc     1392
Leu Val Cys Leu Ala Ile Cys Ile Phe Thr Phe Cys Phe Arg Gly
450                 455                 460 cta cag agt gac cga aat act att cac aag aac ctt tgt atc aac ctt     1440
Leu Gln Ser Asp Arg Asn Thr Ile His Lys Asn Leu Cys Ile Asn Leu
465                 470                 475                 480 ttc att gct gaa ttt att ttc cta ata ggc att gat aag aca aaa tat     1488
Phe Ile Ala Glu Phe Ile Phe Leu Ile Gly Ile Asp Lys Thr Lys Tyr
            485                 490                 495 gcg att gca tgc cca ata ttt gca gga ctt cta cac ttt ttc ttt ttg     1536
Ala Ile Ala Cys Pro Ile Phe Ala Gly Leu Leu His Phe Phe Phe Leu
        500                 505                 510
```

```
gca gct ttt gct tgg atg tgc cta gaa ggt gtg cag ctc tac cta atg      1584
Ala Ala Phe Ala Trp Met Cys Leu Glu Gly Val Gln Leu Tyr Leu Met
        515                 520                 525 tta gtt gaa gtt ttt gaa agt gaa tat tca agg aaa aaa tat tac tat      1632
Leu Val Glu Val Phe Glu Ser Glu Tyr Ser Arg Lys Lys Tyr Tyr Tyr
530                 535                 540 gtt gct ggt tac ttg ttt cct gcc aca gtg gtt gga gtt tca gct gct      1680
Val Ala Gly Tyr Leu Phe Pro Ala Thr Val Val Gly Val Ser Ala Ala
545                 550                 555                 560 att gac tat aag agc tat gga aca gaa aaa gct tgc tgg ctt cat gtt      1728
Ile Asp Tyr Lys Ser Tyr Gly Thr Glu Lys Ala Cys Trp Leu His Val
                565                 570                 575 gat aac tac ttt ata tgg agc ttc att gga cct gtt acc ttc att att      1776
Asp Asn Tyr Phe Ile Trp Ser Phe Ile Gly Pro Val Thr Phe Ile Ile
            580                 585                 590 ctg cta aat att atc ttc ttg gtg atc aca ttg tgc aaa atg gtg aag      1824
Leu Leu Asn Ile Ile Phe Leu Val Ile Thr Leu Cys Lys Met Val Lys
        595                 600                 605 cat tca aac act ttg aaa cca gat tct agc agg ttg gaa aac att aag      1872
His Ser Asn Thr Leu Lys Pro Asp Ser Ser Arg Leu Glu Asn Ile Lys
610                 615                 620 tct tgg gtg ctt ggc gct ttc gct ctt ctg tgt ctt ctt ggc ctc acc      1920
Ser Trp Val Leu Gly Ala Phe Ala Leu Leu Cys Leu Leu Gly Leu Thr
625                 630                 635                 640 tgg tcc ttt ggg ttg ctt ttt att aat gag gag act att gtg atg gca      1968
Trp Ser Phe Gly Leu Leu Phe Ile Asn Glu Glu Thr Ile Val Met Ala
                645                 650                 655 tat ctc ttc act ata ttt aat gct ttc cag gga gtg ttc att ttc atc      2016
Tyr Leu Phe Thr Ile Phe Asn Ala Phe Gln Gly Val Phe Ile Phe Ile
            660                 665                 670 ttt cac tgt gct ctc caa aag aaa gta cga aaa gaa tat ggc aag tgc      2064
Phe His Cys Ala Leu Gln Lys Lys Val Arg Lys Glu Tyr Gly Lys Cys
        675                 680                 685 ttc aga cac tca tac tgc tgt gga ggc ctc cca act gag agt ccc cac      2112
Phe Arg His Ser Tyr Cys Cys Gly Gly Leu Pro Thr Glu Ser Pro His
690                 695                 700 agt tca gtg aag gca tca acc acc aga acc agt gct cgc tat tcc tct      2160
Ser Ser Val Lys Ala Ser Thr Thr Arg Thr Ser Ala Arg Tyr Ser Ser
705                 710                 715                 720 ggc aca cag agt cgt ata aga aga atg tgg aat gat act gtg aga aaa      2208
Gly Thr Gln Ser Arg Ile Arg Arg Met Trp Asn Asp Thr Val Arg Lys
                725                 730                 735 caa tca gaa tct tct ttt atc tca ggt gac atc aat agc act tca aca      2256
Gln Ser Glu Ser Ser Phe Ile Ser Gly Asp Ile Asn Ser Thr Ser Thr
            740                 745                 750 ctt aat caa gga ctg aca tca cat ggt ctg aga gcc cat ctt caa gat      2304
Leu Asn Gln Gly Leu Thr Ser His Gly Leu Arg Ala His Leu Gln Asp
        755                 760                 765 tta tat cat tta gag cta ctc tta ggc cag ata gcc tgagcagaca           2350
Leu Tyr His Leu Glu Leu Leu Leu Gly Gln Ile Ala
770                 775                 780 gacatgatgt gagttgtcca aagacattca ctgaacaatg ccagggatac aagtgccatg    2410
gatactctac cgctaaatgg taattttaac aacagctact cgctgcacaa gggtgactat    2470
aatgacagcg tgcaagttgt ggactgtgga ctaagtctga atgatactgc ttttgagaaa    2530
atgatcattt cagaattagt gcacaacaac ttacggggca gcagcaagac tcacaacctc    2590
gagctcacgc taccagtcaa acctgtgatt ggaggtagca gcagtgaaga tgatgctatt    2650
gtggcagatg cttcatcttt aatgcacagc gacaacccag ggctggagct ccatcacaaa    2710
```

```
gaactcgagg caccacttat tcctcagcgg actcactccc ttctgtacca acccagaag    2770 aaagtgaagt ccgagggaac tgacagctat gtctcccaac tgacagcaga ggctgaagat    2830
cacctacagt cccccaacag agactctctt tatacaagca tgcccaatct tagagactct    2890
ccctatccgg agagcagccc tgacatggaa gaagacctct ctccctccag gaggagtgag    2950
aatgaggaca tttactataa aagcatgcca atcttggag ctggccatca gcttcagatg     3010
tgctaccaga tcagcagggg caatagtgat ggttatataa tccccattaa caaagaaggg    3070
tgtattccag aaggagatgt tagagaagga caaatgcagc tggttacaag tctttaatca    3130
tacagctaag gaattccaag ggccacatgc gagtattaat aaataaagac accattggcc    3190
tgacgcagct ccctcaaact ctgcttgaag agatgactct tgacctgtgg ttctctggtg    3250
taaaaaagat gactgaacct tgcagttctg tgaattttta taaaacatac aaaaactttg    3310
tatatacaca gagtatacta aagtgaatta tttgttacaa agaaaagaga tgccagccag    3370
gtattttaag attctgctgc tgtttagaga aattgtgaaa caagcaaaac aaaactttcc    3430
agccatttta ctgcagcagt ctgtgaacta aatttgtaaa tatggctgca ccattttgt     3490 aggcctgcat tgtattatat acaagacgta ggctttaaaa tcctgtggga caaatttact    3550
gtaccttact attcctgaca agacttggaa aagcaggaga gatattctgc atcagtttgc    3610
agttcactgc aaatctttta cattaaggca aagattgaaa acatgcttaa ccactagcaa    3670
tcaagccaca ggccttattt catatgtttc ctcaactgta caatgaacta ttctcatgaa    3730
aaatggctaa agaaattata ttttgttcta ttgctagggt aaaataaata catttgtgtc    3790
caactgaaat ataattgtca ttaaaataat tttaaagagt gaagaaaata ttgtgaaaag    3850
ctcttggttg cacatgttat gaaatgtttt ttcttacact ttgtcatggt aagttctact    3910
cattttcact tcttttccac tgtatacagt gttctgcttt gacaaagtta gtctttatta    3970
cttacattta aatttcttat tgccaaaaga acgtgtttta tggggagaaa caaactcttt    4030
gaagccagtt atgtcatgcc ttgcacaaaa gtgatgaaat ctagaaaaga ttgtgtgtca    4090
cccctgttta ttcttgaaca gagggcaaag agggcactgg gcacttctca caaactttct    4150
agtgaacaaa aggtgcctat tctttttttaa aaaaaaaaaa                        4190
```

<210> SEQ ID NO 10
<211> LENGTH: 780
<212> TYPE: PRT
<213> ORGANISM: Homo sapiens

<400> SEQUENCE: 10

```
Ala Gln Val Pro Thr Thr Ala Val Thr Ile Thr Ser Ser Ala Glu Leu
 1               5                  10                  15

Phe Lys Thr Ile Ile Ser Thr Thr Ser Thr Thr Ser Gln Lys Gly Pro
            20                  25                  30

Met Ser Thr Thr Val Ala Gly Ser Gln Glu Gly Ser Lys Gly Thr Lys
        35                  40                  45

Pro Pro Pro Ala Val Ser Thr Thr Lys Ile Pro Ile Thr Asn Ile
    50                  55                  60

Phe Pro Leu Pro Glu Arg Phe Cys Glu Ala Leu Asp Ser Lys Gly Ile
65                  70                  75                  80

Lys Trp Pro Gln Thr Gln Arg Gly Met Met Val Glu Arg Pro Cys Pro
                85                  90                  95

Lys Gly Thr Arg Gly Thr Ala Ser Tyr Leu Cys Met Ile Ser Thr Gly
            100                 105                 110
```

```
Thr Trp Asn Pro Lys Gly Pro Asp Leu Ser Asn Cys Thr Ser His Trp
            115                 120                 125

Val Asn Gln Leu Ala Gln Lys Ile Arg Ser Gly Glu Asn Ala Ala Ser
            130                 135                 140

Leu Ala Asn Glu Leu Ala Lys His Thr Lys Gly Pro Val Phe Ala Gly
145                 150                 155                 160

Asp Val Ser Ser Val Arg Leu Met Glu Gln Leu Val Asp Ile Leu
                165                 170                 175

Asp Ala Gln Leu Gln Glu Leu Lys Pro Ser Glu Lys Asp Ser Ala Gly
            180                 185                 190

Arg Ser Tyr Asn Lys Ala Ile Val Asp Thr Val Asp Asn Leu Leu Arg
            195                 200                 205

Pro Glu Ala Leu Glu Ser Trp Lys His Met Asn Ser Ser Glu Gln Ala
            210                 215                 220

His Thr Ala Thr Met Leu Leu Asp Thr Leu Glu Glu Gly Ala Phe Val
225                 230                 235                 240

Leu Ala Asp Asn Leu Leu Glu Pro Thr Arg Val Ser Met Pro Thr Glu
                245                 250                 255

Asn Ile Val Leu Glu Val Ala Val Leu Ser Thr Glu Gly Gln Ile Gln
                260                 265                 270

Asp Phe Lys Phe Pro Leu Gly Ile Lys Gly Ala Gly Ser Ser Ile Gln
            275                 280                 285

Leu Ser Ala Asn Thr Val Lys Gln Asn Ser Arg Asn Gly Leu Ala Lys
            290                 295                 300

Leu Val Phe Ile Ile Tyr Arg Ser Leu Gly Gln Phe Leu Ser Thr Glu
305                 310                 315                 320

Asn Ala Thr Ile Lys Leu Gly Ala Asp Phe Ile Gly Arg Asn Ser Thr
                325                 330                 335

Ile Ala Val Asn Ser His Val Ile Ser Val Ser Ile Asn Lys Glu Ser
                340                 345                 350

Ser Arg Val Tyr Leu Thr Asp Pro Val Leu Phe Thr Leu Pro His Ile
            355                 360                 365

Asp Pro Asp Asn Tyr Phe Asn Ala Asn Cys Ser Phe Trp Asn Tyr Ser
370                 375                 380

Glu Arg Thr Met Met Gly Tyr Trp Ser Thr Gln Gly Cys Lys Leu Val
385                 390                 395                 400

Asp Thr Asn Lys Thr Arg Thr Thr Cys Ala Cys Ser His Leu Thr Asn
                405                 410                 415

Phe Ala Ile Leu Met Ala His Arg Glu Ile Ala Tyr Lys Asp Gly Val
            420                 425                 430

His Glu Leu Leu Leu Thr Val Ile Thr Trp Val Gly Ile Val Ile Ser
            435                 440                 445

Leu Val Cys Leu Ala Ile Cys Ile Phe Thr Phe Cys Phe Phe Arg Gly
            450                 455                 460

Leu Gln Ser Asp Arg Asn Thr Ile His Lys Asn Leu Cys Ile Asn Leu
465                 470                 475                 480

Phe Ile Ala Glu Phe Ile Phe Leu Ile Gly Ile Asp Lys Thr Lys Tyr
            485                 490                 495

Ala Ile Ala Cys Pro Ile Phe Ala Gly Leu Leu His Phe Phe Phe Leu
            500                 505                 510

Ala Ala Phe Ala Trp Met Cys Leu Glu Gly Val Gln Leu Tyr Leu Met
            515                 520                 525
```

```
Leu Val Glu Val Phe Glu Ser Glu Tyr Ser Arg Lys Tyr Tyr Tyr
    530             535             540

Val Ala Gly Tyr Leu Phe Pro Ala Thr Val Gly Val Ser Ala Ala
545             550             555             560

Ile Asp Tyr Lys Ser Tyr Gly Thr Glu Lys Ala Cys Trp Leu His Val
                565             570             575

Asp Asn Tyr Phe Ile Trp Ser Phe Ile Gly Pro Val Thr Phe Ile Ile
            580             585             590

Leu Leu Asn Ile Ile Phe Leu Val Ile Thr Leu Cys Lys Met Val Lys
            595             600             605

His Ser Asn Thr Leu Lys Pro Asp Ser Ser Arg Leu Glu Asn Ile Lys
    610             615             620

Ser Trp Val Leu Gly Ala Phe Ala Leu Leu Cys Leu Leu Gly Leu Thr
625             630             635             640

Trp Ser Phe Gly Leu Leu Phe Ile Asn Glu Glu Thr Ile Val Met Ala
                645             650             655

Tyr Leu Phe Thr Ile Phe Asn Ala Phe Gln Gly Val Phe Ile Phe Ile
                660             665             670

Phe His Cys Ala Leu Gln Lys Lys Val Arg Lys Glu Tyr Gly Lys Cys
        675             680             685

Phe Arg His Ser Tyr Cys Cys Gly Gly Leu Pro Thr Glu Ser Pro His
        690             695             700

Ser Ser Val Lys Ala Ser Thr Thr Arg Thr Ser Ala Arg Tyr Ser Ser
705             710             715             720

Gly Thr Gln Ser Arg Ile Arg Arg Met Trp Asn Asp Thr Val Arg Lys
                725             730             735

Gln Ser Glu Ser Ser Phe Ile Ser Gly Asp Ile Asn Ser Thr Ser Thr
            740             745             750

Leu Asn Gln Gly Leu Thr Ser Gly Leu Arg Ala His Leu Gln Asp
        755             760             765

Leu Tyr His Leu Glu Leu Leu Leu Gly Gln Ile Ala
    770             775             780
```

```
<210> SEQ ID NO 11
<211> LENGTH: 3156
<212> TYPE: DNA
<213> ORGANISM: Homo sapiens
<220> FEATURE:
<221> NAME/KEY: CDS
<222> LOCATION: (49)..(2553)

<400> SEQUENCE: 11
ctgtcccact cactctttcc cctgccgctc ctgccggcag ctccaacc atg gga ggc      57
                                                   Met Gly Gly
                                                     1 cgc gtc ttt ctc gca ttc tgt gtc tgg ctg act ctg ccg gga gct gaa     105
Arg Val Phe Leu Ala Phe Cys Val Trp Leu Thr Leu Pro Gly Ala Glu
      5                  10                  15 acc cag gac tcc agg ggc tgt gcc cgg tgg tgc cct cag aac tcc tcg     153
Thr Gln Asp Ser Arg Gly Cys Ala Arg Trp Cys Pro Gln Asn Ser Ser
 20                  25                  30                  35 tgt gtc aat gcc acc gcc tgt cgc tgc aat cca ggg ttc agc tct ttt     201
Cys Val Asn Ala Thr Ala Cys Arg Cys Asn Pro Gly Phe Ser Ser Phe
                 40                  45                  50 tct gag atc atc acc acc ccg acg gag act tgt gac gac atc aac gag     249
Ser Glu Ile Ile Thr Thr Pro Thr Glu Thr Cys Asp Asp Ile Asn Glu
             55                  60                  65
```

-continued

| | |
|---|---|
| tgt gca aca ccg tcg aaa gtg tca tgc gga aaa ttc tcg gac tgc tgg<br>Cys Ala Thr Pro Ser Lys Val Ser Cys Gly Lys Phe Ser Asp Cys Trp<br>            70                        75                        80 | 297 |
| aac aca gag ggg agc tac gac tgc gtg tgc agc ccg gga tat gag cct<br>Asn Thr Glu Gly Ser Tyr Asp Cys Val Cys Ser Pro Gly Tyr Glu Pro<br>            85                        90                        95 | 345 |
| gtt tct ggg aca aaa aca ttc aag aat gag agc gag aac acc tgt caa<br>Val Ser Gly Thr Lys Thr Phe Lys Asn Glu Ser Glu Asn Thr Cys Gln<br>100                       105                    110               115 | 393 |
| gat gtg gac gaa tgt cag cag aac cca agg ctc tgt aaa agc tac ggc<br>Asp Val Asp Glu Cys Gln Gln Asn Pro Arg Leu Cys Lys Ser Tyr Gly<br>           120                     125                    130 | 441 |
| acc tgc gtc aac acc ctt ggc agc tat acc tgc cag tgc ctg cct ggc<br>Thr Cys Val Asn Thr Leu Gly Ser Tyr Thr Cys Gln Cys Leu Pro Gly<br>               135                     140                   145 | 489 |
| ttc aag ttc ata cct gag gat ccg aag gtc tgc aca gat gtg aat gaa<br>Phe Lys Phe Ile Pro Glu Asp Pro Lys Val Cys Thr Asp Val Asn Glu<br>               150                     155                    160 | 537 |
| tgc acc tcc gga caa aat ccg tgc cac agc tcc acc cac tgc ctc aac<br>Cys Thr Ser Gly Gln Asn Pro Cys His Ser Ser Thr His Cys Leu Asn<br>165                       170                    175 | 585 |
| aac gtg ggc agc tat cag tgt cgc tgc cga ccg ggc tgg caa ccg att<br>Asn Val Gly Ser Tyr Gln Cys Arg Cys Arg Pro Gly Trp Gln Pro Ile<br>180                       185                    190               195 | 633 |
| ccg ggg tcc ccc aat ggc cca aac aat acc gtc tgt gaa gat gtg gac<br>Pro Gly Ser Pro Asn Gly Pro Asn Asn Thr Val Cys Glu Asp Val Asp<br>                    200                     205                   210 | 681 |
| gag tgc agc tcc ggg cag cat cag tgt gac agc tcc acc gtc tgc ttc<br>Glu Cys Ser Ser Gly Gln His Gln Cys Asp Ser Ser Thr Val Cys Phe<br>               215                     220                   225 | 729 |
| aac acc gtg ggt tca tac agc tgc cgc tgc cgc cca ggc tgg aag ccc<br>Asn Thr Val Gly Ser Tyr Ser Cys Arg Cys Arg Pro Gly Trp Lys Pro<br>                 230                     235                   240 | 777 |
| aga cac gga atc ccg aat aac caa aag gac act gtc tgt gaa gat atg<br>Arg His Gly Ile Pro Asn Asn Gln Lys Asp Thr Val Cys Glu Asp Met<br>           245                     250                    255 | 825 |
| act ttc tcc acc tgg acc ccg ccc cct gga gtc cac agc cag acg ctt<br>Thr Phe Ser Thr Trp Thr Pro Pro Pro Gly Val His Ser Gln Thr Leu<br>260                       265                    270               275 | 873 |
| tcc cga ttc ttc gac aaa gtc cag gac ctg ggc aga gac tcc aag aca<br>Ser Arg Phe Phe Asp Lys Val Gln Asp Leu Gly Arg Asp Ser Lys Thr<br>                    280                     285                   290 | 921 |
| agc tca gcc gag gtc acc atc cag aat gtc atc aaa ttg gtg gat gaa<br>Ser Ser Ala Glu Val Thr Ile Gln Asn Val Ile Lys Leu Val Asp Glu<br>               295                     300                   305 | 969 |
| ctg atg gaa gct cct gga gac gta gag gcc ctg gcg cca cct gtc cgg<br>Leu Met Glu Ala Pro Gly Asp Val Glu Ala Leu Ala Pro Pro Val Arg<br>310                       315                    320 | 1017 |
| cac ctc ata gcc acc cag ctg ctc tca aac ctt gaa gat atc atg agg<br>His Leu Ile Ala Thr Gln Leu Leu Ser Asn Leu Glu Asp Ile Met Arg<br>           325                     330                    335 | 1065 |
| atc ctg gcc aag agc ctg cct aaa ggc ccc ttc acc tac att tcc cct<br>Ile Leu Ala Lys Ser Leu Pro Lys Gly Pro Phe Thr Tyr Ile Ser Pro<br>340                       345                    350               355 | 1113 |
| tcg aac aca gag ctg acc ctg atg atc cag gag cgg ggg gac aag aac<br>Ser Asn Thr Glu Leu Thr Leu Met Ile Gln Glu Arg Gly Asp Lys Asn<br>                    360                     365                   370 | 1161 |
| gtc act atg ggt cag agc agc gca cgc atg aag ctg aat tgg gct gtg<br>Val Thr Met Gly Gln Ser Ser Ala Arg Met Lys Leu Asn Trp Ala Val<br>               375                     380                   385 | 1209 |

```
gca gct gga gcc gag gat cca ggc ccc gcc gtg gcg ggc atc ctc tcc    1257
Ala Ala Gly Ala Glu Asp Pro Gly Pro Ala Val Ala Gly Ile Leu Ser
        390                 395                 400 atc cag aac atg acg aca ttg ctg gcc aat gcc tcc ttg aac ctg cat    1305
Ile Gln Asn Met Thr Thr Leu Leu Ala Asn Ala Ser Leu Asn Leu His
    405                 410                 415 tcc aag aag caa gcc gaa ctg gag gag ata tat gaa agc agc atc cgt    1353
Ser Lys Lys Gln Ala Glu Leu Glu Glu Ile Tyr Glu Ser Ser Ile Arg
420                 425                 430                 435 ggt gtc caa ctc aga cgc ctc tct gcc gtc aac tcc atc ttt ctg agc    1401
Gly Val Gln Leu Arg Arg Leu Ser Ala Val Asn Ser Ile Phe Leu Ser
                440                 445                 450 cac aac aac acc aag gaa ctc aac tcc ccc atc ctt ttc gcc ttc tcc    1449
His Asn Asn Thr Lys Glu Leu Asn Ser Pro Ile Leu Phe Ala Phe Ser
            455                 460                 465 cac ctt gag tcc tcc gat ggg gag gcg gga aga gac cct cct gcc aag    1497
His Leu Glu Ser Ser Asp Gly Glu Ala Gly Arg Asp Pro Pro Ala Lys
        470                 475                 480 gac gtg atg cct ggg cca cgg cag gag ctg ctc tgt gcc ttc tgg aag    1545
Asp Val Met Pro Gly Pro Arg Gln Glu Leu Leu Cys Ala Phe Trp Lys
    485                 490                 495 agt gac agc gac agg gga ggg cac tgg gcc acc gag ggc tgc cag gtg    1593
Ser Asp Ser Asp Arg Gly Gly His Trp Ala Thr Glu Gly Cys Gln Val
500                 505                 510                 515 ctg ggc agc aag aac ggc agc acc acc tgc caa tgc agc cac ctg agc    1641
Leu Gly Ser Lys Asn Gly Ser Thr Thr Cys Gln Cys Ser His Leu Ser
                520                 525                 530 agc ttt gcg atc ctt atg gct cat tat gac gtg gag gac tgg aag ctg    1689
Ser Phe Ala Ile Leu Met Ala His Tyr Asp Val Glu Asp Trp Lys Leu
            535                 540                 545 acc ctg atc acc agg gtg gga ctg gcg ctg tca ctc ttc tgc ctg ctg    1737
Thr Leu Ile Thr Arg Val Gly Leu Ala Leu Ser Leu Phe Cys Leu Leu
        550                 555                 560 ctg tgc atc ctc act ttc ctg ctg gtg cgg ccc atc cag ggc tcg cgc    1785
Leu Cys Ile Leu Thr Phe Leu Leu Val Arg Pro Ile Gln Gly Ser Arg
    565                 570                 575 acc acc ata cac ctg cac ctc tgc atc tgc ctc ttc gtg ggc tcc acc    1833
Thr Thr Ile His Leu His Leu Cys Ile Cys Leu Phe Val Gly Ser Thr
580                 585                 590                 595 atc ttc ctg gcc ggc atc gag aac gaa ggc ggc cag gtg ggg ctg cgc    1881
Ile Phe Leu Ala Gly Ile Glu Asn Glu Gly Gly Gln Val Gly Leu Arg
                600                 605                 610 tgc cgc ctg gtg gcc ggg ctg ctg cac tac tgt ttc ctg gcc gcc ttc    1929
Cys Arg Leu Val Ala Gly Leu Leu His Tyr Cys Phe Leu Ala Ala Phe
            615                 620                 625 tgc tgg atg agc ctc gaa ggc ctg gag ctc tac ttt ctt gtg gtg cgc    1977
Cys Trp Met Ser Leu Glu Gly Leu Glu Leu Tyr Phe Leu Val Val Arg
        630                 635                 640 gtg ttc caa ggc cag ggc ctg agt acg cgc tgg ctc tgc ctg atc ggc    2025
Val Phe Gln Gly Gln Gly Leu Ser Thr Arg Trp Leu Cys Leu Ile Gly
    645                 650                 655 tat ggc gtg ccc ctg ctc atc gtg ggc gtc tcg gct gcc atc tac agc    2073
Tyr Gly Val Pro Leu Leu Ile Val Gly Val Ser Ala Ala Ile Tyr Ser
660                 665                 670                 675 aag ggc tac ggc cgc ccc aga tac tgc tgg ttg gac ttt gag cag ggc    2121
Lys Gly Tyr Gly Arg Pro Arg Tyr Cys Trp Leu Asp Phe Glu Gln Gly
                680                 685                 690 ttc ctc tgg agc ttc ttg gga cct gtg acc ttc atc att ttg tgc aat    2169
Phe Leu Trp Ser Phe Leu Gly Pro Val Thr Phe Ile Ile Leu Cys Asn
```

|     |     |     |     |     |     |     |     |     |     |     |     |     |     |     |     |      |
| --- | --- | --- | --- | --- | --- | --- | --- | --- | --- | --- | --- | --- | --- | --- | --- | ---- |
|     |     |     |     |     | 695 |     |     |     |     | 700 |     |     |     |     | 705 |      |
| gct | gtc | att | ttc | gtg | act | acc | gtc | tgg | aag | ctc | act | cag | aag | ttt | tct | 2217 |
| Ala | Val | Ile | Phe | Val | Thr | Thr | Val | Trp | Lys | Leu | Thr | Gln | Lys | Phe | Ser |      |
|     |     |     | 710 |     |     |     |     | 715 |     |     |     |     | 720 |     |     |      |
| gaa | atc | aat | cca | gac | atg | aag | aaa | tta | aag | aag | gcg | agg | gcg | ctg | acc | 2265 |
| Glu | Ile | Asn | Pro | Asp | Met | Lys | Lys | Leu | Lys | Lys | Ala | Arg | Ala | Leu | Thr |      |
|     | 725 |     |     |     |     | 730 |     |     |     |     | 735 |     |     |     |     |      |
| atc | acg | gcc | atc | gcg | cag | ctc | ttc | ctg | ttg | ggc | tgc | acc | tgg | gtc | ttt | 2313 |
| Ile | Thr | Ala | Ile | Ala | Gln | Leu | Phe | Leu | Leu | Gly | Cys | Thr | Trp | Val | Phe |      |
| 740 |     |     |     |     | 745 |     |     |     |     | 750 |     |     |     |     | 755 |      |
| ggc | ctg | ttc | atc | ttc | gac | gat | cgg | agc | ttg | gtg | ctg | acc | tat | gtg | ttt | 2361 |
| Gly | Leu | Phe | Ile | Phe | Asp | Asp | Arg | Ser | Leu | Val | Leu | Thr | Tyr | Val | Phe |      |
|     |     |     |     | 760 |     |     |     |     | 765 |     |     |     |     | 770 |     |      |
| acc | atc | ctc | aac | tgc | ctg | cag | ggc | gcc | ttc | ctc | tac | ctg | ctg | cac | tgc | 2409 |
| Thr | Ile | Leu | Asn | Cys | Leu | Gln | Gly | Ala | Phe | Leu | Tyr | Leu | Leu | His | Cys |      |
|     |     |     |     | 775 |     |     |     |     | 780 |     |     |     |     | 785 |     |      |
| ctg | ctc | aac | aag | aag | gtt | cgg | gaa | gaa | tac | cgg | aag | tgg | gcc | tgc | cta | 2457 |
| Leu | Leu | Asn | Lys | Lys | Val | Arg | Glu | Glu | Tyr | Arg | Lys | Trp | Ala | Cys | Leu |      |
|     |     |     | 790 |     |     |     |     | 795 |     |     |     |     | 800 |     |     |      |
| gtt | gct | ggg | ggg | agc | aag | tac | tca | gaa | ttc | acc | tcc | acc | acg | tct | ggc | 2505 |
| Val | Ala | Gly | Gly | Ser | Lys | Tyr | Ser | Glu | Phe | Thr | Ser | Thr | Thr | Ser | Gly |      |
|     |     | 805 |     |     |     |     | 810 |     |     |     |     | 815 |     |     |     |      |
| act | ggc | cac | aat | cag | acc | cgg | gcc | ctc | agg | gca | tca | gag | tcc | ggc | ata | 2553 |
| Thr | Gly | His | Asn | Gln | Thr | Arg | Ala | Leu | Arg | Ala | Ser | Glu | Ser | Gly | Ile |      |
| 820 |     |     |     |     | 825 |     |     |     |     | 830 |     |     |     |     | 835 |      |

| | |
|---|---|
| tgaaggcgca tggttctgga cggcccagca gctcctgtgg ccacagcagc tttgtacacg | 2613 |
| aagaccatcc atcctccctt cgtccaccac tctactccct ccaccctccc tccctgatcc | 2673 |
| cgtgtgccac caggagggag tggcagctat agtctggcac caaagtccag gacacccagt | 2733 |
| ggggtggagt cggagccact ggtcctgctg ctggctgcct ctctgctcca ccttgtgacc | 2793 |
| cagggtgggg acaggggctg gcccagggct gcaatgcagc atgttgccct ggcacctgtg | 2853 |
| gccagtactc gggacagact aagggcgctt gtcccatcct ggacttttcc tctcatgtct | 2913 |
| ttgctgcaga actgaagaga ctaggcgctg ggctcagct tccctcttaa gctaagactg | 2973 |
| atgtcagagg ccccatggcg aggccccttg gggccactgc ctgaggctca cggtacagag | 3033 |
| gcctgccctg cctggccggg caggaggttc tcactgttgt gaaggttgta gacgttgtgt | 3093 |
| aatgtgtttt tatctgttaa aatttttcag tgttgacact taaaattaaa cacatgcata | 3153 |
| cag | 3156 |

<210> SEQ ID NO 12
<211> LENGTH: 835
<212> TYPE: PRT
<213> ORGANISM: Homo sapiens

<400> SEQUENCE: 12

Met Gly Gly Arg Val Phe Leu Ala Phe Cys Val Trp Leu Thr Leu Pro
 1               5                  10                  15

Gly Ala Glu Thr Gln Asp Ser Arg Gly Cys Ala Arg Trp Cys Pro Gln
             20                  25                  30

Asn Ser Ser Cys Val Asn Ala Thr Ala Cys Arg Cys Asn Pro Gly Phe
         35                  40                  45

Ser Ser Phe Ser Glu Ile Ile Thr Thr Pro Thr Glu Thr Cys Asp Asp
     50                  55                  60

Ile Asn Glu Cys Ala Thr Pro Ser Lys Val Ser Cys Gly Lys Phe Ser
 65                  70                  75                  80

-continued

```
Asp Cys Trp Asn Thr Glu Gly Ser Tyr Asp Cys Val Cys Ser Pro Gly
                 85                   90                   95

Tyr Glu Pro Val Ser Gly Thr Lys Thr Phe Lys Asn Glu Ser Glu Asn
            100                 105                 110

Thr Cys Gln Asp Val Asp Glu Cys Gln Gln Asn Pro Arg Leu Cys Lys
        115                 120                 125

Ser Tyr Gly Thr Cys Val Asn Thr Leu Gly Ser Tyr Thr Cys Gln Cys
    130                 135                 140

Leu Pro Gly Phe Lys Phe Ile Pro Glu Asp Pro Lys Val Cys Thr Asp
145                 150                 155                 160

Val Asn Glu Cys Thr Ser Gly Gln Asn Pro Cys His Ser Ser Thr His
                165                 170                 175

Cys Leu Asn Asn Val Gly Ser Tyr Gln Cys Arg Cys Arg Pro Gly Trp
            180                 185                 190

Gln Pro Ile Pro Gly Ser Pro Asn Gly Pro Asn Asn Thr Val Cys Glu
        195                 200                 205

Asp Val Asp Glu Cys Ser Ser Gly Gln His Gln Cys Asp Ser Ser Thr
    210                 215                 220

Val Cys Phe Asn Thr Val Gly Ser Tyr Ser Cys Arg Cys Arg Pro Gly
225                 230                 235                 240

Trp Lys Pro Arg His Gly Ile Pro Asn Asn Gln Lys Asp Thr Val Cys
                245                 250                 255

Glu Asp Met Thr Phe Ser Thr Trp Thr Pro Pro Gly Val His Ser
            260                 265                 270

Gln Thr Leu Ser Arg Phe Phe Asp Lys Val Gln Asp Leu Gly Arg Asp
        275                 280                 285

Ser Lys Thr Ser Ser Ala Glu Val Thr Ile Gln Asn Val Ile Lys Leu
    290                 295                 300

Val Asp Glu Leu Met Glu Ala Pro Gly Asp Val Glu Ala Leu Ala Pro
305                 310                 315                 320

Pro Val Arg His Leu Ile Ala Thr Gln Leu Leu Ser Asn Leu Glu Asp
                325                 330                 335

Ile Met Arg Ile Leu Ala Lys Ser Leu Pro Lys Gly Pro Phe Thr Tyr
            340                 345                 350

Ile Ser Pro Ser Asn Thr Glu Leu Thr Leu Met Ile Gln Glu Arg Gly
        355                 360                 365

Asp Lys Asn Val Thr Met Gly Gln Ser Ser Ala Arg Met Lys Leu Asn
    370                 375                 380

Trp Ala Val Ala Ala Gly Ala Glu Asp Pro Gly Pro Ala Val Ala Gly
385                 390                 395                 400

Ile Leu Ser Ile Gln Asn Met Thr Thr Leu Leu Ala Asn Ala Ser Leu
                405                 410                 415

Asn Leu His Ser Lys Lys Gln Ala Glu Leu Glu Glu Ile Tyr Glu Ser
            420                 425                 430

Ser Ile Arg Gly Val Gln Leu Arg Arg Leu Ser Ala Val Asn Ser Ile
        435                 440                 445

Phe Leu Ser His Asn Asn Thr Lys Glu Leu Asn Ser Pro Ile Leu Phe
    450                 455                 460

Ala Phe Ser His Leu Glu Ser Ser Asp Gly Ala Gly Arg Asp Pro
465                 470                 475                 480

Pro Ala Lys Asp Val Met Pro Gly Pro Arg Gln Glu Leu Leu Cys Ala
                485                 490                 495

Phe Trp Lys Ser Asp Ser Asp Arg Gly Gly His Trp Ala Thr Glu Gly
```

```
             500                 505                 510
Cys Gln Val Leu Gly Ser Lys Asn Gly Ser Thr Thr Cys Gln Cys Ser
            515                 520                 525

His Leu Ser Ser Phe Ala Ile Leu Met Ala His Tyr Asp Val Glu Asp
    530                 535                 540

Trp Lys Leu Thr Leu Ile Thr Arg Val Gly Leu Ala Leu Ser Leu Phe
545                 550                 555                 560

Cys Leu Leu Cys Ile Leu Thr Phe Leu Leu Val Arg Pro Ile Gln
                565                 570                 575

Gly Ser Arg Thr Thr Ile His Leu His Leu Cys Ile Cys Leu Phe Val
            580                 585                 590

Gly Ser Thr Ile Phe Leu Ala Gly Ile Glu Asn Glu Gly Gly Gln Val
        595                 600                 605

Gly Leu Arg Cys Arg Leu Val Ala Gly Leu Leu His Tyr Cys Phe Leu
    610                 615                 620

Ala Ala Phe Cys Trp Met Ser Leu Glu Gly Leu Glu Leu Tyr Phe Leu
625                 630                 635                 640

Val Val Arg Val Phe Gln Gly Gln Gly Leu Ser Thr Arg Trp Leu Cys
                645                 650                 655

Leu Ile Gly Tyr Gly Val Pro Leu Leu Ile Val Gly Val Ser Ala Ala
            660                 665                 670

Ile Tyr Ser Lys Gly Tyr Gly Arg Pro Arg Tyr Cys Trp Leu Asp Phe
        675                 680                 685

Glu Gln Gly Phe Leu Trp Ser Phe Leu Gly Pro Val Thr Phe Ile Ile
    690                 695                 700

Leu Cys Asn Ala Val Ile Phe Val Thr Thr Val Trp Lys Leu Thr Gln
705                 710                 715                 720

Lys Phe Ser Glu Ile Asn Pro Asp Met Lys Lys Leu Lys Lys Ala Arg
                725                 730                 735

Ala Leu Thr Ile Thr Ala Ile Ala Gln Leu Phe Leu Leu Gly Cys Thr
            740                 745                 750

Trp Val Phe Gly Leu Phe Ile Phe Asp Asp Arg Ser Leu Val Leu Thr
        755                 760                 765

Tyr Val Phe Thr Ile Leu Asn Cys Leu Gln Gly Ala Phe Leu Tyr Leu
    770                 775                 780

Leu His Cys Leu Leu Asn Lys Lys Val Arg Glu Glu Tyr Arg Lys Trp
785                 790                 795                 800

Ala Cys Leu Val Ala Gly Gly Ser Lys Tyr Ser Glu Phe Thr Ser Thr
                805                 810                 815

Thr Ser Gly Thr Gly His Asn Gln Thr Arg Ala Leu Arg Ala Ser Glu
            820                 825                 830

Ser Gly Ile
        835

<210> SEQ ID NO 13
<211> LENGTH: 867
<212> TYPE: DNA
<213> ORGANISM: Homo sapiens

<400> SEQUENCE: 13
tttagaacct gaggccttct gtatcacgcg tgtggagttt cagctgctat tgactataag    60
agctatggaa cagaaaaagc ttgctggctt catgttgata actactttat atggagcttc   120
attggacctg ttaccttcat tattctgcta aatattatct tcttggtgat cacattgtgc   180
```

-continued

```
aaaatggtga agcattcaaa cactttgaaa ccagattcta gcaggttgga aaacattaag    240
tcttggggtg cttggcgctt tcgctcttct gtgtcttctt ggcctcacct gggtcctttg    300
gggttgcttt ttattaatga gggagactat tgtggatggg catatctctt tcacttatat    360
ttaattgctt tccgggggag tgttccattt tccatctttc cactgtgctc tccaaaagga    420
agtaatgatc tatatcatat atcttgatct cagcttcaaa attgctactt agctaggtat    480
atatatagta gaagatttat agtaatcaac tatctcttct ctcctagtaa gtactaatcg    540
aattcggcac gagaatcctc gagttttttt tttttttttt tttatttagt tccataaatt    600
aatattctat ttactctatc attaatacaa tgaaagttat aattaaaata taatagttat    660
cggcactaaa ttctattgca ggatattcat tgcaggccta tgcaggataa tagcacctat    720
gccgcctatg caaggcaagg atgtcctcaa tgaaggagac acgctcctga actcaagggc    780
aatgaaggca cgctcgcgca cgctcaggat aactcaggga tagatcaatt aagggtaaat    840
cggtaaatca ggctccaaaa gggaaaa                                       867
```

<210> SEQ ID NO 14
<211> LENGTH: 20
<212> TYPE: DNA
<213> ORGANISM: Artificial Sequence
<220> FEATURE:
<223> OTHER INFORMATION: Description of Artificial Sequence: primer
<400> SEQUENCE: 14

```
tggagtttca gctgctattg                                                20
```

<210> SEQ ID NO 15
<211> LENGTH: 20
<212> TYPE: DNA
<213> ORGANISM: Artificial Sequence
<220> FEATURE:
<223> OTHER INFORMATION: Description of Artificial Sequence: primer
<400> SEQUENCE: 15

```
tgcccatcca caatagtctc                                                20
```

<210> SEQ ID NO 16
<211> LENGTH: 3165
<212> TYPE: DNA
<213> ORGANISM: Homo sapiens
<400> SEQUENCE: 16

```
aagaaagagt ccagccgagt atacctgact gatcctgtgc tttttaccct gccacacatt     60
gatcctgaca attatttcaa tgcaaactgc tccttctgga actactcaga gagaactatg    120
atgggatatt ggtctaccca gggctgcaag ctggttgaca ctaataaaac tcgaacaacg    180
tgtgcatgca gccacctaac caattttgca attctcatgg cccacaggga aattgcatat    240
aaagatggcg ttcatgaatt acttcttaca gtcatcacct gggtgggaat tgtcatttcc    300
cttgtttgcc tggctatctg catcttcacc ttctgctttt tccgtggcct acagagtgac    360
cgaaatacta ttcacaagaa cctttgtatc aaccttttca ttgctgaatt tattttccta    420
ataggcattg ataagacaaa atatgcgatt gcatgcccaa tatttgcagg acttctacac    480
ttttttcttt tggcagcttt tgcttggatg tgcctagaag gtgtgcagct ctacctaatg    540
ttagttgaag ttttttgaaag tgaatattca aggaaaaata ttactatgtt gctggttact    600
tgtttcctgc cacagtggtt ggagtttcag ctgctattga ctataagagc tatggaacag    660
aaaaagcttg ctggcttcat gttgataact actttatatg gagcttcatt ggacctgtta    720
```

```
ccttcattat tctgctaaat attatcttct tggtgatcac attgtgcaaa atggtgaagc    780
attcaaacac tttgaaacca gattctagca ggttggaaaa cattaagtct tgggtgcttg    840
gcgctttcgc tcttctgtgt cttcttggcc tcacctggtc ctttgggttg cttttttatta  900 atgaggagac tattgtgatg gcatatctct tcactatatt taatgctttc cagggagtgt   960
tcattttcat ctttcactgt gctctccaaa agaaagtacg aaaagaatat ggcaagtgct  1020
tcagacactc atactgctgt ggaggcctcc caactgagag tccccacagt tcagtgaagg  1080
catcaaccac cagaaccagt gctcgctatt cctctggcac acaggacatt cactgaacaa  1140
tgccagggat acaagtgcca tggatactct accgctaaat ggtaatttta acaacagcta  1200
ctcgctgcac aagggtgact ataatgacag cgtgcaagtt gtggactgtg gactaagtct  1260
gaatgatact gcttttgaga aatgatcat ttcagaatta gtgcacaaca acttacgggg   1320
cagcagcaag actcacaacc tcgagctcac gctaccagtc aaacctgtga ttggaggtag  1380
cagcagtgaa gatgatgcta ttgtggcaga tgcttcatct ttaatgcaca gcgacaaccc  1440
agggctggag ctccatcaca aagaactcga ggcaccactt attcctcagc ggactcactc  1500
ccttctgtac caaccccaga agaaagtgaa gtccgaggga actgacagct atgtctccca  1560
actgacagca gaggctgaag atcacctaca gtcccccaac agagactctc tttatacaag  1620
catgcccaat cttagagact ctccctatcc ggagagcagc cctgacatgg aagaagacct  1680
ctctccctcc aggaggagtg agaatgagga catttactat aaaagcatgc caaatcttgg  1740
agctggccat cagcttcaga tgtgctacca gatcagcagg ggcaatagtg atggttatat  1800
aatccccatt aacaagaag ggtgtattcc agaaggagat gttagagaag acaaatgca    1860 gctggttaca agtctttaat catacagcta aggaattcca agggccacat gcgagtatta  1920
ataaataaag acaccattgg cctgacgcag ctccctcaaa ctctgcttga agagatgact  1980
cttgacctgt ggttctctgg tgtaaaaaag atgactgaac cttgcagttc tgtgaatttt  2040
tataaaacat acaaaaactt tgtatataca cagagtatac taaagtgaat tatttgttac  2100
aaagaaaaga gatgccagcc aggtattta agattctgct gctgtttaga gaaattgtga   2160
aacaagcaaa acaaaacttt ccagccattt tactgcagca gtctgtgaac taaatttgta  2220
aatatggctg caccatttttt gtaggcctgc attgtattat atacaagacg taggctttaa  2280
aatcctgtgg gacaaattta ctgtacctta ctattcctga caagacttgg aaaagcagga  2340
gagatattct gcatcagttt gcagttcact gcaaatcttt tacattaagg caaagattga  2400
aaacatgctt aaccactagc aatcaagcca caggccttat ttcatatgtt tcctcaactg  2460
tacaatgaac tattctcatg aaaaatggct aaagaaatta tattttgttc tattgctagg  2520
gtaaaataaa tacatttgtg tccaactgaa atataattgt cattaaaata attttaaaga  2580
gtgaagaaaa tattgtgaaa agctcttggt tgcacatgtt atgaaatgtt ttttcttaca  2640
ctttgtcatg gtaagttcta ctcatttca cttcttttcc actgtataca gtgttctgct   2700
ttgacaaagt tagtctttat tacttacatt taaatttctt attgccaaaa gaacgtgttt  2760
tatggggaga acaaactct ttgaagccag ttatgtcatg ccttgcacaa agtgatgaa    2820 atctagaaaa gattgtgtgt cacccctgtt tattcttgaa cagagggcaa agagggcact  2880
gggcacttct cacaaacttt ctagtgaaca aaaggtgcct attctttttt aaaaaaataa  2940
aataaaacat aaatattact cttccatatt ccttctgcct atatttagta attaatttat  3000
tttatgataa agttctaatg aaatgtaaat tgtttcagca aaattctgct ttttttcat   3060
```

-continued

```
ccctttgtgt aaacctgtta ataatgagcc catcactaat atccagtgta aagtttaaca    3120
cggtttgaca gtaaataaat gtgaattttt tcaaaaaaaa aaaa                     3165
```

<210> SEQ ID NO 17
<211> LENGTH: 25
<212> TYPE: DNA
<213> ORGANISM: Artificial Sequence
<220> FEATURE:
<223> OTHER INFORMATION: Description of Artificial Sequence: primer

<400> SEQUENCE: 17

```
gtgatccagc tacagttgtg ctcat                                          25
```

<210> SEQ ID NO 18
<211> LENGTH: 26
<212> TYPE: DNA
<213> ORGANISM: Artificial Sequence
<220> FEATURE:
<223> OTHER INFORMATION: Description of Artificial Sequence: primer

<400> SEQUENCE: 18

```
ctaatgcttc acagaatctc tctggc                                         26
```

<210> SEQ ID NO 19
<211> LENGTH: 5693
<212> TYPE: DNA
<213> ORGANISM: Rattus rattus
<220> FEATURE:
<221> NAME/KEY: CDS
<222> LOCATION: (425)..(4822)

<400> SEQUENCE: 19

```
gagctctgac gccgccccg cccctccgcc tccacgcctc gctcccggg aggggcgcag      60 acccgcgcgc ccggggccgg ggccgcctcc ggagcgccgc gatccgcctt ttctttcctt    120 tttttccct tcccttcttc ccttttaaat tttggttggt ggcggcagtg ctgggccgga    180
ggaaagaagg gacacggagt cctccctcgc tcagccaccc cctccccgct tcccctggg    240 ccgggctccg ggagatgtgc cggcgggg gcccggcttc gcggagccgc gggaggagcg    300
cgcacggccg accccgaagc gccgctggac aggctggtgg gccaggcctt ggtaccctgg    360
tgatgcgggg caaggccccc cccacagtcc gctgagatca ccgtgcccgc ccctggcctt    420
```

```
cgcc atg gcc cgc ttg gct gca gca ctc tgg agt ctc tgt gtg acg act    469
     Met Ala Arg Leu Ala Ala Ala Leu Trp Ser Leu Cys Val Thr Thr
      1               5                  10                  15 gtc ctc gtc acc tct gct acc caa ggc ctg agc cgg gct gga ctc cca    517
Val Leu Val Thr Ser Ala Thr Gln Gly Leu Ser Arg Ala Gly Leu Pro
            20                  25                  30 ttt gga ttg atg cgc cgg gag cta gca tgc gaa ggc tac ccc att gag    565
Phe Gly Leu Met Arg Arg Glu Leu Ala Cys Glu Gly Tyr Pro Ile Glu
        35                  40                  45 ctg cgg tgc ccg ggc agt gac gtc atc atg gtg gag aat gca aac tat    613
Leu Arg Cys Pro Gly Ser Asp Val Ile Met Val Glu Asn Ala Asn Tyr
    50                  55                  60 ggg cgc aca gat gac aag atc tgc gat gcc gac cct ttt cag atg gag    661
Gly Arg Thr Asp Asp Lys Ile Cys Asp Ala Asp Pro Phe Gln Met Glu
65                  70                  75 aac gtg cag tgc tac ctg cct gac gcc ttc aaa atc atg tca cag aga    709
Asn Val Gln Cys Tyr Leu Pro Asp Ala Phe Lys Ile Met Ser Gln Arg
 80                  85                  90                  95 tgt aat aac cga acc cag tgt gtg gtg gtg gcc ggc tct gac gcc ttt    757
Cys Asn Asn Arg Thr Gln Cys Val Val Val Ala Gly Ser Asp Ala Phe
```

```
                    100                 105                 110
cct gac ccc tgt cct gga acc tac aag tac ctg gag gtg cag tac gac         805
Pro Asp Pro Cys Pro Gly Thr Tyr Lys Tyr Leu Glu Val Gln Tyr Asp
            115                 120                 125 tgt gtc cct tac atc ttc gtg tgc cca ggg aca ctg cag aag gtg ctg         853
Cys Val Pro Tyr Ile Phe Val Cys Pro Gly Thr Leu Gln Lys Val Leu
        130                 135                 140 gag ccc acc tcc aca cat gaa tcg gag cac cag tct ggc gca tgg tgc         901
Glu Pro Thr Ser Thr His Glu Ser Glu His Gln Ser Gly Ala Trp Cys
    145                 150                 155 aag gac cca ctg cag gca ggt gac cgt atc tac gtt atg ccc tgg atc         949
Lys Asp Pro Leu Gln Ala Gly Asp Arg Ile Tyr Val Met Pro Trp Ile
160                 165                 170                 175 ccc tac cgc acg gac aca ctg acc gag tat gct tcc tgg gag gac t at        997
Pro Tyr Arg Thr Asp Thr Leu Thr Glu Tyr Ala Ser Trp Glu Asp Tyr
                180                 185                 190 gtg gct gca cgc cac acc acc acg tac aga ctg ccc aac cgt gta gat         1045
Val Ala Ala Arg His Thr Thr Thr Tyr Arg Leu Pro Asn Arg Val Asp
            195                 200                 205 ggc act ggc ttt gtg gta tat gat ggt gcc gtc ttc tat aac aag gaa         1093
Gly Thr Gly Phe Val Val Tyr Asp Gly Ala Val Phe Tyr Asn Lys Glu
        210                 215                 220 cgt act cgc aac att gtc aaa tat gac ctg cgg acc cgc atc aag agc         1141
Arg Thr Arg Asn Ile Val Lys Tyr Asp Leu Arg Thr Arg Ile Lys Ser
    225                 230                 235 gga gaa aca gtc ata aac aca gcc aac tac cac gac acc tca cct tat         1189
Gly Glu Thr Val Ile Asn Thr Ala Asn Tyr His Asp Thr Ser Pro Tyr
240                 245                 250                 255 cgc tgg gga ggc aaa acc gac att gac ctg gca gtg gat gag aac ggg         1237
Arg Trp Gly Gly Lys Thr Asp Ile Asp Leu Ala Val Asp Glu Asn Gly
                260                 265                 270 ctg tgg gtc atc tat gcc acc gag ggg aac aac ggg cgt ctg gtg gtg         1285
Leu Trp Val Ile Tyr Ala Thr Glu Gly Asn Asn Gly Arg Leu Val Val
            275                 280                 285 agc cag ctc aac ccc tac aca ctg cgt ttc gag ggc acc tgg gaa aca         1333
Ser Gln Leu Asn Pro Tyr Thr Leu Arg Phe Glu Gly Thr Trp Glu Thr
        290                 295                 300 ggc tat gac aag cgc tca gcc tcc aat gcc ttc atg gtg tgt ggt gtc         1381
Gly Tyr Asp Lys Arg Ser Ala Ser Asn Ala Phe Met Val Cys Gly Val
    305                 310                 315 ctc tat gtg ctg cgc tct gtt tat gtg gat gac gac agt gag gca gca         1429
Leu Tyr Val Leu Arg Ser Val Tyr Val Asp Asp Asp Ser Glu Ala Ala
320                 325                 330                 335 ggc aac cgc gtg gac tat gcc ttt aac acc aat gca aac cga gag gag         1477
Gly Asn Arg Val Asp Tyr Ala Phe Asn Thr Asn Ala Asn Arg Glu Glu
                340                 345                 350 ccc gtc agt ctc gcc ttc ccc aac ccc tac cag ttt gta tct tct gtt         1525
Pro Val Ser Leu Ala Phe Pro Asn Pro Tyr Gln Phe Val Ser Ser Val
            355                 360                 365 gac tac aat ccc cgg gac aac cag ctg tat gtg tgg aac aac tat ttc         1573
Asp Tyr Asn Pro Arg Asp Asn Gln Leu Tyr Val Trp Asn Asn Tyr Phe
        370                 375                 380 gtg gtg cgc tac agc ctg gag ttt gga ccc cca gat ccc agt gct ggc         1621
Val Val Arg Tyr Ser Leu Glu Phe Gly Pro Pro Asp Pro Ser Ala Gly
    385                 390                 395 cca gcc act tcc cca cct ctc agt acc acc acc gct cgg cct acg             1669
Pro Ala Thr Ser Pro Pro Leu Ser Thr Thr Thr Ala Arg Pro Thr
400                 405                 410                 415 ccc ctc acc agc aca gcc tca cct gca gcc acc act cca ctc cgc cgg         1717
```

```
                                                          -continued

Pro Leu Thr Ser Thr Ala Ser Pro Ala Ala Thr Thr Pro Leu Arg Arg
                420             425             430 gcg ccc ctc acc acg cac cca gta ggt gcc atc aac cag ctg gga cct      1765
Ala Pro Leu Thr Thr His Pro Val Gly Ala Ile Asn Gln Leu Gly Pro
            435             440             445 gac ctg cct cca gcc aca gcc cca gca ccc agt acc cgg cgg cct cca      1813
Asp Leu Pro Pro Ala Thr Ala Pro Ala Pro Ser Thr Arg Arg Pro Pro
        450             455             460 gcc ccc aat ctg cat gtg tcc cct gag ctc ttc tgt gaa ccc cga gag      1861
Ala Pro Asn Leu His Val Ser Pro Glu Leu Phe Cys Glu Pro Arg Glu
465             470             475 gtc cgg cgg gtc cag tgg cca gct acc cag cag ggt atg ctg gta gag      1909
Val Arg Arg Val Gln Trp Pro Ala Thr Gln Gln Gly Met Leu Val Glu
480             485             490             495 aga cct tgc ccc aag gga act cga gga att gcc tcg ttc cag tgc ctc      1957
Arg Pro Cys Pro Lys Gly Thr Arg Gly Ile Ala Ser Phe Gln Cys Leu
                500             505             510 cca gct ctg ggg ctc tgg aat cct cgg ggc cct gac ctc agc aac tgc      2005
Pro Ala Leu Gly Leu Trp Asn Pro Arg Gly Pro Asp Leu Ser Asn Cys
            515             520             525 act tcc ccc tgg gtc aac caa gtc gcc cag aag atc aag agt gga gag      2053
Thr Ser Pro Trp Val Asn Gln Val Ala Gln Lys Ile Lys Ser Gly Glu
        530             535             540 aat gca gcc aac att gct agt gag ctg gcc cgc cac acg cgg ggc tcc      2101
Asn Ala Ala Asn Ile Ala Ser Glu Leu Ala Arg His Thr Arg Gly Ser
545             550             555 atc tat gct ggg gac gtg tcc tca tcg gtg aag ctg atg gag caa ctg      2149
Ile Tyr Ala Gly Asp Val Ser Ser Ser Val Lys Leu Met Glu Gln Leu
560             565             570             575 cta gat atc ctg gat gcc cag ctc cag gcc cta cgg ccc att gaa cga      2197
Leu Asp Ile Leu Asp Ala Gln Leu Gln Ala Leu Arg Pro Ile Glu Arg
                580             585             590 gag tca gct ggc aag aac tac aat aag atg cac aag cga gag aga acc      2245
Glu Ser Ala Gly Lys Asn Tyr Asn Lys Met His Lys Arg Glu Arg Thr
            595             600             605 tgc aag gac tat atc aag gct gtg gtg gag aca gtg gac aac ctg ctt      2293
Cys Lys Asp Tyr Ile Lys Ala Val Val Glu Thr Val Asp Asn Leu Leu
        610             615             620 cgg cca gag gca ctt gag tca tgg aaa gac atg aat gcc acc gaa cag      2341
Arg Pro Glu Ala Leu Glu Ser Trp Lys Asp Met Asn Ala Thr Glu Gln
625             630             635 gtc cat acg gcc acc atg ctc cta gat gtc tta gag gag ggt gcc ttc      2389
Val His Thr Ala Thr Met Leu Leu Asp Val Leu Glu Glu Gly Ala Phe
640             645             650             655 ctg ctg gcc gac aat gtc aga gaa cct gct cgc ttc ttg gct gcc aag      2437
Leu Leu Ala Asp Asn Val Arg Glu Pro Ala Arg Phe Leu Ala Ala Lys
                660             665             670 cag aat gtg gtc ctg gag gtc act gtc ctg agc aca gag ggt caa gtg      2485
Gln Asn Val Val Leu Glu Val Thr Val Leu Ser Thr Glu Gly Gln Val
            675             680             685 cag gag ttg gtg ttc ccc cag gag tat gcc agt gag agc tcc att cag      2533
Gln Glu Leu Val Phe Pro Gln Glu Tyr Ala Ser Glu Ser Ser Ile Gln
        690             695             700 ctg tcc gcc aac acc atc aag cag aac agc cgc aat ggt gtg gtg aag      2581
Leu Ser Ala Asn Thr Ile Lys Gln Asn Ser Arg Asn Gly Val Val Lys
705             710             715 gtt gtc ttc att ctc tac aac aac ctg ggc ctc ttc ttg tcc acg gag      2629
Val Val Phe Ile Leu Tyr Asn Asn Leu Gly Leu Phe Leu Ser Thr Glu
720             725             730             735
```

```
aat gcc aca gtg aag ctg gca ggt gag gca ggg acc ggt ggc cct gga    2677
Asn Ala Thr Val Lys Leu Ala Gly Glu Ala Gly Thr Gly Gly Pro Gly
            740                 745                 750 ggt gcc tcc ctg gtg gtt aac tca cag gtc atc gca gca tcc atc aat    2725
Gly Ala Ser Leu Val Val Asn Ser Gln Val Ile Ala Ala Ser Ile Asn
            755                 760                 765 aag gag tcc agc cgt gtc ttc ctc atg gac cct gtc atc ttt act gtg    2773
Lys Glu Ser Ser Arg Val Phe Leu Met Asp Pro Val Ile Phe Thr Val
            770                 775                 780 gcc cac ttg gag gcc aag aac cac ttc aat gca aac tgc tcc ttc tgg    2821
Ala His Leu Glu Ala Lys Asn His Phe Asn Ala Asn Cys Ser Phe Trp
            785                 790                 795 aac tac tca gag cgc tcc atg ctg ggc tac tgg tca acc cag ggc tgc    2869
Asn Tyr Ser Glu Arg Ser Met Leu Gly Tyr Trp Ser Thr Gln Gly Cys
800                 805                 810                 815 cga ctg gtg gag tcc aat aag acc cat acc aca tgt gcc tgc agc cac    2917
Arg Leu Val Glu Ser Asn Lys Thr His Thr Thr Cys Ala Cys Ser His
            820                 825                 830 ctc acc aac ttc gca gtg ctc atg gct cac cga gag atc tac caa ggc    2965
Leu Thr Asn Phe Ala Val Leu Met Ala His Arg Glu Ile Tyr Gln Gly
            835                 840                 845 cgt att aat gag ctg ttg ctg tca gtc atc acc tgg gtt ggc att gtc    3013
Arg Ile Asn Glu Leu Leu Leu Ser Val Ile Thr Trp Val Gly Ile Val
            850                 855                 860 atc tcc ctg gtc tgt ctg gct atc tgc atc tcc acc ttc tgc ttc ctg    3061
Ile Ser Leu Val Cys Leu Ala Ile Cys Ile Ser Thr Phe Cys Phe Leu
865                 870                 875 cgg ggc ctg cag acc gac cgc aac acc atc cac aag aac ctg tgc atc    3109
Arg Gly Leu Gln Thr Asp Arg Asn Thr Ile His Lys Asn Leu Cys Ile
880                 885                 890                 895 aac ctc ttc ctt gca gag ctg ctc ttc ctg gtt gga ata gac aaa act    3157
Asn Leu Phe Leu Ala Glu Leu Leu Phe Leu Val Gly Ile Asp Lys Thr
            900                 905                 910 cag tat gag gtc gcc tgc cct atc ttt gcg ggc ctg ctg cac tac ttc    3205
Gln Tyr Glu Val Ala Cys Pro Ile Phe Ala Gly Leu Leu His Tyr Phe
            915                 920                 925 ttc ctg gcc gcc ttc tcc tgg ctg tgc cta gag ggc gtg cac ctc tac    3253
Phe Leu Ala Ala Phe Ser Trp Leu Cys Leu Glu Gly Val His Leu Tyr
            930                 935                 940 ctc ctg ctg gtc gag gtg ttc gag agc gaa tat tca cgc acc aag tac    3301
Leu Leu Leu Val Glu Val Phe Glu Ser Glu Tyr Ser Arg Thr Lys Tyr
945                 950                 955 tat tac ctg ggc ggc tac tgc ttc cca gcc ctg gtg gta ggc atc gca    3349
Tyr Tyr Leu Gly Gly Tyr Cys Phe Pro Ala Leu Val Val Gly Ile Ala
960                 965                 970                 975 gcc gcc att gac tac cga agc tac ggc act gag aag gcc tgc tgg ctg    3397
Ala Ala Ile Asp Tyr Arg Ser Tyr Gly Thr Glu Lys Ala Cys Trp Leu
            980                 985                 990 agg gtg gat aac tat ttc atc tgg agc ttc att ggg ccc gtc tcc ttt    3445
Arg Val Asp Asn Tyr Phe Ile Trp Ser Phe Ile Gly Pro Val Ser Phe
            995                 1000                1005 gtt att gtg gtg aac ctg gtg ttc ctc atg gtg acc ctg cac aag atg    3493
Val Ile Val Val Asn Leu Val Phe Leu Met Val Thr Leu His Lys Met
            1010                1015                1020 atc cga agc tca tcc gtg ctc aag cct gac tcc agc cgc ctt gac aac    3541
Ile Arg Ser Ser Ser Val Leu Lys Pro Asp Ser Ser Arg Leu Asp Asn
            1025                1030                1035 atc aag tcc tgg gcg ctg ggt gcc att gca ctg ctc ttc ctg ctg ggc    3589
Ile Lys Ser Trp Ala Leu Gly Ala Ile Ala Leu Leu Phe Leu Leu Gly
1040                1045                1050                1055
```

```
ctc acc tgg gct ttc ggc ctc ctc ttc atc aac aag gag tca gta gta    3637
Leu Thr Trp Ala Phe Gly Leu Leu Phe Ile Asn Lys Glu Ser Val Val
            1060                1065                1070 atg gct tac ctc ttc aca acc ttc aac gcc ttc cag ggg gtc ttc atc    3685
Met Ala Tyr Leu Phe Thr Thr Phe Asn Ala Phe Gln Gly Val Phe Ile
        1075                1080                1085 ttt gtc ttt cac tgc gcc tta cag aaa aag gtg cac aag gag tac agc    3733
Phe Val Phe His Cys Ala Leu Gln Lys Lys Val His Lys Glu Tyr Ser
    1090                1095                1100 aag tgc ctg cgt cac tcc tac tgc tgc att cgc tcc cca cct ggg ggg    3781
Lys Cys Leu Arg His Ser Tyr Cys Cys Ile Arg Ser Pro Pro Gly Gly
1105                1110                1115 gct cac ggc tcc ctt aag acc tca gcc atg cga agt aac acc cgc tac    3829
Ala His Gly Ser Leu Lys Thr Ser Ala Met Arg Ser Asn Thr Arg Tyr
1120                1125                1130                1135 tac aca ggg acc cag agc cga atc cgg agg atg tgg aat gac acc gtg    3877
Tyr Thr Gly Thr Gln Ser Arg Ile Arg Arg Met Trp Asn Asp Thr Val
            1140                1145                1150 agg aag cag aca gag tcg tcc ttt atg gca ggg gac atc aac agc acc    3925
Arg Lys Gln Thr Glu Ser Ser Phe Met Ala Gly Asp Ile Asn Ser Thr
        1155                1160                1165 ccc acc ctg aac cga ggt acc atg ggg aac cac cta ctg acc aac cct    3973
Pro Thr Leu Asn Arg Gly Thr Met Gly Asn His Leu Leu Thr Asn Pro
    1170                1175                1180 gtg cta cag ccc cgt ggg ggc act agc cca tac aat aca ctc att gca    4021
Val Leu Gln Pro Arg Gly Gly Thr Ser Pro Tyr Asn Thr Leu Ile Ala
1185                1190                1195 gag tct gtg ggc ttc aat ccc tcc tcg ccc cca gtc ttc aac tcc cca    4069
Glu Ser Val Gly Phe Asn Pro Ser Ser Pro Pro Val Phe Asn Ser Pro
1200                1205                1210                1215 gga agc tac agg gaa cct aag cac ccc ttg ggc ggc cgg gaa gcc tgt    4117
Gly Ser Tyr Arg Glu Pro Lys His Pro Leu Gly Gly Arg Glu Ala Cys
            1220                1225                1230 ggc atg gac aca ctg ccc ctt aat ggc aac ttc aac aac agc tac tcc    4165
Gly Met Asp Thr Leu Pro Leu Asn Gly Asn Phe Asn Asn Ser Tyr Ser
        1235                1240                1245 ttg cga agt ggt gat ttc cct ccg ggg gat ggg ggt cct gag cca ccc    4213
Leu Arg Ser Gly Asp Phe Pro Pro Gly Asp Gly Gly Pro Glu Pro Pro
    1250                1255                1260 cga ggc cga aac cta gcg gat gct gcg gcc ttt gag aag atg atc atc    4261
Arg Gly Arg Asn Leu Ala Asp Ala Ala Ala Phe Glu Lys Met Ile Ile
1265                1270                1275 tca gag ctg gtg cac aac aac ctt cgg ggg gcc agt ggg ggc gcc aaa    4309
Ser Glu Leu Val His Asn Asn Leu Arg Gly Ala Ser Gly Gly Ala Lys
1280                1285                1290                1295 ggt cct cca cca gag cct cct gtg cca ccc gtg cca gga gtc agt gag    4357
Gly Pro Pro Pro Glu Pro Pro Val Pro Pro Val Pro Gly Val Ser Glu
            1300                1305                1310 gac gag gct ggt ggg cct ggg ggt gct gac cgg gct gag att gaa ctt    4405
Asp Glu Ala Gly Gly Pro Gly Gly Ala Asp Arg Ala Glu Ile Glu Leu
        1315                1320                1325 ctc tac aag gcc ctg gag gag cca ctg ctg ctg ccc cgg gcc cag tcg    4453
Leu Tyr Lys Ala Leu Glu Glu Pro Leu Leu Leu Pro Arg Ala Gln Ser
    1330                1335                1340 gtg ctg tac cag agt gat ctg gat gag tcg gag agc tgt acg gca gag    4501
Val Leu Tyr Gln Ser Asp Leu Asp Glu Ser Glu Ser Cys Thr Ala Glu
1345                1350                1355 gat ggg gcc acc agc cgg ccc ctc tcc tcc cct ccc ggc cgg gac tcc    4549
Asp Gly Ala Thr Ser Arg Pro Leu Ser Ser Pro Pro Gly Arg Asp Ser
```

```
                                                                -continued 1360           1365           1370           1375 ctc tat gcc agc ggg gcc aac ctg cgg gac tcg ccc tcc tac ccg gac        4597
Leu Tyr Ala Ser Gly Ala Asn Leu Arg Asp Ser Pro Ser Tyr Pro Asp
            1380                1385                1390 agc agc ccc gaa ggg cct aat gag gcc ctg ccc cct ccc cca cct gct        4645
Ser Ser Pro Glu Gly Pro Asn Glu Ala Leu Pro Pro Pro Pro Pro Ala
        1395                1400                1405 ccc cct ggg ccc cca gaa atc tac tac acc tct cgc ccg ccg gcc ctg        4693
Pro Pro Gly Pro Pro Glu Ile Tyr Tyr Thr Ser Arg Pro Pro Ala Leu
    1410                1415                1420 gtg gct cgg aat ccc cta cag ggc tac tac cag gtg cgg cgg ccc agc        4741
Val Ala Arg Asn Pro Leu Gln Gly Tyr Tyr Gln Val Arg Arg Pro Ser
1425                1430                1435 cat gag ggc tac ctg gca gcc ccc agc ctt gag ggg cca ggg ccc gat        4789
His Glu Gly Tyr Leu Ala Ala Pro Ser Leu Glu Gly Pro Gly Pro Asp
1440                1445                1450                1455 ggg gat ggg caa atg cag ttg gtc act agt ctc tgagggggcct catggaccag      4842
Gly Asp Gly Gln Met Gln Leu Val Thr Ser Leu
                1460                1465 aggcctggcc agggagggaa tccaggaggg gctctggtgg gagcagagac tgatggaggc       4902
agtggctggt gggccactct ctccaggtgc ccctctgcct gtgggcccca cagtcccctt       4962
ggggactatg acctgggccc caggtgccag ggttagtaga caggggtttcc accagccaca     5022 agccccagct tctttagggg agtgcattga ggagaagccc ccaggggccct aggagtgagg     5082 gagaagctgg taggtgtgac caacgtccaa agctccctcc ctttggaggg agaaagcaag      5142
ggataaggct tccctaggtg tacaggggtg gccacttttg aggtggccga agccttgcag      5202
gatacaccct atctgctgct catcttcttc gtccaccaga aaggagcagt gggacagatg      5262
gacaggtcct tccatgctac agttccttgc ttcttggaga ctgggcctaa catcctgaga     5322
gagcccaggc ccaggggatg gatggggttg tgagggctgg tggttaatgg tggaactttc     5382
tctgaagctc ctttctccct tgctattggt ccctatctcc cgagcaagcc tacccctaaac   5442 ccccagagtg cacccaatga ccccctccct tgggggtgact cctgatgaag cacaactccc    5502
cgcagggccc caacccactg cagtggccat atttgggcag ttcccagtcc tgtgggctgg    5562
gctatctggg gagcagatgt ggggtctggg gctccctgag gagtgggtcc tgggtttgga    5622
tctttcccta gggggtcctc ttaccctttct cttcctcccc tattgctgta aatatttcaa    5682
caaaatggaa a                                                          5693

<210> SEQ ID NO 20
<211> LENGTH: 1466
<212> TYPE: PRT
<213> ORGANISM: Rattus rattus

<400> SEQUENCE: 20

Met Ala Arg Leu Ala Ala Ala Leu Trp Ser Leu Cys Val Thr Thr Val
1               5                   10                  15

Leu Val Thr Ser Ala Thr Gln Gly Leu Ser Arg Ala Gly Leu Pro Phe
            20                  25                  30

Gly Leu Met Arg Arg Glu Leu Ala Cys Glu Gly Tyr Pro Ile Glu Leu
        35                  40                  45

Arg Cys Pro Gly Ser Asp Val Ile Met Val Glu Asn Ala Asn Tyr Gly
    50                  55                  60

Arg Thr Asp Asp Lys Ile Cys Asp Ala Asp Pro Phe Gln Met Glu Asn
65                  70                  75                  80
```

-continued

```
Val Gln Cys Tyr Leu Pro Asp Ala Phe Lys Ile Met Ser Gln Arg Cys
                85                  90                  95

Asn Asn Arg Thr Gln Cys Val Val Ala Gly Ser Asp Ala Phe Pro
            100                 105                 110

Asp Pro Cys Pro Gly Thr Tyr Lys Tyr Leu Glu Val Gln Tyr Asp Cys
        115                 120                 125

Val Pro Tyr Ile Phe Val Cys Pro Gly Thr Leu Gln Lys Val Leu Glu
    130                 135                 140

Pro Thr Ser Thr His Glu Ser Glu His Gln Ser Gly Ala Trp Cys Lys
145                 150                 155                 160

Asp Pro Leu Gln Ala Gly Asp Arg Ile Tyr Val Met Pro Trp Ile Pro
                165                 170                 175

Tyr Arg Thr Asp Thr Leu Thr Glu Tyr Ala Ser Trp Glu Asp Tyr Val
                180                 185                 190

Ala Ala Arg His Thr Thr Thr Tyr Arg Leu Pro Asn Arg Val Asp Gly
            195                 200                 205

Thr Gly Phe Val Val Tyr Asp Gly Ala Val Phe Tyr Asn Lys Glu Arg
    210                 215                 220

Thr Arg Asn Ile Val Lys Tyr Asp Leu Arg Thr Arg Ile Lys Ser Gly
225                 230                 235                 240

Glu Thr Val Ile Asn Thr Ala Asn Tyr His Asp Thr Ser Pro Tyr Arg
                245                 250                 255

Trp Gly Gly Lys Thr Asp Ile Asp Leu Ala Val Asp Glu Asn Gly Leu
            260                 265                 270

Trp Val Ile Tyr Ala Thr Glu Gly Asn Asn Gly Arg Leu Val Val Ser
    275                 280                 285

Gln Leu Asn Pro Tyr Thr Leu Arg Phe Glu Gly Thr Trp Glu Thr Gly
    290                 295                 300

Tyr Asp Lys Arg Ser Ala Ser Asn Ala Phe Met Val Cys Gly Val Leu
305                 310                 315                 320

Tyr Val Leu Arg Ser Val Tyr Val Asp Asp Ser Glu Ala Ala Gly
                325                 330                 335

Asn Arg Val Asp Tyr Ala Phe Asn Thr Asn Ala Asn Arg Glu Glu Pro
            340                 345                 350

Val Ser Leu Ala Phe Pro Asn Pro Tyr Gln Phe Val Ser Ser Val Asp
    355                 360                 365

Tyr Asn Pro Arg Asp Asn Gln Leu Tyr Val Trp Asn Asn Tyr Phe Val
    370                 375                 380

Val Arg Tyr Ser Leu Glu Phe Gly Pro Pro Asp Pro Ser Ala Gly Pro
385                 390                 395                 400

Ala Thr Ser Pro Pro Leu Ser Thr Thr Thr Ala Arg Pro Thr Pro
            405                 410                 415

Leu Thr Ser Thr Ala Ser Pro Ala Ala Thr Thr Pro Leu Arg Arg Ala
            420                 425                 430

Pro Leu Thr Thr His Pro Val Gly Ala Ile Asn Gln Leu Gly Pro Asp
            435                 440                 445

Leu Pro Pro Ala Thr Ala Pro Ala Pro Ser Thr Arg Arg Pro Pro Ala
    450                 455                 460

Pro Asn Leu His Val Ser Pro Glu Leu Phe Cys Glu Pro Arg Glu Val
465                 470                 475                 480

Arg Arg Val Gln Trp Pro Ala Thr Gln Gln Gly Met Leu Val Glu Arg
                485                 490                 495

Pro Cys Pro Lys Gly Thr Arg Gly Ile Ala Ser Phe Gln Cys Leu Pro
```

```
                  500                 505                 510
        Ala Leu Gly Leu Trp Asn Pro Arg Gly Pro Asp Leu Ser Asn Cys Thr
                515                 520                 525

Ser Pro Trp Val Asn Gln Val Ala Gln Lys Ile Lys Ser Gly Glu Asn
                530                 535                 540

Ala Ala Asn Ile Ala Ser Glu Leu Ala Arg His Thr Arg Gly Ser Ile
        545                 550                 555                 560

Tyr Ala Gly Asp Val Ser Ser Val Lys Leu Met Glu Gln Leu Leu
                        565                 570                 575

Asp Ile Leu Asp Ala Gln Leu Gln Ala Leu Arg Pro Ile Glu Arg Glu
                        580                 585                 590

Ser Ala Gly Lys Asn Tyr Asn Lys Met His Lys Arg Glu Arg Thr Cys
                        595                 600                 605

Lys Asp Tyr Ile Lys Ala Val Val Glu Thr Val Asp Asn Leu Leu Arg
                        610                 615                 620

Pro Glu Ala Leu Glu Ser Trp Lys Asp Met Asn Ala Thr Glu Gln Val
        625                 630                 635                 640

His Thr Ala Thr Met Leu Leu Asp Val Leu Glu Glu Gly Ala Phe Leu
                        645                 650                 655

Leu Ala Asp Asn Val Arg Glu Pro Ala Arg Phe Leu Ala Ala Lys Gln
                        660                 665                 670

Asn Val Val Leu Glu Val Thr Val Leu Ser Thr Glu Gly Gln Val Gln
                        675                 680                 685

Glu Leu Val Phe Pro Gln Glu Tyr Ala Ser Glu Ser Ser Ile Gln Leu
                690                 695                 700

Ser Ala Asn Thr Ile Lys Gln Asn Ser Arg Asn Gly Val Val Lys Val
        705                 710                 715                 720

Val Phe Ile Leu Tyr Asn Asn Leu Gly Leu Phe Leu Ser Thr Glu Asn
                        725                 730                 735

Ala Thr Val Lys Leu Ala Gly Glu Ala Gly Thr Gly Gly Pro Gly Gly
                        740                 745                 750

Ala Ser Leu Val Val Asn Ser Gln Val Ile Ala Ala Ser Ile Asn Lys
                        755                 760                 765

Glu Ser Ser Arg Val Phe Leu Met Asp Pro Val Ile Phe Thr Val Ala
                770                 775                 780

His Leu Glu Ala Lys Asn His Phe Asn Ala Asn Cys Ser Phe Trp Asn
        785                 790                 795                 800

Tyr Ser Glu Arg Ser Met Leu Gly Tyr Trp Ser Thr Gln Gly Cys Arg
                        805                 810                 815

Leu Val Glu Ser Asn Lys Thr His Thr Thr Cys Ala Cys Ser His Leu
                        820                 825                 830

Thr Asn Phe Ala Val Leu Met Ala His Arg Glu Ile Tyr Gln Gly Arg
                        835                 840                 845

Ile Asn Glu Leu Leu Leu Ser Val Ile Thr Trp Val Gly Ile Val Ile
        850                 855                 860

Ser Leu Val Cys Leu Ala Ile Cys Ile Ser Thr Phe Cys Phe Leu Arg
        865                 870                 875                 880

Gly Leu Gln Thr Asp Arg Asn Thr Ile His Lys Asn Leu Cys Ile Asn
                        885                 890                 895

Leu Phe Leu Ala Glu Leu Leu Phe Leu Val Gly Ile Asp Lys Thr Gln
                        900                 905                 910

Tyr Glu Val Ala Cys Pro Ile Phe Ala Gly Leu Leu His Tyr Phe Phe
                915                 920                 925
```

-continued

```
Leu Ala Ala Phe Ser Trp Leu Cys Leu Glu Gly Val His Leu Tyr Leu
    930                 935                 940
Leu Leu Val Glu Val Phe Glu Ser Glu Tyr Ser Arg Thr Lys Tyr Tyr
945                 950                 955                 960
Tyr Leu Gly Gly Tyr Cys Phe Pro Ala Leu Val Val Gly Ile Ala Ala
            965                 970                 975
Ala Ile Asp Tyr Arg Ser Tyr Gly Thr Glu Lys Ala Cys Trp Leu Arg
            980                 985                 990
Val Asp Asn Tyr Phe Ile Trp Ser Phe Ile Gly Pro Val Ser Phe Val
            995                 1000                1005
Ile Val Val Asn Leu Val Phe Leu Met Val Thr Leu His Lys Met Ile
    1010                1015                1020
Arg Ser Ser Ser Val Leu Lys Pro Asp Ser Ser Arg Leu Asp Asn Ile
1025                1030                1035                1104
Lys Ser Trp Ala Leu Gly Ala Ile Ala Leu Leu Phe Leu Leu Gly Leu
                1045                1050                1055
Thr Trp Ala Phe Gly Leu Leu Phe Ile Asn Lys Glu Ser Val Val Met
                1060                1065                1070
Ala Tyr Leu Phe Thr Thr Phe Asn Ala Phe Gln Gly Val Phe Ile Phe
    1075                1080                1085
Val Phe His Cys Ala Leu Gln Lys Lys Val His Lys Glu Tyr Ser Lys
    1090                1095                1100
Cys Leu Arg His Ser Tyr Cys Cys Ile Arg Ser Pro Pro Gly Gly Ala
1105                1110                1115                1112
His Gly Ser Leu Lys Thr Ser Ala Met Arg Ser Asn Thr Arg Tyr Tyr
                1125                1130                1135
Thr Gly Thr Gln Ser Arg Ile Arg Arg Met Trp Asn Asp Thr Val Arg
            1140                1145                1150
Lys Gln Thr Glu Ser Ser Phe Met Ala Gly Asp Ile Asn Ser Thr Pro
            1155                1160                1165
Thr Leu Asn Arg Gly Thr Met Gly Asn His Leu Leu Thr Asn Pro Val
    1170                1175                1180
Leu Gln Pro Arg Gly Gly Thr Ser Pro Tyr Asn Thr Leu Ile Ala Glu
1185                1190                1195                1120
Ser Val Gly Phe Asn Pro Ser Ser Pro Pro Val Phe Asn Ser Pro Gly
            1205                1210                1215
Ser Tyr Arg Glu Pro Lys His Pro Leu Gly Gly Arg Glu Ala Cys Gly
            1220                1225                1230
Met Asp Thr Leu Pro Leu Asn Gly Asn Phe Asn Asn Ser Tyr Ser Leu
    1235                1240                1245
Arg Ser Gly Asp Phe Pro Pro Gly Asp Gly Pro Glu Pro Pro Arg
    1250                1255                1260
Gly Arg Asn Leu Ala Asp Ala Ala Ala Phe Glu Lys Met Ile Ile Ser
1265                1270                1275                1128
Glu Leu Val His Asn Asn Leu Arg Gly Ala Ser Gly Ala Lys Gly
                1285                1290                1295
Pro Pro Pro Glu Pro Pro Val Pro Pro Val Pro Gly Val Ser Glu Asp
            1300                1305                1310
Glu Ala Gly Gly Pro Gly Gly Ala Asp Arg Ala Glu Ile Glu Leu Leu
    1315                1320                1325
Tyr Lys Ala Leu Glu Glu Pro Leu Leu Leu Pro Arg Ala Gln Ser Val
    1330                1335                1340
```

```
Leu Tyr Gln Ser Asp Leu Asp Glu Ser Glu Ser Cys Thr Ala Glu Asp
1345                1350                1355                1136

Gly Ala Thr Ser Arg Pro Leu Ser Ser Pro Gly Arg Asp Ser Leu
            1365                1370                1375

Tyr Ala Ser Gly Ala Asn Leu Arg Asp Ser Pro Ser Tyr Pro Asp Ser
        1380                1385                1390

Ser Pro Glu Gly Pro Asn Glu Ala Leu Pro Pro Pro Pro Ala Pro
    1395                1400                1405

Pro Gly Pro Pro Glu Ile Tyr Tyr Thr Ser Arg Pro Pro Ala Leu Val
    1410                1415                1420

Ala Arg Asn Pro Leu Gln Gly Tyr Tyr Gln Val Arg Arg Pro Ser His
1425                1430                1435                1144

Glu Gly Tyr Leu Ala Ala Pro Ser Leu Glu Gly Pro Gly Pro Asp Gly
            1445                1450                1455

Asp Gly Gln Met Gln Leu Val Thr Ser Leu
            1460                1465

<210> SEQ ID NO 21
<211> LENGTH: 829
<212> TYPE: DNA
<213> ORGANISM: Homo sapiens

<400> SEQUENCE: 21
agtggttgga gtttcagctg ctattgacta taagagctat ggaacagaaa aagcttgctg      60
gcttcatgtt gataactact ttatatggag cttcattgga cctgttacct tcattattct    120
gctaaatatt atcttcttgg tgatcacatt gtgcaaaatg gtgaagcatt caaacacttt    180
gaaaccagat tctagcaggt tggaaaacat taagtcttgg gtgcttggcg ctttcgctct    240
tctgtgtctt cttggcctca cctggtcctt tgggttgctt tttattaatg aggagactat    300
tgtgatggca tatctcttca ctatatttaa tgctttccag ggagtgttca ttttcatctt    360
tcactgtgct ctccaaaaga agtacgaaa agaatatggc aagtgcttca gacactcata    420
ctgctgtgga ggcctcccaa ctgagagtcc ccacagttca gtgaaggcat caaccaccag    480
aaccagtgct cgctattcct ctggcacaca gagtcgtata agaagaatgt ggaatgatac    540
tgtgagaaaa caatcagaat cttctttat ctcaggtgac atcaatagca cttcaacact     600
taatcaagga cattcactga caatgccag ggatacaagt gccatggata tctaccgct      660 aaatggtaat tttaacaaca gctactcgct gcacaagggt gactataatg acagcgtgca    720
agttgtggac tgtggactaa gtctgaatga tactgctttt gagaaaatga tcatttcaga    780
attagtgcac aacaacttac ggggcagcag caagactcac aacctcgag                829

<210> SEQ ID NO 22
<211> LENGTH: 429
<212> TYPE: DNA
<213> ORGANISM: Homo sapiens

<400> SEQUENCE: 22
ggggactggt gcccccacgc gtgtcagcac ggggttggtc agcaggtggt tccccatggt     60
acctcggttc agggtggggg tgctgttgat gtcacccgcc atgaaggagg actccgtctg    120
tttcctcaca gtgtcattcc acatcctccg aattcggctc tgggtccctg tgtagtagcg    180
ggtgttgctt cgcatggctg aggtcttgag ggatccgtga gtgccccgg gtgggatgcg     240 gatgcagcag taggagtgac gcaggcactt gctgtactcc ttgtgcacct tcttctgtaa    300
ggcgcagtga agacgaaga tgaagacccc ctggaaggcg ttgaaggtgg tgaagagata    360
```

```
ggccatgacc accgactcct tgttgatgaa gaggaggccg aaagcccagg tgaggcccag    420
caggaacag                                                           429
```

```
<210> SEQ ID NO 23
<211> LENGTH: 280
<212> TYPE: DNA
<213> ORGANISM: Homo sapiens

<400> SEQUENCE: 23
ctgagtcttg tcgatcccga ccaggaagag cagctcagcc aggaagaggt tgatgcacag     60
gttcttgtgg atggtgttgc ggtcggtctg cagcccccgc agaagcagaa ggtggagatg    120
cagatggcca agcagaccag ggagatcaca atgcccaccc aggtgatgac cgacagcagc    180
agctcgttga tgcggccctg gtagatctca cggtgagcca tgagcacagc gaagttggtg    240
aggtggctgc aggcacacgt ggtatgggtc ttgttggact                          280

<210> SEQ ID NO 24
<211> LENGTH: 24
<212> TYPE: DNA
<213> ORGANISM: Artificial Sequence
<220> FEATURE:
<223> OTHER INFORMATION: Description of Artificial Sequence: primer

<400> SEQUENCE: 24
tcttcagctg agctcttcaa aacc                                           24

<210> SEQ ID NO 25
<211> LENGTH: 24
<212> TYPE: DNA
<213> ORGANISM: Artificial Sequence
<220> FEATURE:
<223> OTHER INFORMATION: Description of Artificial Sequence: primer

<400> SEQUENCE: 25
ggttttgaag agctcagctg aaga                                           24

<210> SEQ ID NO 26
<211> LENGTH: 51
<212> TYPE: DNA
<213> ORGANISM: Artificial Sequence
<220> FEATURE:
<223> OTHER INFORMATION: Description of Artificial Sequence: primer

<400> SEQUENCE: 26
cagcagggat ccaccatggt gtcttctggt tgcagaatgc gaagtctgtg g             51

<210> SEQ ID NO 27
<211> LENGTH: 55
<212> TYPE: DNA
<213> ORGANISM: Artificial Sequence
<220> FEATURE:
<223> OTHER INFORMATION: Description of Artificial Sequence: primer

<400> SEQUENCE: 27
gacgatgacg cggccgccta ttaaagactt gtaaccagct gcatttgtcc ttctc         55

<210> SEQ ID NO 28
<211> LENGTH: 27
<212> TYPE: DNA
<213> ORGANISM: Artificial Sequence
<220> FEATURE:
<223> OTHER INFORMATION: Description of Artificial Sequence: primer
```

```
<400> SEQUENCE: 28
tacaaccatg ggcacaactg tagctgg                                          27

<210> SEQ ID NO 29
<211> LENGTH: 34
<212> TYPE: DNA
<213> ORGANISM: Artificial Sequence
<220> FEATURE:
<223> OTHER INFORMATION: Description of Artificial Sequence: primer

<400> SEQUENCE: 29
tacaagatct agcagatagc caggcaaaca aggg                                  34

<210> SEQ ID NO 30
<211> LENGTH: 439
<212> TYPE: DNA
<213> ORGANISM: Homo sapiens

<400> SEQUENCE: 30
aaaagcagta tcattcagac ttagtccaca gtccacaact tgcacgctgt cattatagtc      60
acccttgtgc agcgagtagt gtntgttaaa attaccattt agcggtagag tatccatggc     120
acttgtatcc ctgggcattg ttcagtgaat gtccttgatt aagtgttgaa gtgctattga     180
tgtcacctga gataaaagaa gattctgatt gttttctcac agtatcattc cacattcttc     240
ttatacggac tctgtgtgcc agagggaata gcgagcactg ggttctgggt gggttgatgc     300
cttcactgaa ctgtgggggg actctcaggt tggggagggc ctncacaggc agtatggagg     360
tgtcttgaag gcactttgcc ataattcttt ttcgtacctt tccttttggg agagcacagt     420
gaaagntgga aaattgacc                                                  439

<210> SEQ ID NO 31
<211> LENGTH: 27
<212> TYPE: DNA
<213> ORGANISM: Artificial Sequence
<220> FEATURE:
<223> OTHER INFORMATION: Description of Artificial Sequence: primer

<400> SEQUENCE: 31
tacaaccatg ggcacaactg tagctgg                                          27

<210> SEQ ID NO 32
<211> LENGTH: 34
<212> TYPE: DNA
<213> ORGANISM: Artificial Sequence
<220> FEATURE:
<223> OTHER INFORMATION: Description of Artificial Sequence: primer

<400> SEQUENCE: 32
tacaagatct agcagatagc caggcaaaca aggg                                  34

<210> SEQ ID NO 33
<211> LENGTH: 5598
<212> TYPE: DNA
<213> ORGANISM: Homo sapiens
<220> FEATURE:
<221> NAME/KEY: CDS
<222> LOCATION: (407)..(3748)

<400> SEQUENCE: 33
cggcgaacag acgttctttc tcctccatgc agttacacaa aaggagggct acggaaacta      60
aaagtttcgg ggcctctggc tcggtgtgtg gagaaaagag aaaacctgga gacgggatat     120
```

```
-continued gaagatcaat gatgcagact gatggtcttg atgaagctgg gcatttataa ctagattcat      180
taaggaatac aaagaaaata cttaaaggga tcaataatgg tgtcttctgg ttgcagaatg      240
cgaagtctgt ggtttatcat tgtaatcagc ttcttaccaa atacagaagg tttcagcaga      300
gcagctttac catttgggct ggtgaggcga gaattatcct gtgaaggtta ttctatagat      360
ctgcgatgcc cgggcagtga tgtcatcatg attgagagcg ctaact atg gtc gga         415
                                                   Met Val Gly
                                                     1 cgg atg aca aga ttt gtg atg ctg acc cat ttc aga tgg gag aat aca        463
Arg Met Thr Arg Phe Val Met Leu Thr His Phe Arg Trp Glu Asn Thr
      5                  10                  15 gac tgc tac ctc ccc gat gcc ttc aaa att atg act caa agg tgc aac        511
Asp Cys Tyr Leu Pro Asp Ala Phe Lys Ile Met Thr Gln Arg Cys Asn
 20                  25                  30                  35 aat cga aca cag tgt ata gta gtt act ggg tca gat gtg ttt cct gat        559
Asn Arg Thr Gln Cys Ile Val Val Thr Gly Ser Asp Val Phe Pro Asp
                 40                  45                  50 cca tgt cct gga aca tac aaa tac ctt gaa gtc caa tat gaa tgt gtc        607
Pro Cys Pro Gly Thr Tyr Lys Tyr Leu Glu Val Gln Tyr Glu Cys Val
             55                  60                  65 cct tac att ttt gtg tgt cct ggg acc ttg aaa gca att gtg gac tca        655
Pro Tyr Ile Phe Val Cys Pro Gly Thr Leu Lys Ala Ile Val Asp Ser
         70                  75                  80 cca tgt ata tat gaa gct gaa caa aag gcg ggt gct tgg tgc aag gac        703
Pro Cys Ile Tyr Glu Ala Glu Gln Lys Ala Gly Ala Trp Cys Lys Asp
     85                  90                  95 cct ctt cag gct gca gat aaa att tat ttc atg ccc tgg act ccc tat        751
Pro Leu Gln Ala Ala Asp Lys Ile Tyr Phe Met Pro Trp Thr Pro Tyr
100                 105                 110                 115 cgt acc gat act tta ata gaa tat gct tct tta gaa gat ttc caa aat        799
Arg Thr Asp Thr Leu Ile Glu Tyr Ala Ser Leu Glu Asp Phe Gln Asn
                120                 125                 130 agt cgc caa aca aca aca tat aaa ctt cca aat cga gta gat ggt act        847
Ser Arg Gln Thr Thr Thr Tyr Lys Leu Pro Asn Arg Val Asp Gly Thr
            135                 140                 145 gga ttt gtg gtg tat gat ggt gct gtc ttc ttt aac aaa gaa aga acg        895
Gly Phe Val Val Tyr Asp Gly Ala Val Phe Phe Asn Lys Glu Arg Thr
        150                 155                 160 agg aat att gtg aaa ttt gac ttg agg act aga att aag agt ggc gag        943
Arg Asn Ile Val Lys Phe Asp Leu Arg Thr Arg Ile Lys Ser Gly Glu
165                 170                 175 gcc ata att aac tat gcc aac tac cat gat acc tca cca tac aga tgg        991
Ala Ile Ile Asn Tyr Ala Asn Tyr His Asp Thr Ser Pro Tyr Arg Trp
180                 185                 190                 195 gga gga aag act gat atc gac cta gca gtt gat gaa aat ggt tta tgg       1039
Gly Gly Lys Thr Asp Ile Asp Leu Ala Val Asp Glu Asn Gly Leu Trp
                200                 205                 210 gtc att tac gcc act gaa cag aac aat gga atg ata gtt att agc cag       1087
Val Ile Tyr Ala Thr Glu Gln Asn Asn Gly Met Ile Val Ile Ser Gln
            215                 220                 225 ctg aat cca tac act ctt cga ttt gaa gca acg tgg gag act gta tac       1135
Leu Asn Pro Tyr Thr Leu Arg Phe Glu Ala Thr Trp Glu Thr Val Tyr
        230                 235                 240 gac aaa cgt gcc gca tca aat gct ttt atg ata tgc gga gtc ctc tat       1183
Asp Lys Arg Ala Ala Ser Asn Ala Phe Met Ile Cys Gly Val Leu Tyr
245                 250                 255 gtg gtt agg tca gtt tat caa gac aat gaa agt gaa aca ggc aag aac       1231
Val Val Arg Ser Val Tyr Gln Asp Asn Glu Ser Glu Thr Gly Lys Asn
                265                 270                 275
260
```

```
tca att gat tac att tat aat acc cga tta aac cga gga gaa tat gta    1279
Ser Ile Asp Tyr Ile Tyr Asn Thr Arg Leu Asn Arg Gly Glu Tyr Val
                    280                 285                 290 gac gtt ccc ttc ccc aac cag tat cag tat att gct gca gtg gat tac    1327
Asp Val Pro Phe Pro Asn Gln Tyr Gln Tyr Ile Ala Ala Val Asp Tyr
                295                 300                 305 aat cca aga gat aac caa ctt tac gtg tgg aac aat aac ttc att tta    1375
Asn Pro Arg Asp Asn Gln Leu Tyr Val Trp Asn Asn Asn Phe Ile Leu
                    310                 315                 320 cga tat tct ctg gag ttt ggt cca cct gat cct gcc caa gtg cct acc    1423
Arg Tyr Ser Leu Glu Phe Gly Pro Pro Asp Pro Ala Gln Val Pro Thr
        325                 330                 335 aca gct gtg aca ata act tct tca gct gag ctg ttc aaa acc ata ata    1471
Thr Ala Val Thr Ile Thr Ser Ser Ala Glu Leu Phe Lys Thr Ile Ile
340                 345                 350                 355 tca acc aca agc act act tca cag aaa ggc ccc atg agc aca act gta    1519
Ser Thr Thr Ser Thr Thr Ser Gln Lys Gly Pro Met Ser Thr Thr Val
                    360                 365                 370 gct gga tca cag gaa gga agc aaa ggg aca aaa cca cct cca gca gtt    1567
Ala Gly Ser Gln Glu Gly Ser Lys Gly Thr Lys Pro Pro Pro Ala Val
            375                 380                 385 tct aca acc aaa att cca cct ata aca aat att ttt ccc ctg cca gag    1615
Ser Thr Thr Lys Ile Pro Pro Ile Thr Asn Ile Phe Pro Leu Pro Glu
        390                 395                 400 aga ttc tgt gaa gca tta gac tcc aag ggg ata aag tgg cct cag aca    1663
Arg Phe Cys Glu Ala Leu Asp Ser Lys Gly Ile Lys Trp Pro Gln Thr
405                 410                 415 caa agg gga atg atg gtt gaa cga cca tgc cct aag gga aca aga gga    1711
Gln Arg Gly Met Met Val Glu Arg Pro Cys Pro Lys Gly Thr Arg Gly
420                 425                 430                 435 act gcc tca tat ctc tgc atg att tcc act gga aca tgg aac cct aag    1759
Thr Ala Ser Tyr Leu Cys Met Ile Ser Thr Gly Thr Trp Asn Pro Lys
                440                 445                 450 ggc ccc gat ctt agc aac tgt acc tca cac tgg gtg aat cag ctg gct    1807
Gly Pro Asp Leu Ser Asn Cys Thr Ser His Trp Val Asn Gln Leu Ala
            455                 460                 465 cag aag atc aga agc gga gaa aat gct gct agt ctt gcc aat gaa ctg    1855
Gln Lys Ile Arg Ser Gly Glu Asn Ala Ala Ser Leu Ala Asn Glu Leu
        470                 475                 480 gct aaa cat acc aaa ggg cca gtg ttt gct ggg gat gta agt tct tca    1903
Ala Lys His Thr Lys Gly Pro Val Phe Ala Gly Asp Val Ser Ser Ser
485                 490                 495 gtg aga ttg atg gag cag ttg gtg gac atc ctt gat gca cag ctg cag    1951
Val Arg Leu Met Glu Gln Leu Val Asp Ile Leu Asp Ala Gln Leu Gln
500                 505                 510                 515 gaa ctg aaa cct agt gaa aaa gat tca gct gga cgg agt tat aac aag    1999
Glu Leu Lys Pro Ser Glu Lys Asp Ser Ala Gly Arg Ser Tyr Asn Lys
                520                 525                 530 gca att gtt gac aca gtg gac aac ctt ctg aga cct gaa gct ttg gaa    2047
Ala Ile Val Asp Thr Val Asp Asn Leu Leu Arg Pro Glu Ala Leu Glu
            535                 540                 545 tca tgg aaa cat atg aat tct tct gaa caa gca cat act gca aca atg    2095
Ser Trp Lys His Met Asn Ser Ser Glu Gln Ala His Thr Ala Thr Met
        550                 555                 560 tta ctc gat aca ttg gaa gaa gga gct ttt gtc cta gct gac aat ctt    2143
Leu Leu Asp Thr Leu Glu Glu Gly Ala Phe Val Leu Ala Asp Asn Leu
565                 570                 575 tta gaa cca aca agg gtc tca atg ccc aca gaa aat att gtc ctg gaa    2191
Leu Glu Pro Thr Arg Val Ser Met Pro Thr Glu Asn Ile Val Leu Glu
```

```
580                 585                 590                 595 gtt gcc gta ctc agt aca gaa gga cag atc caa gac ttt aaa ttt cct    2239
Val Ala Val Leu Ser Thr Glu Gly Gln Ile Gln Asp Phe Lys Phe Pro
                600                 605                 610 ctg ggc atc aaa gga gca ggc agc tca atc caa ctg tcc gca aat acc    2287
Leu Gly Ile Lys Gly Ala Gly Ser Ser Ile Gln Leu Ser Ala Asn Thr
                615                 620             625 gtc aaa cag aac agc agg aat ggg ctt gca aag ttg gtg ttc atc att    2335
Val Lys Gln Asn Ser Arg Asn Gly Leu Ala Lys Leu Val Phe Ile Ile
            630                 635                 640 tac cgg agc ctg gga cag ttc ctt agt aca gaa aat gca acc att aaa    2383
Tyr Arg Ser Leu Gly Gln Phe Leu Ser Thr Glu Asn Ala Thr Ile Lys
        645                 650                 655 ctg ggt gct gat ttt att ggt cgt aat agc acc att gca gtg aac tct    2431
Leu Gly Ala Asp Phe Ile Gly Arg Asn Ser Thr Ile Ala Val Asn Ser
660                 665                 670                 675 cac gtc att tca gtt tca atc aat aaa gag tcc agc cga gta tac ctg    2479
His Val Ile Ser Val Ser Ile Asn Lys Glu Ser Ser Arg Val Tyr Leu
                680                 685                 690 act gat cct gtg ctt ttt acc ctg cca cac att gat cct gac aat tat    2527
Thr Asp Pro Val Leu Phe Thr Leu Pro His Ile Asp Pro Asp Asn Tyr
                695                 700                 705 ttc aat gca aac tgc tcc ttc tgg aac tac tca gag aga act atg atg    2575
Phe Asn Ala Asn Cys Ser Phe Trp Asn Tyr Ser Glu Arg Thr Met Met
            710                 715                 720 gga tat tgg tct acc cag ggc tgc aag ctg gtt gac act aat aaa act    2623
Gly Tyr Trp Ser Thr Gln Gly Cys Lys Leu Val Asp Thr Asn Lys Thr
        725                 730                 735 cga aca acg tgt gca tgc agc cac cta acc aat ttt gca att ctc atg    2671
Arg Thr Thr Cys Ala Cys Ser His Leu Thr Asn Phe Ala Ile Leu Met
740                 745                 750                 755 gcc cac agg gaa att gca tat aaa gat ggc gtt cat gaa tta ctt ctt    2719
Ala His Arg Glu Ile Ala Tyr Lys Asp Gly Val His Glu Leu Leu Leu
                760                 765                 770 aca gtc atc acc tgg gtg gga att gtc att tcc ctt gtt tgc ctg gct    2767
Thr Val Ile Thr Trp Val Gly Ile Val Ile Ser Leu Val Cys Leu Ala
                775                 780                 785 atc tgc atc ttc acc ttc tgc ttt ttc cgt ggc cta cag agt gac cga    2815
Ile Cys Ile Phe Thr Phe Cys Phe Phe Arg Gly Leu Gln Ser Asp Arg
            790                 795                 800 aat act att cac aag aac ctt tgt atc aac ctt ttc att gct gaa ttt    2863
Asn Thr Ile His Lys Asn Leu Cys Ile Asn Leu Phe Ile Ala Glu Phe
        805                 810                 815 att ttc cta ata ggc att gat aag aca aaa tat gcg att gca tgc cca    2911
Ile Phe Leu Ile Gly Ile Asp Lys Thr Lys Tyr Ala Ile Ala Cys Pro
820                 825                 830                 835 ata ttt gca gga ctt cta cac ttt ttc ttt ttg gca gct ttt gct tgg    2959
Ile Phe Ala Gly Leu Leu His Phe Phe Phe Leu Ala Ala Phe Ala Trp
                840                 845                 850 atg tgc cta gaa ggt gtg cag ctc tac cta atg tta gtt gaa gtt ttt    3007
Met Cys Leu Glu Gly Val Gln Leu Tyr Leu Met Leu Val Glu Val Phe
                855                 860                 865 gaa agt gaa tat tca agg aaa aaa tat tac tat gtt gct ggt tac ttg    3055
Glu Ser Glu Tyr Ser Arg Lys Lys Tyr Tyr Tyr Val Ala Gly Tyr Leu
            870                 875                 880 ttt cct gcc aca gtg gtt gga gtt tca gct gct att gac tat aag agc    3103
Phe Pro Ala Thr Val Val Gly Val Ser Ala Ala Ile Asp Tyr Lys Ser
        885                 890                 895 tat gga aca gaa aaa gct tgc tgg ctt cat gtt gat aac tac ttt ata    3151
```

-continued

| | |
|---|---|
| Tyr Gly Thr Glu Lys Ala Cys Trp Leu His Val Asp Asn Tyr Phe Ile<br>900              905                    910               915 | |
| tgg agc ttc att gga cct gtt acc ttc att att ctg cta aat att atc<br>Trp Ser Phe Ile Gly Pro Val Thr Phe Ile Ile Leu Leu Asn Ile Ile<br>                920                       925               930 | 3199 |
| ttc ttg gtg atc aca ttg tgc aaa atg gtg aag cat tca aac act ttg<br>Phe Leu Val Ile Thr Leu Cys Lys Met Val Lys His Ser Asn Thr Leu<br>        935                    940                     945 | 3247 |
| aaa cca gat tct agc agg ttg gaa aac att aag tct tgg gtg ctt ggc<br>Lys Pro Asp Ser Ser Arg Leu Glu Asn Ile Lys Ser Trp Val Leu Gly<br>950              955                    960 | 3295 |
| gct ttc gct ctt ctg tgt ctt ctt ggc ctc acc tgg tcc ttt ggg ttg<br>Ala Phe Ala Leu Leu Cys Leu Leu Gly Leu Thr Trp Ser Phe Gly Leu<br>        965                    970                     975 | 3343 |
| ctt ttt att aat gag gag act att gtg atg gca tat ctc ttc act ata<br>Leu Phe Ile Asn Glu Glu Thr Ile Val Met Ala Tyr Leu Phe Thr Ile<br>980              985                    990               995 | 3391 |
| ttt aat gct ttc cag gga gtg ttc att ttc atc ttt cac tgt gct ctc<br>Phe Asn Ala Phe Gln Gly Val Phe Ile Phe Ile Phe His Cys Ala Leu<br>            1000                 1005               1010 | 3439 |
| caa aag aaa gta cga aaa gaa tat ggc aag tgc ttc aga cac tca tac<br>Gln Lys Lys Val Arg Lys Glu Tyr Gly Lys Cys Phe Arg His Ser Tyr<br>            1015                 1020               1025 | 3487 |
| tgc tgt gga ggc ctc cca act gag agt ccc cac agt tca gtg aag gca<br>Cys Cys Gly Gly Leu Pro Thr Glu Ser Pro His Ser Ser Val Lys Ala<br>        1030                 1035               1040 | 3535 |
| tca acc acc aga acc agt gct cgc tat tcc tct ggc aca cag agt cgt<br>Ser Thr Thr Arg Thr Ser Ala Arg Tyr Ser Ser Gly Thr Gln Ser Arg<br>    1045                 1050               1055 | 3583 |
| ata aga aga atg tgg aat gat act gtg aga aaa caa tca gaa tct tct<br>Ile Arg Arg Met Trp Asn Asp Thr Val Arg Lys Gln Ser Glu Ser Ser<br>1060              1065                    1070               1075 | 3631 |
| ttt atc tca ggt gac atc aat agc act tca aca ctt aat caa gga ctg<br>Phe Ile Ser Gly Asp Ile Asn Ser Thr Ser Thr Leu Asn Gln Gly Leu<br>            1080                 1085               1090 | 3679 |
| aca tca cat ggt ctg aga gcc cat ctt caa gat tta tat cat tta gag<br>Thr Ser His Gly Leu Arg Ala His Leu Gln Asp Leu Tyr His Leu Glu<br>        1095                 1100               1105 | 3727 |
| cta ctc tta ggc cag ata gcc tgagcagaca gacatgatgt gagttgtcca<br>Leu Leu Leu Gly Gln Ile Ala<br>1110 | 3778 |
| aagacattca ctgaacaatg ccagggatac aagtgccatg gatactctac cgctaaatgg | 3838 |
| taattttaac aacagctact cgctgcacaa gggtgactat aatgacagcg tgcaagttgt | 3898 |
| ggactgtgga ctaagtctga atgatactgc ttttgagaaa atgatcattt cagaattagt | 3958 |
| gcacaacaac ttacggggca gcagcaagac tcacaacctc gagctcacgc taccagtcaa | 4018 |
| acctgtgatt ggaggtagca gcagtgaaga tgatgctatt gtggcagatg cttcatcttt | 4078 |
| aatgcacagc gacaacccag ggctggagct ccatcacaaa gaactcgagg caccacttat | 4138 |
| tcctcagcgg actcactccc ttctgtacca accccagaag aaagtgaagt ccgagggaac | 4198 |
| tgacagctat gtctcccaac tgacagcaga ggctgaagat cacctacagt cccccaacag | 4258 |
| agactctctt tatacaagca tgcccaatct tagagactct ccctatccgg agagcagccc | 4318 |
| tgacatggaa gaagacctct ctccctccag gaggagtgag aatgaggaca tttactataa | 4378 |
| aagcatgcca aatcttggag ctggccatca gcttcgatg tgctaccaga tcagcagggg | 4438 |
| caatagtgat ggttatataa tccccattaa caaagaaggg tgtattccag aaggagatgt | 4498 |

-continued

| | |
|---|---|
| tagagaagga caaatgcagc tggttacaag tctttaatca tacagctaag gaattccaag | 4558 |
| ggccacatgc gagtattaat aaataaagac accattggcc tgacgcagct ccctcaaact | 4618 |
| ctgcttgaag agatgactct tgacctgtgg ttctctggtg taaaaaagat gactgaacct | 4678 |
| tgcagttctg tgaatttta taaaacatac aaaaactttg tatatacaca gagtatacta | 4738 |
| aagtgaatta tttgttacaa agaaaagaga tgccagccag gtatttaag attctgctgc | 4798 |
| tgtttagaga aattgtgaaa caagcaaaac aaaactttcc agccatttta ctgcagcagt | 4858 |
| ctgtgaacta aatttgtaaa tatggctgca ccattttgt aggcctgcat tgtattatat | 4918 |
| acaagacgta ggctttaaaa tcctgtggga caaatttact gtaccttact attcctgaca | 4978 |
| agacttggaa aagcaggaga gatattctgc atcagtttgc agttcactgc aaatctttta | 5038 |
| cattaaggca aagattgaaa acatgcttaa ccactagcaa tcaagccaca ggccttattt | 5098 |
| catatgtttc ctcaactgta caatgaacta ttctcatgaa aaatggctaa agaaattata | 5158 |
| ttttgttcta ttgctagggt aaaataaata catttgtgtc caactgaaat ataattgtca | 5218 |
| ttaaaataat tttaaagagt gaagaaaata ttgtgaaaag ctcttggttg cacatgttat | 5278 |
| gaaatgtttt ttcttacact ttgtcatggt aagttctact cattttcact tcttttccac | 5338 |
| tgtatacagt gttctgcttt gacaaagtta gtctttatta cttacattta aatttcttat | 5398 |
| tgccaaaaga acgtgtttta tggggagaaa caaactcttt gaagccagtt atgtcatgcc | 5458 |
| ttgcacaaaa gtgatgaaat ctagaaaaga ttgtgtgtca ccctgtttta ttcttgaaca | 5518 |
| gagggcaaag agggcactgg gcacttctca caaactttct agtgaacaaa aggtgcctat | 5578 |
| tcttttttaa aaaaaaaaa | 5598 |

<210> SEQ ID NO 34
<211> LENGTH: 1114
<212> TYPE: PRT
<213> ORGANISM: Homo sapiens

<400> SEQUENCE: 34

Met Val Gly Arg Met Thr Arg Phe Val Met Leu Thr His Phe Arg Trp
1               5                   10                  15

Glu Asn Thr Asp Cys Tyr Leu Pro Asp Ala Phe Lys Ile Met Thr Gln
            20                  25                  30

Arg Cys Asn Asn Arg Thr Gln Cys Ile Val Val Thr Gly Ser Asp Val
        35                  40                  45

Phe Pro Asp Pro Cys Pro Gly Thr Tyr Lys Tyr Leu Glu Val Gln Tyr
    50                  55                  60

Glu Cys Val Pro Tyr Ile Phe Val Cys Pro Gly Thr Leu Lys Ala Ile
65                  70                  75                  80

Val Asp Ser Pro Cys Ile Tyr Glu Ala Glu Gln Lys Ala Gly Ala Trp
                85                  90                  95

Cys Lys Asp Pro Leu Gln Ala Ala Asp Lys Ile Tyr Phe Met Pro Trp
            100                 105                 110

Thr Pro Tyr Arg Thr Asp Thr Leu Ile Glu Tyr Ala Ser Leu Glu Asp
        115                 120                 125

Phe Gln Asn Ser Arg Gln Thr Thr Tyr Lys Leu Pro Asn Arg Val
    130                 135                 140

Asp Gly Thr Gly Phe Val Val Tyr Asp Gly Ala Val Phe Phe Asn Lys
145                 150                 155                 160

Glu Arg Thr Arg Asn Ile Val Lys Phe Asp Leu Arg Thr Arg Ile Lys
                165                 170                 175

```
Ser Gly Glu Ala Ile Ile Asn Tyr Ala Asn Tyr His Asp Thr Ser Pro
            180                 185                 190

Tyr Arg Trp Gly Gly Lys Thr Asp Ile Asp Leu Ala Val Asp Glu Asn
            195                 200                 205

Gly Leu Trp Val Ile Tyr Ala Thr Glu Gln Asn Asn Gly Met Ile Val
            210                 215                 220

Ile Ser Gln Leu Asn Pro Tyr Thr Leu Arg Phe Glu Ala Thr Trp Glu
225                 230                 235                 240

Thr Val Tyr Asp Lys Arg Ala Ala Ser Asn Ala Phe Met Ile Cys Gly
                245                 250                 255

Val Leu Tyr Val Val Arg Ser Val Tyr Gln Asp Asn Glu Ser Glu Thr
            260                 265                 270

Gly Lys Asn Ser Ile Asp Tyr Ile Tyr Asn Thr Arg Leu Asn Arg Gly
            275                 280                 285

Glu Tyr Val Asp Val Pro Phe Pro Asn Gln Tyr Gln Tyr Ile Ala Ala
            290                 295                 300

Val Asp Tyr Asn Pro Arg Asp Asn Gln Leu Tyr Val Trp Asn Asn Asn
305                 310                 315                 320

Phe Ile Leu Arg Tyr Ser Leu Glu Phe Gly Pro Asp Pro Ala Gln
                325                 330                 335

Val Pro Thr Thr Ala Val Thr Ile Thr Ser Ser Ala Glu Leu Phe Lys
            340                 345                 350

Thr Ile Ile Ser Thr Thr Ser Thr Thr Ser Gln Lys Gly Pro Met Ser
            355                 360                 365

Thr Thr Val Ala Gly Ser Gln Glu Gly Ser Lys Gly Thr Lys Pro Pro
            370                 375                 380

Pro Ala Val Ser Thr Thr Lys Ile Pro Pro Ile Thr Asn Ile Phe Pro
385                 390                 395                 400

Leu Pro Glu Arg Phe Cys Glu Ala Leu Asp Ser Lys Gly Ile Lys Trp
                405                 410                 415

Pro Gln Thr Gln Arg Gly Met Met Val Glu Arg Pro Cys Pro Lys Gly
            420                 425                 430

Thr Arg Gly Thr Ala Ser Tyr Leu Cys Met Ile Ser Thr Gly Thr Trp
            435                 440                 445

Asn Pro Lys Gly Pro Asp Leu Ser Asn Cys Thr Ser His Trp Val Asn
450                 455                 460

Gln Leu Ala Gln Lys Ile Arg Ser Gly Glu Asn Ala Ala Ser Leu Ala
465                 470                 475                 480

Asn Glu Leu Ala Lys His Thr Lys Gly Pro Val Phe Ala Gly Asp Val
                485                 490                 495

Ser Ser Ser Val Arg Leu Met Glu Gln Leu Val Asp Ile Leu Asp Ala
            500                 505                 510

Gln Leu Gln Glu Leu Lys Pro Ser Glu Lys Asp Ser Ala Gly Arg Ser
            515                 520                 525

Tyr Asn Lys Ala Ile Val Asp Thr Val Asp Asn Leu Leu Arg Pro Glu
            530                 535                 540

Ala Leu Glu Ser Trp Lys His Met Asn Ser Ser Glu Gln Ala His Thr
545                 550                 555                 560

Ala Thr Met Leu Leu Asp Thr Leu Glu Glu Gly Ala Phe Val Leu Ala
                565                 570                 575

Asp Asn Leu Leu Glu Pro Thr Arg Val Ser Met Pro Thr Glu Asn Ile
            580                 585                 590

Val Leu Glu Val Ala Val Leu Ser Thr Glu Gly Gln Ile Gln Asp Phe
```

-continued

```
              595                 600                 605
Lys Phe Pro Leu Gly Ile Lys Gly Ala Gly Ser Ser Ile Gln Leu Ser
    610                 615                 620
Ala Asn Thr Val Lys Gln Asn Ser Arg Asn Gly Leu Ala Lys Leu Val
625                 630                 635                 640
Phe Ile Ile Tyr Arg Ser Leu Gly Gln Phe Leu Ser Thr Glu Asn Ala
                    645                 650                 655
Thr Ile Lys Leu Gly Ala Asp Phe Ile Gly Arg Asn Ser Thr Ile Ala
                660                 665                 670
Val Asn Ser His Val Ile Ser Val Ser Ile Asn Lys Glu Ser Ser Arg
                675                 680                 685
Val Tyr Leu Thr Asp Pro Val Leu Phe Thr Leu Pro His Ile Asp Pro
690                 695                 700
Asp Asn Tyr Phe Asn Ala Asn Cys Ser Phe Trp Asn Tyr Ser Glu Arg
705                 710                 715                 720
Thr Met Met Gly Tyr Trp Ser Thr Gln Gly Cys Lys Leu Val Asp Thr
                    725                 730                 735
Asn Lys Thr Arg Thr Thr Cys Ala Cys Ser His Leu Thr Asn Phe Ala
                740                 745                 750
Ile Leu Met Ala His Arg Glu Ile Ala Tyr Lys Asp Gly Val His Glu
                755                 760                 765
Leu Leu Leu Thr Val Ile Thr Trp Val Gly Ile Val Ile Ser Leu Val
770                 775                 780
Cys Leu Ala Ile Cys Ile Phe Thr Phe Cys Phe Arg Gly Leu Gln
785                 790                 795                 800
Ser Asp Arg Asn Thr Ile His Lys Asn Leu Cys Ile Asn Leu Phe Ile
                    805                 810                 815
Ala Glu Phe Ile Phe Leu Ile Gly Ile Asp Lys Thr Lys Tyr Ala Ile
                820                 825                 830
Ala Cys Pro Ile Phe Ala Gly Leu Leu His Phe Phe Leu Ala Ala
                835                 840                 845
Phe Ala Trp Met Cys Leu Glu Gly Val Gln Leu Tyr Leu Met Leu Val
                850                 855                 860
Glu Val Phe Glu Ser Glu Tyr Ser Arg Lys Lys Tyr Tyr Tyr Val Ala
865                 870                 875                 880
Gly Tyr Leu Phe Pro Ala Thr Val Val Gly Val Ser Ala Ala Ile Asp
                    885                 890                 895
Tyr Lys Ser Tyr Gly Thr Glu Lys Ala Cys Trp Leu His Val Asp Asn
                900                 905                 910
Tyr Phe Ile Trp Ser Phe Ile Gly Pro Val Thr Phe Ile Ile Leu Leu
                915                 920                 925
Asn Ile Ile Phe Leu Val Ile Thr Leu Cys Lys Met Val Lys His Ser
                930                 935                 940
Asn Thr Leu Lys Pro Asp Ser Ser Arg Leu Glu Asn Ile Lys Ser Trp
945                 950                 955                 960
Val Leu Gly Ala Phe Ala Leu Leu Cys Leu Leu Gly Leu Thr Trp Ser
                    965                 970                 975
Phe Gly Leu Leu Phe Ile Asn Glu Glu Thr Ile Val Met Ala Tyr Leu
                980                 985                 990
Phe Thr Ile Phe Asn Ala Phe Gln Gly Val Phe Ile Phe Ile Phe His
                995                 1000                1005
Cys Ala Leu Gln Lys Lys Val Arg Lys Glu Tyr Gly Lys Cys Phe Arg
1010                1015                1020
```

His Ser Tyr Cys Cys Gly Gly Leu Pro Thr Glu Ser Pro His Ser Ser
1025                1030                1035                1040

Val Lys Ala Ser Thr Thr Arg Thr Ser Ala Arg Tyr Ser Ser Gly Thr
            1045                1050                1055

Gln Ser Arg Ile Arg Arg Met Trp Asn Asp Thr Val Arg Lys Gln Ser
        1060                1065                1070

Glu Ser Ser Phe Ile Ser Gly Asp Ile Asn Ser Thr Ser Thr Leu Asn
    1075                1080                1085

Gln Gly Leu Thr Ser His Gly Leu Arg Ala His Leu Gln Asp Leu Tyr
    1090                1095                1100

His Leu Glu Leu Leu Leu Gly Gln Ile Ala
1105                1110

<210> SEQ ID NO 35
<211> LENGTH: 28
<212> TYPE: DNA
<213> ORGANISM: Artificial Sequence
<220> FEATURE:
<223> OTHER INFORMATION: Description of Artificial Sequence: primer

<400> SEQUENCE: 35
gggcctcacc tgggctttcg gcctcctc                                        28

<210> SEQ ID NO 36
<211> LENGTH: 28
<212> TYPE: DNA
<213> ORGANISM: Artificial Sequence
<220> FEATURE:
<223> OTHER INFORMATION: Description of Artificial Sequence: primer

<400> SEQUENCE: 36
ggactggtgc ccccacgcgt gtcagcac                                        28

<210> SEQ ID NO 37
<211> LENGTH: 24
<212> TYPE: DNA
<213> ORGANISM: Artificial Sequence
<220> FEATURE:
<223> OTHER INFORMATION: Description of Artificial Sequence: primer

<400> SEQUENCE: 37
ccaacaagac ccataccagc tgtg                                            24

<210> SEQ ID NO 38
<211> LENGTH: 22
<212> TYPE: DNA
<213> ORGANISM: Artificial Sequence
<220> FEATURE:
<223> OTHER INFORMATION: Description of Artificial Sequence: primer

<400> SEQUENCE: 38
ctgagtcttg tcgatcccga cc                                              22

<210> SEQ ID NO 39
<211> LENGTH: 349
<212> TYPE: DNA
<213> ORGANISM: Homo sapiens

<400> SEQUENCE: 39
aagcttggca cgagggtcta tgtgcatttt ggaattactc acctgatacc atgaatggca     60
gctggtcttc agagggctgt gagctgacat actcaaatga gacccacacc tcatgccgct    120

```
gtaatcacct gacacatttt gcaattttga tgtcctctgg tccttccatt ggtattaaag      180
attataatat tcttacaagg gatcactcaa ctaggaataa ttatttcact gatttgtctt      240
gccatatgca tttttacctt ctggttcttc agtgaaattc aaagcaccag gacaacaatt      300
cacaaaaatc tttgctggta gcctatttct tgctgaactt ggtttttct                 349
```

<210> SEQ ID NO 40
<211> LENGTH: 359
<212> TYPE: DNA
<213> ORGANISM: Homo sapiens

<400> SEQUENCE: 40

```
cagggaatgt ttatatttat tttccattgt gtcctacaga agaaggtacg aaaagagtat       60
gggaaatgcc tgcgaacaca ttgctgtagt ggcaaaagta cagagagttc cattggttca      120
gggaaaacat ctggttctcg aactcctgga cgctactcca caggctcaca gagcganatt      180
ccgtagaatg tggaatgaca cggttcgaaa gcagtcagag tcttcctttta ttactggaga    240 cataaacagt tcagcgtcac tcaacagaga ggggcttctg aacaatgcca ggggatacaa      300
gtgtcatgga tactctacca ctgaatgggt aaccatgggc aatagttaca gcattgcca      359
```

<210> SEQ ID NO 41
<211> LENGTH: 480
<212> TYPE: DNA
<213> ORGANISM: Homo sapiens

<400> SEQUENCE: 41

```
tttttttttc tactacatta acaggactca aattctggag gaacagaaag cagactatat       60
gtgcaatgct agtatctgta cattacatag aaattgctca acttctttttt ctgccattag     120 ttttatcatc agttaataca gcaaatcata aaatatgcat ttagcatata attctagaat      180
tcccctccat ttcattatta attttgttgt tttattttgt tttccacagc tattccagct      240
gtgggtgaaa ttcaggttgt gagtgaccaa aaaccctatg tgatacagtt ttgctttgct     300
cttatgtttg tttgtgcagg cactccaatc taggatgcag cattgttact aatttcagac      360
aattgttctg ggccttttna aaaggcgggt ccntgttaat tttaggtaac acggcatcgg      420
ggtggtttaa agcntacaca acctattnca caggggccca tgggggggcct ttttcttcaa     480
```

<210> SEQ ID NO 42
<211> LENGTH: 466
<212> TYPE: DNA
<213> ORGANISM: Homo sapiens

<400> SEQUENCE: 42

```
ngcgaaacga anngtnctt ctagnaactt caggcttgca acaacacang ggggtgggac       60
agcagtgggt gctatgttga agaaggtgat ggggacaatg tcacctgtat ctgtgaccac     120
ctaacatcat tctccatcct catgtcccct gactccccag atcctagttc tctcctggga      180
atactcctgg atattatttc ttatgttggg gtgggctttt ccatcttgag cttggcagcc      240
tgtctagttg tggaagctgt ggtgtggaaa tcggtgacca agaatcggac ttcttatatg      300
cgccacacct gcatagtgaa tatcgctgcc tcccttctgg tccgccaaca cctggttcat      360
tgtnggtcgc tggccatcca ggacaatccg ctacatactc tgcaagacag cctgtgtggc      420
tgccaccttc ttcaatccac ttcttctanc tcagcgtctt cttctn                    466
```

<210> SEQ ID NO 43

<211> LENGTH: 403
<212> TYPE: DNA
<213> ORGANISM: Homo sapiens

<400> SEQUENCE: 43

```
ttttttttttc ctgggaatat attttttttaa ttggttgatt tgcttcgttc aaagcgctta      60
gaatggaaga tttagtttga ggaggggcag gtttgggggt aggctcagcg ggcatagtgg     120
ccacaagaag atgcccatct cacacctgga gacgtccatg agcacctcga agctggccgt     180
ntggctgcac tggcgtacga catgggtccg gttcctggac aggagcttga agccccgggc     240
aggaccaccc tcccgtccca ctgacactgc gtagagaagg gagaagaggc aggggtgaga     300
cggttccctc cgcccatgtc tnttgggggc antctttncc cgggccctgg ggacttccca     360
ggccattcct gggccaaaac caaacagcag gtattagttg agt                       403
```

<210> SEQ ID NO 44
<211> LENGTH: 358
<212> TYPE: DNA
<213> ORGANISM: Homo sapiens

<400> SEQUENCE: 44

```
ttttgagagg tttggctttt tttaatctgc ttccaaaaca aagcctcgat gatcaggcat       60
aaaatgagac ttccaatgga gatacccagt cccacatagg tgatccattt tacaacgggg     120
aagattgtag aggggacaaa aggtgacatc aatatggaga aggaggtcaa gtgagtacat     180
tggcacgtca cgatgtcttg agtttcattc actaggtggc agcctgcatc gttccactgc     240
aaatgactga aatcccaaaa cacacaatga ggctggctca ggtttgactc tatcttggaa     300
aaaaatagga aaacttcatt tatggaatag ttttgaataa ccgtggatat cacaggtc       358
```

<210> SEQ ID NO 45
<211> LENGTH: 556
<212> TYPE: DNA
<213> ORGANISM: Homo sapiens

<400> SEQUENCE: 45

```
gctggctgcc gagccagtgc catcttcctg cacttctccc tgctcacctg cctttcctgg      60
atgggcctcg aggggtacaa cctctaccga ctcgtggtgg aggtctttgg cacctatgtc     120
cctggctacc tactcaagct gagcgccatg ggctggggct tccccatctt tctggtgacg     180
ctggtggccc tggtggatgt ggacaactat ggccccatca tcttggctgt gcataggact     240
ccagagggcg tcatctaccc ttccatgtgc tggatccggg actccctggt cagctacatc     300
accaacctgg gcctcttcag cctggtgttt ctgttcaaca tggccatgct agccaccatg     360
gtggtgcaga tcctgcggct gcgcccccac acccaaaagt ggtcacatgt gctgacactg     420
ctgggcctca gcctggtcct tggcctgccc tgggccttga ccttcttctc ctttgcttct     480
ggcaccttcc agcttgtcgt cctctacctt ttcagcatca tcacctcctt ccaaggcttc     540
ctcatcttca tctggt                                                     556
```

<210> SEQ ID NO 46
<211> LENGTH: 324
<212> TYPE: DNA
<213> ORGANISM: Homo sapiens

<400> SEQUENCE: 46

```
gatccccatt gcgccantgn ggactactcc agagcagatg ccagctcagg agtctgggnc      60
actgaaaatt gccagaccct ggagacccag gcagctcaca cccgctgcca gtgccagcac     120
```

-continued

| | |
|---|---|
| ctgtccacct tgctgtact agcccagccg cccaaggacc tgaccctgga gctggcgggc | 180 |
| tcccctcgg tccccctggt gatcggctgt gcagtgtcgt gcatggcgct gctcaccctg | 240 |
| ctcgccatct atgccgcctt tggaggttc ataaaatctg aacgctccat catcttgctg | 300 |
| aacttntgcc tgtccatctt ggca | 324 |

<210> SEQ ID NO 47
<211> LENGTH: 391
<212> TYPE: DNA
<213> ORGANISM: Homo sapiens

<400> SEQUENCE: 47

| | |
|---|---|
| ttaaagcata actgtatttt tnnttttagg gccttattga tgttttgccg ttccaatgta | 60 |
| tgcatttttt nactcaataa acttgtctta attttaaata tggggcttcc ttggacctgt | 120 |
| ctgcgccatc ttctctgtga atttagttct ctttctggtg actctctgga ttttnaaaaa | 180 |
| cagactctcc tccctcaata gtgaagtgtc caccctccgg aacacaaggt ccgggagcaa | 240 |
| tatgggaaat ggtccaaagg gatcaggaaa ttgaaaactg agtctgagat gcacacactc | 300 |
| tccagcagtg ctaaggctga caactccaaa cccagcacgg gtaactagaa aaatcttctg | 360 |
| aataagatct tcccctttgc ccgtgggaaa t | 391 |

<210> SEQ ID NO 48
<211> LENGTH: 5749
<212> TYPE: DNA
<213> ORGANISM: Homo sapiens

<400> SEQUENCE: 48

| | |
|---|---|
| ggaaagcgga aagaggaaaa agcataagct tgagccttcc gatccgacca cgaatactcc | 60 |
| tgtaataaac ccaccgcccc aacaaatctg ccatagcagc cgccgccgcc gccggtcact | 120 |
| tctcgtctca gcgctttctt tgcttcttgg tttgttgggg gtagcttta tgaaacaaat | 180 |
| ctttgctatt aagccactta cattttgggg ggttccttag agtctcccctt gggggggctt | 240 |
| ctccctccct ttagccccc tcggtttgga ggttggattc agttggatac ggcgcaaggt | 300 |
| tctgggctcc tgctggcttt ttttttcctct ctctcatcga cccccctttg gttcccaccc | 360 |
| cccacctttt gcttttcgta tgtatgcatt tttaaaaata aatcctgatt ttggaagctg | 420 |
| agccggggaa aatgggcaac ggtgattggg accgaagggg agtctctccg tcactgttgc | 480 |
| tgggacgcgt gcctgtgctg gtgtcttaga gcaagagcct ccctgagctt tcggagtgga | 540 |
| agaacagtgg aagagactgc agcctaaaga cttttaaaat taacttggca tcacttttat | 600 |
| cagctcaaag gctaaacaaa caaacaaaag cagtgtcatt tattctaaga ataacttct | 660 |
| taaaggttaa agctgaaaaa tattcaagtt attttggat aacaacttac agaggccaaa | 720 |
| tgacatagga tgaaggctgt tcgtaacctg ctgatttata tattttccac ctatctcctg | 780 |
| gttatgtttg gattaatgc tgcccaagac ttctggtgtt caactttggt gaagggagtc | 840 |
| atttatggat cgtattctgt aagtgaaatg tttcctaaaa actttacaaa ctgcacttgg | 900 |
| acgctggaaa atccagatcc aaccaaatat agcatttacc tgaaattttc caaaaggac | 960 |
| cttagctgct ctaacttttc actcctggct tatcagtttg atcatttttc ccatgaaaaa | 1020 |
| ataaaggatc ttttaagaaa gaatcattct ataatgcaac tctgcaattc caagaatgct | 1080 |
| ttcgtttttc tacagtatga taaaaatttt attcaaatac gtcgagtatt tccaactaat | 1140 |
| ttcccaggat tacagaaaaa aggggaagaa gatcagaaat cttttttga gttttggta | 1200 |

-continued

```
ttgaacaagg tcagcccaag ccagtttggt tgccatgtat tatgtacttg gttggagagc     1260
tgcttaaaat cagaaaatgg gagaacagaa tcatgtggga tcatgtatac aaaatgcacc     1320
tgccctcagc atttgggaga gtgggggatc gacgaccagt cgctgatttt gttaaataac     1380
gtggtgttac ccctgaatga gcagacagag ggctgcctga cccaggagct gcaaaccacc     1440
caagtctgca atcttaccag ggaggccaag cgaccaccca agaagaatt tggaatgatg      1500 ggagatcata caattaaaag tcagcgacct cgatctgttc atgaaaaaag ggtccctcag     1560
gaacaagctg atgctgctaa atttatggca caaactggtg aatctggtgt ggaagagtgg     1620
tcccagtgga gcacatgttc ggttacttgt ggtcaagggt cgcaggtgcg aaccagaact     1680
tgtgtatcac cttacgggac acactgcagc ggcccattaa gagaatcaag ggtttgcaat     1740
aacactgccc tctgtccagt acacggagta tgggaggaat ggtcaccatg gagtttatgt     1800
tcatttacat gtggtcgagg ccaaagaaca agaacaaggt catgcacacc tcctcagtat     1860
ggaggaaggc cgtgtgaagg acctgaaaca catcataagc cttgtaatat tgctctttgc     1920
ccagttgatg gacagtggca agagtggagt tcgtggagcc agtgctcagt aacgtgctcg     1980
aatgggactc agcagagaag ccggcagtgc actgcagctg cccatggagg ctccgaatgc     2040
agagggccat gggcagaaag cagagagtgc tataaccctg aatgtacagc caatggtcaa     2100
tggaatcagt ggggtcattg gagtggttgt tccaagtcct gtgatggcgg ctgggaaagg     2160
cgaataagga cctgtcaggg tgcagtgata acagggcagc aatgtgaagg aacgggcgaa     2220
gaagtgagaa gatgcagtga gcagcgatgc cctgcacctt atgaaatatg ccctgaggat     2280
tatctgatgt cgatggtgtg gaaaagaact ccagcaggcg acttggcatt caatcaatgt     2340
cccctgaatg ccacaggcac cactagcaga cgctgctctc tcagtcttca tggagtggcc     2400
ttctgggaac agccgagctt tgcaagatgc atatcaaatg agtacagaca cttgcagcat     2460
tcaattaaag agcaccttgc taaggggcag cgaatgctgg caggtgatgg aatgtcccag     2520
gtgaccaaga cactgttgga tttaactcag agaaaaaatt tctatgcagg cgatcttctg     2580
atgtctgtgg agatcctgag aaatgtgaca gacacattta aaagggcaag ttacatccct     2640
gcatctgatg gtgtccagat ttatccaggg tcaatagagt taatgcaggt gattgaagat     2700
tttatacaca ttgttggaat ggggatgatg gactttcaga attcatactt aatgactgga     2760
aatgtagtgg ctagtattca gaagcttcct gcagcctctg ttctaacaga catcaacttt     2820
ccaatgaaag gacggaaggg aatggttgac tgggcaagaa actcagaaga tagggtagta     2880
attccaaaaa gcattttcac tccggtgtca tcaaaagaat tagatgaatc atctgtattt     2940
gttcttggcg cagtcctata caaaaactta gatctaattt tgcccacttt gagaaattat     3000
actgtcatta attccaaaat catcgtggtc acaataaggc ctgaacccaa acaaccgat     3060 tcgtttctgg agatagaact agctcatttg gctaatggta cttgaatcc ctattgtgta     3120 ttgtgggatg actccaaaac gaacgagtct ttgggaacgt ggtccaccca gggatgtaaa     3180
actgtgctta ccgatgcatc ccatacgaaa tgcttatgtg atcgtctctc taccttcgcc     3240
attttggctc agcaacctag agaaataatc atggaatcct ctggcacacc ttcagttacc     3300
ctaatagtag gcagtggtct ttcttgcttg gccttgatta ccctagcagt tgtctatgca     3360
gcattatgga ggtacatacg ctctgagaga tccataatac taattaactt ctgcctgtct     3420
atcatctcat ccaatatcct catactggtt ggacagactc agacacataa taagagtatc     3480
tgcacaacca ccactgcatt tttgcacttt ttcttcctgg cttcattctg ttgggttttg     3540
actgaggcgt ggcaatcata tatggctgta actggaaaaa ttaggacacg gcttataaga     3600
```

```
aaacgctttt tgtgccttgg atggggtaag catattgata taccgtttca tgctcttctc    3660
aaaatgacgt tgaacacaca ttagaaagca gtcatgagtg attagacaca ggctactttg    3720
tgtctaattt aatctatgga agtgaaaata catgagctgg tcagttttga acattcattg    3780
gtcatttgga actttaaaag gaagtaagta ttgaatgctc atttagctag tcagttaaca    3840
ttcaacagtg tctagatagt atgaaatgag accccgagat gcctacacac agaaaaacag    3900
tgctctctgt taatattttc tgaaagtgca aaataccttta aaattttcaa ggcctaatgt    3960
gtgatggttc actaggcatg tactcccacc aagaaaactt agaagatttc atttcaagaa    4020
atctcaaagc aattaaagaa taaaagcgat tcatttcata gggagaacac catctagaga    4080
attaatgaaa cctcacagct tgttgacctg gtcctcaaaa gcagaaacag aattgctgac    4140
agactgagaa ctaattcttt acttgtgttt attaagaagt ttctctcaaa ttgcctcatg    4200
acatggacat ctcaaagatc tatattatag ggccaattct aatgatagcc tagttaattt    4260
aagaagctac ttttagaaaa agcccaaata tacaataata tctactgtat tagaagactg    4320
gcatatggga tgctaggagg aacctggaa attacaaata agtgtgctta taacaattcc    4380
agaattattt aggctggaaa aatatgatca agaacacgta aatattattc attaggtttc    4440
agcaaggtct attatgtcta gctaataaat taggacttta tccacagaca aatgaaaaag    4500
caattaataa gaagttgaag agtaggccag acatggtggc tcacgcctgt aatcctagca    4560
ctttgggaaa ccaaggcggg tggactacct gagcgtgggt ggactacctg agcgcgggtg    4620
gactacctga gcacgggagt tcgagattag cctgagcaat atggcaaaac cccatctcta    4680
ccaaaaatgc aaaaaattag ccgggagtga tggcacatac ctgtagtccc agctactcgg    4740
gaggctaagg tgggaggatt gcatgagcct gggaagtgga ggttgcagtg agccaagatc    4800
acaccacgac actccaactt gtgtcacaga gtaagaccct atctcacacc aacacaaaag    4860
ttgaagactt tgttctactt agaatttcat caaattttttg tctaaatttc ctgacaaagg    4920
ccttctaaag ttgagatagt atttaaatca agggacactt ttgccatgaa ttagtaccat    4980
tctaagaaat acagaataca ggtaaaagaa cacattttttt gatgaagaac aaaacatggt    5040
gattttcaag attagtgact accttgttta aaattattac taaagatttt gaggagaggg    5100
ttcacagaca gtctccgtat ttacagctaa tattaaacta ctctaggtag caaaaacctg    5160
aactgatggt gctaaagtat cagaaagttt atgggttggc agaatagtgg tgtgtgtgtt    5220
tcattatgaa caagtacaat aaaatgaatc tagaaaaaat ttaatctaaa ttgtatgaaa    5280
taaatactat taattcttca gttataaccc atgaggaatt ttttttttcct aatgaacttg    5340 gtccagtcaa tcaaaaaaaa tcaacaaatg acatgtgtgg aggaagagga gaaggaggga    5400
caagaagagg agaaacagaa ggaggaaagg gaagaggagg aaagggagga taaggatgag    5460
gaggggacta tatttttata attttatata catatatgta tagtcaccag tgtttgttta    5520
acactatggt gtgtccttct gagatgtttt ccatagttct tgtcattaaa tctcatgaag    5580
gaatgtgatg ccactagaga aggctcacag aagagaatag caggaggtat gtgaaatgat    5640
agtaagaaag aagacagaca gaggacatac aataaaatga ttagatgacg gatttttcaa    5700
ccggaaaagg caaacatgat cttcctgaaa agaaggcata accaaaact              5749
```

<210> SEQ ID NO 49
<211> LENGTH: 21
<212> TYPE: DNA
<213> ORGANISM: Artificial Sequence
<220> FEATURE:

```
<223> OTHER INFORMATION: Description of Artificial Sequence: primer

<400> SEQUENCE: 49
tcagacactc atactgctgt g                                              21

<210> SEQ ID NO 50
<211> LENGTH: 19
<212> TYPE: DNA
<213> ORGANISM: Artificial Sequence
<220> FEATURE:
<223> OTHER INFORMATION: Description of Artificial Sequence: primer

<400> SEQUENCE: 50
cacagtccac aacttgcac                                                 19

<210> SEQ ID NO 51
<211> LENGTH: 40
<212> TYPE: DNA
<213> ORGANISM: Artificial Sequence
<220> FEATURE:
<223> OTHER INFORMATION: Description of Artificial Sequence: primer

<400> SEQUENCE: 51
gacgctggtc gactaggtgg ctgcatgcac acgttgttcg                          40

<210> SEQ ID NO 52
<211> LENGTH: 37
<212> TYPE: DNA
<213> ORGANISM: Artificial Sequence
<220> FEATURE:
<223> OTHER INFORMATION: Description of Artificial Sequence: primer

<400> SEQUENCE: 52
cctaccacag ctgtgacaat aacttcttca gctgagc                             37

<210> SEQ ID NO 53
<211> LENGTH: 16
<212> TYPE: PRT
<213> ORGANISM: Homo sapiens

<400> SEQUENCE: 53

Cys Leu Gln Asp Leu Tyr His Leu Glu Leu Leu Leu Gly Gln Ile Ala
 1               5                  10                  15

<210> SEQ ID NO 54
<211> LENGTH: 15
<212> TYPE: PRT
<213> ORGANISM: Homo sapiens

<400> SEQUENCE: 54

Cys Thr Arg Thr Ser Ala Arg Tyr Ser Ser Thr Gln Asp Ile His
 1               5                  10                  15

<210> SEQ ID NO 55
<211> LENGTH: 16
<212> TYPE: PRT
<213> ORGANISM: Homo sapiens

<400> SEQUENCE: 55

Cys Glu Gly Asp Val Arg Glu Gly Gln Met Gln Leu Val Thr Ser Leu
 1               5                  10                  15

<210> SEQ ID NO 56
<211> LENGTH: 16
<212> TYPE: PRT
```

```
<213> ORGANISM: Homo sapiens

<400> SEQUENCE: 56

Cys Ser Arg Ile Arg Arg Met Trp Asn Asp Thr Val Arg Lys Gln Ser
  1               5                  10                  15

<210> SEQ ID NO 57
<211> LENGTH: 5610
<212> TYPE: DNA
<213> ORGANISM: Homo sapiens
<220> FEATURE:
<221> NAME/KEY: CDS
<222> LOCATION: (281)..(4687)

<400> SEQUENCE: 57 ctaattttg  gtcggcggcg  gtgctgggcc  aggggaagga  agggacacgg  aggccgccct     60
cgtcccgcca  cctcctaccc  gcttccccc   agccccggct  ccgggagatg  tgccgggcgg   120
ggggcccggg  ttcgccgagc  cgcaggagag  acacgctggg  ccgaccccag  agaggcgctg   180
gacaggctgg  tggtccaggc  cgtggtgcct  gccaggtgat  gtgggcaaa   gccccccgca   240 caggccactg  agagctccgg  acacgcaccc  ggctgccacc atg gcc cgc cta gcc       295
                                               Met Ala Arg Leu Ala
                                                 1               5 gca gtg ctc tgg aat ctg tgt gtc acc gcc gtg ctg gtc acc tcg gcc          343
Ala Val Leu Trp Asn Leu Cys Val Thr Ala Val Leu Val Thr Ser Ala
                10                  15                  20 acc caa ggc ctg agc cgg gcc ggg ctc ccg ttc ggg ctg atg cgc cgg          391
Thr Gln Gly Leu Ser Arg Ala Gly Leu Pro Phe Gly Leu Met Arg Arg
             25                  30                  35 gag ctg gcg tgt gaa ggc tac ccc atc gag ctg cgg tgc ccc ggc agc          439
Glu Leu Ala Cys Glu Gly Tyr Pro Ile Glu Leu Arg Cys Pro Gly Ser
         40                  45                  50 gac gtc atc atg gtg gag aat gcc aac tac ggg cgc acg gac gac aag          487
Asp Val Ile Met Val Glu Asn Ala Asn Tyr Gly Arg Thr Asp Asp Lys
     55                  60                  65 att tgc gat gct gac cct ttc cag atg gag aat gtg cag tgc tac ctg          535
Ile Cys Asp Ala Asp Pro Phe Gln Met Glu Asn Val Gln Cys Tyr Leu
 70                  75                  80                  85 ccg gac gcc ttc aag atc atg tca cag agg tgt aac aac cgc acc cag          583
Pro Asp Ala Phe Lys Ile Met Ser Gln Arg Cys Asn Asn Arg Thr Gln
                 90                  95                 100 tgc gtg gtg gtc gcc ggc tcg gat gcc ttt cct gac ccc tgt cct ggg          631
Cys Val Val Val Ala Gly Ser Asp Ala Phe Pro Asp Pro Cys Pro Gly
            105                 110                 115 acc tac aag tac ctg gag gtg cag tac gac tgt gtc ccc tac atc ttc          679
Thr Tyr Lys Tyr Leu Glu Val Gln Tyr Asp Cys Val Pro Tyr Ile Phe
        120                 125                 130 gtg tgc cca ggg acc ctg cag aag gtg ctg gag ccc acc tcg aca cac          727
Val Cys Pro Gly Thr Leu Gln Lys Val Leu Glu Pro Thr Ser Thr His
    135                 140                 145 gag tca gag cac cag tct ggc gca tgg tgc aag gac ccg ctg cag gcg          775
Glu Ser Glu His Gln Ser Gly Ala Trp Cys Lys Asp Pro Leu Gln Ala
150                 155                 160                 165 ggt gac cgc atc tac gtg atg ccc tgg atc ccc tac cgc acg gac aca          823
Gly Asp Arg Ile Tyr Val Met Pro Trp Ile Pro Tyr Arg Thr Asp Thr
                170                 175                 180 ctg act gag tat gcc tcg tgg gag gac tac gtg gcc gcc cgc cac acc          871
Leu Thr Glu Tyr Ala Ser Trp Glu Asp Tyr Val Ala Ala Arg His Thr
            185                 190                 195 acc acc tac cgc ctg ccc aac cgc gtg gat ggc aca ggc ttt gtg gtc          919
```

-continued

```
Thr Thr Tyr Arg Leu Pro Asn Arg Val Asp Gly Thr Gly Phe Val Val
        200                 205                 210 tac gat ggt gcc gtc ttg tac aac aag gag cgc acg cgc aac atc gtc        967
Tyr Asp Gly Ala Val Leu Tyr Asn Lys Glu Arg Thr Arg Asn Ile Val
215                 220                 225 aag tat gac cta cgg acg cgc atc aag agc ggg gag acg gtc atc aat       1015
Lys Tyr Asp Leu Arg Thr Arg Ile Lys Ser Gly Glu Thr Val Ile Asn
230                 235                 240                 245 acc gcc aac tac cat gac acc tcg ccc tac cgc tgg ggc gga aag acc       1063
Thr Ala Asn Tyr His Asp Thr Ser Pro Tyr Arg Trp Gly Gly Lys Thr
                250                 255                 260 gac att gac ctg gcg gtg gac gag aac ggg ctg tgg gtc atc tac gcc       1111
Asp Ile Asp Leu Ala Val Asp Glu Asn Gly Leu Trp Val Ile Tyr Ala
            265                 270                 275 act gag ggc aac aac ggg cgg ctg gtg gtg agc cag ctg aac ccc tac       1159
Thr Glu Gly Asn Asn Gly Arg Leu Val Val Ser Gln Leu Asn Pro Tyr
        280                 285                 290 aca ctg cgc ttt gag ggc acg tgg gag acg ggt tac gac aag cgc tcg       1207
Thr Leu Arg Phe Glu Gly Thr Trp Glu Thr Gly Tyr Asp Lys Arg Ser
295                 300                 305 gca tcc aac gcc ttc atg gtg tgt ggg gtc ctg tac gtc ctg cgt tcc       1255
Ala Ser Asn Ala Phe Met Val Cys Gly Val Leu Tyr Val Leu Arg Ser
310                 315                 320                 325 gtg tac gtg gat gat gac agc gag gcg gct ggc aac cgc gtg gac tat       1303
Val Tyr Val Asp Asp Asp Ser Glu Ala Ala Gly Asn Arg Val Asp Tyr
                330                 335                 340 gcc ttc aac acc aat gcc aac cgc gag gag cct gtc agc ctc acc ttc       1351
Ala Phe Asn Thr Asn Ala Asn Arg Glu Glu Pro Val Ser Leu Thr Phe
            345                 350                 355 ccc aac ccc tac cag ttc atc tcc tcc gtt gac tac aac cct cgc gac       1399
Pro Asn Pro Tyr Gln Phe Ile Ser Ser Val Asp Tyr Asn Pro Arg Asp
        360                 365                 370 aac cag ctg tac gtc tgg aac aac tat ttc gtg gtg cgc tac agc ctg       1447
Asn Gln Leu Tyr Val Trp Asn Asn Tyr Phe Val Val Arg Tyr Ser Leu
375                 380                 385 gag ttc ggg ccg ccc gac ccc agt gct ggc cca gcc act tcc cca ccc       1495
Glu Phe Gly Pro Pro Asp Pro Ser Ala Gly Pro Ala Thr Ser Pro Pro
390                 395                 400                 405 ctc agc acg acc acc aca gcc agg ccc acg ccc ctc acc agc aca gcc       1543
Leu Ser Thr Thr Thr Thr Ala Arg Pro Thr Pro Leu Thr Ser Thr Ala
                410                 415                 420 tcg ccc gca gcc acc acc ccg ctc cgc cgg gca ccc ctc acc acg cac       1591
Ser Pro Ala Ala Thr Thr Pro Leu Arg Arg Ala Pro Leu Thr Thr His
            425                 430                 435 cca gtg ggt gcc atc aac cag ctg gga cct gat ctg cct cca gcc aca       1639
Pro Val Gly Ala Ile Asn Gln Leu Gly Pro Asp Leu Pro Pro Ala Thr
        440                 445                 450 gcc cca gtc ccc agc acc cgg cgg ccc cca gcc ccg aat cta cac gtg       1687
Ala Pro Val Pro Ser Thr Arg Arg Pro Pro Ala Pro Asn Leu His Val
455                 460                 465 tcc cct gag ctc ttc tgc gag ccc cga gag gta cgg cgg gtc cag tgg       1735
Ser Pro Glu Leu Phe Cys Glu Pro Arg Glu Val Arg Arg Val Gln Trp
470                 475                 480                 485 ccg gcc acc cag cag ggc atg ctg gtg gag agg ccc tgc ccc aag ggg       1783
Pro Ala Thr Gln Gln Gly Met Leu Val Glu Arg Pro Cys Pro Lys Gly
                490                 495                 500 act cga gga att gcc tcc ttc cag tgt cta cca gcc ttg ggg ctc tgg       1831
Thr Arg Gly Ile Ala Ser Phe Gln Cys Leu Pro Ala Leu Gly Leu Trp
            505                 510                 515
```

-continued

| | |
|---|---|
| aac ccc cgg ggc cct gac ctc agc aac tgc acc tcc ccc tgg gtc aac<br>Asn Pro Arg Gly Pro Asp Leu Ser Asn Cys Thr Ser Pro Trp Val Asn<br>520                        525                    530 | 1879 |
| cag gtg gcc cag aag atc aag agt ggg gag aac gcg gcc aac atc gcc<br>Gln Val Ala Gln Lys Ile Lys Ser Gly Glu Asn Ala Ala Asn Ile Ala<br>535                        540                    545 | 1927 |
| agc gag ctg gcc cga cac acc cgg ggc tcc atc tac gcg ggg gac gtc<br>Ser Glu Leu Ala Arg His Thr Arg Gly Ser Ile Tyr Ala Gly Asp Val<br>550                   555                   560                  565 | 1975 |
| tcc tcc tct gtg aag ctg atg gag cag ctg ctg gac atc ctg gat gcc<br>Ser Ser Ser Val Lys Leu Met Glu Gln Leu Leu Asp Ile Leu Asp Ala<br>                570                   575                   580 | 2023 |
| cag ctg cag gcc ctg cgg ccc atc gag cgc gag tca gcc ggc aag aac<br>Gln Leu Gln Ala Leu Arg Pro Ile Glu Arg Glu Ser Ala Gly Lys Asn<br>585                        590                   595 | 2071 |
| tac aac aag atg cac aag cga gag aga act tgt aag gat tat atc aag<br>Tyr Asn Lys Met His Lys Arg Glu Arg Thr Cys Lys Asp Tyr Ile Lys<br>                600                   605                   610 | 2119 |
| gcc gtg gtg gag aca gtg gac aat ctg ctc cgg cca gaa gct ctg gag<br>Ala Val Val Glu Thr Val Asp Asn Leu Leu Arg Pro Glu Ala Leu Glu<br>615                        620                    625 | 2167 |
| tcc tgg aag gac atg aat gcc acg gag cag gtg cac acg gcc acc atg<br>Ser Trp Lys Asp Met Asn Ala Thr Glu Gln Val His Thr Ala Thr Met<br>630                        635                    640                  645 | 2215 |
| ctc ctc gac gtc ctg gag gag ggc gcc ttc ctg ctg gcc gac aat gtc<br>Leu Leu Asp Val Leu Glu Glu Gly Ala Phe Leu Leu Ala Asp Asn Val<br>                650                   655                   660 | 2263 |
| agg gag cct gcc cgc ttc ctg gct gcc aag gag aac gtg gtc ctg gag<br>Arg Glu Pro Ala Arg Phe Leu Ala Ala Lys Glu Asn Val Val Leu Glu<br>665                        670                    675 | 2311 |
| gtc aca gtc ctg aac aca gag ggc cag gtg cag gag ctg gtg ttc ccc<br>Val Thr Val Leu Asn Thr Glu Gly Gln Val Gln Glu Leu Val Phe Pro<br>                680                   685                   690 | 2359 |
| cag gag gag tac ccg aga aag aac tcc atc cag ctg tct gcc aaa acc<br>Gln Glu Glu Tyr Pro Arg Lys Asn Ser Ile Gln Leu Ser Ala Lys Thr<br>695                        700                    705 | 2407 |
| atc aag cag aac agc cgc aat ggg gtg gtc aaa gtt gtc ttc atc ctc<br>Ile Lys Gln Asn Ser Arg Asn Gly Val Val Lys Val Val Phe Ile Leu<br>710                        715                   720                  725 | 2455 |
| tac aac aac ctg ggc ctc ttc ctg tcc acg gag aat gcc aca gtg aag<br>Tyr Asn Asn Leu Gly Leu Phe Leu Ser Thr Glu Asn Ala Thr Val Lys<br>                730                   735                   740 | 2503 |
| ctg gcc ggc gaa gca ggc ccg ggt ggc cct ggg ggc gcc tct cta gtg<br>Leu Ala Gly Glu Ala Gly Pro Gly Gly Pro Gly Gly Ala Ser Leu Val<br>745                        750                    755 | 2551 |
| gtg aac tca cag gtc atc gca gca tcc atc aac aag gag tcc agc cgc<br>Val Asn Ser Gln Val Ile Ala Ala Ser Ile Asn Lys Glu Ser Ser Arg<br>                760                   765                   770 | 2599 |
| gtc ttc ctc atg gac cct gtc atc ttc acc gtg gcc cac ctg gag gac<br>Val Phe Leu Met Asp Pro Val Ile Phe Thr Val Ala His Leu Glu Asp<br>775                        780                    785 | 2647 |
| aag aac cac ttc aat gct aac tgc tcc ttc tgg aac tac tcg gag cgt<br>Lys Asn His Phe Asn Ala Asn Cys Ser Phe Trp Asn Tyr Ser Glu Arg<br>790                        795                   800                  805 | 2695 |
| tcc atg ctg ggc tac tgg tcg acc caa ggc tgc cgc ctg gtg gag tcc<br>Ser Met Leu Gly Tyr Trp Ser Thr Gln Gly Cys Arg Leu Val Glu Ser<br>                810                   815                   820 | 2743 |
| aac aag acc cat acc acg tgt gcc tgc agc cac ctc acc aac ttc gct<br>Asn Lys Thr His Thr Thr Cys Ala Cys Ser His Leu Thr Asn Phe Ala<br>825                        830                    835 | 2791 |

```
gtg ctc atg gct cac cgt gag atc tac cag ggc cgc atc aac gag ctg    2839
Val Leu Met Ala His Arg Glu Ile Tyr Gln Gly Arg Ile Asn Glu Leu
            840                 845                 850 ctg ctg tcg gtc atc acc tgg gtg ggc att gtg atc tcc ctg gtc tgc    2887
Leu Leu Ser Val Ile Thr Trp Val Gly Ile Val Ile Ser Leu Val Cys
        855                 860                 865 ttg gcc atc tgc atc tcc acc ttc tgc ttc ctg cgg ggg ctg cag acc    2935
Leu Ala Ile Cys Ile Ser Thr Phe Cys Phe Leu Arg Gly Leu Gln Thr
    870                 875                 880                 885 gac cgc aac acc atc cac aag aac ctg tgc atc aac ctc ttc ctg gct    2983
Asp Arg Asn Thr Ile His Lys Asn Leu Cys Ile Asn Leu Phe Leu Ala
                890                 895                 900 gag ctg ctc ttc ctg gtc ggg atc gac aag act cag tat gag att gcc    3031
Glu Leu Leu Phe Leu Val Gly Ile Asp Lys Thr Gln Tyr Glu Ile Ala
            905                 910                 915 tgc ccc atc ttc gcc ggc ctg ctg cac tat ttc ttc ctg gct gcc ttc    3079
Cys Pro Ile Phe Ala Gly Leu Leu His Tyr Phe Phe Leu Ala Ala Phe
        920                 925                 930 tcc tgg ctg tgc ctg gag ggc gtg cac ctc tac ctg cta cta gtg gag    3127
Ser Trp Leu Cys Leu Glu Gly Val His Leu Tyr Leu Leu Val Glu
    935                 940                 945 gtg ttt gag agc gag tat tcc cgc acc aag tac tac tac ctg ggt ggc    3175
Val Phe Glu Ser Glu Tyr Ser Arg Thr Lys Tyr Tyr Tyr Leu Gly Gly
950                 955                 960                 965 tac tgc ttc ccg gcc ctg gtg gtg ggc atc gcg gct gcc att gac tac    3223
Tyr Cys Phe Pro Ala Leu Val Val Gly Ile Ala Ala Ala Ile Asp Tyr
            970                 975                 980 cgc agc tac ggc acc gag aag gcc tgc tgg ctc cga gtg gac aat tac    3271
Arg Ser Tyr Gly Thr Glu Lys Ala Cys Trp Leu Arg Val Asp Asn Tyr
        985                 990                 995 ttc atc tgg agt ttc atc ggg cca gtc tcc ttc gtt atc gtg gtc aac    3319
Phe Ile Trp Ser Phe Ile Gly Pro Val Ser Phe Val Ile Val Val Asn
    1000                1005                1010 ctg gtg ttc ctc atg gtg acc ctg cac aag atg atc cga agc tca tct    3367
Leu Val Phe Leu Met Val Thr Leu His Lys Met Ile Arg Ser Ser Ser
    1015                1020                1025 gtg ctc aag ccc gac tcc agc cgc ctg gac aac att aaa tcc tgg gcg    3415
Val Leu Lys Pro Asp Ser Ser Arg Leu Asp Asn Ile Lys Ser Trp Ala
1030                1035                1040                1045 ctg ggg gcc atc gcg ctg ctg ttc ctg ctg ggc ctc acc tgg gct ttc    3463
Leu Gly Ala Ile Ala Leu Leu Phe Leu Leu Gly Leu Thr Trp Ala Phe
            1050                1055                1060 ggc ctc ctc ttc atc aac aag gag tcg gtg gtc atg gcc tat ctc ttc    3511
Gly Leu Leu Phe Ile Asn Lys Glu Ser Val Val Met Ala Tyr Leu Phe
        1065                1070                1075 acc acc ttc aac gcc ttc cag ggg gtc ttc atc ttc gtc ttt cac tgc    3559
Thr Thr Phe Asn Ala Phe Gln Gly Val Phe Ile Phe Val Phe His Cys
    1080                1085                1090 gcc tta cag aag aag gtg cac aag gag tac agc aag tgc ctg cgt cac    3607
Ala Leu Gln Lys Lys Val His Lys Glu Tyr Ser Lys Cys Leu Arg His
    1095                1100                1105 tcc tac tgc tgc atc cgc tcc cca ccc ggg ggc act cac gga tcc ctc    3655
Ser Tyr Cys Cys Ile Arg Ser Pro Pro Gly Gly Thr His Gly Ser Leu
1110                1115                1120                1125 aag acc tca gcc atg cga agc aac acc cgc tac tac aca ggg acc cag    3703
Lys Thr Ser Ala Met Arg Ser Asn Thr Arg Tyr Tyr Thr Gly Thr Gln
            1130                1135                1140 agc cga att cgg agg atg tgg aat gac act gtg agg aaa cag acg gag    3751
Ser Arg Ile Arg Arg Met Trp Asn Asp Thr Val Arg Lys Gln Thr Glu
```

-continued

|     |     |     |     |     |     |     |     |     |     |     |     |     |     |     |     |      |
| --- | --- | --- | --- | --- | --- | --- | --- | --- | --- | --- | --- | --- | --- | --- | --- | ---- |
|     |     |     | 1145 |     |     |     |     | 1150 |     |     |     |     | 1155 |     |     |      |
| tcc | tcc | ttc | atg | gcg | ggt | gac | atc | aac | agc | acc | ccc | acc | ctg | aac | cga | 3799 |
| Ser | Ser | Phe | Met | Ala | Gly | Asp | Ile | Asn | Ser | Thr | Pro | Thr | Leu | Asn | Arg |      |
|     |     |     | 1160 |     |     |     |     | 1165 |     |     |     |     | 1170 |     |     |      |
| ggt | acc | atg | ggg | aac | cac | ctg | ctg | acc | aac | ccc | gtg | ctg | cag | ccc | cgt | 3847 |
| Gly | Thr | Met | Gly | Asn | His | Leu | Leu | Thr | Asn | Pro | Val | Leu | Gln | Pro | Arg |      |
|     | 1175 |    |     |     |     | 1180 |    |     |     |     | 1185 |    |     |     |     |      |
| ggg | ggc | acc | agt | ccc | tac | aac | acc | ctc | atc | gcc | gag | tca | gtg | ggc | ttc | 3895 |
| Gly | Gly | Thr | Ser | Pro | Tyr | Asn | Thr | Leu | Ile | Ala | Glu | Ser | Val | Gly | Phe |      |
| 1190 |   |     |     |     | 1195 |    |     |     |     | 1200 |    |     |     |     | 1205 |      |
| aat | ccc | tcc | tcg | ccc | cct | gtc | ttc | aac | tcc | cca | ggg | agc | tac | cgg | gaa | 3943 |
| Asn | Pro | Ser | Ser | Pro | Pro | Val | Phe | Asn | Ser | Pro | Gly | Ser | Tyr | Arg | Glu |      |
|     |     |     | 1210 |    |     |     |     | 1215 |    |     |     |     | 1220 |    |     |      |
| ccc | aag | cac | ccc | ttg | gga | ggc | cgg | gaa | gcc | tgt | ggc | atg | gac | acc | ctg | 3991 |
| Pro | Lys | His | Pro | Leu | Gly | Gly | Arg | Glu | Ala | Cys | Gly | Met | Asp | Thr | Leu |      |
|     |     |     | 1225 |    |     |     |     | 1230 |    |     |     |     | 1235 |    |     |      |
| ccc | ctg | aac | ggc | aac | ttc | aat | aac | agt | tac | tcc | ttg | cga | agt | ggg | gat | 4039 |
| Pro | Leu | Asn | Gly | Asn | Phe | Asn | Asn | Ser | Tyr | Ser | Leu | Arg | Ser | Gly | Asp |      |
|     |     |     | 1240 |    |     |     |     | 1245 |    |     |     |     | 1250 |    |     |      |
| ttc | cct | ccc | ggg | gat | ggg | ggc | cct | gag | ccg | ccc | cga | ggc | cgg | aac | cta | 4087 |
| Phe | Pro | Pro | Gly | Asp | Gly | Gly | Pro | Glu | Pro | Pro | Arg | Gly | Arg | Asn | Leu |      |
|     | 1255 |    |     |     |     | 1260 |    |     |     |     | 1265 |    |     |     |     |      |
| gcc | gat | gcg | gcg | gcc | ttt | gag | aag | atg | atc | atc | tca | gag | ctg | gtg | cac | 4135 |
| Ala | Asp | Ala | Ala | Ala | Phe | Glu | Lys | Met | Ile | Ile | Ser | Glu | Leu | Val | His |      |
| 1270 |   |     |     |     | 1275 |    |     |     |     | 1280 |    |     |     |     | 1285 |      |
| aac | aac | ctg | cgg | ggg | agc | agc | agc | gcg | gcc | aag | ggc | cct | cca | ccg | cct | 4183 |
| Asn | Asn | Leu | Arg | Gly | Ser | Ser | Ser | Ala | Ala | Lys | Gly | Pro | Pro | Pro | Pro |      |
|     |     |     | 1290 |    |     |     |     | 1295 |    |     |     |     | 1300 |    |     |      |
| gag | ccc | cct | gtg | cca | cct | gtg | cca | ggg | ggc | ggg | ggc | gag | gaa | gag | gcg | 4231 |
| Glu | Pro | Pro | Val | Pro | Pro | Val | Pro | Gly | Gly | Gly | Gly | Glu | Glu | Glu | Ala |      |
|     |     |     | 1305 |    |     |     |     | 1310 |    |     |     |     | 1315 |    |     |      |
| ggc | ggg | ccc | ggg | ggt | gct | gac | cgg | gcc | gag | att | gaa | ctt | ctc | tat | aag | 4279 |
| Gly | Gly | Pro | Gly | Gly | Ala | Asp | Arg | Ala | Glu | Ile | Glu | Leu | Leu | Tyr | Lys |      |
|     | 1320 |    |     |     |     | 1325 |    |     |     |     | 1330 |    |     |     |     |      |
| gcc | ctg | gag | gag | cct | ctg | ctg | ctg | ccc | cgg | gcc | cag | tcg | gtg | ctg | tac | 4327 |
| Ala | Leu | Glu | Glu | Pro | Leu | Leu | Leu | Pro | Arg | Ala | Gln | Ser | Val | Leu | Tyr |      |
|     | 1335 |    |     |     |     | 1340 |    |     |     |     | 1345 |    |     |     |     |      |
| cag | agc | gat | ctg | gac | gag | tcg | gag | agc | tgc | acg | gcc | gag | gac | ggc | gcc | 4375 |
| Gln | Ser | Asp | Leu | Asp | Glu | Ser | Glu | Ser | Cys | Thr | Ala | Glu | Asp | Gly | Ala |      |
| 1350 |   |     |     |     | 1355 |    |     |     |     | 1360 |    |     |     |     | 1365 |      |
| acc | agc | cgg | ccc | ctc | tcc | tcc | cct | cct | ggc | cgg | gac | tcc | ctc | tat | gcc | 4423 |
| Thr | Ser | Arg | Pro | Leu | Ser | Ser | Pro | Pro | Gly | Arg | Asp | Ser | Leu | Tyr | Ala |      |
|     |     |     | 1370 |    |     |     |     | 1375 |    |     |     |     | 1380 |    |     |      |
| agc | ggg | gcc | aac | ctg | cgg | gac | tca | ccc | tcc | tac | ccg | gac | agc | agc | cct | 4471 |
| Ser | Gly | Ala | Asn | Leu | Arg | Asp | Ser | Pro | Ser | Tyr | Pro | Asp | Ser | Ser | Pro |      |
|     | 1385 |    |     |     |     | 1390 |    |     |     |     | 1395 |    |     |     |     |      |
| gag | ggg | ccc | agt | gag | gcc | ctg | ccc | cca | ccc | cct | ccc | gca | ccc | ccc | ggc | 4519 |
| Glu | Gly | Pro | Ser | Glu | Ala | Leu | Pro | Pro | Pro | Pro | Pro | Ala | Pro | Pro | Gly |      |
|     | 1400 |    |     |     |     | 1405 |    |     |     |     | 1410 |    |     |     |     |      |
| ccc | ccc | gaa | atc | tac | tac | acc | tcg | cgc | ccg | cca | gcc | ctg | gtg | gcc | cgg | 4567 |
| Pro | Pro | Glu | Ile | Tyr | Tyr | Thr | Ser | Arg | Pro | Pro | Ala | Leu | Val | Ala | Arg |      |
|     | 1415 |    |     |     |     | 1420 |    |     |     |     | 1425 |    |     |     |     |      |
| aat | ccc | ctg | cag | ggc | tac | tac | cag | gtg | cgg | cgt | cct | agc | cac | gag | ggc | 4615 |
| Asn | Pro | Leu | Gln | Gly | Tyr | Tyr | Gln | Val | Arg | Arg | Pro | Ser | His | Glu | Gly |      |
| 1430 |   |     |     |     | 1435 |    |     |     |     | 1440 |    |     |     |     | 1445 |      |
| tac | ctg | gca | gcc | cca | ggc | ctt | gag | ggg | cca | ggg | ccc | gat | ggg | gac | ggg | 4663 |
| Tyr | Leu | Ala | Ala | Pro | Gly | Leu | Glu | Gly | Pro | Gly | Pro | Asp | Gly | Asp | Gly |      |
|     |     |     | 1450 |    |     |     |     | 1455 |    |     |     |     | 1460 |    |     |      |
| cag | atg | cag | ctg | gtc | acc | agt | ctc | tgagggcacc | tcatggacca | gggctggtg |   |     |     |     |     | 4717 |

```
Gln Met Gln Leu Val Thr Ser Leu
        1465 gcccaggcca gggagggaac cctgggcagg gctctggtgg gagagggaga cagatggagg    4777 cagtggctgg tgggccactc tctccaggtg cccctcagcc atgggcccta cagtcccctc    4837 agggactct  aacctggggg cctgaggtgc caggggttcac agacagggtt tcccaccagc    4897 cacacgcacc agctctattt gggggaagtg tagtgaggag gagcccagag acccccaggg    4957 gagtgaggag ggagaacttg gaagggtgca gcccacttcc agactctccc ctctcccacc    5017 cttctaccct gtgaagggaa atgagggctt tagtttcctg ggcagggagg ggcagcttct    5077 gaggttgcca aaggcccca  ctggatggaa cctgttagct gctcctctcc gcagccagaa    5137 atgctgccgg ctgcacccag agggagcagt gaggcaggac agatggacag gttcctcctg    5197 cgctgtaatt ccctgctccc tggagactgg gaaaaggccg cagggcaggg ggactgggcg    5257 gtggtggctg gtggtttaaa ggttgaactt tctctgaagc tcctttcccc ttgctcttgg    5317 tccctgcccc gcaagcaaac ctgcccctc  tgcctcccag tgcacccaat gacccctcc    5377 cttggggcga ctcctgatga agcacaactc cccgcagggc ccccagccca caggggtggc    5437 catatttggg cagttcccag tctgtgggc  tcggctatct ggggagcaga ttttgggtct    5497 ggatctccct ggggagtggg tcctgggctt ggatctttcc ctaggggcc  ctcttactcc    5557 ttcctctctc ctcctccttc cccattgctg taaatatttc aacgaaatgg aaa           5610

<210> SEQ ID NO 58
<211> LENGTH: 1469
<212> TYPE: PRT
<213> ORGANISM: Homo sapiens

<400> SEQUENCE: 58

Met Ala Arg Leu Ala Ala Val Leu Trp Asn Leu Cys Val Thr Ala Val
 1               5                  10                  15

Leu Val Thr Ser Ala Thr Gln Gly Leu Ser Arg Ala Gly Leu Pro Phe
            20                  25                  30

Gly Leu Met Arg Arg Glu Leu Ala Cys Glu Gly Tyr Pro Ile Glu Leu
        35                  40                  45

Arg Cys Pro Gly Ser Asp Val Ile Met Val Glu Asn Ala Asn Tyr Gly
    50                  55                  60

Arg Thr Asp Asp Lys Ile Cys Asp Ala Asp Pro Phe Gln Met Glu Asn
65                  70                  75                  80

Val Gln Cys Tyr Leu Pro Asp Ala Phe Lys Ile Met Ser Gln Arg Cys
                85                  90                  95

Asn Asn Arg Thr Gln Cys Val Val Ala Gly Ser Asp Ala Phe Pro
            100                 105                 110

Asp Pro Cys Pro Gly Thr Tyr Lys Tyr Leu Glu Val Gln Tyr Asp Cys
        115                 120                 125

Val Pro Tyr Ile Phe Val Cys Pro Gly Thr Leu Gln Lys Val Leu Glu
    130                 135                 140

Pro Thr Ser Thr His Glu Ser Glu His Gln Ser Gly Ala Trp Cys Lys
145                 150                 155                 160

Asp Pro Leu Gln Ala Gly Asp Arg Ile Tyr Val Met Pro Trp Ile Pro
                165                 170                 175

Tyr Arg Thr Asp Thr Leu Thr Glu Tyr Ala Ser Trp Glu Asp Tyr Val
            180                 185                 190

Ala Ala Arg His Thr Thr Thr Tyr Arg Leu Pro Asn Arg Val Asp Gly
        195                 200                 205
```

-continued

```
Thr Gly Phe Val Val Tyr Asp Gly Ala Val Leu Tyr Asn Lys Glu Arg
    210                 215                 220
Thr Arg Asn Ile Val Lys Tyr Asp Leu Arg Thr Arg Ile Lys Ser Gly
225                 230                 235                 240
Glu Thr Val Ile Asn Thr Ala Asn Tyr His Asp Thr Ser Pro Tyr Arg
                245                 250                 255
Trp Gly Gly Lys Thr Asp Ile Asp Leu Ala Val Asp Glu Asn Gly Leu
                260                 265                 270
Trp Val Ile Tyr Ala Thr Glu Gly Asn Asn Gly Arg Leu Val Val Ser
                275                 280                 285
Gln Leu Asn Pro Tyr Thr Leu Arg Phe Glu Gly Thr Trp Glu Thr Gly
    290                 295                 300
Tyr Asp Lys Arg Ser Ala Ser Asn Ala Phe Met Val Cys Gly Val Leu
305                 310                 315                 320
Tyr Val Leu Arg Ser Val Tyr Val Asp Asp Ser Glu Ala Ala Gly
                325                 330                 335
Asn Arg Val Asp Tyr Ala Phe Asn Thr Asn Ala Asn Arg Glu Glu Pro
                340                 345                 350
Val Ser Leu Thr Phe Pro Asn Pro Tyr Gln Phe Ile Ser Ser Val Asp
    355                 360                 365
Tyr Asn Pro Arg Asp Asn Gln Leu Tyr Val Trp Asn Asn Tyr Phe Val
    370                 375                 380
Val Arg Tyr Ser Leu Glu Phe Gly Pro Pro Asp Pro Ser Ala Gly Pro
385                 390                 395                 400
Ala Thr Ser Pro Pro Leu Ser Thr Thr Thr Ala Arg Pro Thr Pro
                405                 410                 415
Leu Thr Ser Thr Ala Ser Pro Ala Ala Thr Thr Pro Leu Arg Arg Ala
                420                 425                 430
Pro Leu Thr Thr His Pro Val Gly Ala Ile Asn Gln Leu Gly Pro Asp
            435                 440                 445
Leu Pro Pro Ala Thr Ala Pro Val Pro Ser Thr Arg Arg Pro Pro Ala
450                 455                 460
Pro Asn Leu His Val Ser Pro Glu Leu Phe Cys Glu Pro Arg Glu Val
465                 470                 475                 480
Arg Arg Val Gln Trp Pro Ala Thr Gln Gln Gly Met Leu Val Glu Arg
                485                 490                 495
Pro Cys Pro Lys Gly Thr Arg Gly Ile Ala Ser Phe Gln Cys Leu Pro
                500                 505                 510
Ala Leu Gly Leu Trp Asn Pro Arg Gly Pro Asp Leu Ser Asn Cys Thr
                515                 520                 525
Ser Pro Trp Val Asn Gln Val Ala Gln Lys Ile Lys Ser Gly Glu Asn
530                 535                 540
Ala Ala Asn Ile Ala Ser Glu Leu Ala Arg His Thr Arg Gly Ser Ile
545                 550                 555                 560
Tyr Ala Gly Asp Val Ser Ser Val Lys Leu Met Glu Gln Leu Leu
                565                 570                 575
Asp Ile Leu Asp Ala Gln Leu Gln Ala Leu Arg Pro Ile Glu Arg Glu
                580                 585                 590
Ser Ala Gly Lys Asn Tyr Asn Lys Met His Lys Arg Glu Arg Thr Cys
                595                 600                 605
Lys Asp Tyr Ile Lys Ala Val Val Glu Thr Val Asp Asn Leu Leu Arg
610                 615                 620
```

-continued

```
Pro Glu Ala Leu Glu Ser Trp Lys Asp Met Asn Ala Thr Glu Gln Val
625                 630                 635                 640

His Thr Ala Thr Met Leu Leu Asp Val Leu Glu Glu Gly Ala Phe Leu
            645                 650                 655

Leu Ala Asp Asn Val Arg Glu Pro Ala Arg Phe Leu Ala Ala Lys Glu
                660                 665                 670

Asn Val Val Leu Glu Val Thr Val Leu Asn Thr Glu Gly Gln Val Gln
            675                 680                 685

Glu Leu Val Phe Pro Gln Glu Glu Tyr Pro Arg Lys Asn Ser Ile Gln
690                 695                 700

Leu Ser Ala Lys Thr Ile Lys Gln Asn Ser Arg Asn Gly Val Val Lys
705                 710                 715                 720

Val Val Phe Ile Leu Tyr Asn Asn Leu Gly Leu Phe Leu Ser Thr Glu
                725                 730                 735

Asn Ala Thr Val Lys Leu Ala Gly Glu Ala Gly Pro Gly Gly Pro Gly
            740                 745                 750

Gly Ala Ser Leu Val Val Asn Ser Gln Val Ile Ala Ala Ser Ile Asn
            755                 760                 765

Lys Glu Ser Ser Arg Val Phe Leu Met Asp Pro Val Ile Phe Thr Val
770                 775                 780

Ala His Leu Glu Asp Lys Asn His Phe Asn Ala Asn Cys Ser Phe Trp
785                 790                 795                 800

Asn Tyr Ser Glu Arg Ser Met Leu Gly Tyr Trp Ser Thr Gln Gly Cys
                805                 810                 815

Arg Leu Val Glu Ser Asn Lys Thr His Thr Thr Cys Ala Cys Ser His
            820                 825                 830

Leu Thr Asn Phe Ala Val Leu Met Ala His Arg Glu Ile Tyr Gln Gly
            835                 840                 845

Arg Ile Asn Glu Leu Leu Leu Ser Val Ile Thr Trp Val Gly Ile Val
850                 855                 860

Ile Ser Leu Val Cys Leu Ala Ile Cys Ile Ser Thr Phe Cys Phe Leu
865                 870                 875                 880

Arg Gly Leu Gln Thr Asp Arg Asn Thr Ile His Lys Asn Leu Cys Ile
                885                 890                 895

Asn Leu Phe Leu Ala Glu Leu Leu Phe Leu Val Gly Ile Asp Lys Thr
            900                 905                 910

Gln Tyr Glu Ile Ala Cys Pro Ile Phe Ala Gly Leu Leu His Tyr Phe
            915                 920                 925

Phe Leu Ala Ala Phe Ser Trp Leu Cys Leu Glu Gly Val His Leu Tyr
930                 935                 940

Leu Leu Leu Val Glu Val Phe Glu Ser Glu Tyr Ser Arg Thr Lys Tyr
945                 950                 955                 960

Tyr Tyr Leu Gly Gly Tyr Cys Phe Pro Ala Leu Val Val Gly Ile Ala
                965                 970                 975

Ala Ala Ile Asp Tyr Arg Ser Tyr Gly Thr Glu Lys Ala Cys Trp Leu
            980                 985                 990

Arg Val Asp Asn Tyr Phe Ile Trp Ser Phe Ile Gly Pro Val Ser Phe
            995                 1000                1005

Val Ile Val Val Asn Leu Val Phe Leu Met Val Thr Leu His Lys Met
    1010                1015                1020

Ile Arg Ser Ser Ser Val Leu Lys Pro Asp Ser Ser Arg Leu Asp Asn
1025                1030                1035                1040

Ile Lys Ser Trp Ala Leu Gly Ala Ile Ala Leu Leu Phe Leu Leu Gly
```

-continued

```
                 1045                1050                1055
Leu Thr Trp Ala Phe Gly Leu Leu Phe Ile Asn Lys Glu Ser Val Val
             1060                1065                1070
Met Ala Tyr Leu Phe Thr Thr Phe Asn Ala Phe Gln Gly Val Phe Ile
    1075                1080                1085
Phe Val Phe His Cys Ala Leu Gln Lys Lys Val His Lys Glu Tyr Ser
    1090                1095                1100
Lys Cys Leu Arg His Ser Tyr Cys Cys Ile Arg Ser Pro Pro Gly Gly
1105                1110                1115                1120
Thr His Gly Ser Leu Lys Thr Ser Ala Met Arg Ser Asn Thr Arg Tyr
             1125                1130                1135
Tyr Thr Gly Thr Gln Ser Arg Ile Arg Arg Met Trp Asn Asp Thr Val
             1140                1145                1150
Arg Lys Gln Thr Glu Ser Ser Phe Met Ala Gly Asp Ile Asn Ser Thr
             1155                1160                1165
Pro Thr Leu Asn Arg Gly Thr Met Gly Asn His Leu Leu Thr Asn Pro
    1170                1175                1180
Val Leu Gln Pro Arg Gly Gly Thr Ser Pro Tyr Asn Thr Leu Ile Ala
1185                1190                1195                1200
Glu Ser Val Gly Phe Asn Pro Ser Ser Pro Val Phe Asn Ser Pro
             1205                1210                1215
Gly Ser Tyr Arg Glu Pro Lys His Pro Leu Gly Gly Arg Glu Ala Cys
             1220                1225                1230
Gly Met Asp Thr Leu Pro Leu Asn Gly Asn Phe Asn Asn Ser Tyr Ser
             1235                1240                1245
Leu Arg Ser Gly Asp Phe Pro Pro Gly Asp Gly Pro Glu Pro Pro
    1250                1255                1260
Arg Gly Arg Asn Leu Ala Asp Ala Ala Ala Phe Glu Lys Met Ile Ile
1265                1270                1275                1280
Ser Glu Leu Val His Asn Asn Leu Arg Gly Ser Ser Ser Ala Ala Lys
             1285                1290                1295
Gly Pro Pro Pro Pro Glu Pro Pro Val Pro Pro Val Pro Gly Gly Gly
             1300                1305                1310
Gly Glu Glu Glu Ala Gly Gly Pro Gly Gly Ala Asp Arg Ala Glu Ile
             1315                1320                1325
Glu Leu Leu Tyr Lys Ala Leu Glu Glu Pro Leu Leu Leu Pro Arg Ala
    1330                1335                1340
Gln Ser Val Leu Tyr Gln Ser Asp Leu Asp Glu Ser Glu Ser Cys Thr
1345                1350                1355                1360
Ala Glu Asp Gly Ala Thr Ser Arg Pro Leu Ser Ser Pro Pro Gly Arg
             1365                1370                1375
Asp Ser Leu Tyr Ala Ser Gly Ala Asn Leu Arg Asp Ser Pro Ser Tyr
    1380                1385                1390
Pro Asp Ser Ser Pro Glu Gly Pro Ser Glu Ala Leu Pro Pro Pro Pro
    1395                1400                1405
Pro Ala Pro Pro Gly Pro Pro Glu Ile Tyr Tyr Thr Ser Arg Pro Pro
    1410                1415                1420
Ala Leu Val Ala Arg Asn Pro Leu Gln Gly Tyr Tyr Gln Val Arg Arg
1425                1430                1435                1440
Pro Ser His Glu Gly Tyr Leu Ala Ala Pro Gly Leu Glu Gly Pro Gly
             1445                1450                1455
Pro Asp Gly Asp Gly Gln Met Gln Leu Val Thr Ser Leu
             1460                1465
```

<210> SEQ ID NO 59
<211> LENGTH: 1548
<212> TYPE: DNA
<213> ORGANISM: Homo sapiens
<220> FEATURE:
<221> NAME/KEY: CDS
<222> LOCATION: (1)..(798)

<400> SEQUENCE: 59

| | | | | | | | | | | | | | | | | |
|---|---|---|---|---|---|---|---|---|---|---|---|---|---|---|---|---|
| gag | ggg | ctt | ctg | aac | aat | gcc | agg | gat | aca | agt | gtc | atg | gat | act | cta | 48 |
| Glu | Gly | Leu | Leu | Asn | Asn | Ala | Arg | Asp | Thr | Ser | Val | Met | Asp | Thr | Leu | |
| 1 | | | | 5 | | | | | 10 | | | | | 15 | | |
| cca | ctg | aat | ggt | aac | cat | ggc | aat | agt | tac | agc | att | gcc | agc | ggc | gaa | 96 |
| Pro | Leu | Asn | Gly | Asn | His | Gly | Asn | Ser | Tyr | Ser | Ile | Ala | Ser | Gly | Glu | |
| | | | 20 | | | | | 25 | | | | | 30 | | | |
| tac | ctg | agc | aac | tgt | gtg | caa | atc | ata | gac | cgt | ggc | tat | aac | cat | aac | 144 |
| Tyr | Leu | Ser | Asn | Cys | Val | Gln | Ile | Ile | Asp | Arg | Gly | Tyr | Asn | His | Asn | |
| | | 35 | | | | | 40 | | | | | 45 | | | | |
| gag | acc | gcc | cta | gag | aaa | aag | att | ctg | aag | gaa | ctc | act | tcc | aac | tat | 192 |
| Glu | Thr | Ala | Leu | Glu | Lys | Lys | Ile | Leu | Lys | Glu | Leu | Thr | Ser | Asn | Tyr | |
| | 50 | | | | | 55 | | | | | 60 | | | | | |
| atc | cct | tct | tac | ctg | aac | aac | cat | gag | cgc | tcc | agt | gaa | cag | aac | agg | 240 |
| Ile | Pro | Ser | Tyr | Leu | Asn | Asn | His | Glu | Arg | Ser | Ser | Glu | Gln | Asn | Arg | |
| 65 | | | | | 70 | | | | | 75 | | | | | 80 | |
| aat | ctg | atg | aac | aag | ctg | gtg | aat | aac | ctt | ggc | agt | gga | agg | gaa | gat | 288 |
| Asn | Leu | Met | Asn | Lys | Leu | Val | Asn | Asn | Leu | Gly | Ser | Gly | Arg | Glu | Asp | |
| | | | | 85 | | | | | 90 | | | | | 95 | | |
| gat | gcc | att | gtc | ctg | gat | gat | gcc | acc | tcg | ttt | aac | cac | gag | gag | agt | 336 |
| Asp | Ala | Ile | Val | Leu | Asp | Asp | Ala | Thr | Ser | Phe | Asn | His | Glu | Glu | Ser | |
| | | | 100 | | | | | 105 | | | | | 110 | | | |
| ttg | ggc | ctg | gaa | ctc | att | cat | gag | gaa | tct | gat | gct | cct | ttg | ctg | ccc | 384 |
| Leu | Gly | Leu | Glu | Leu | Ile | His | Glu | Glu | Ser | Asp | Ala | Pro | Leu | Leu | Pro | |
| | | 115 | | | | | 120 | | | | | 125 | | | | |
| cca | aga | gta | tac | tcc | acc | gag | aac | cac | cag | cca | cac | cat | tat | acc | aga | 432 |
| Pro | Arg | Val | Tyr | Ser | Thr | Glu | Asn | His | Gln | Pro | His | His | Tyr | Thr | Arg | |
| | 130 | | | | | 135 | | | | | 140 | | | | | |
| agg | cgg | atc | ccc | caa | gac | cac | agt | gag | agc | ttt | ttc | cct | ttg | cta | acc | 480 |
| Arg | Arg | Ile | Pro | Gln | Asp | His | Ser | Glu | Ser | Phe | Phe | Pro | Leu | Leu | Thr | |
| 145 | | | | | 150 | | | | | 155 | | | | | 160 | |
| aac | gag | cag | aca | gaa | gat | ctc | cag | tca | ccc | cat | aga | gac | tct | ctc | tat | 528 |
| Asn | Glu | Gln | Thr | Glu | Asp | Leu | Gln | Ser | Pro | His | Arg | Asp | Ser | Leu | Tyr | |
| | | | | 165 | | | | | 170 | | | | | 175 | | |
| acc | agc | atg | ccg | aca | ctg | gct | ggt | gtg | gcc | gcc | aca | gag | agt | gtt | acc | 576 |
| Thr | Ser | Met | Pro | Thr | Leu | Ala | Gly | Val | Ala | Ala | Thr | Glu | Ser | Val | Thr | |
| | | | 180 | | | | | 185 | | | | | 190 | | | |
| acc | agc | acc | cag | acc | gaa | ccc | cca | ccg | gcc | aaa | tgt | ggt | gat | gcc | gaa | 624 |
| Thr | Ser | Thr | Gln | Thr | Glu | Pro | Pro | Pro | Ala | Lys | Cys | Gly | Asp | Ala | Glu | |
| | | 195 | | | | | 200 | | | | | 205 | | | | |
| gat | gtt | tac | tac | aaa | agc | atg | cca | aac | cta | ggc | tcc | aga | aac | cac | gtc | 672 |
| Asp | Val | Tyr | Tyr | Lys | Ser | Met | Pro | Asn | Leu | Gly | Ser | Arg | Asn | His | Val | |
| | 210 | | | | | 215 | | | | | 220 | | | | | |
| cat | cag | ctg | cat | act | tac | tac | cag | cta | ggt | cgc | ggc | agc | agt | gat | gga | 720 |
| His | Gln | Leu | His | Thr | Tyr | Tyr | Gln | Leu | Gly | Arg | Gly | Ser | Ser | Asp | Gly | |
| 225 | | | | | 230 | | | | | 235 | | | | | 240 | |
| ttt | ata | gtt | cct | cca | aac | aaa | gat | ggg | acc | cct | ccc | gag | gga | agt | tca | 768 |
| Phe | Ile | Val | Pro | Pro | Asn | Lys | Asp | Gly | Thr | Pro | Pro | Glu | Gly | Ser | Ser | |
| | | | | 245 | | | | | 250 | | | | | 255 | | |
| aaa | gga | ccg | gct | cat | ttg | gtc | act | agt | cta | tagaagatga | | cacagaaatt | | | | 818 |
| Lys | Gly | Pro | Ala | His | Leu | Val | Thr | Ser | Leu | | | | | | | |
| | | | 260 | | | | | 265 | | | | | | | | |

```
ggaaccaaca aaactgctaa caccttgttg actgttctga gttgatataa gcagtggtaa    878
taatgtgtgt actcctaaat ctttatgctg tcctctaaag acaaacacaa actctcagac    938
tttttttttt ttaatgggat ttttaggtca gcccagggga gaaagataac tgctaaaatt    998
cccctgtacc ccatccttc ttgtcctttc cccttcagat ggagacttca ttatgttaat    1058
gaacaagata tgaagaaaat ggcactcatt gtggccttgt tgaattatgt tgtgtatgtt    1118
ttaacatctc tgatgctgtg ttactaaaat tacaaggacc tgcttttaa aaggccagaa     1178
caattgtctg aaattagtaa caatgctgca tctagattgg agtgctgcac aaacaaacat    1238
aagagcaaag caaaactgta tcacataggg ttttggtca ctcacaacct gaattcacca     1298
cagctggaat agctgtggaa aacaaaataa aacaacaaaa ttaataatga aatggagggg    1358
aattctagaa ttatatgcta aatgcatatt ttatgatttg ctgtattaac tgatgataaa    1418
actaatggca gaaaagaag ttgagcaatt tctatgtaat gtacagatac tagcattgca     1478
catatagtct gctttctgtt cctccagaat ttgagtcctg ttaatgtagt agaaaaaaaa    1538
aaaaaaaaaa                                                          1548
```

<210> SEQ ID NO 60
<211> LENGTH: 266
<212> TYPE: PRT
<213> ORGANISM: Homo sapiens

<400> SEQUENCE: 60

```
Glu Gly Leu Leu Asn Asn Ala Arg Asp Thr Ser Val Met Asp Thr Leu
 1               5                  10                  15

Pro Leu Asn Gly Asn His Gly Asn Ser Tyr Ser Ile Ala Ser Gly Glu
            20                  25                  30

Tyr Leu Ser Asn Cys Val Gln Ile Ile Asp Arg Gly Tyr Asn His Asn
        35                  40                  45

Glu Thr Ala Leu Glu Lys Lys Ile Leu Lys Glu Leu Thr Ser Asn Tyr
    50                  55                  60

Ile Pro Ser Tyr Leu Asn Asn His Glu Arg Ser Ser Glu Gln Asn Arg
65                  70                  75                  80

Asn Leu Met Asn Lys Leu Val Asn Asn Leu Gly Ser Gly Arg Glu Asp
                85                  90                  95

Asp Ala Ile Val Leu Asp Asp Ala Thr Ser Phe Asn His Glu Glu Ser
            100                 105                 110

Leu Gly Leu Glu Leu Ile His Glu Glu Ser Asp Ala Pro Leu Leu Pro
        115                 120                 125

Pro Arg Val Tyr Ser Thr Glu Asn His Gln Pro His Tyr Thr Arg
    130                 135                 140

Arg Arg Ile Pro Gln Asp His Ser Glu Ser Phe Phe Pro Leu Leu Thr
145                 150                 155                 160

Asn Glu Gln Thr Glu Asp Leu Gln Ser Pro His Arg Asp Ser Leu Tyr
                165                 170                 175

Thr Ser Met Pro Thr Leu Ala Gly Val Ala Ala Thr Glu Ser Val Thr
            180                 185                 190

Thr Ser Thr Gln Thr Glu Pro Pro Ala Lys Cys Gly Asp Ala Glu
        195                 200                 205

Asp Val Tyr Tyr Lys Ser Met Pro Asn Leu Gly Ser Arg Asn His Val
    210                 215                 220

His Gln Leu His Thr Tyr Tyr Gln Leu Gly Arg Gly Ser Ser Asp Gly
225                 230                 235                 240
```

```
Phe Ile Val Pro Pro Asn Lys Asp Gly Thr Pro Pro Glu Gly Ser Ser
                245                 250                 255

Lys Gly Pro Ala His Leu Val Thr Ser Leu
        260                 265
```

<210> SEQ ID NO 61
<211> LENGTH: 28
<212> TYPE: DNA
<213> ORGANISM: Artificial Sequence
<220> FEATURE:
<223> OTHER INFORMATION: Description of Artificial Sequence: primer

<400> SEQUENCE: 61
atataagctt gctgccacca tggcccgc                                        28

<210> SEQ ID NO 62
<211> LENGTH: 20
<212> TYPE: DNA
<213> ORGANISM: Artificial Sequence
<220> FEATURE:
<223> OTHER INFORMATION: Description of Artificial Sequence: primer

<400> SEQUENCE: 62
atgacccaca gcccgttctc                                                 20

<210> SEQ ID NO 63
<211> LENGTH: 16
<212> TYPE: PRT
<213> ORGANISM: Homo sapiens

<400> SEQUENCE: 63

```
Cys Pro Gly Pro Asp Gly Asp Gly Gln Met Gln Leu Val Thr Ser Leu
 1               5                  10                  15
```

<210> SEQ ID NO 64
<211> LENGTH: 16
<212> TYPE: PRT
<213> ORGANISM: Homo sapiens

<400> SEQUENCE: 64

```
Cys Pro Glu Gly Ser Ser Lys Gly Pro Ala His Leu Val Thr Ser Leu
 1               5                  10                  15
```